United States Patent
Yang et al.

(10) Patent No.: US 11,426,471 B2
(45) Date of Patent: *Aug. 30, 2022

(54) TARGETED PROTEIN CONTRAST AGENTS, METHODS OF MAKING, AND USES THEREOF

(71) Applicant: Georgia State University Research Foundation, Inc., Atlanta, GA (US)

(72) Inventors: Jenny Jie Yang, Atlanta, GA (US); Fan Pu, Atlanta, GA (US); Shenghui Xue, Atlanta, GA (US); Jingjuan Qiao, Atlanta, GA (US); Shanshan Tan, Atlanta, GA (US); Mani Salarian, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 7 days.

This patent is subject to a terminal disclaimer.

(21) Appl. No.: 17/015,633

(22) Filed: Sep. 9, 2020

(65) Prior Publication Data

US 2021/0038746 A1    Feb. 11, 2021

Related U.S. Application Data

(62) Division of application No. 15/572,863, filed as application No. PCT/US2016/031900 on May 11, 2016, now Pat. No. 10,814,020.

(60) Provisional application No. 62/159,685, filed on May 11, 2015.

(51) Int. Cl.
| | |
|---|---|
| *A61K 49/14* | (2006.01) |
| *A61K 49/12* | (2006.01) |
| *A61K 49/16* | (2006.01) |
| *C07K 14/76* | (2006.01) |
| *C01G 99/00* | (2010.01) |

(52) U.S. Cl.
CPC .......... *A61K 49/143* (2013.01); *A61K 49/126* (2013.01); *A61K 49/16* (2013.01); *C01G 99/006* (2013.01); *C07K 14/76* (2013.01); *C07K 2319/32* (2013.01); *C07K 2319/33* (2013.01); *C07K 2319/70* (2013.01)

(58) Field of Classification Search
CPC ...... A61K 49/00; A61K 49/143; A61K 49/16; A61K 2123/00; A61K 2121/00; A61K 49/126; C07K 14/76; C07K 2319/32; C07K 2319/33; C07K 2319/70; C01G 99/006
USPC ...... 424/1.49, 1.65, 1.69, 9.1, 9.2, 9.3, 9.36, 424/1.11, 9.323
See application file for complete search history.

(56) References Cited

U.S. PATENT DOCUMENTS

| | | | | |
|---|---|---|---|---|
| 9,956,304 | B2* | 5/2018 | Yang | A61K 49/14 |
| 10,814,020 | B2* | 10/2020 | Yang | A61K 49/126 |
| 10,849,993 | B2* | 12/2020 | Yang | A61K 49/126 |
| 2003/0220482 | A1 | 11/2003 | Huang et al. | |
| 2005/0250700 | A1 | 11/2005 | Sato et al. | |
| 2009/0274625 | A1 | 11/2009 | Denmeade et al. | |

FOREIGN PATENT DOCUMENTS

| | | |
|---|---|---|
| WO | WO2007081751 A2 | 7/2007 |
| WO | 2009146099 | 12/2009 |
| WO | 2013184786 A2 | 12/2013 |

OTHER PUBLICATIONS

Non-Final Office Action of U.S. Appl. No. 17/015,571, dated Dec. 29, 2021, 11 pages.
International Search Report for PCT/US2016/031900 dated Oct. 28, 2016.
Yang et al., "Rational Design of Protein-based MRI Contrast Agents." JACS. (2008) 130:92670-9267.
Yang et al., "Rational Design of a Calcium-Binding Protein." JACS. (2003) 125:6165-6171.
Ye et al., "Probing Site-Specific Calmodulin Calcium and Lanthanide Affinity by Grafting." JACS. (2005) 127:3743-3750.
Li et al., "Rational design of a conformation-switchable Ca2+and Tb3+-binding protein without the use of multiple coupled metal-binding sites." FEBS. (2008) 275:5048-5061.
Li et al., "PEGylation of Protein-based MRI Contrast Agents Improves Relaxivities and Biocompatibilities." J. Inorg. Biochem. (2012) 107:111-118.
Xue et al. "Design of a novel class of protein-based magnetic resonance imaging contrast agents for the molecular imaging of cancer biomarkers." Interdiscip. Rev. Nanomed. Nanobiotechnol. (2013) 5(2):163-179.
Xue et al., "Design of ProCAs (Protein-based Gd3+ MRI Contrast Agents) with High Dose Efficiency and Capability for Molecular Imaging of Cancer Biomarkers." Medicinal Res. Rev. (2014) 34:1070-1099.
Pfuhl et al., "NMR exchange broadening arising from specific low affinity protein self-association: Analysis of nitrogen-15 nuclear relaxation for rat CD2 domain 1." J. Biomol. NMR (1999) 14(4):307-320.
Davis et al., "The role of charge residues mediating low affinity protein-protein recognition at the cell surface by CD2." PNAS (1998) 95(10):5490-5494.
Evans et al., "Crystal Structure and Binding Properties of the CD2 and CD244 (2B4)-binding Protein CD48." J. Biol. Chem. (2006) 281(39):29309-29320.
Luo et al., "Structure-Function Study and Anti-HIV Activity of Synthetic Peptide Analogues Derived from Viral Chemokine vMIP-II." Biochem. (2000) 39:13545-13550.

(Continued)

*Primary Examiner* — D. L. Jones
(74) *Attorney, Agent, or Firm* — Meunier Carlin & Curfman LLC

(57) ABSTRACT

Provided herein are protein contrast agents and targeted protein contrast agents, formulations thereof, and methods of use, including but not limited to, as a magnetic resonance imaging contrast agent.

8 Claims, 80 Drawing Sheets

Specification includes a Sequence Listing.

(56) References Cited

OTHER PUBLICATIONS

Qiao et al, "Molecular imaging of EGFR/HER2 cancer biomarkers by protein MRI contrast agents." J. Biol. Inorg. Chem. (2014) 19(2): 259-270.
European Search Report dated Nov. 26, 2018 for Application No. 16793465.2.
Shenghui Xue; et al: "Protein MRI contrast agent with unprecedented metal selectivity and sensitivity for liver cancer imaging", Proceedings of the National Academy of Sciences of the United Stated of America, vol. 112, No. 21, May 13, 2015 (May 13, 2015), pp. 6607-6612,XP055524448, US ISSN: 0027-8424, DOI: 10.1073/pnas.1423021112, The whole document.
Shen, et al., "Evaluation of Phage Display Discovered Peptides as Ligands for Prostate-Specific Membrane Antigen (PSMA)," PLoS ONE, 2013, pp. 1-10, vol. 8, No. 7, doi: 10.1371/journal.pone.0068339.

\* cited by examiner

FIG. 1A

FIG. 1B linker

| Contrast Agent | $r_1$ (mM$^{-1}$S$^{-1}$) | $r_2$ (mM$^{-1}$S$^{-1}$) | Kd (Tb$^{3+}$) (M) | Kd (Gd$^{3+}$) (M) | Kd (Ca$^{2+}$) (M) | Kd (Zn$^{2+}$) (M) | PSMA Affinity (µM) |
|---|---|---|---|---|---|---|---|
| ProCA32.WP.PSMA | 24.38 ± 0.08 | 33.5 ± 0.1 | 6.8 ± 0.2 x 10$^{-22}$ | 2.40 ± 0.25x10$^{-22}$ | 1.2 ± 0.03 x 10$^{-8}$ | 1.4 ± 0.03 x 10$^{-6}$ | |
| ProCA32.562.PSMA | 21.5 | 29.8 | 2.53 ± 0.25 x 10$^{-22}$ | 2.53 x 10$^{-22}$ | 1.4 ± 0.01 x 10$^{-8}$ | 2.5 ± 0.05 x 10$^{-6}$ | |
| ProCA32.564.PSMA | 27.6 | 37.9 | 3.25 ± 0.03 x 10$^{-22}$ | 9.03 x 10$^{-22}$ | 1.7 ± 0.02 x 10$^{-8}$ | 1.6 ± 0.04 x 10$^{-6}$ | 0.52 ± 0.04 |

| $y = m3*m0^{m2}/(m1^{m2}+m0^{m2})+m...$ | | |
|---|---|---|
| | Value | Error |
| m1 | 6.8555e-22 | 2.9149e-22 |
| m2 | 0.97375 | 0.21466 |
| m3 | 1.2085 | 0.24367 |
| m4 | 0.031603 | 0.036874 |
| Chisq | 0.012636 | NA |
| R | 0.9936 | NA |

$$y = m3 \cdot m0^{m2}/(m1^{m2}+m0^{m2})+m...$$

| | Value | Error |
|---|---|---|
| m1 | 1.2783e-08 | 9.7492e-10 |
| m2 | 1.0399 | 0.075259 |
| m3 | 0.98677 | 0.026352 |
| m4 | -0.021554 | 0.01899 |
| Chisq | 0.013481 | NA |
| R | 0.99755 | NA |

| y = m4-((M2+M0+M1)-sqrt((M2+... | | |
|---|---|---|
| | Value | Error |
| m1 | 2.1597 | 0.28834 |
| m2 | 2.1091 | 0.29844 |
| m4 | 0.91049 | 0.023381 |
| Chisq | 0.02162 | NA |
| R | 0.9941 | NA |

| | Value | Error |
|---|---|---|
| \multicolumn{3}{c}{$y = m3*m0^{m2}/(m1^{m2}+m0^{m2})+m...$} | | |
| m1 | 1.4297e-08 | 1.0272e-09 |
| m2 | 1.1111 | 0.079531 |
| m3 | 0.98039 | 0.02515 |
| m4 | -0.01953 | 0.017583 |
| Chisq | 0.012348 | NA |
| R | 0.99765 | NA |

| y = m4-((M2+M0+M1)-sqrt((M2+... | | |
|---|---|---|
| | Value | Error |
| m1 | 2.3624 | 0.21109 |
| m2 | 7.7966 | 0.51376 |
| m4 | 0.97891 | 0.0044667 |
| Chisq | 0.0022799 | NA |
| R | 0.99959 | NA |

ProCA32.WP, $Kd_{Zn^{2+}} = 1.6 \times 10^{-6}$ M

FIG. 32B

| Contrast Agent | r1 (mM$^{-1}$S$^{-1}$) | r2 (mM$^{-1}$S$^{-1}$) | Kd (Tb$^{3+}$)(M) | Kd (Gd$^{3+}$)(M) | Kd (Ca$^{2+}$)(M) | Kd (Zn$^{2+}$)(M) | PSMA Affinity (uM) |
|---|---|---|---|---|---|---|---|
| ProCA32 .WP | 24.38 ± 0.08 | 33.5 ± 0.1 | 6.8 ± 0.2x10$^{-22}$ | 2.40 ± 0.25x10$^{-22}$ | 1.2 ± 0.03x10$^{-8}$ | 1.4 ± 0.03x10$^{-6}$ | |
| ProCA32 .562 | 21.5 | 29.8 | 2.53 ± 0.25x10$^{-22}$ | 2.53x10$^{-22}$ | 1.4 ± 0.01x10$^{-8}$ | 2.5 ± 0.05x10$^{-6}$ | |
| ProCA32 .564 | 27.6 | 37.9 | 3.25 ± 0.03x10$^{-22}$ | 9.03 x10$^{-22}$ | 1.7 ± 0.02x10$^{-8}$ | 1.6 ± 0.04x10$^{-6}$ | 0.52± 0.04 |

FIG. 33

| Association Constant | ProCA32.562 | ProCA32.564 | ProCA32.WP |
|---|---|---|---|
| $Ka1\ (Ca^{2+})$ | $1.1 \pm 0.01 \times 10^8$ M | $1.04 \pm 0.02 \times 10^8$ M | $1.5 \pm 0.03 \times 10^8$ M |
| $Ka2\ (Ca^{2+})$ | $4.1 \pm 0.01 \times 10^7$ M | $3.30 \pm 0.02 \times 10^7$ M | $4.1 \pm 0.03 \times 10^7$ M |

FIG. 34

$K_d$ Values for Peptides Binding to VEGF-R2[a]

| monomeric peptides | $K_d$ (nM) |
|---|---|
| (1) Ac-GDSRVCWEDSWGGEVCFRYDPGGGKNH$_2$ | 70 |
| (2) Ac-AGPTWCEDDWYYCWITGTGGGKNH$_2$ | 280 |
| (4) Ac-AGPTWCEDDWTYCWLPGTGGGKNH$_2$ | 3 |
| homo-bivalent (4) + (4) | 5 |
| homo-bivalent (1) + (1) | 185 |
| hetero-bivalent (1) + (2) | 0.6 |
| hetero-bivalent (1) + (4) | 0.6 |

[a] Bivalents were linked as in Figure 5. $K_d$ was measured by fluorescence polarization for monomers and SPR (Biacore) for bivalent molecules.[16]

FIG. 35

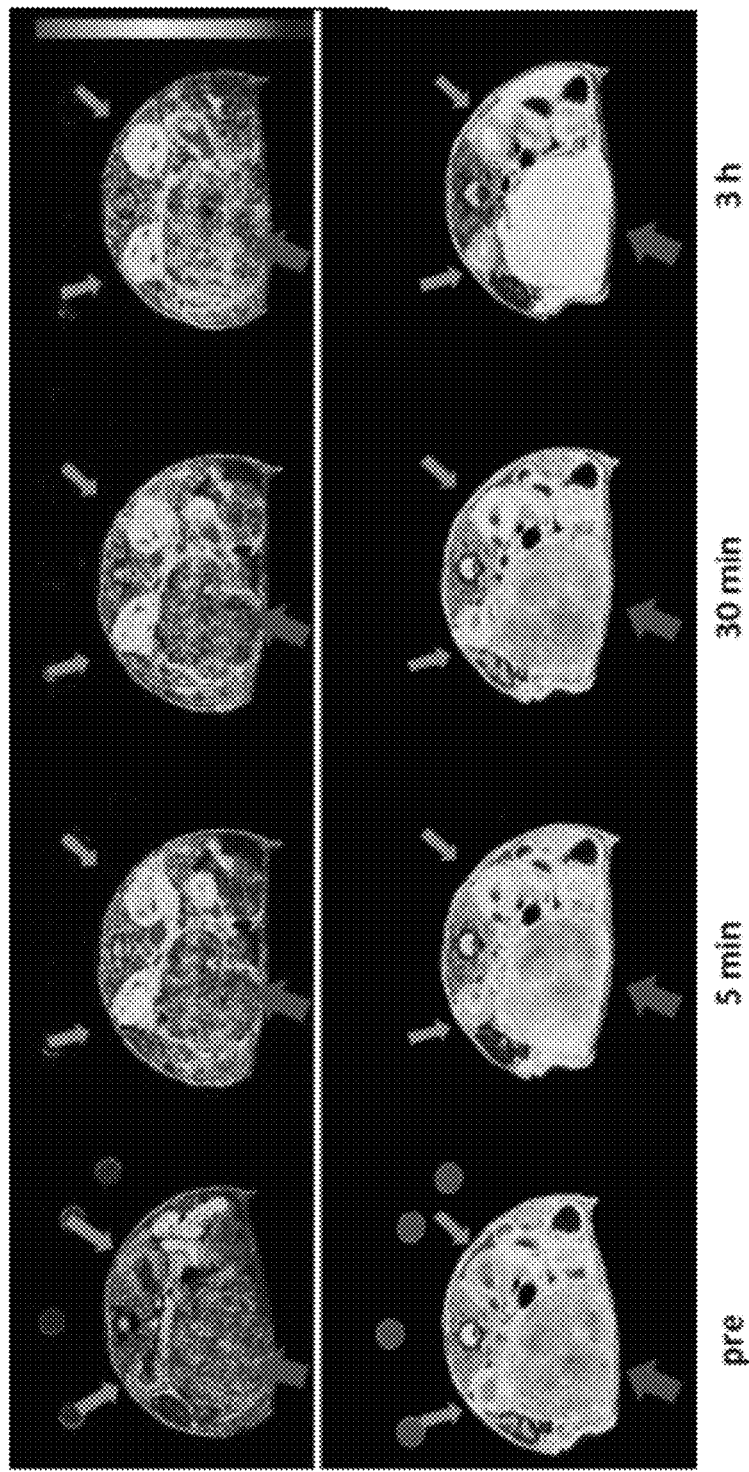

| peptides | sequence | CXCR4 binding as characterized by 12G5 mAb (IC50, nM) | x-fold increase |
|---|---|---|---|
| V1 (parent) | LGASWHRPDKCCLGYQKRPLP | 640 | NA |
| V1-L1A | AGASWHRPDKCCLGYQKRPLP | 18,500 | ~29 |
| V1-W5A | LGASAHRPDKCCLGYQKRPLP | 2,300 | ~4 |
| V1-R7A | LGASWHAPDKCCLGYQKRPLP | 41,800 | ~65 |
| V1-K9A | LGASWHRPDACCLGYQKRPLP | >100,000 | >156 (dec) |
| V1-C11A | LGASWHRPDKCALGYQKRPLP | 84 | ~7 (inc) |
| V1-Q16A | LGASWHRPDKCCLGYAKRPLP | 450 | ~1.5 |
| V1-R18A | LGASWHRPDKCCLGYQK

4°C

ProCA32.V1.CXCR4

Negative control

4°C

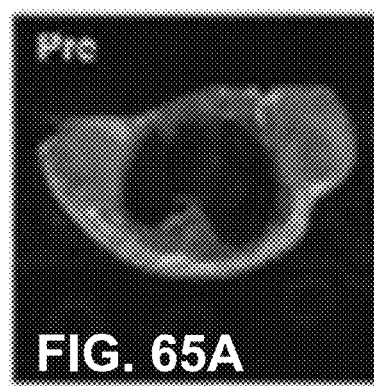
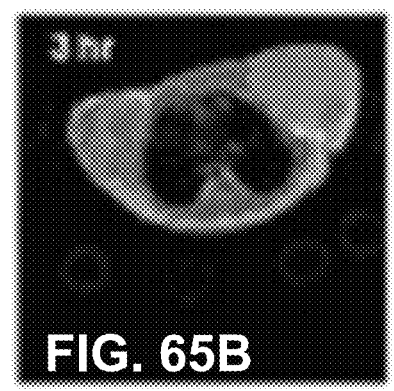
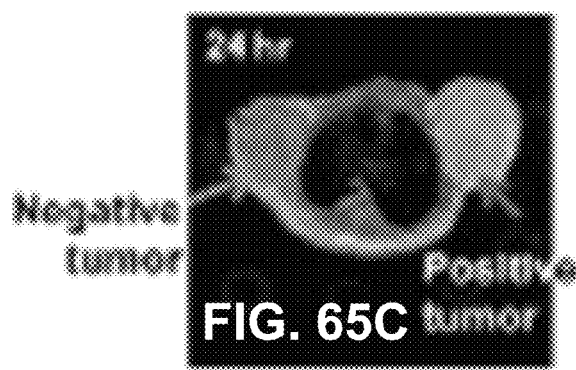
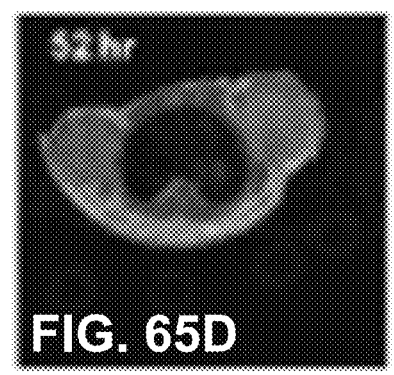
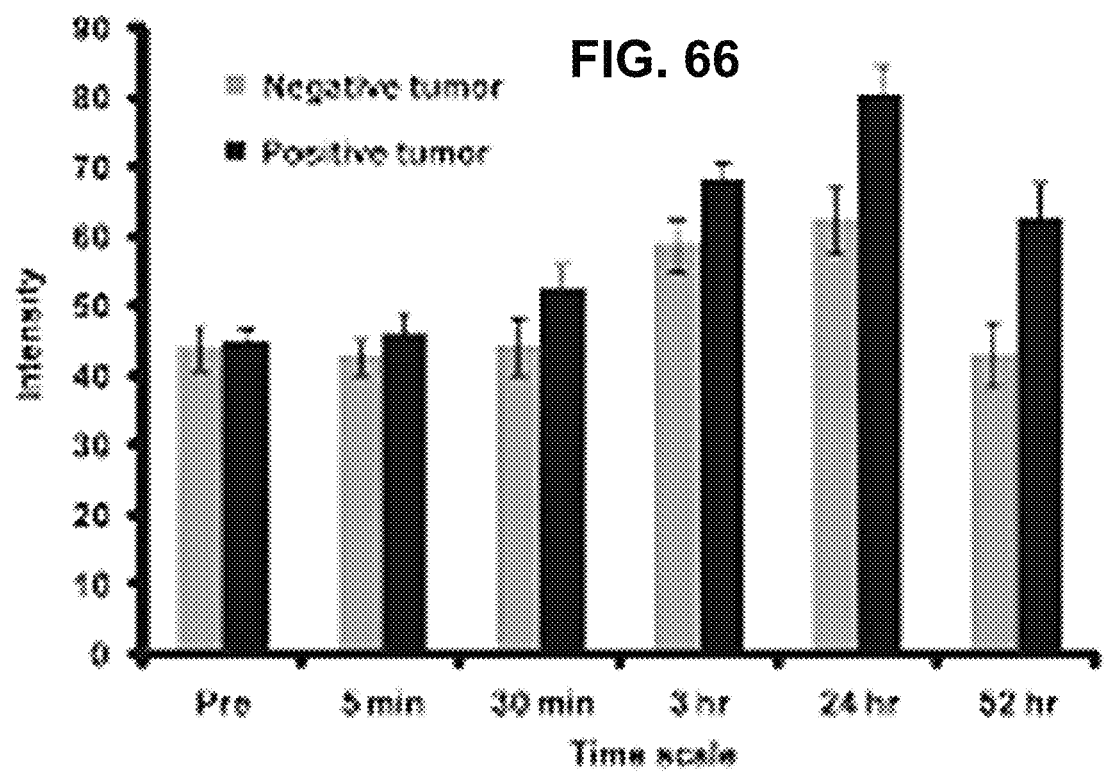

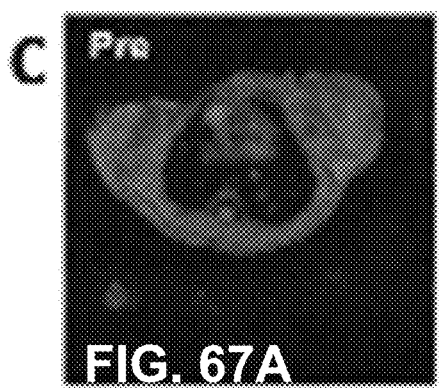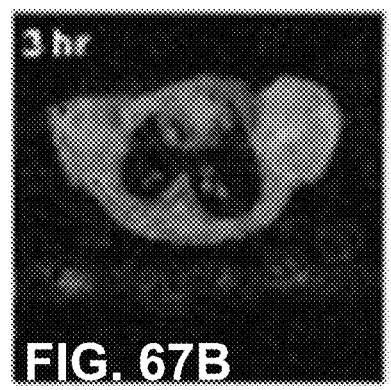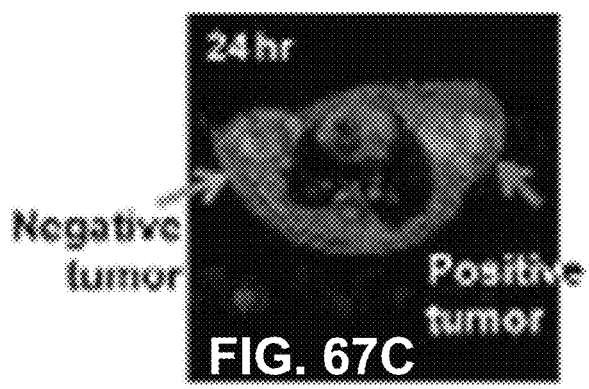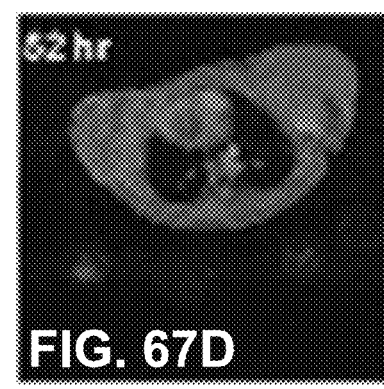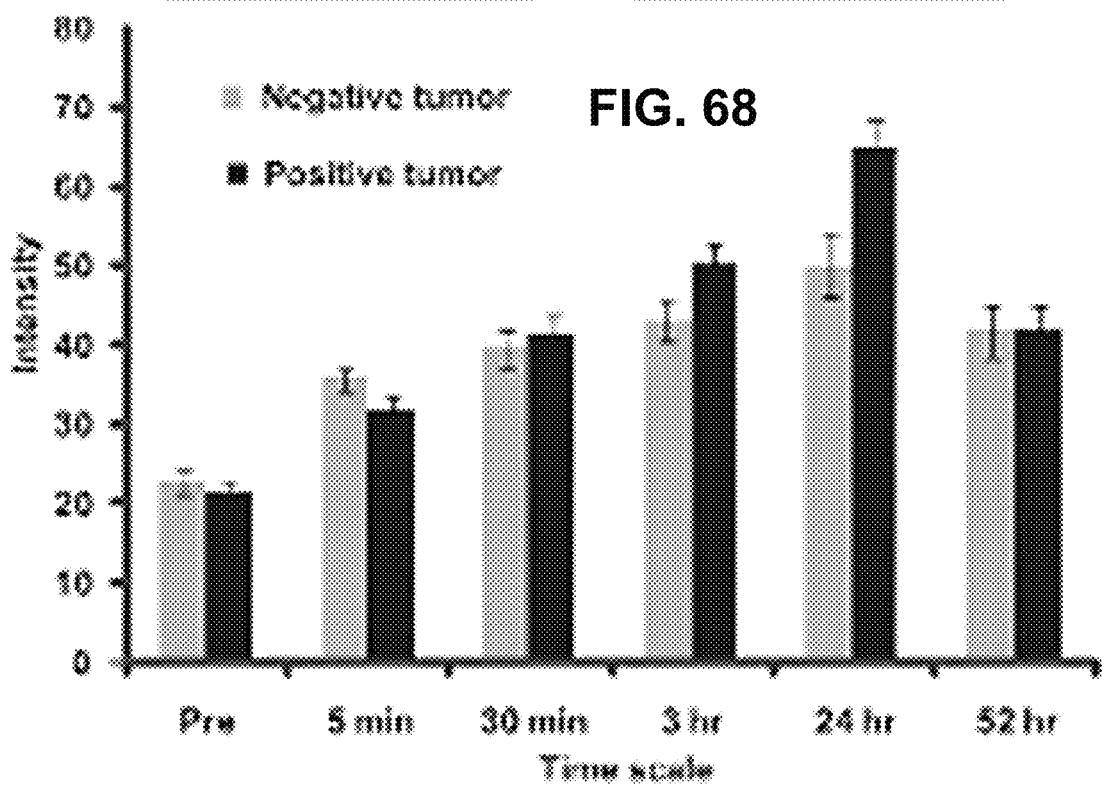

|       | Concentration |
|-------|---------------|
| 7E15  | 133.84 µM     |
| G10   | 97.86 µM      |
| B10   | 82.73 µM      |

FIG. 71

| $K_d$ (M) | Gd-DTPA (M) | ProCA32 (M) | hCA32 (M) |
|---|---|---|---|
| $Tb^{3+}$ | $9.55 \times 10^{-22}$ | $1.21 \pm 0.33 \times 10^{-21}$ | $9.82 \pm 0.5 \times 10^{-22}$ |
| $Gd^{3+}$ | $1.86 \times 10^{-21}$ | $2.79 \pm 0.36 \times 10^{-22}$ | $2.59 \pm 0.1 \times 10^{-22}$ |
| $Ca^{2+}$ | $1.51 \times 10^{-10}$ | $3.57 \pm 0.01 \times 10^{-9}$ | $1.35 \times 10^{-8}$ |
| $Zn^{2+}$ | $6.31 \times 10^{-19}$ | $6.00 \pm 2.0 \times 10^{-8}$ | $1.42 \pm 0.18 \times 10^{-6}$ |
| Log ($K_{Gd}/K_{Ca}$) | 10.9 | 13.1 | 13.72 |
| Log ($K_{Gd}/K_{Zn}$) | 2.5 | 14.3 | 15.34 |

FIG. 82

T2-weighted

T1-weighted

SEQ ID No. 1 TNALETWGAL GQDINLDIPS FQMSDDDIDI KWEKTSDKKK IAQFRKEKET FKEKDTYELL 60
SEQ ID No. 2 TNALETWGAL GQDIELNIPS FQMSDDDIDI KWEKTSDKKK IAQFRKEKET FKEKDTYELD 60
SEQ ID No. 3 GSRDSGTVWG ALGHGIELNI PNFQMTDDID EVRWERGSTL VAEFKRKMKP FLKSGAFEID 60

SEQ ID No. 1 KNGTLKIKHL KTDDQDIYKV SIYDTKGKNV LEKIFDLKIQ E 101
SEQ ID No. 2 KNGDLDIKHL KTDDQDIYKV SIYDTKGKNV LEKIFDLKIQ E 101
SEQ ID No. 3 ANGDLDIKNL TRDDSGTYNV TVYSTNGTRI LNKALDLRIL E 101

FIG. 86

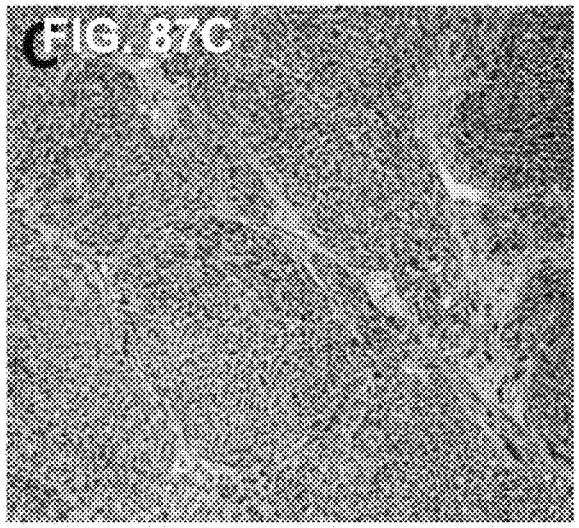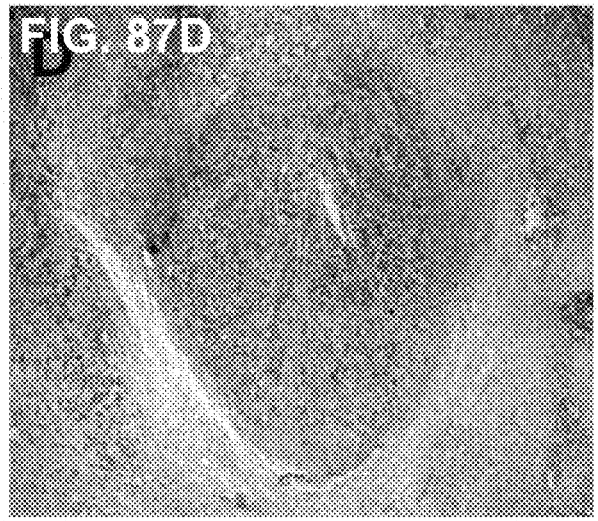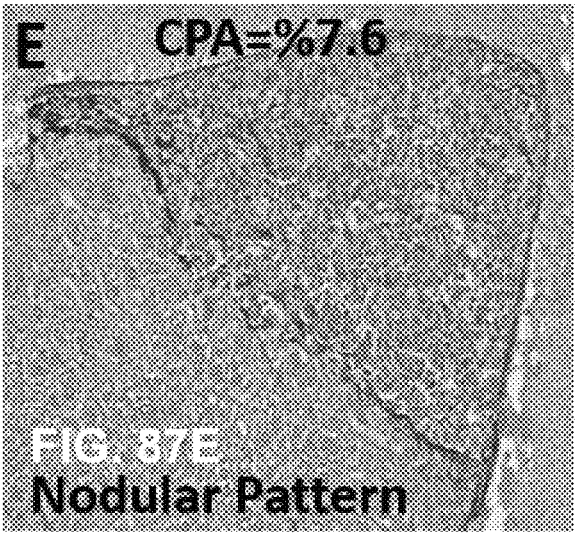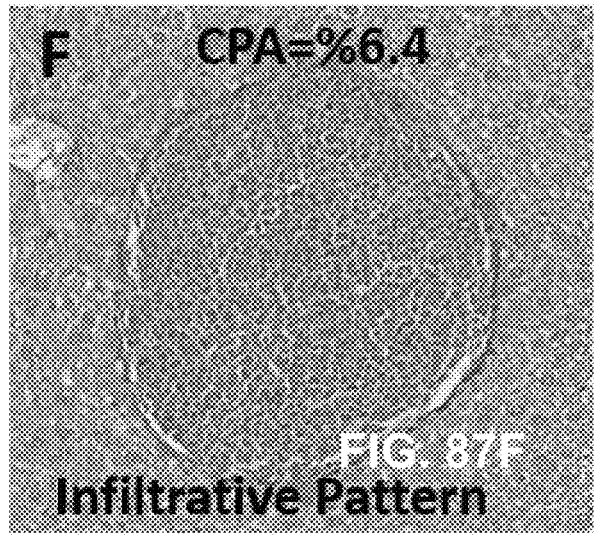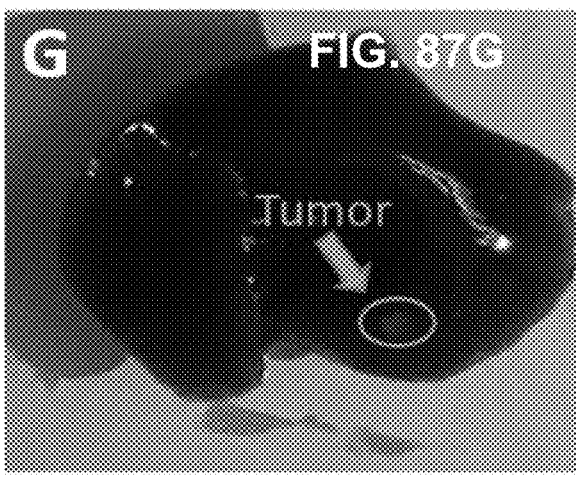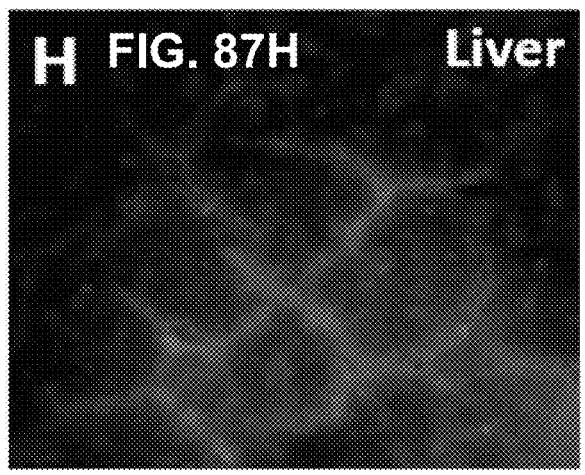

FIG. 88B
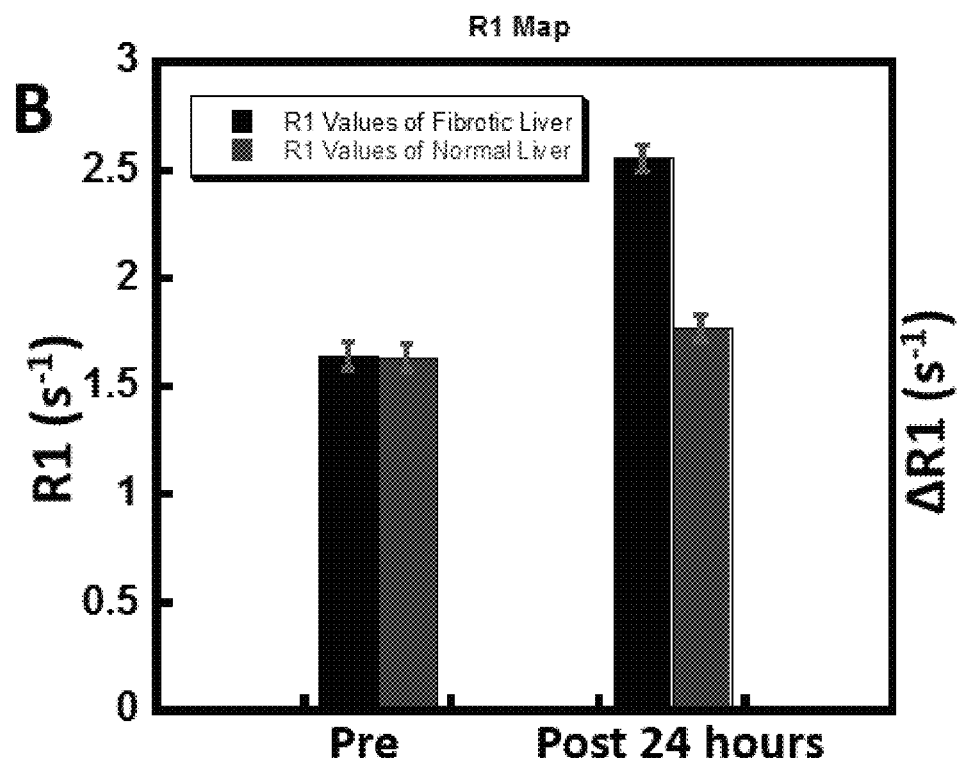
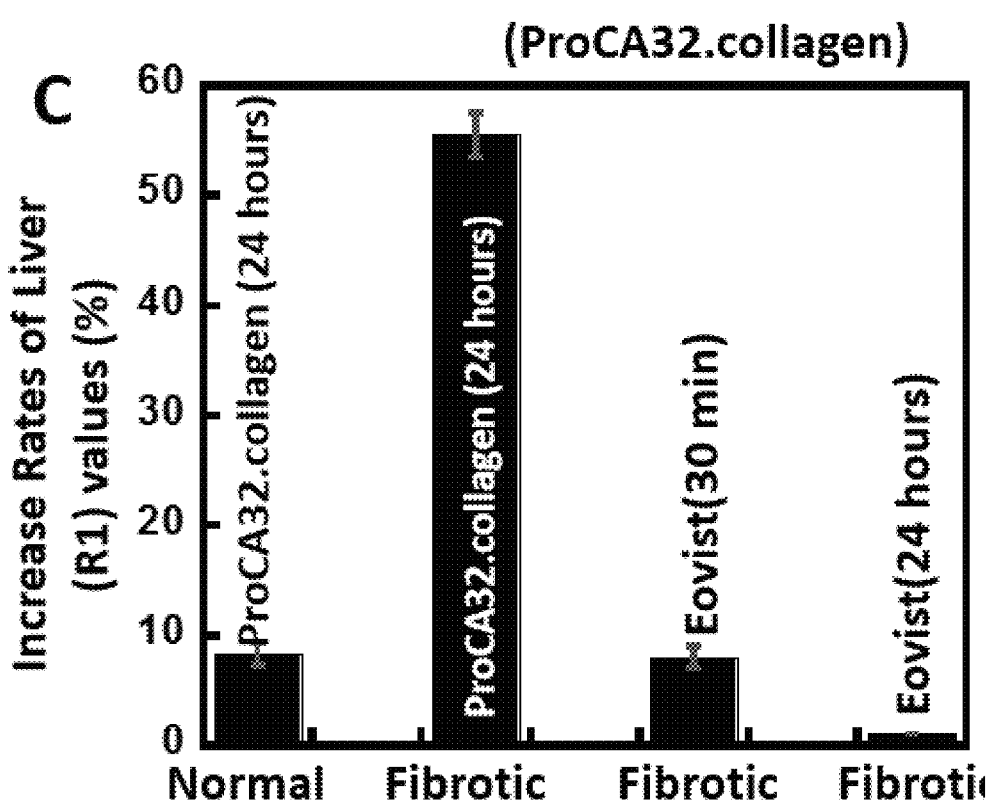
FIG. 88C

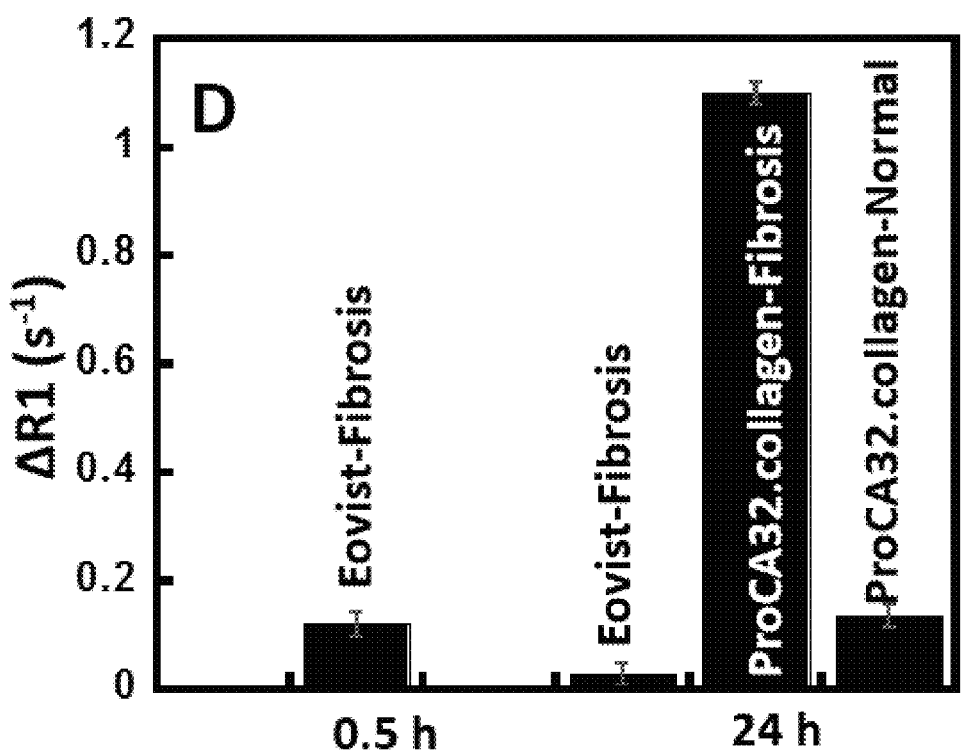
FIG. 88D
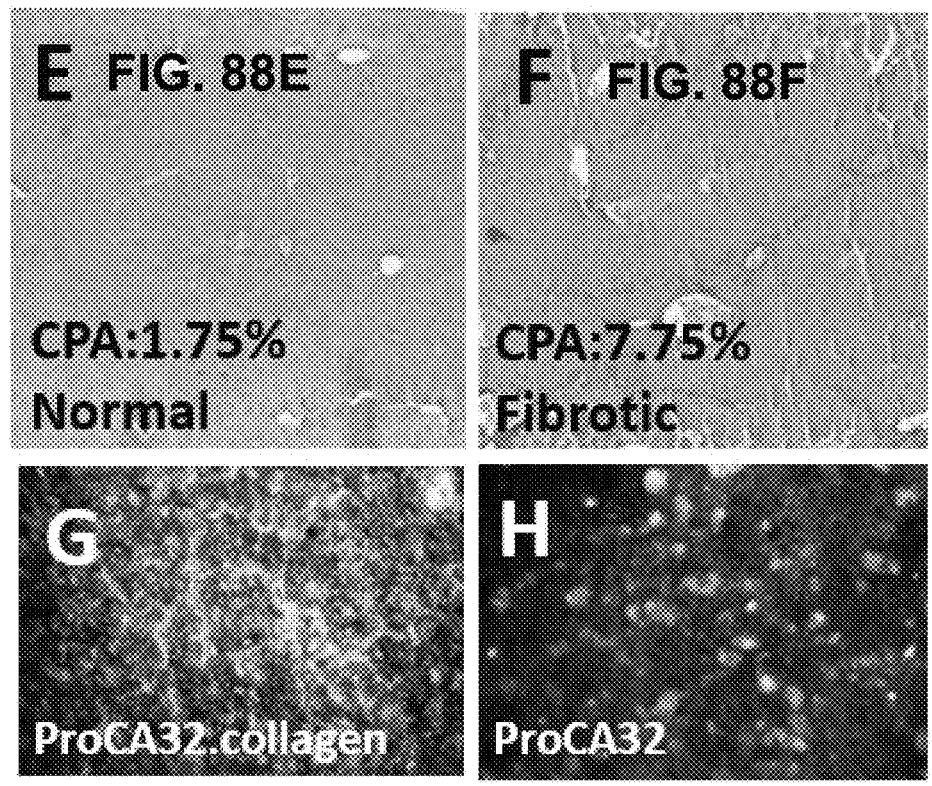
FIG. 88G  FIG. 88H

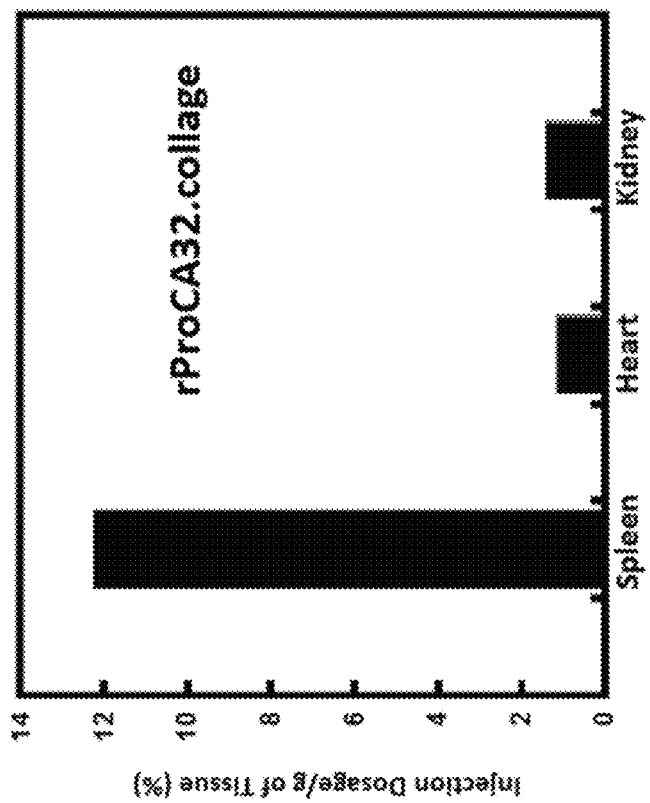
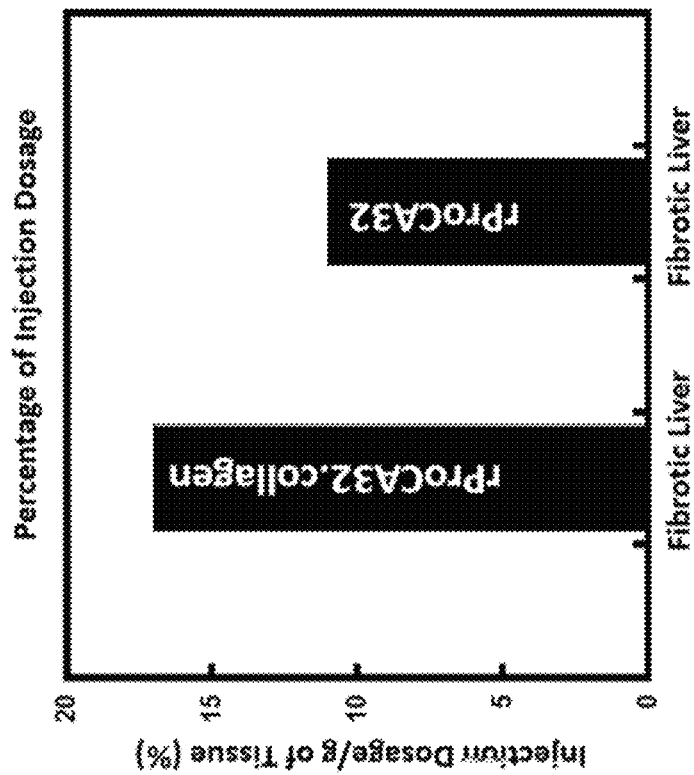
FIG. 89B
FIG. 89A

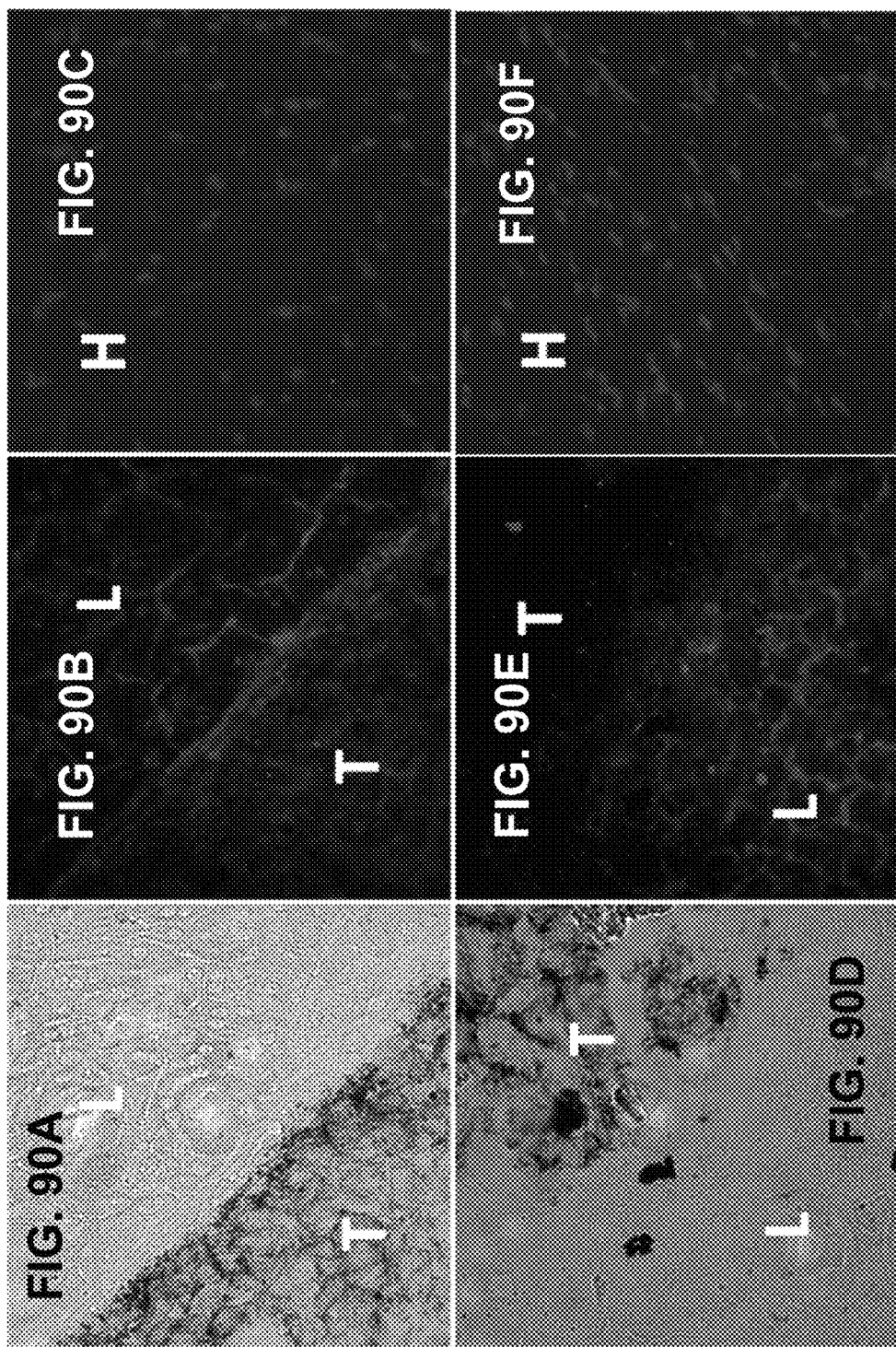

TARGETED PROTEIN CONTRAST AGENTS, METHODS OF MAKING, AND USES THEREOF

CROSS-REFERENCE TO RELATED APPLICATIONS

This application is a divisional of co-pending U.S. patent application Ser. No. 15/572,863, filed on Nov. 9, 2017, entitled "TARGETED PROTEIN CONTRAST AGENTS, METHODS OF MAKING, AND USES THEREOF," which is the 35 U.S.C. § 371 national stage application of PCT Application No. PCT/US2016/031900, filed May 11, 2016, where the PCT claims the benefit of and priority to U.S. Provisional Patent Application No. 62/159,685, filed on May 11, 2015, entitled "TARGETED PROTEIN CONTRAST AGENTS, METHODS OF MAKING, AND USES THEREOF," which are herein incorporated by reference in their entireties.

STATEMENT REGARDING FEDERALLY SPONSORED RESEARCH OR DEVELOPMENT

This invention was made with Government support under contracts EB007268, GM062999, CA118113, R41CA183376, and R01GM081749 awarded by the National Institutes of Health. The Government has certain rights in the invention.

BACKGROUND

Magnetic Resonance Imaging (MRI) is a powerful and highly utilized imaging technique for both research and clinical applications. As such, there exists a need for improved contrast agents for use with MRI.

SUMMARY

Provided herein are protein contrast agents having a modified parvalbumin polypeptide or a fragment thereof, wherein the modified parvalbumin polypeptide or the fragment thereof contains a paramagnetic metal binding site consisting of one or more amino acid residues of the modified parvalbumin polypeptide or fragment thereof; and a targeting moiety, wherein the targeting moiety operatively linked to the modified parvalbumin polypeptide or the fragment thereof. The modified parvalbumin polypeptide or fragment thereof has a sequence according to SEQ ID NO. 10 The targeting moiety is selected from the group of a PSMA binding peptide, a V1 peptide or variant thereof, gastrin releasing peptide, a HER2-specific affibody, a EGFR-specific affibody, a VEGFR binding peptide, fibronectin, integrin, collagen, and combinations thereof. The targeting moiety can have a sequence according to any one of SEQ ID NOs.: 14-66. The targeting moiety can be directly fused or indirectly linked via a flexible peptide linker to the C-terminus, N-terminus, or both the C-terminus and the N-terminus of the modified parvalbumin polypeptide or fragment thereof. The targeting moiety can be directly fused or indirectly linked via a flexible peptide linker to one or more amino acids between the C terminus and the N terminus of the modified parvalbumin polypeptide or fragment thereof. The protein contrast agent can further contain a paramagnetic ion, wherein the paramagnetic ion is directly bound to at least one amino acid of the modified parvalbumin polypeptide or fragment thereof. The paramagnetic ion can be $Gd^{3+}$. The protein contrast agent can be PEGylated. The hydrophobicity of the protein contrast agent can be altered via an insertion, deletion, or substitution of an amino acid in the protein contrast agent. The hydrophilicity of the protein contrast agent can be altered via insertion, deletion, or substitution of an amino acid in the protein contrast agent. The modified parvalbumin polypeptide or fragment thereof comprises S56D and a F103W mutations or structural equivalents thereof.

Also provided herein pharmaceutical compositions having protein contrast agents having a modified parvalbumin polypeptide or a fragment thereof, wherein the modified parvalbumin polypeptide or the fragment thereof contains a paramagnetic metal binding site consisting of one or more amino acid residues of the modified parvalbumin polypeptide or fragment thereof; and a targeting moiety, wherein the targeting moiety operatively linked to the modified parvalbumin polypeptide or the fragment thereof.

Also provided herein are methods of administering a protein contrast agent having a modified parvalbumin polypeptide or a fragment thereof, wherein the modified parvalbumin polypeptide or the fragment thereof contains a paramagnetic metal binding site consisting of one or more amino acid residues of the modified parvalbumin polypeptide or fragment thereof; and a targeting moiety, wherein the targeting moiety operatively linked to the modified parvalbumin polypeptide or the fragment thereof to a subject and imaging at least a portion of the subject using magnetic resonance imaging.

Also provided herein are protein contrast agents having a modified calmodulin polypeptide or a fragment thereof, wherein the modified calmodulin polypeptide or the fragment thereof contains a paramagnetic metal binding site consisting of one or more amino acid residues of the modified calmodulin polypeptide or fragment thereof; and a targeting moiety, wherein the targeting moiety operatively linked to the modified calmodulin polypeptide or the fragment thereof. The modified calmodulin polypeptide or fragment thereof has a sequence according to SEQ ID NO.: 13. The targeting moiety can be selected from the group of: a PSMA binding peptide, a V1 peptide or variant thereof, gastrin releasing peptide, a HER2-specific affibody, a EGFR-specific affibody, a VEGFR binding peptide, fibronectin, integrin, collagen, and combinations thereof. The targeting moiety can have a sequence according to any one of SEQ ID NOs.: 14-66. The targeting moiety can be directly fused or indirectly linked via a flexible peptide linker to the C-terminus, N-terminus, or both the C-terminus and the N-terminus of the modified calmodulin polypeptide or fragment thereof. The targeting moiety can be directly fused or indirectly linked via a flexible peptide linker to one or more amino acids between the C terminus and the N terminus of the modified calmodulin polypeptide or fragment thereof. The protein contrast agent can further have a paramagnetic ion, wherein the paramagnetic ion is directly bound to at least one amino acid of the modified calmodulin polypeptide or fragment thereof. The paramagnetic ion can be $Gd^{3+}$. The protein contrast agent can be PEGylated. The hydrophobicity of the protein contrast agent or portion thereof can be altered via an insertion, deletion, or substitution of an amino acid in the protein contrast agent. The hydrophilicity of the protein contrast agent is altered via insertion, deletion, or substitution of an amino acid in the protein contrast agent. The protein contrast agent has a sequence according to SEQ ID NO.: 70.

Also provided herein are pharmaceutical compositions having a protein contrast agent having a modified calmodulin polypeptide or a fragment thereof, wherein the modified calmodulin polypeptide or the fragment thereof contains a paramagnetic metal binding site consisting of one or more amino acid residues of the modified calmodulin polypeptide or fragment thereof; and a targeting moiety, wherein the targeting moiety operatively linked to the modified calmodulin polypeptide or the fragment thereof and a pharmaceutically acceptable carrier.

Also provided herein are methods of administering a protein contrast agent having a modified calmodulin polypeptide or a fragment thereof, wherein the modified calmodulin polypeptide or the fragment thereof contains a paramagnetic metal binding site consisting of one or more amino acid residues of the modified calmodulin polypeptide or fragment thereof; and a targeting moiety, wherein the targeting moiety operatively linked to the modified calmodulin polypeptide or the fragment thereof to a subject and imaging at least a portion of the subject using magnetic resonance imaging.

Also provided herein are protein contrast agents having a modified CD2 polypetpide or a fragment thereof, wherein the modified CD2 polypeptide or the fragment thereof contains a paramagnetic metal binding site consisting of one or more amino acid residues of the modified CD2 polypeptide or fragment thereof; and a targeting moiety, wherein the targeting moiety operatively linked to the modified CD2 polypeptide or the fragment thereof. The modified CD2 polypeptide or fragment thereof can have a sequence according to any one of SEQ ID NOs.: 1-3, 7-9, or 12. The targeting moiety is selected from the group consisting of: a PSMA binding peptide, a V1 peptide or variant thereof, gastrin releasing peptide, a HER2-specific affibody, a EGFR-specific affibody, a VEGFR binding peptide, fibronectin, integrin, collagen, and combinations thereof. The targeting moiety can have a sequence according to any one of SEQ ID NOs.: 14-66. The targeting moiety can be directly fused or indirectly linked via a flexible peptide linker to the C-terminus, N-terminus, or both the C-terminus and the N-terminus of the modified CD2 polypeptide or fragment thereof. The targeting moiety can be directly fused or indirectly linked via a flexible peptide linker to one or more amino acids between the C terminus and the N terminus of the modified CD2 polypeptide or fragment thereof. The protein contrast agent can further have a paramagnetic ion, wherein the paramagnetic ion is directly bound to at least one amino acid of the modified CD2 polypeptide or fragment thereof. The paramagnetic ion can be $Gd^{3+}$. The protein contrast agent can be PEGylated. The hydrophobicity of the protein contrast agent or portion thereof is altered via an insertion, deletion, or substitution of an amino acid in the protein contrast agent. The hydrophilicity of the protein contrast agent is altered via insertion, deletion, or substitution of an amino acid in the protein contrast agent. The modified CD2 polypeptide or fragment thereof comprises N15E, D17N, L60D, T64D and K66D mutations as compared to domain 1 of wild-type D2. The protein contrast agent can have a sequence according to any one of SEQ ID NOs. 1-3.

Also provided herein are pharmaceutical compositions containing a protein contrast agent having a modified CD2 polypetpide or a fragment thereof, wherein the modified CD2 polypeptide or the fragment thereof contains a paramagnetic metal binding site consisting of one or more amino acid residues of the modified CD2 polypeptide or fragment thereof; and a targeting moiety, wherein the targeting moiety operatively linked to the modified CD2 polypeptide or the fragment thereof and a pharmaceutically acceptable carrier.

Also provided herein are methods of administering a protein contrast agent having a modified CD2 polypetpide or a fragment thereof, wherein the modified CD2 polypeptide or the fragment thereof contains a paramagnetic metal binding site consisting of one or more amino acid residues of the modified CD2 polypeptide or fragment thereof; and a targeting moiety, wherein the targeting moiety operatively linked to the modified CD2 polypeptide or the fragment thereof to a subject and imaging at least a portion of the subject using magnetic resonance imaging.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 1A and 1B show a schematic of some embodiments of a targeted protein contrast agent having a targeting moiety directly (FIG. 1A) or indirectly (FIG. 1B) linked to a protein contrast agent (ProCA).

FIGS. 32A-32B demonstrating Fluozin-1 and ProCA32.564 competition for zinc.

FIG. 33 shows a table demonstrating a summary of relaxivities and metal binding affinities of various targeted protein contrast agents.

FIG. 34 shows a table demonstrating association constants for $Ca^{2+}$ for varying targeted protein contrast agents.

FIG. 35 shows a table demonstrating Kd values for VEGFR binding peptides.

FIGS. 39A and 39B show imaging VEGFR2 expression in tumors using ProCA32.VEGFR2.

FIG. 41 shows a table demonstrating various V1 and V1 variant peptides.

FIG. 56A shows a MRI image of the mice before injection of HER-2 targeted ProCA1. FIG. 56B shows a MRI image of the mice at 3 hours post injection of HER-2 targeted ProCA1. FIG. 56C shows a MRI image of the mice at 24 hours post injection of HER-2 targeted ProCA1. HER-2 Positive tumor shows much enhanced MRI signal. FIG. 56D shows a MRI image of the mice at 52 hours post injection of HER-2 targeted ProCA1.

FIG. 57A shows MRI image of the mice before injection of HER-2 targeted ProCA1. FIG. 57B shows a MRI image of the mice at 3 hours post injection of HER-2 targeted ProCA1. FIG. 57C shows a MRI image of the mice at 24 hours post injection of HER-2 targeted ProCA1. HER-2 Positive tumor shows much enhanced MRI signal. FIG. 57D. MRI image of the mice at 52 hours post injection of HER-2 targeted ProCA1.

FIG. 62 demonstrates the step which rat ProCA1 was purified by FPLC equipped with a SP column.

FIGS. 65A-65D show MRI scans demonstrating imaging of HER2 positive and negative tumors in SKOV-3 tumors on mice pre and at various time points post administration of a rat ProCA1-Affi.

FIG. 66 shows a graph demonstrating signal intensity of HER2 positive and negative SKOV-3 tumors on mice pre and at various time points post administration of a rat-ProCA1-Affi.

FIGS. 67A-67D show MRI scans demonstrating imaging of HER2 positive and negative MFS-MB-231 tumors on mice pre and at various time points post administration of a rat ProCA1-Affi.

FIG. 68 shows a graph demonstrating signal intensity of HER2 positive and negative MFS-MB-231 tumors on mice pre and at various time points post administration of a rat ProCA1-Affi.

FIG. 71 shows a table demonstrating the concentration of the purified ProCA1 (7E15) and the ProCA1.G10 and ProCA1.B10 variants.

FIG. 82 shows a table demonstration various metal binding affinities for ProCA32 and hCA32.

FIG. 86 shows a sequence for human CD2 domain 1 (SEQ ID NO.: 1) and a modified human CD2 domain 1 (SEQ ID NO.: 3) and rat CD2 domain 1 (SEQ ID NO.: 2) that contains mutations to include a metal binding site. The underlined residues are those mutated for metal binding. Besides the 6 underlined and bolded amino acids, 58E and 62N can also contribute to the metal binding pocket.

FIGS. 88A-H demonstrate the R1 map of fibrotic and normal liver before and after injection of rProCA32.collagen (24 hours) and Eovist (30 min) (FIG. 88A), R1 values of fibrotic and normal liver before and 24 hours after injection of rProCA32.collagen (FIG. 88B), the percent increase rate in R1 of normal and fibrotic liver before and after injection of rProCA32.collagen (24 hours) and Eovist (30 min and 24 hours) (FIG. 88C), ΔR1 of Eovist (30 min and 24 h post injection) and rProCA32.collagen (24 hours post injection) of fibrotic and normal liver. FIG. 88E. Representative Sirius Red histology of normal (FIG. 88D) and fibrotic liver tissues (FIG. 88F), and Immunofluorescence staining of fibrotic liver tissue with rProCA32.collagen and rProCA32 (red) and collagen type I (green) along with nucleus (blue) (FIGS. 88G and 88H).

FIGS. 89A-89B show graphs demonstrating the injection dosages per gram of tissue for ProCA32.collagen.

FIGS. 90A-F show images demonstrating targeting by ProCA32.CXCR4.

DETAILED DESCRIPTION

Figures 2A, 2B:
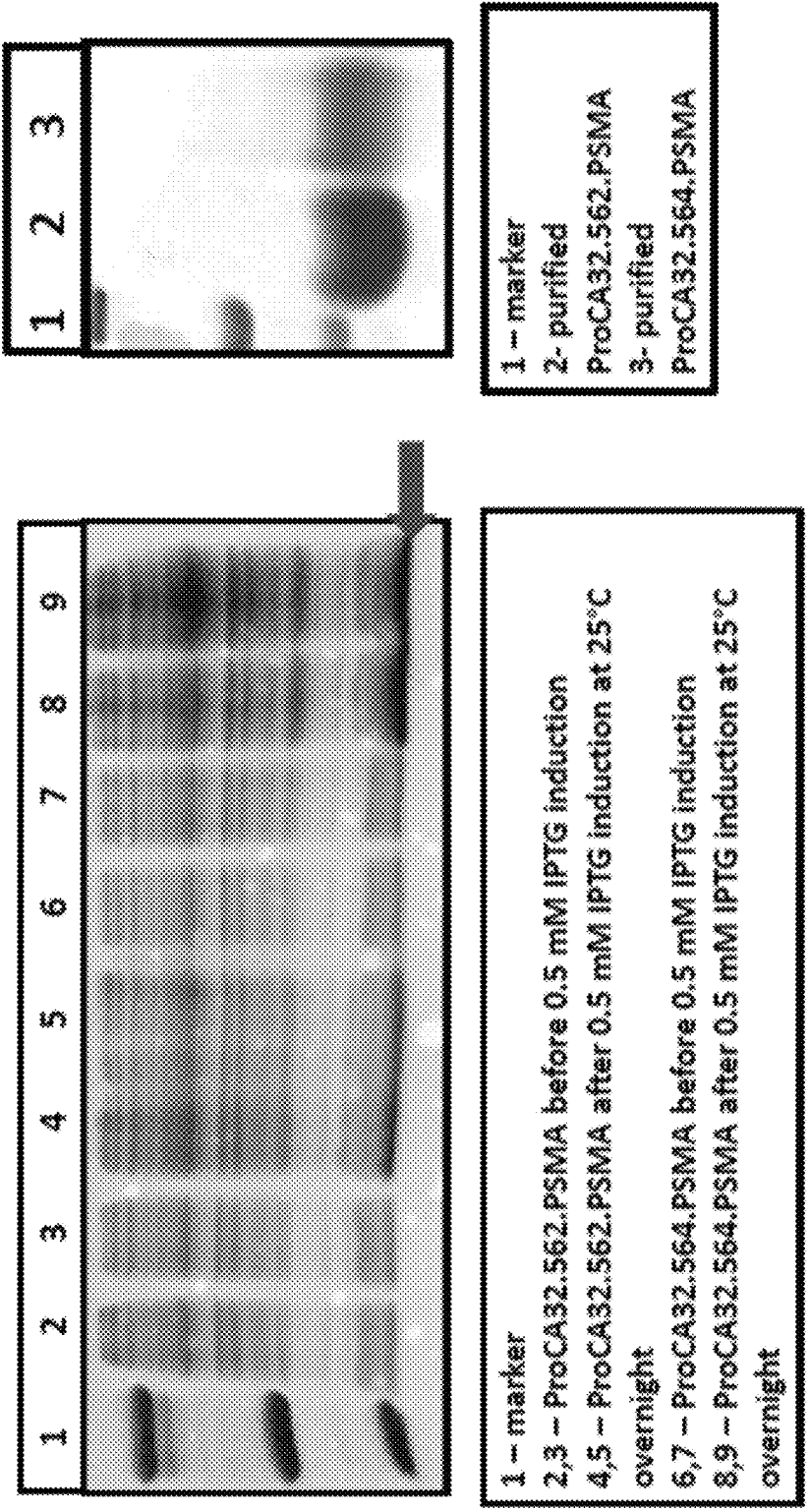
FIGS. 2A and 2B demonstrate expression (FIG. 2A) and purification (FIG. 2B) of ProCA32.562.PSMA and ProCA32.564.PSMA.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "control" is an alternative subject or sample used in an experiment for comparison purpose and included to minimize or distinguish the effect of variables other than an independent variable.

As used herein, "about," "approximately," and the like, when used in connection with a numerical variable, generally refers to the value of the variable and to all values of the variable that are within the experimental error (e.g., within the 95% confidence interval for the mean) or within +-10% of the indicated value, whichever is greater.

As used herein, "effective amount" is an amount sufficient to effect beneficial or desired results. An effective amount can be administered in one or more administrations, applications, or dosages.

As used herein, "administering" can refer to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "preventative" refers to hindering or stopping a disease or condition before it occurs or while the disease or condition is still in the sub-clinical phase.

As used herein, "therapeutic" can refer to treating or curing a disease or condition.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

The terms "operatively linked" or "operatively coupled" as used herein can refer to the association of nucleic acid sequences on a single nucleic acid fragment so that the function of one is regulated by the other. For example, a promoter is operatively linked with a coding sequence when it is capable of regulating the expression of that coding sequence (i.e., the coding sequence is under the transcriptional control of the promoter). Coding sequences can be operatively linked to regulatory sequences in a sense or antisense orientation. In one example, the complementary RNA regions can be operatively linked, either directly or indirectly, 5' to the target mRNA, or 3' to the target mRNA, or within the target mRNA, or a first complementary region is 5' and its complement is 3' to the target mRNA. The term "operatively linked" as used herein can also refer to the direct or indirect linkage of any two nucleic acid sequences on a singly nucleic acid fragment such that they are indirectly or directly physically connected on the same nucleic acid fragment. The term "operatively linked" as used herein can also refer to the insertion of a nucleic acid within the 5' and 3' end of another nucleic or the direct coupling of a nucleic acid to the 5' or 3' end of another nucleic acid. The term "operatively linked" and the like can refer to the coupling of one or more functional polypeptide unit (e.g. a ProCA or a targeting moiety) to one or more other functional polypeptide directly via a peptide bond between the two or more functional polypeptides. The term "operatively linked" can also refer to the indirect coupling of one or more functional polypeptides through a linker, such as a peptide linker.

As used herein, "specific binding," "specifically bind," and the like refer to binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins. As another non-limiting example, a miRNA can specifically bind preferably to a miRNA target and not to a non-specific nucleic acid sequence or if binding to a non-specific nucleic acid sequence occurs that no change in the expression or function of the non-specific nucleic acid can be observed or detected.

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" can refer to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic RNA molecule including but not limited to tRNA, siRNA, piRNA, miRNA, long-non-coding RNA and shRNA.

As used herein, "deoxyribonucleic acid (DNA)" and "ribonucleic acid (RNA)" generally refer to any polyribonucleotide or polydeoxyribonucleotide, which can be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers or coding mRNA (messenger RNA).

As used herein, "nucleic acid sequence" and "oligonucleotide" also encompasses a nucleic acid and polynucleotide as defined elsewhere herein.

As used herein, "DNA molecule" includes nucleic acids/polynucleotides that are made of DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotide" as that term is intended herein.

As used herein, "pharmaceutically acceptable carrier, diluent, binders, lubricants, glidants, preservative, flavoring agent, coloring agent, and excipient" refers to a carrier, diluent, binder, lubricant, glidant, preservative, flavoring agent, coloring agent, or excipient that is useful in preparing a pharmaceutical formulation that is generally safe, non-toxic, and is neither biologically or otherwise undesirable, and includes a carrier or excipient that is acceptable for veterinary use as well as human pharmaceutical use.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain. The terms "treating", "treatment," and the like as used herein can refer to both therapeutic treatment and prophylactic or preventative measures. Those in need of treatment include those already with the disorder as well as those in which the disorder is to be prevented.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein with reference to the relationship between DNA, cDNA, cRNA, RNA, and protein/peptides, "corresponding to" or "encoding" can refer to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "identity," can refer to a relationship between two or more polypeptide sequences, as determined by comparing the sequences. In the art, "identity" also refers to the degree of sequence relatedness between polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties.

The terms "sufficient" and "effective", as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "organism", "host", and "subject" can refer to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, "patient" can refer to an organism, host, or subject in need of diagnosis, prognosis, treatment, and/or prevention.

As used herein, "peptide" can refer to chains of at least 2 amino acids that are short, relative to a protein or polypeptide.

As used herein, "Protein Contrast Agent (ProCA)" can refer to a polypeptide that contains a paramagnetic or superparamagnetic binding site, where the binding site is made of one or more amino acids within the polypeptide. The one or more amino acids that make up the binding site can be contiguous or non-contiguous within the polypeptide.

Discussion

Magnetic resonance imaging (MRI) is a powerful imaging technique that uses a magnetic field and radio waves to create high resolution images of the organs and tissues of the body. In operation, the magnetic field produced by an MRI machine realigns hydrogen atoms in the body. Radio waves cause the aligned atoms to produce very faint signals, which are then used to create cross-sectional MRI images. MRI machines can also be used to produce 3-D images of organs and other tissues. MRI provides a noninvasive examination tool that is used widely to diagnose a variety of problems and has proven to be a powerful research tool in the medical field.

MRI contrast agents are compounds and compositions that can be administered to a subject to increase the visibility of internal body structures when using MRI. Most MRI contrast agents work by shortening the T1 relaxation time of protons inside tissues via interactions with contrast agent. Conventional contrast agents are paramagnetic metals, such as gadolinium, (Gd) and manganese (Mn), or superparamagnetic metals (iron oxide and iron platinum). While remarkable progress for developing conventional contrast agents has been made, MRI contrast agents capable of molecular imaging with high sensitivity and specificity remain elusive to the market.

There have been many efforts in improving relaxivity of MRI contrast agents by covalently linking Gd-chelates to nano-carriers, such as dendrimers, liposomes, nanoparticle emulsions, viral capsids, and nanotubes. Non-covalent binding between Gd chelators and protein, such as MS-325, have shown an increase in relaxivity. Despite this, there have been little efforts made on using protein residues to function as ligands to bind a paramagenetic or superparamagnetic metals.

Recently protein based MRI contrast agents (ProCAs) have been described (e.g. Xue et al. 2013. Interdiscip Rev Nanomed nanobiotechnol. 5(2):163-179). The ProCAs can have several desirable capabilities for use in MRI and can have sufficient sensitivity and specificity to image diseases and disorders in a subject. ProCAs can exhibit higher relaxivity and dose efficiency than conventional contrast agents. Although these first generation ProCAs have potential for use as a contrast agent, there still exists a need for ProCAs with improved relaxivity profiles. Further it is also desirable in some cases for the protein contrast agent to target specific tissues or cells so as to noninvasively provide further information regarding a subject, such as tumor type.

With that said, described herein are ProCAs that can be configured to bind a paramagnetic metal and formulations thereof. The ProCAs can be operatively linked to a targeting moiety. Also described herein are methods of using the ProCAs as contrast agents in a subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Protein Based Contrast Agents (ProCAs)

The ProCAs described herein include a polypeptide instead of small chelators that can be configured to bind a paramagnetic or superparamagnetic ion. Exemplary paramagnetic or superparamagnetic ions include, but are not limited to, paramagnetic or super paramagnetic ions of Gd, Fe, Mn, Li, O, Na, Mg, Al, Mo, Sn, Ca, Co, Ni, Sr, Ru, Rh, Pd, Ba, Ce, Nd, Sm, Eu, Tb, Dy, Ho, Er, Tm, W, Os, In, and Pt. Synthetic proteins can be engineered to include one or more metal binding sites. Such methods of engineering a metal binding site can be as described in Yang et al., (2008) JACS. 130:92670-9267; Yang et al., (2003) JACS. 125: 6165-6171; Ye et al., (2005) JACS. 127: 3743-3750, Li et al. (2008) FEBS. 275:5048-5061; Xue et al., 2014 Medicinal Res. Rev. 34:1070-1099; and elsewhere herein. The ProCAs can be configured such that they bind the paramagnetic or super paramagnetic ion with a greater affinity that a physiological ion, such as Ca or Zn.

The ProCAs can be further modified with polyethylene glycol (PEG) to improve biocompatibility, serum stability, solubility, circulation time, immunogenicity (i.e. decrease immunogenicity), modulate hydrophobicity/hydrophilicity, and relaxivity (see e.g. Li et al., 2012. J. Inorg. Biochem. 107(1) 111-118). Techniques for PEGylating proteins will be appreciated by those of ordinary skill in the art. In embodiments, the ProCA can be PEGylated using PEG ranging in molecular weight from 0.25 to 30 kDa. The PEG molecules used for PEGylation can be straight chain, branched, or a combination of both types. PEGylation can occur at one or more sites on the ProCA at lysine residues and/or Cys residues of the ProCA. The ProCA can be a protein that contains one or more EF-1 hand motifs. In some embodiments, the ProCAs can be generated using metalloproteins that can contain one or more EF-1 hand domains (see e.g. Xue et al. 2014. Med Res. Rev. 34(5):1070-1099 and Xue et al. 2013. Interdiscip. Rev. Nanomed. Nanobiotechnol. 2013. 5(2):163-179). In some embodiments, the ProCA can be based on a calmodulin protein, parvalbumin protein, a CD2 protein, or any fragment thereof. Non-limiting example polypeptide sequences for the ProCA can be found in Table 1.

The amino acid residues of the ProCAs can be modified to modulate the hydrophobicity/hydrophilicity of the ProCAs. The ProCA can be lysine modified using hydrophilic modification. Other amino acids can be added, deleted and/or substituted to modulate the hydophilicity/hydrophobicity of the ProCA. In some embodiments, the ProCAs described herein, including but not limited to ProCA, can be hydrophobic modified. In some embodiments, the ProCAs the hydrophobic residues (including, but not limited to, Val, Ile, Leu, and Met) can be changed, substituted, or otherwise modified, to reduce undesired interactions, improve solubility, stability, and/or maintain the status of the monomer or oligomer.

ProCA1 and Variants Thereof

The ProCA can be a CD2 protein or include or be composed substantially entirely of a fragment thereof (also referred to herein as ProCA1). In some embodiments, the ProCA can be a modified CD2 protein or fragment thereof, where the modification can be one or more mutations in domain 1 of the CD2. In some embodiments, the ProCA can include domain 1 of a CD2 protein that is modified to bind a paramagnetic or super paramagnetic ions. In embodiments, the ProCA can include a mutated domain 1 of a CD2 protein that has a binding pocket formed by a group of carboxyl side chains (E15, D56, D58, D62, and D64). This ProCA is also referred to herein as ProCA1 or ProCA1 7E15. ProCA1 can have a 14-20 fold improvement of both r1 and r2 relaxivities compared with current clinically used contrast agents such as Gd-DTPA.

In some embodiments, the ProCA can be a variant of a ProCA described herein, including but not limited to ProCA1. The ProCA1 can be lysine modified using hydrophilic modification. Other amino acids can be added, deleted and/or substituted to modulate the hydophilicity/hrdophobicity of the ProCA1. In some embodiments, the ProCAs described herein, including but not limited to ProCA1, can be hydrophobic modified. In some embodiments, the ProCAs the hydrophobic residues (including, but not limited to, Val, Ile, Leu, and Met) can be changed, substituted, or otherwise modified, to reduce undesired interactions, improve solubility, stability, and/or maintain the status of the monomer or oligomer. Alteration of the hydrophobic interactions in the ProCA, can be modified by deletion of one or more hydrophobic residues. Alteration of the hydrophobic interactions in the ProCA, can be accomplished by insertion of non-hydrophobic residues in to the ProCA, such that hydrophobicity in one or more regions of the ProCA is altered. Alteration of the hydrophobic interactions can also be accomplished by substitution of one or more hydrophobic residues with a non-hydrophobic residues. Hydrophobic and non-hydrophobic residues will be appreciated by those of ordinary skill in the art. In embodiments wherein the ProCA is ProCA1, several of the residues that can form a dimer (see e.g., Pfuhl et al., 1999. J. Biomol. NMR 14(4):307-320; Davis et al., 1998. PNAS 95(10):5490-5494; Evans et al., 2006. J. Biol. Chem. 281(39):29309-29320).

In other embodiments, ProCA1 can be mutated to form variants of ProCA1. In some embodiments, the variants can have increased r1 and/or r2 relaxivities as compared to ProCA1 and/or current clinically used contrast agents. In embodiments, the ProCA1 variants can include a targeting moiety and/or one or more flexible peptide linkers between S52 and $A_{53}$ of the ProCA1 (See Table 1). Embodiments of such ProCA1 variants are as follows (italics in the sequences indicate flexible peptide linker, underline indicates targeting moiety). In other embodiments, the ProCA1 can include one or more targeting moieties directly fused to or indirectly linked via a flexible peptide linker at its C and/or N-terminus. These embodiments are discussed in greater detail below.

(ProCA1.B14) SEQ ID NO.: 4:
MRDSGTVWGALGHGIELNIPNFQMTDDIDEVRWERGSTLVAEFKRKMKPF

LKS*GGSGGE*QRLGNQWAVGHLM*GGSGG*AFEIDANGDLDIKNLTRDDSGTY

NVTVYSTNGTRILNKALDLRILE (ProCA1.B10) SEQ ID NO.: 5:
MRDSGTVWGALGHGIELNIPNFQMTDDIDEVRWERGSTLVAEFKRKMKPF

LKS*GGSGG*GNQWAVGHLM*GGSGG*AFEIDANGDLDIKNLTRDDSGTYNVTV

YSTNGTRILNKALDLRILE (ProCA1.G10) SEQ ID NO.: 6:
MRDSGTVWGALGHGIELNIPNFQMTDDIDEVRWERGSTLVAEFKRKMKPF

LKS*GGSGG*GNHWAVGHLM*GGSGG*AFEIDANGDLDIKNLTRDDSGTYNVTV

YSTNGTRILNKALDLRILE

In embodiments, the ProCA1 or variant thereof can be PEGylated (Li et al. (2012) J. Inorg. Biochem. 107:111-118). Techniques for PEGylating proteins will be appreciated by those of skill in the art. The ProCA1 or variant thereof can be further modified with polyethylene glycol (PEG) to improve biocompatibility, serum stability, solubility, circulation time, immunogenicity (i.e. decrease immunogenicity), and relaxivity (see e.g. Li et al., 2012. J. Inorg. Biochem. 107(1) 111-118) and/or hydrophobicity and/or hydrophilicity of ProCA1. Techniques for PEGylating proteins will be appreciated by those of ordinary skill in the art. In embodiments, the ProCA1 or variant thereof can be PEGylated using PEG ranging in molecular weight from 0.25 to 30 kDa. The PEG molecules used for PEGylation can be straight chain, branched, or a combination of both types. PEGylation can occur at one or more sites on the ProCA1 or variant at lysine residues and/or Cys residues of the ProCA1.

ProCA32 and Variants Thereof

In other embodiments, the ProCA can be, include, or be composed entirely of parvalbumin or a fragment thereof. (also referred to herein as ProCA30). ProCA32 can contain an S56D and an F103W mutation in the α-parvalbumin polypeptide. The native α-parvalbumin polypeptide sequences are generally known in the art. For example, rat α-parvalbumin GenBank Accession number is AAI26091.1 and human α-parvalbumin GenBank Accession number is CAA44792.1. In embodiments, the ProCA32 can be PEGylated. Methods of PEGylating proteins are generally known in the art and will be instantly appreciated by one of ordinary skill in the art. In embodiments, the ProCA32 can be PEGylated using PEG ranging in molecular weight from 0.5 to 20 kDa. In embodiments, the ProCA32 or variant thereof can be PEGylated (Li et al. (2012) J. Inorg. Biochem. 107:111-118). Techniques for PEGylating proteins will be appreciated by those of skill in the art. The ProCA32 or variant thereof can be further modified with polyethylene glycol (PEG) to improve biocompatibility, serum stability, solubility, circulation time, immunogenicity (i.e. decrease immunogenicity), and relaxivity (see e.g. Li et al., 2012. J. Inorg. Biochem. 107(1) 111-118) and/or modify the hydrophobicity and/or hydrophilicity of the ProCA32 or fragment thereof. Techniques for PEGylating proteins will be appreciated by those of ordinary skill in the art. In embodiments, the ProCA32 or variant can be PEGylated using PEG ranging in molecular weight from 0.25 to 30 kDa. The PEG molecules used for PEGylation can be straight chain, branched, or a combination of both types. PEGylation can occur at one or more sites on the ProCA32 or variant at lysine residues and/or Cys residues of the ProCA32.

ProCA2 and Variant's Thereof

In other embodiments, the ProCA can be, include, or be composed entirely of calmodulin or a fragment thereof, such as an EF-1 domain. In some embodiments, the calmodulin or fragment thereof is as shown in Table 1. In some embodiments, the calmodulin or fragment thereof is modified to bind a paramagnetic or superparamagnetic ion.

The ProCA2 can be lysine modified using hydrophilic modification. Other amino acids can be added, deleted and/or substituted to modulate the hydophilicity/hrdopobicity of the ProCA2. In some embodiments, the ProCAs described herein, including but not limited to ProCA2, can be hydrophobic modified. In some embodiments, the hydrophobic residues (including, but not limited to, Val, Ile, Leu, and Met) can be changed, substituted, or otherwise modified, to reduce undesired interactions, improve solubility, stability, and/or maintain the status of the monomer or oligomer. Alteration of the hydrophobic interactions in the ProCA2, can be modified by deletion of one or more hydrophobic residues. Alteration of the hydrophobic interactions in the ProCA2, can be accomplished by insertion of non-hydrophobic residues in to the ProCA2, such that hydrophobicity in one or more regions of the ProCA2 is altered. Alteration of the hydrophobic interactions can also be accomplished by substitution of one or more hydrophobic residues with a non-hydrophobic residues. Hydrophobic and non-hydrophobic residues will be appreciated by those of ordinary skill in the art.

Alteration of the hydrophobic interactions in the ProCA2, such as in the central-helix region of the calmodulin protein, can be modified by deletion of one or more hydrophobic residues. Alteration of the hydrophobic interactions in the ProCA2, such as in the central-helix region of the calmodulin protein, can be accomplished by insertion of non-hydrophobic residues in to the ProCA2, such that hydrophobicity in one or more regions of the ProCA2 is altered. Alteration of the hydrophobic interactions can also be accomplished by substitution of one or more hydrophobic residues with a non-hydrophobic residues. Hydrophobic and non-hydrophobic residues will be appreciated by those of ordinary skill in the art.

In embodiments, the ProCA2 can be PEGylated. Methods of PEGylating proteins are generally known in the art and will be instantly appreciated by one of ordinary skill in the art. In embodiments, the ProCA2 can be PEGylated using PEG ranging in molecular weight from 0.5 to 20 kDa. In embodiments, the ProCA2 or variant thereof can be PEGylated (Li et al. (2012) J. Inorg. Biochem. 107:111-118). Techniques for PEGylating proteins will be appreciated by those of skill in the art. The ProCA2 or variant thereof can be further modified with polyethylene glycol (PEG) to improve biocompatibility, serum stability, solubility, circulation time, immunogenicity (i.e. decrease immunogenicity), and relaxivity (see e.g. Li et al., 2012. J. Inorg. Biochem. 107(1) 111-118) and/or modify the hydrophobicity and/or hydrophilicity of the ProCA2 or fragment thereof. Techniques for PEGylating proteins will be appreciated by those of ordinary skill in the art. In embodiments, the ProCA2 or variant can be PEGylated using PEG ranging in molecular weight from 0.25 to 30 kDa. The PEG molecules used for PEGylation can be straight chain, branched, or a combination of both types. PEGylation can occur at one or more sites on the ProCA2 or variant at lysine residues and/or Cys residues of the ProCA2.

TABLE 1

Protein Contrast Agents (ProCAs)

| Alias in Application | SEQ ID NO.: | Polypeptide Sequence |
|---|---|---|
| rProCA1 (rat ProCA1) | 7 | MRDSGTVWGALGHG IELNIPNFQMTDDI DEVRWERGSTLVAE FKRKMKPFLKSGAF EIDANGDLDIKNLT RDDSGTYNVTVYST NGTRILNKALDLRI LE |
| ProCA1 human ProCA1; hProCA1 | 8 | $R_1$DSGTVWGALGHG IELNIPNFQMTDDI DEVRWERGSTLVAE FKRKMKPFLKS$_{52}$ $A_{53}$FEIDANGDLDI NLTRDDSGTYNVTV KYSTNGTRILNKAL DLRILE |

TABLE 1-continued

Protein Contrast Agents (ProCAs)

| Alias in Application | SEQ ID NO.: | Polypeptide Sequence |
|---|---|---|
| rProCA32 (rat ProCA32) (mutations from rat ProCA30 are underlined) | 9 | MSMTDLLSAEDIKK AIGAFTAADSFDHK KFFQMVGLKKKSAD DVKKVFHILDKDK_D_ GFIEEDELGSILK_G_ FSSDARDLSAKETK TLMAAGDKDGDGKI GVEEWSTLVAES |
| ProCA32 (human ProCA32); α-parvalbumin with S55D and F102W mutations (mutations underlined); hProCA32 | 10 | MS1MTDLLSAEDIK KAIGAFTAADSFDH KKFFQMVGLKKKSA DDVKKVFHILDKDK D55GFIEEDELGSI LKGFSSDARDLSAK ETKTLMAAGDKDGD GKIGVEE_W_STLVAE S |
| Rat CD2 domain 1 | 11 | TNALETWGALGQDI NLDIPSFQMSDDID DIKWEKTSDKKKIA QFRKEKETFKEKDT YELLKNGTLKIKHL KTDDQDIYKVSIYD TKGKNVLEKIFDLK IQE |
| Rat CD2 domain 1 (residues mutated from rat CD2 domain 1 are shown in bold and underlined) | 12 | TNALETWGALGQDI ELDNPSFQMSDDID DIKWEKTSDKKKIA QFRKEKETFKEKDT YELDKNGDLDIKHL K**TDDQDIYKVSIYD TKGKNVLEKIFDLK IQE |
| ProCA2 (calmodulin based ProCA) | 13 | ADQLTEEQIAEFKE AFSLFDKDGDGTIT TKELGTVMRSLGQN PTEAELQDMINEVD ADGDGTIDFPEFLT MMARK |

Targeted ProCAs

The ProCA can be modified such that it can target a specific cell or tissue. For example, the ProCA polypeptide can contain amino acid residue deletions, additions, or modifications that alter the hydrophobicity and/or hydrophilicty of the polypeptide or region thereof.

Figures 1A, 1B:
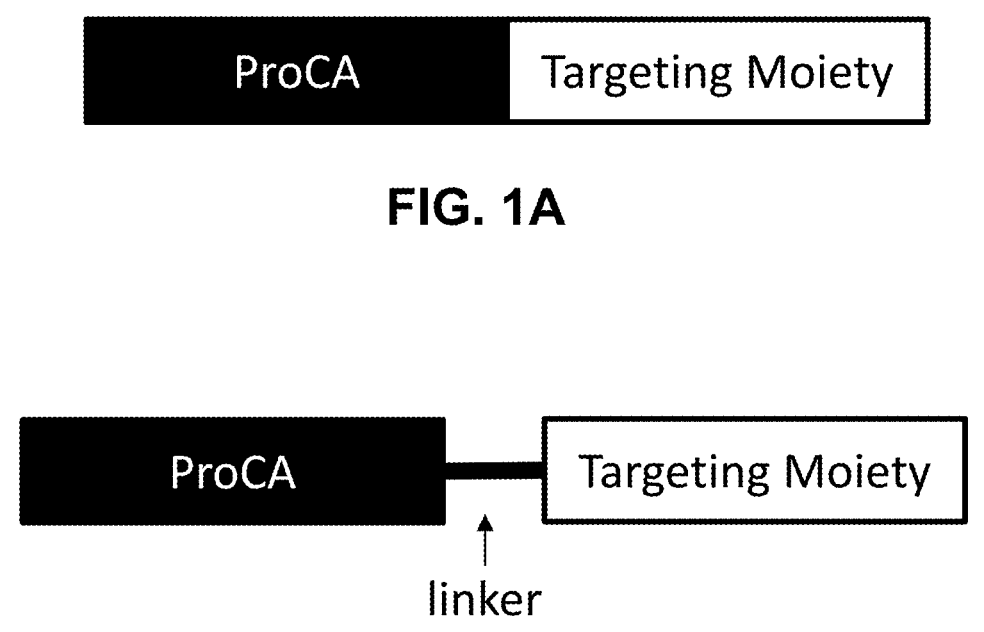

In other embodiments, the ProCA, including but not limited to, ProCA1, ProCA32, and variants thereof, can further contain a peptide or polypeptide targeting moiety that is directly fused to the N- and/or C-terminus of the ProCA. (See e.g. FIG. 1A) In some embodiments, the ProCA can further contain a peptide or polypeptide targeting moiety and/or one or more flexible peptide linkers that can be inserted between any two amino acids of the ProCA, such that the ProCA can still bind a metal. In some embodiments, the peptide or polypeptide targeting moiety and/or one or more flexible linkers can be inserted between S52 and A53 or equivalent position in ProCA backbone. Suitable targeting moieties can include but are not limited to: a PSMA binding peptide (can target PSMA), a V1 peptide or variant thereof (can target CXCR4), gastrin releasing peptide (GRP), bombesin (e.g. 14 amino acid bombesin and 10 amino acid bombesis) an affibody (including, but not limited to, a HER2 and EGFR specific affibodies, a VEGFR binding peptide (targets VEGFR), collagen, integrin, fibronectin, and combinations thereof In further embodiments, the ProCA can be indirectly linked at its N- and/or C-terminus to a targeting moiety via a suitable linker (See e.g. FIG. 1B). The linker can be flexible. The linker can be reversible. The linker can be a peptide or polypeptide. Non-limiting linkers are shown in Table 3.

TABLE 2

Peptide (including affibodies) Targeting Moieties

| Target | Alias within application (if any) | Sequence | SEQ ID NO. |
|---|---|---|---|
| PSMA | Sau.PSMA; Sau | WQPDTAHHWATL | 14 |
| PSMA | WP.PSMA; PSMAWP; WP | AEWWQPDTAHHWATLPDP | 15 |
| PSMA | 562.PSMA; 562 | SHSFSVGSGDHSPFT | 16 |
| PSMA | 563.PSMA; 563 | GRFTGGTGRLLRIS | 17 |
| PSMA | 564.PMSA; 564 | LSFFSCWLRRSFSLT | 18 |
| PSMA | | LPIFKVDFGDHSPFT | 19 |
| PSMA | | ARMFLLFLMACIGCY | 20 |
| PSMA | | SHSFSVGSGDSPFT | 21 |

TABLE 2-continued

Peptide (including affibodies) Targeting Moieties

| Target | Alias within application (if any) | Sequence | SEQ ID NO. |
|---|---|---|---|
| PSMA | | SHSFSVGSGSGDHSP | 22 |
| PSMA | | EVPRLSLLAVFLVVM | 23 |
| PSMA | | EVPRLSLLAVFLCNG | 24 |
| PSMA | | EVPRLSLLAVFLVAN | 25 |
| PSMA | | GRFLTGGTGRLLRIS | 26 |
| PSMA | | MAEWQPDTAHHWATLPDP | 27 |
| PSMA | | SHSFSVGSGDGSPF | 28 |
| VEGFR2 (targeting moiety 1) | | GDSRVCWEDSWGGEVCFRYDPGGGK | 29 |
| VEGFR2 (targeting moiety 2) | | AGPKWCEEDWYYCMITGTGGGK | 30 |
| VEGFR2 (targeting moiety 3) | | AGPTWCEDDWYYCWLPGTGGGK | 31 |
| VEGFR2 | | Homo-bivalent VEGFR2 (targeting moiety 1) + VEGFR2 (targeting moiety 1) | 32 |
| VEGFR2 | | Homo-bivalent VEGFR2 (targeting moiety 3) + VEGFR2 (targeting moiety 3) | 33 |
| VEGFR2 | | Hetero-bivalent VEGFR2 (targeting moiety 1) + VEGFR2 (targeting moiety 2) | 34 |
| VEGFR2 | | Hetero-bivalent VEGFR2 (targeting moiety 1) + VEGFR2 (targeting moiety 3) | 35 |
| CXCR4 | V1 (parent) | LGASWHRPDKCCLGYQKRPLP | 36 |
| CXCR4 | V1-L1 A | AGASWHRPDKCCLGYQKRPLP | 37 |
| CXCR4 | V1-W5A | LGASAHRPDKCCLGYQKRPLP | 38 |
| CXCR4 | V1-R7A | LGASWHAPDKCCLGYQKRPLP | 39 |
| CXCR4 | V1-K9A | LGASWHRPDACCLGYQKRPLP | 40 |
| CXCR4 | V1-C11A | LGASWHRPDKACLGYQKRPLP | 41 |
| CXCR4 | V1-Q16A | LGASWHRPDKCCLGYAKRPLP | 42 |
| CXCR4 | V1-R18A | LGASWHRPDKCCLGYQKAPLP | 43 |
| CXCR4 | V1-C11AC12A | LGASWHRPDKAALGYQKRPLP | 44 |
| CXCR4 | V1-C11G | LGASWHRPDKGCLGYQKRPLP | 45 |
| CXCR4 | V1-C11F | LGASWHRPDKFCLGYQKRPLP | 46 |
| CXCR4 | V1-C11AC12G | LGASWHRPDKAGLGYQKRPLP | 47 |
| CXCR4 | V1-C11AC12F | LGASWHRPDKAFLGYQKRPLP | 48 |
| CXCR4 | V1a | MLGASWHRPDKCCLGYQ | 49 |

TABLE 2-continued

Peptide (including affibodies) Targeting Moieties

| Target | Alias within application (if any) | Sequence | SEQ ID NO. |
|---|---|---|---|
| CXCR4 | V1a-C11F | MLGASWHRPDKFCLGYQ | 50 |
| CXCR4 | V1a-C12F | MLGASWHRPDKCFLGYQ | 51 |
| CXCR4 | V1a-C11A | MLGASWHRPDKACLGYQ | 52 |
| CXCR4 | V1a-C12A | MLGASWHRPDKCALGYQ | 53 |
| HER2 | Affi342 | VDNKFNKEMRNAYWEIALLPNLNNQQKRA FIRSLYDDPSQSANLLAEAKKLNDAQAPK | 54 |
| EGFR | Affi1907 | VDNKFNKEMWAAWEEIRNLPNLNGWQMTA FIASLVDDPSQSANLLAEAKKLNDAQAPK | 55 |
| Bombesin Receptor(s) | Bombesin, B14 (14 amino acid peptide) | EQRLGNQWAVGHLM | 56 |
| Bombesin Receptor(s) | Bombesin, B10 (10 amino acid peptide) | GNQWAVGHLM | 57 |
| Gastrin releasing peptide receptors, including bombesin receptors | Gastrin-releasing peptide (GRP) | GNHWAVGHLM | 58 |
| Collagen Type I | parent | KKWHCYTYFPHHYCVYG | 59 |
| Collagen type I | G17Y | KKWHCYTYFPHHYCVYY | 60 |
| Collagen type I | G17W | KKWHCYTYFPHHYCVYW | 61 |
| Collagen type I | G17F | KKWHCYTYFPHHYCVYF | 62 |
| Collagen type I | K1G | GKWHCYTYFPHHYCVYG | 63 |
| Collagen type I | K1G-Y8K | GKWHCYTKFPHHYCLYG | 64 |
| Collagen type I | K1G-V15L | GKWHCYTYFPHHYCLYG | 65 |
| Integrin $\alpha_v\beta_3$ | | RGDRGDRGDRGD | 66 |

TABLE 3

Linkers

| Linker | SEQ ID NO.: |
|---|---|
| GGG | 67 |
| GGSGG | 68 |
| GSGS | 69 |

ProCA Formulations

Also provided herein are pharmaceutical formulations containing an amount of a ProCA and/or targeted ProCA as described herein. The amount can be an effective amount. Pharmaceutical formulations can be formulated for delivery via a variety of routes and can contain a pharmaceutically acceptable carrier. Techniques and formulations generally can be found in Remmington's Pharmaceutical Sciences, Meade Publishing Co., Easton, Pa. (20th Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

The pharmaceutical formulations can be administered to a subject in need thereof. The subject in need thereof can have a disease, disorder, or a symptom thereof or be suspected of having a disease, disorder, or a symptom thereof. Example disease or disorder can include, but are not limited to, a cardiovascular disease, a pulmonary disease, a brain disease, a renal disease, a liver disease, a blood disease, a nervous system disease, an intestinal disease, an ocular disease, and cancer. The pharmaceutical formulations can be disposed on or otherwise coupled to or integrated with a medical device, such as, but not limited to, catheters or stents, such that the pharmaceutical formulation is eluted from the medical device over a time period. The pharmaceutical formulation can therefore be delivered to a subject in need thereof during and/or after a procedure such as an angioplasty, vein draft or organ transplant. Other procedures where such a medical device would be useful will be appreciated by those of skill in the art.

A pharmaceutical formulation can be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. The construct, biologic molecules and pharmaceutical formulations thereof described herein can be disposed on or otherwise integrated with or coupled to a medical device such as, but not limited to, a catheter or stent, such that the construct, biological molecule can be released to the surrounding local area or systemically over a period of time after insertion or implantation into a subject in need thereof. These can also be referred to as drug eluting medical devices.

Pharmaceutical formulations suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). Injectable pharmaceutical formulations can be sterile and can be fluid to the extent that easy syringability exists. Injectable pharmaceutical formulations can be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of injectable compositions can be brought about by incorporating an agent which delays absorption, for example, aluminum monostearate and gelatin.

Sterile injectable solutions can be prepared by incorporating any of the compositions or recombinant polypeptides as described herein in an amount in an appropriate solvent with one or a combination of ingredients enumerated herein, as required, followed by filtered sterilization. Generally, dispersions can be prepared by incorporating the nucleic acid vectors into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated can be used in the formulation. Such penetrants are generally known in the art, and include, for example, for transmucosal administration, detergents, bile salts, and fluidic acid derivatives. Transmucosal administration can be accomplished through the use of nasal sprays or suppositories. For transdermal the compositions or recombinant polypeptides described herein can be formulated into ointments, salves, gels, or creams as generally known in the art. In some embodiments, the compositions or recombinant polypeptides can be applied via transdermal delivery systems, which can slowly release the compositions or recombinant polypeptides for percutaneous absorption. Permeation enhancers can be used to facilitate transdermal penetration of the active factors in the conditioned media. Transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Administration of the compositions or recombinant polypeptides described herein is not restricted to a single route, but may encompass administration by multiple routes. For instance, exemplary administrations by multiple routes include, among others, a combination of intradermal and intramuscular administration, or intradermal and subcutaneous administration. Multiple administrations may be sequential or concurrent. Other modes of application by multiple routes will be apparent to the skilled artisan.

The pharmaceutical formulations can be administered to a subject by any suitable method that allows the agent to exert its effect on the subject in vivo. For example, the formulations or other compositions described herein can be administered to the subject by known procedures including, but not limited to, by oral administration, sublingual or buccal administration, parenteral administration, transdermal administration, via inhalation, via nasal delivery, vaginally, rectally, and intramuscularly. The formulations or other compositions described herein can be administered parenterally, by epifascial, intracapsular, intracutaneous, subcutaneous, intradermal, intrathecal, intramuscular, intraperitoneal, intrasternal, intravascular, intravenous, parenchymatous, and/or sublingual delivery. Delivery can be by injection, infusion, catheter delivery, or some other means, such as by tablet or spray.

For oral administration, a formulation as described herein can be presented as capsules, tablets, powders, granules, or as a suspension or solution. The formulation can contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration by through a route other than the alimentary canal), the formulations described herein can be combined with a sterile aqueous solution that is isotonic with the blood of the subject. Such a formulation can be prepared by dissolving the active ingredient in water containing physiologically-compatible substances, such as sodium chloride, glycine and the like, and having a buffered pH compatible with physiological conditions, so as to produce an aqueous solution, then rendering the solution sterile. The formulation can be presented in unit or multi-dose containers, such as sealed ampoules or vials. The formulation can be delivered by injection, infusion, or other means known in the art.

For transdermal administration, the formulation described herein can be combined with skin penetration enhancers, such as propylene glycol, polyethylene glycol, isopropanol, ethanol, oleic acid, N-methylpyrrolidone and the like, which increase the permeability of the skin to the nucleic acid vectors of the invention and permit the nucleic acid vectors to penetrate through the skin and into the bloodstream. The formulations and/or compositions described herein can be further combined with a polymeric substance, such as ethylcellulose, hydroxypropyl cellulose, ethylene/vinyl acetate, polyvinyl pyrrolidone, and the like, to provide the composition in gel form, which can be dissolved in a solvent, such as methylene chloride, evaporated to the desired viscosity and then applied to backing material to provide a patch.

Dosage Forms

The pharmaceutical formulations or compositions described herein can be provided in unit dose form such as a tablet, capsule or single-dose injection or infusion vial. Where appropriate, the dosage forms described herein can be microencapsulated. The dosage form can also be prepared to prolong or sustain the release of any ingredient. In some embodiments, the complexed active agent can be the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

In some embodiments, such as for treatments of plants, the topical formulation of a composition or pharmaceutical formulation described herein can be further formulated as a spray and can include a suitable surfactant, wetting agent, adjuvants/surfactant (stickers, extender, plant penetrant, compatibility agents, buffers, drift control additives, and defoaming agents), or any combination thereof so as to formulated as a spray. The compounds, any optional auxiliary active ingredient, suitable surfactant, wetting agent, adjuvants, or any combination thereof can be formulated as a solution, suspension, or emulsion. The spray dosage from can be administered through a spraying device. In some embodiments, the spraying device can be configured to generate the sprayable formulation as a liquid solution is contacted with the complexed active agent compound or formulation thereof. In other embodiments, the sprayable dosage form is pre-made prior to spraying. As such, the spraying device can act solely as an applicator for these embodiments.

In further embodiments, such as for treatments of plants (e.g. such as a herbicide), the dosage form of composition or pharmaceutical formulation described herein thereof can be further formulated as a dust and can include a suitable dry inert carrier (e.g. talc chalk, clay, nut hull, volcanic ash, or any combination thereof so as to be formulated as a dust. The dust can contain dust particles of varying sizes. In some embodiments, the particle size can be substantially homogenous. In other embodiments, the particle size can be heterogeneous. Dosage forms adapted as a dust can contain one or more adjuvants/surfactants (stickers, extender, plant penetrant, compatibility agents, buffers, drift control additives, and defoaming agents).

In some embodiments, the dosage form can be formulated as a bait. In these embodiments, the complexed active agent compound or other formulation thereof can be further formulated to include a food or other attractive substance that can attract one or more insect or other pest. The bait dosage form can be formulated as a dust, paste, gel, or granule. Dosage forms adapted as baits can contain one or more adjuvants/surfactants (stickers, extender, plant penetrant, compatibility agents, buffers, drift control additives, and defoaming agents).

In additional embodiments, the dosage form can be formulated as granules or pellets that can be applied to the environment. These dosage formulations are similar to dust formulations, but the particles are larger and heavier. The granules can be applied to soil or other environmental area. Dosage forms adapted as granules or pellets can contain one or more adjuvants/surfactants (stickers, extender, plant penetrant, compatibility agents, buffers, drift control additives, and defoaming agents).

The dusts, granules, and pellets described herein can be formulated as wettable dusts, granules, and pellets, soluble dusts granules, and pellets, and/or water-dispersible granules, and/or dry flowables.

The dosage form can be adapted for impregnating (saturating) an object or device, which then can be carried by, worn, or otherwise coupled to an organism in need thereof. In some embodiments, the dosage form can be impregnated onto a collar, bracelet, patch, adhesive tape, livestock ear tags, clothing, blankets, plastics, nets, and paints. The composition or pharmaceutical formulation thereof can be formulated and impregnated in the object or device such that the composition or pharmaceutical formulation evaporates over time, which releases the composition and/or pharmaceutical formulation into the air and/or environment surrounding the organism and/or onto the organism.

The dosage form can be adapted as a fumigant, which is a formulation that forms a gas when utilized or applied. In some embodiments, the composition and/or pharmaceutical formulation thereof can be supplied as a liquid when packaged under pressure and change to a gas when they are released. In other embodiments, the composition and/or pharmaceutical formulation thereof can be supplied as a volatile liquid when enclosed in a container (not under pressure). Others can be formulated as solids that release gases when applied under conditions of high humidity or in the presence of high water vapor. Dosage forms adapted as fumigants can contain one or more adjuvants/surfactants (stickers, extender, plant penetrant, compatibility agents, buffers, drift control additives, and defoaming agents).

Effective Amounts

The pharmaceutical formulations can contain an effective amount of a ProCA and/or targeted ProCA described herein and/or an effective amount of an auxiliary agent. In some embodiments, the effective amount ranges from about 0.001 pg to about 1,000 g or more of a composition described herein. In some embodiments, the effective amount of the composition described herein can range from about 0.001 mg/kg body weight to about 1,000 mg/kg body weight. In yet other embodiments, the effective amount of the composition can range from about 1% w/w to about 99% or more w/w, w/v, or v/v of the total pharmaceutical formulation. The effective amount of the ProCAs described herein can range from about 0.5 µM to 20 mM. The effective amount of the ProCAs described herein can range from about 0.5 umol/kg to about 0.3 mmol/kg Combination Therapy The pharmaceutical formulations or other compositions described herein can be administered to a subject either as a single agent, or in combination with one or more other agents. Additional agents include but are not limited to DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and $\beta_2$-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Methods of Using the ProCAs

The ProCAs and targeted ProCAs as described herein can be used in imaging methods including, but not limited to MRI. In embodiments, the ProCA, targeted ProCA, or formulation thereof can be administered to a subject. After administration, the subject can be imaged using MRI or other imaging technique. Imaging can occur immediately, simultaneously, or at some other time (e.g. 5, 10, 15, 20, 30, 40, 45, 50, 55, 60, 90, 120, 240, 360 or more minutes) post administration. In this way, the ProCAs and targeted ProCAs provided herein can be useful in the diagnosis, treatment, and/or prevention of diseases and disorders such as cancer, including but not limited to, cancer of the prostate, breast, liver, kidney, brain, and lung, and liver fibrosis.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1. PSMA Targeted ProCAs

FIGS. 2A and 2B demonstrate expression (FIG. 2A) and purification (FIG. 2B) of ProCA32.562.PSMA and ProCA32.564.PSMA. E. coli competent cell strain BL21 (DE3)plysS was transformed with plasmids of ProCA32.562.PSMA and ProCA32.564.PSMA. The protein expression was induced by 0.5 mM isopropyl β-D-1-thiogalactopyranoside (IPTG) when the bacterial growth is up to the exponential phase. After IPTG induction, the culture temperature was maintained at 37° C. for 3 h, and then decreased to 25° C. overnight. Cell pellets were re-suspended in PBS buffer supplemented with benzonuclease and phenylmethanesulfonyl fluoride and were completely broken by a sonicator and cell disruptor. The supernatant of bacteria lysates was boiled at 90-95° C. for 10 min. The precipitates after boiling were removed by centrifuge. The supernatant was mixed with 3% streptomycin sulphate and placed at 4° C. overnight to precipitate DNA in the solution. On the next day, the precipitate DNA was removed by centrifuge and the supernatant was dialyzed in 10 mM HEPES buffer (pH 8.0) at 4° C. overnight. After dialysis, the protein solution was filtered by a 0.45 μm filter and further purified by fast protein liquid chromatography (FPLC) equipped with a HiTrap Q HP column. The purified protein MRI contrast agents by FPLC were confirmed by SDS-PAGE and UV spectrum. $Gd^{3+}$ was loaded with these protein MRI contrast agents at a 2:1 ratio.

Figure 3A:
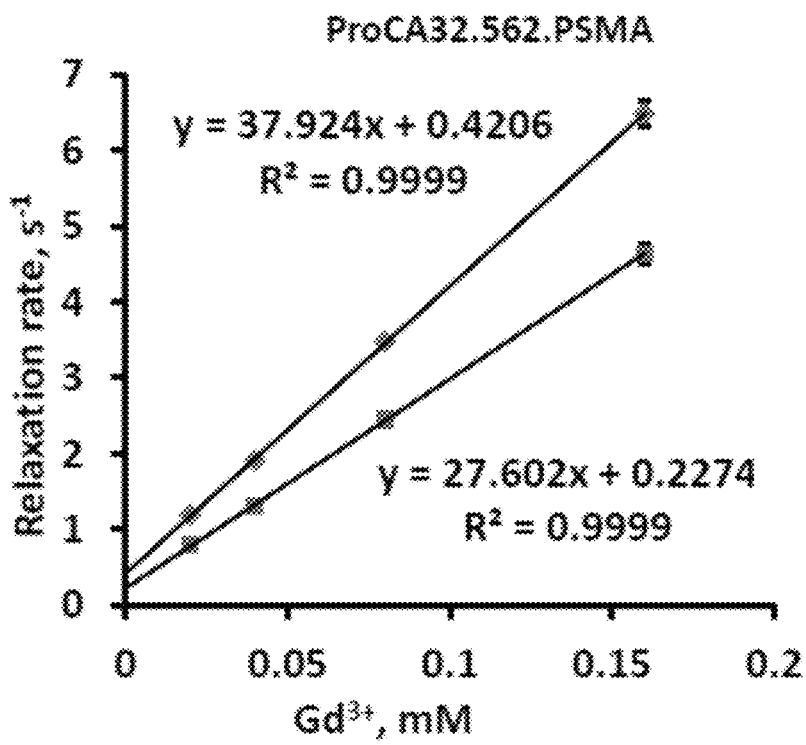
FIGS. 3A and 3B show graphs demonstrating the relaxivity measurements (r1 and r2) of ProCA32.562.PSMA (FIG. 3A) and ProCA32.564.PSMA (FIG. 3B) at about 37° C. under 60 M Hz by Bruker Minispec in 10 mM HEPES at pH 7.2.
Figure 3B:
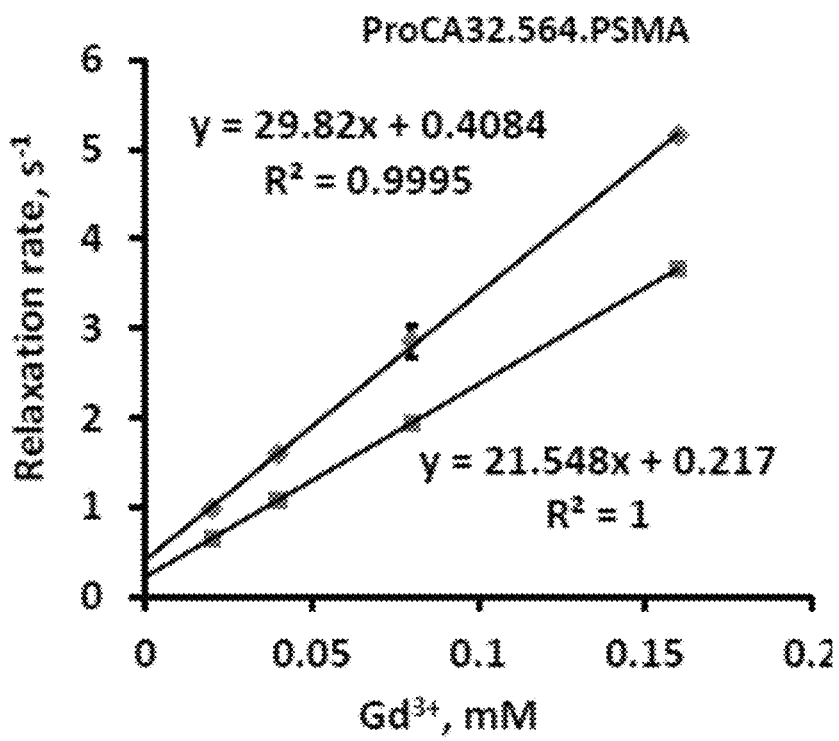

The r1 and r2 relaxivities for ProCA32.562.PSMA and ProCA32.564.PSMA were evaluated. Different concentrations of ProCAs (ProCA32.562.PSMA and ProCA32.564.PSMA) were mixed with $GdCl_3$ at a 1:2 ratio. The $T_1$ and $T_2$ relaxation times of water in the presence or absence of ProCAs were measured at 37° C. by using a 1.4 T Bruker Minispec using saturation recovery and CPMG sequence, respectively. The $T_1$ and $T_2$ of Gd-DTPA and ProCA32.562 were also measured by using a 7 T-Agilent scanner using saturation recovery and spin echo sequence. FIGS. 3A and 3B show graphs demonstrating the relaxivity measurements (r1 and r2) of ProCA32.562.PSMA (FIG. 3A) and ProCA32.564.PSMA (FIG. 3B) at about 37° C. under 60 M Hz by Bruker Minispec in 10 mM HEPES at pH 7.2.

The $Tb^{3+}$ binding affinity of ProCA32.562.PSMA and ProCA32.564.PSMA using a $Tb^{3+}$-DTPA buffer system. The $K_d$ of ProCA32 variants to $Tb^{3+}$ was determined using Gd-DTPA buffer system, which contains 50 mM HEPES, 100 mM NaCl, 5 mM DTPA and 30 μM of ProCA32 variants (562 and 564) at pH 7.0. In this procedure, 5 mM $TbCl_3$ was titrated into the system to generate a free $Gd^{3+}$ concentration ranging from $10^{-23}$ to $10^{-18}$ M. $K_d$ of ProCA32 variants to $Tb^{3+}$ was determined by Hill equation.

Determination of the $Tb^{3+}$ binding affinity of ProCAs was based on the $Tb^{3+}$ luminescence resonance energy transfer (LRET) experiment. Briefly, 30 μM ProCAs were prepared in 5 mM DTPA, 50 mM HEPES, 150 mM NaCl at pH 7.2. The ratio of Tb-DTPA concentration ([Tb-DTPA]) and free DTPA concentration ($[DTPA]_{free}$) were controlled free, by titration of $TbCl_3$ in the system. The protein-$Tb^{3+}$ LRET emission spectra were collected between 520 and 580 nm using an excitation wavelength of 280 nm. The free $Tb^{3+}$ concentrations ($[Tb]_{free}$) in each titration point were calculated by Equation 1 (Eq.1) free, $$[Tb]_{free} = K_{d_{Tb,DTPA}} \times \frac{[Tb-DTPA]}{[DTPA]_{free}} \quad \text{(Eq. 1)}$$

Where $K_{dTb,DTPA}$ is the dissociation constant between $Tb^{3+}$ and DTPA based on National Institute of Standards and Technology Standard Reference Database 46. The dissociation constant between $Tb^{3+}$ and ProCA ($K_{dTb,ProCA}$) is calculated by the Hill equation (Eq. 2).

$$f = \frac{[Tb]_{free}^n}{K_{d_{Tb,ProCA}}^n + [Tb]_{free}^n} \quad \text{(Eq. 2)}$$

Where f is the fractional change of the LRET signal at each titration point and n is the hill number.

Figure 4A:
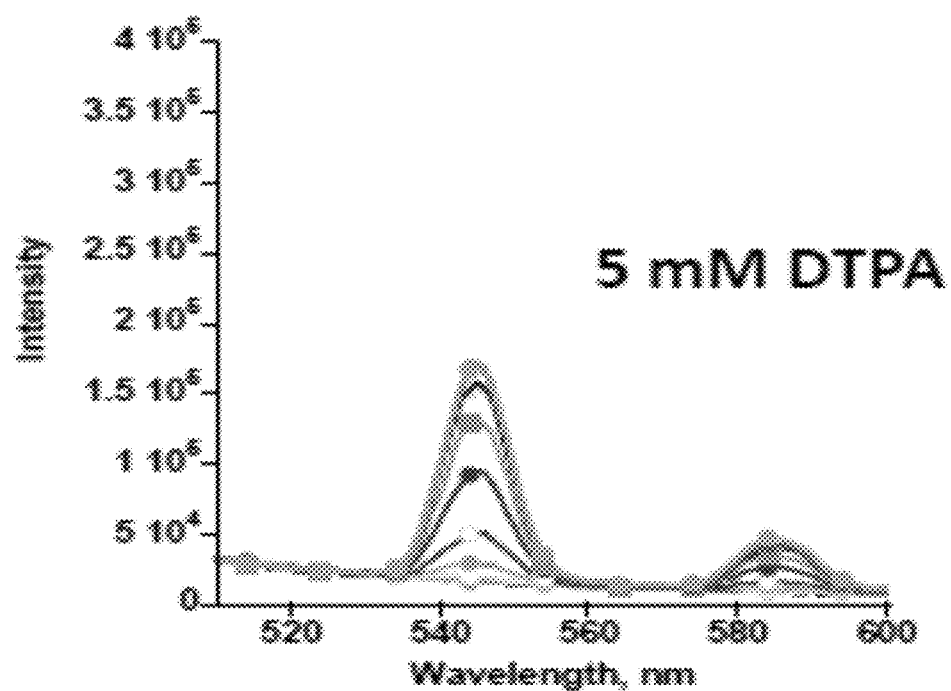
FIGS. 4A-4D show graphs demonstrating $Tb^{3+}$ binding affinity of ProCA32.562.PSMA and ProCA32.564.PSMA using a $Tb^{3+}$-DTPA buffer system.
Figure 4B:
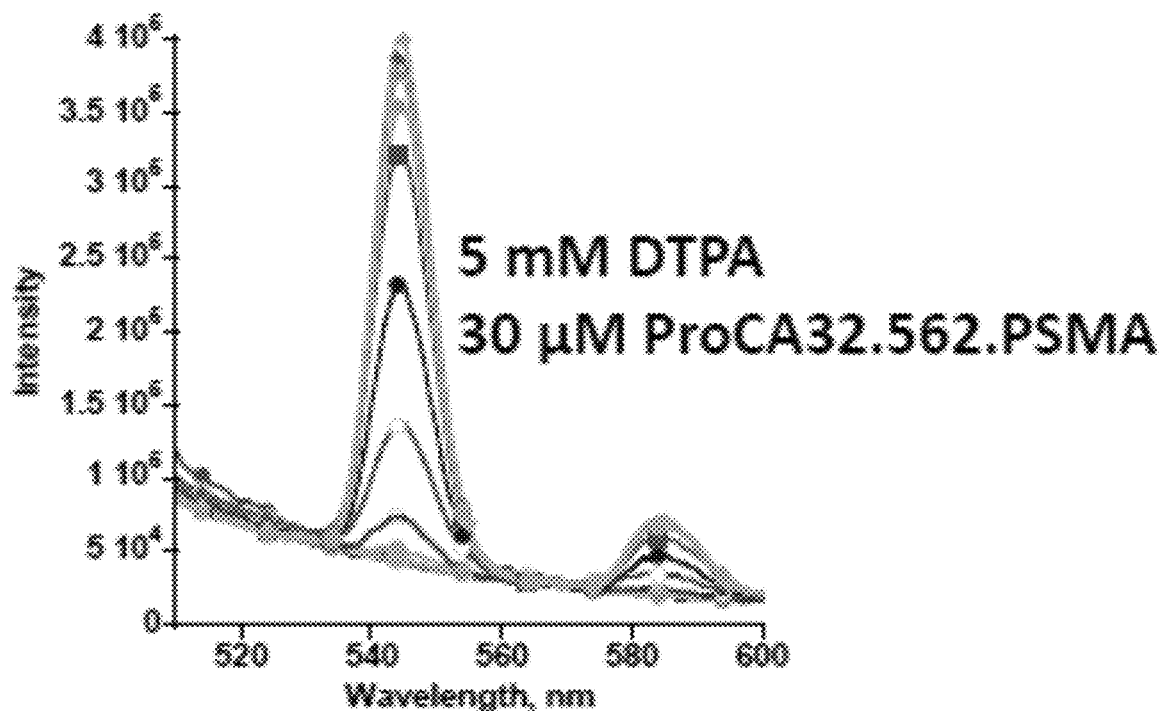
Figure 4C:
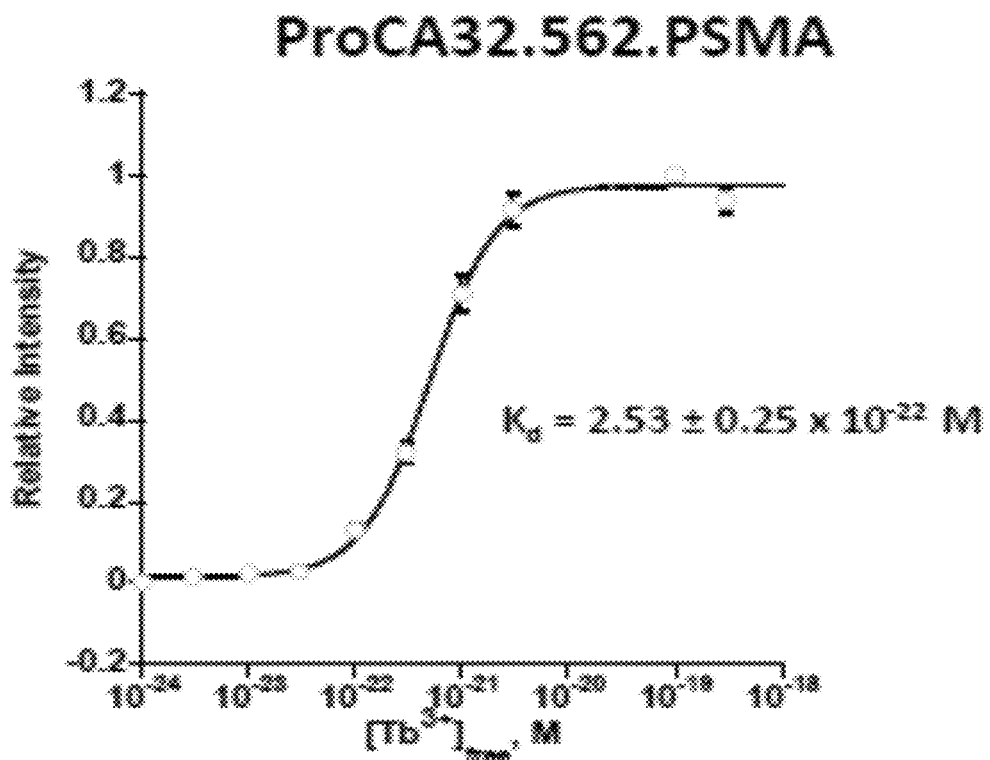
Figure 4D:
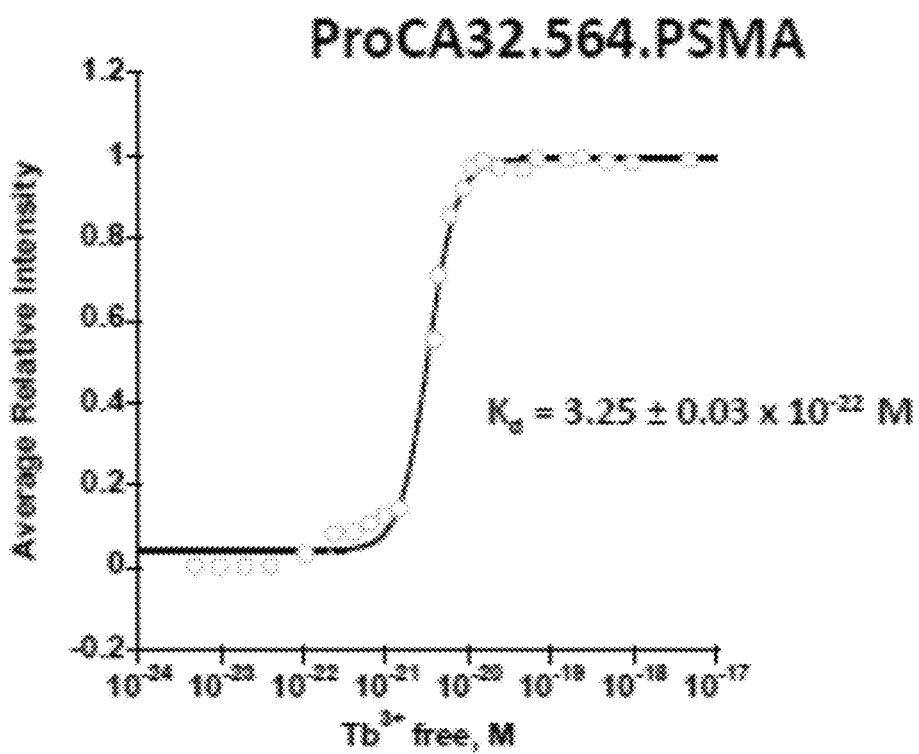

$Gd^{3+}$ binding affinities to ProCAs were measured by the LRET competition method. Briefly, 10 μM of ProCA and 20 μM $Tb^{3+}$ were incubated with 0 to 200 μM of $GdCl_3$ at room temperature overnight. The $Tb^{3+}$ LRET spectra were collected between 520 and 580 nm using an excitation wavelength of 280 nm. The apparent dissociation constants ($K_{dapp}$) were calculated by fitting the plot of LRET peak intensities over different concentrations of $Gd^{3+}$ (Equation 3, Eq. 3) and the dissociation constants of $Gd^{3+}$ to ProCAs ($K_{dGd,ProCA}$) were calculated by Equation 4 (Eq. 4)

$$f = \frac{([Tb]_T + [Gd]_T + K_{d_{app}}) - \sqrt{([Tb]_T + [Gd]_T + K_{d_{app}})^2 - 4 \times [Tb]_T \times [Gd]_T}}{2 \times [Tb]_T} \quad \text{(Eq. 3)}$$

$$K_{d_{Gd,ProCA}} = K_{d_{app}} \times \frac{K_{d_{Tb,ProCA}}}{K_{d_{TB,ProCA}} + [Tb]_T}, \quad \text{(Eq. 4)}$$

where f is the fractional change of the LRET signal, $[Tb]_T$ is the total $Tb^{3+}$ concentration, $[Gd]_T$ is the total $Gd^{3+}$ concentration in each titration point, and $K_{dGd,ProCA}$ is the dissociation constant between $Gd^{3+}$ and ProCA determined by equation (2). FIGS. 4A-4D show graphs demonstrating $Tb^{3+}$ binding affinity of ProCA32.562.PSMA and ProCA32.564.PSMA using a $Tb^{3+}$-DTPA buffer system. FIG. 4A shows the signal of $Tb^{3+}$ in buffer without the protein. FIG. 4B demonstrates the $Tb^{3+}$ in the presence of the protein. FIGS. 4C and 4D show the normalized data for each ProCA.32 variant. The fluorescence spectrums were collected under excitation wavelength of 280 nm and an emission wavelength of between 500-600 nm. This results indicate that ProCA32.562.PSMA and ProCA32.564.PSMA can have a strong Gd3+ affinity for in vitro and in vivo applications.

Figure 5A:
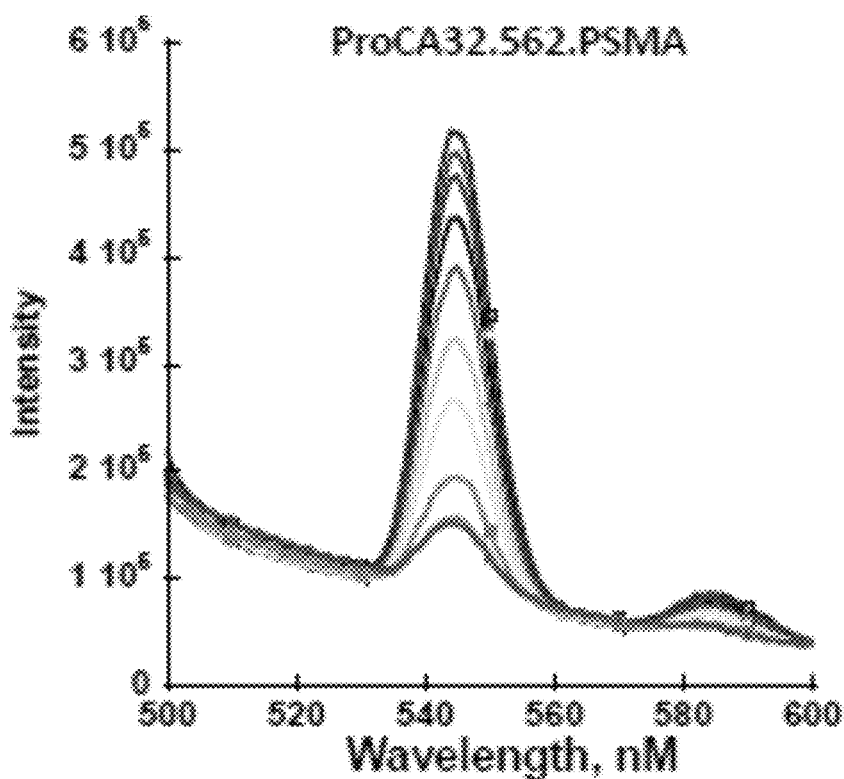
FIGS. 5A-5D show graphs demonstrating $Gd^{3+}$ binding affinity of ProCA32.562.PSMA and ProCA32.564.PSMA using a $Tb^{3+}$ competition assay.
Figure 5B:
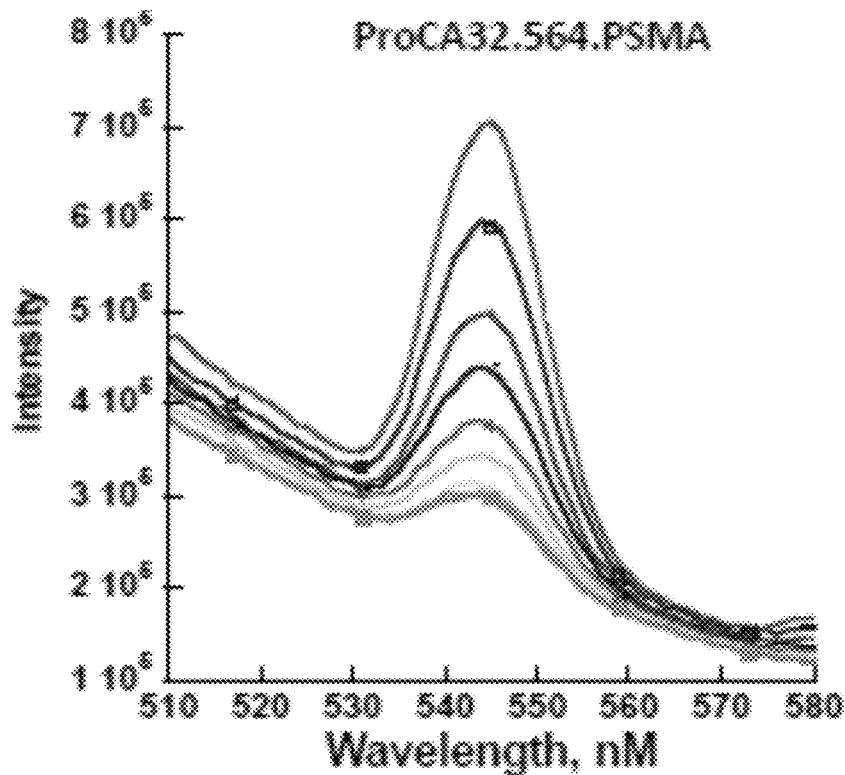
Figure 5C:
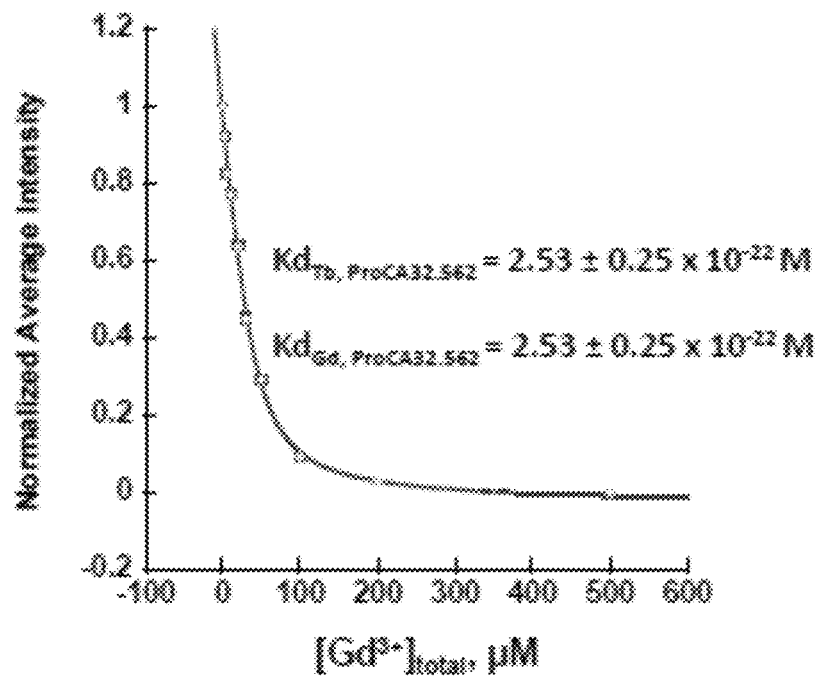
Figure 5D:
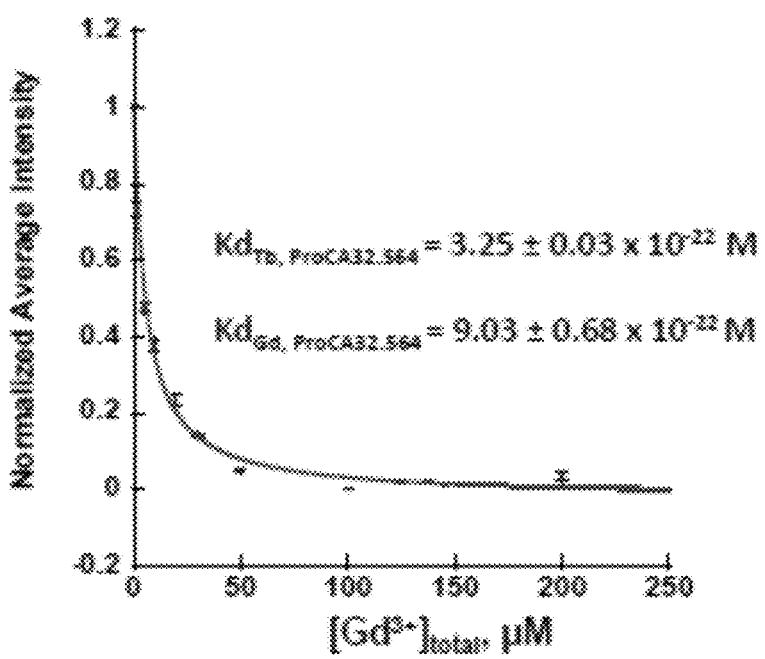

The $Gd^{3+}$ binding affinity of ProCA32.562.PSMA and ProCA32.564.PSMA was evaluated using a $Tb^{3+}$ competition assay. This experiment was performed in PTI using excitation wavelength of 280 nm by incubating different concentrations of $Gd^{3+}$ in 50 mM HEPES, 100 mM NaCl, 10 μM ProCA variants and 20 μM $Tb^{3+}$. Since $Gd^{3+}$ variants can compete $Tb^{3+}$ out of the metal binding pocket in ProCA variants, $Tb^{3+}$ shows decreased fluorescence signal as $Gd^{3+}$ concentration increases. FIGS. 5A-5B demonstrate the decrease in $Tb^{3+}$ signal in each ProCA variants and FIGS. 5C and 5D demonstrate the normalized signal of $Tb^{3+}$ after adding different amount of $Gd^{3+}$. The fluorescence spectrum were collected under excitation wavelength of 280 nm, and emission wavelength between 500-600 nm for ProCA32.562.PSMA and 510-580 nm for ProCA32.564.PSMA. FIGS. 5A-5D show graphs demonstrating $Gd^{3+}$ binding affinity of ProCA32.562.PSMA and ProCA32.564.PSMA using a $Tb^{3+}$ competition assay.

Figure 6:
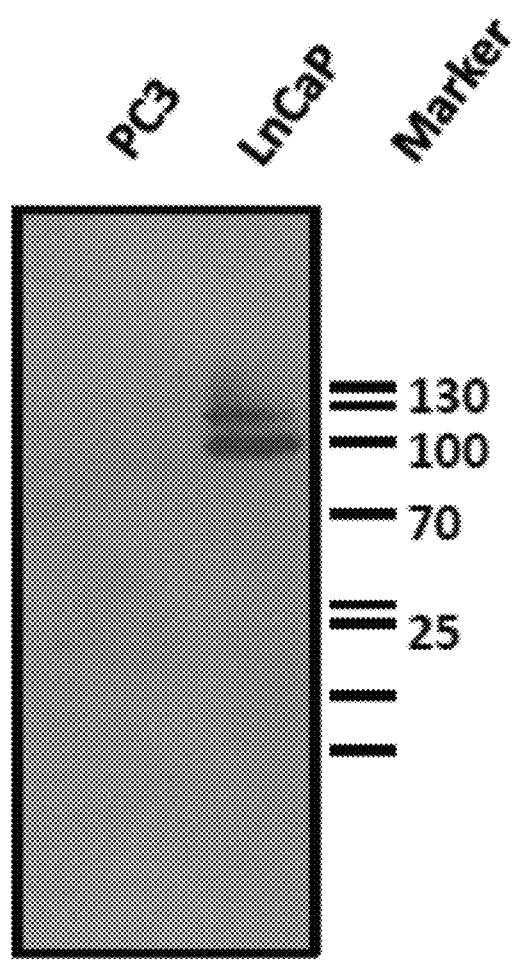
FIG. 6 demonstrates PSMA protein expression in LNCaP and PC3 cells.

FIG. 6 demonstrates PSMA protein expression in LNCaP and PC3 cells. To detect the PSMA expression in LnCaP cells, proteins were separated in 15% SDS-PAGE and then transferred onto the membrane. After blocking with 5% non-fat milk, the PSMA was visualized by monoclonal PSMA antibody (ABCaM 1:1000 dilution) and HRP-conjugated goat-anti-rabbit antibody (BioRad 1:10,000). PC3 cell lysate was used as a negative control, which does not have any bands, indicating that PC3 cells do not have PSMA expression.

Figure 7:
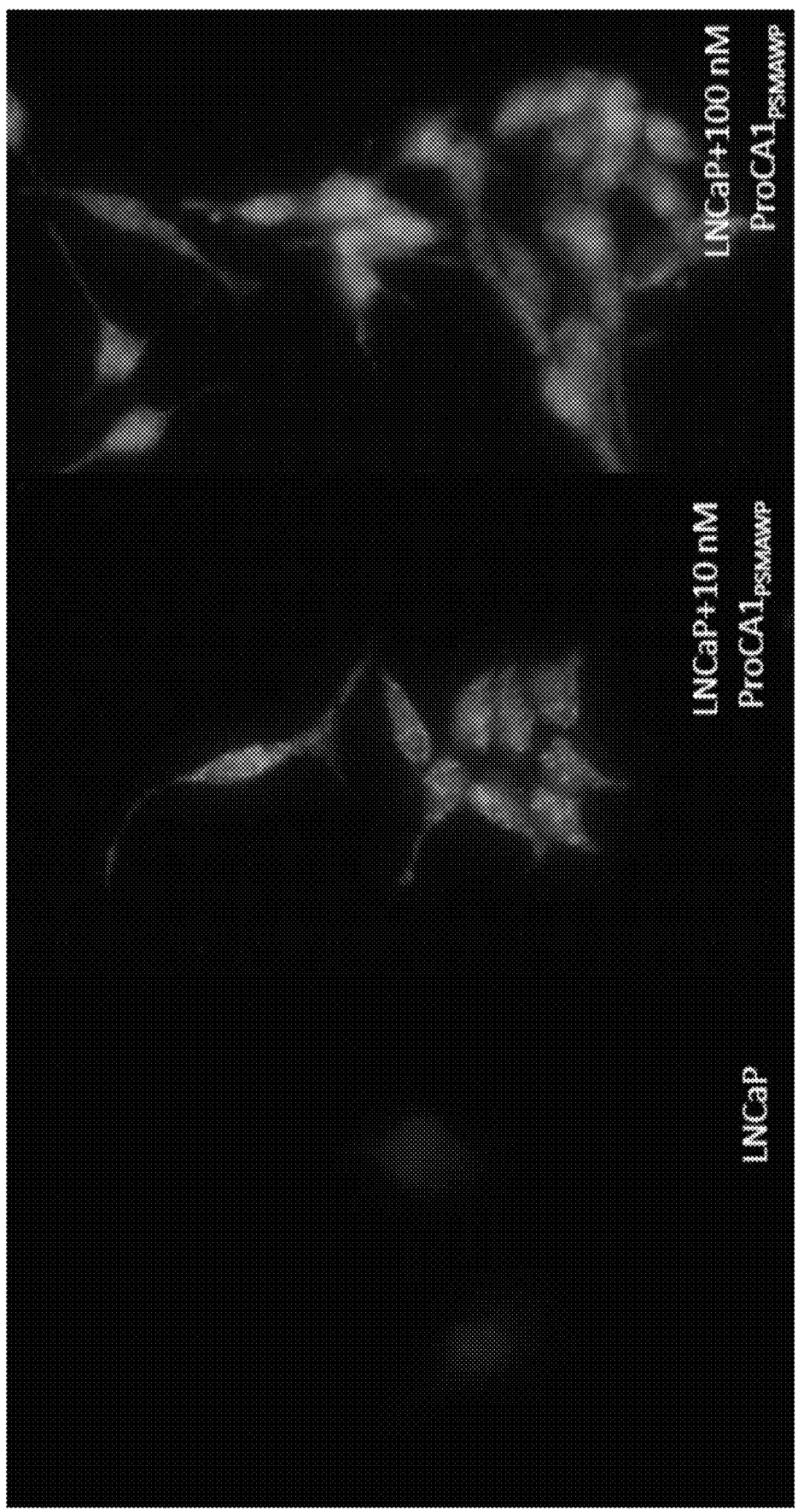
FIG. 7 shows a fluorescent micrographic image demonstrating ProCA1.WP.PSMA interaction with LNCaP cells.

The interaction between ProCA1PSMAwp and PSMA was confirmed by fluorescence imaging using a Zeiss fluorescence microscope. ProCA1PSMAwp was incubated with LNCAP cells first and then was out. These cells was then stained by fluorescence antibody and fixed before imaging The LNCaP shows enhanced green fluorescence after incubating with 10 nM or 100 nM of ProCA1PSMAwp. 100 nM ProCA1PSMAwp shows the highest fluorescence intensity. FIG. 7 shows a fluorescent micrographic image demonstrating ProCA1.WP.PSMA interaction with LNCaP cells. Without being bound by theory, these results suggest that ProCA1PSMAwp bond to PSMA positive cells.

Figure 8A:
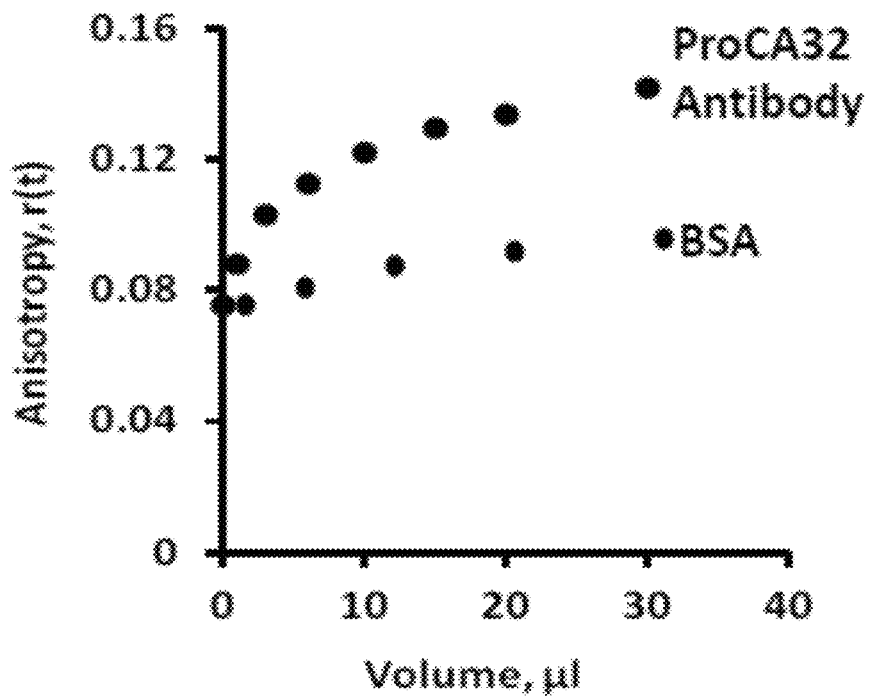
FIGS. 8A-8B show graphs demonstrating probe interaction between ProCA32.562.PSMA (FIG. 8A) or ProCA32.564.PSMA (FIG. 8B) as determined by anisotropy.
Figure 8B:
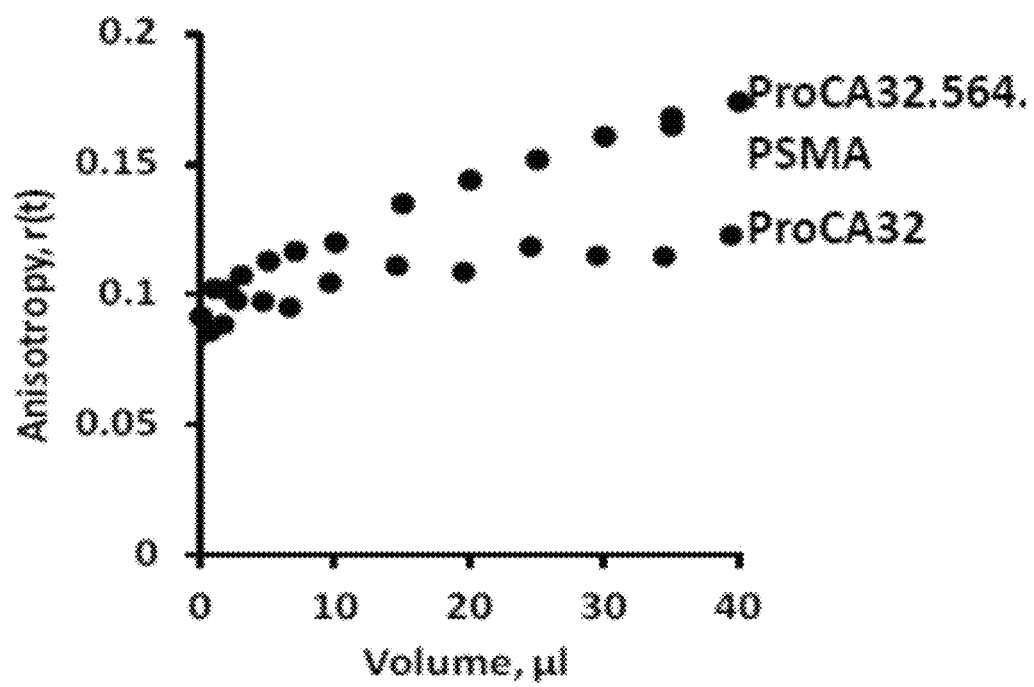

The probe interaction between ProCA32.562.PSMA or ProCA32.564.PSMA and PSMA was examined using anisotropy. ProCA32 variants were labeled with fluorescein. The basic mechanism of fluorescence anisotropy is based on rotational motions decreased when fluorescein-labeled ProCA32 bind to PSMA. Initially, 1% BSA and rabbit-anti-mouse ProCA32 antibody (homemade) were chosen as negative or positive controls, respectively with the concentration of ProCA32 at 15 μM. Then, different concentrations of antibody or BSA were titrated to ProCA32 in the fluorescence cuvette. The anisotropy signal of ProCA32 interacting with antibody or BSA was collected by fluorometer. FIGS. 8A-8B show graphs demonstrating probe interaction between ProCA32.562.PSMA (FIG. 8A) or ProCA32.564.PSMA and PSMA (FIG. 8B) as determined by anisotropy. Without being bound by theory, these results further indicate that PSMA targeted contrast agents bond the PSMA positive cells.

Figure 9:
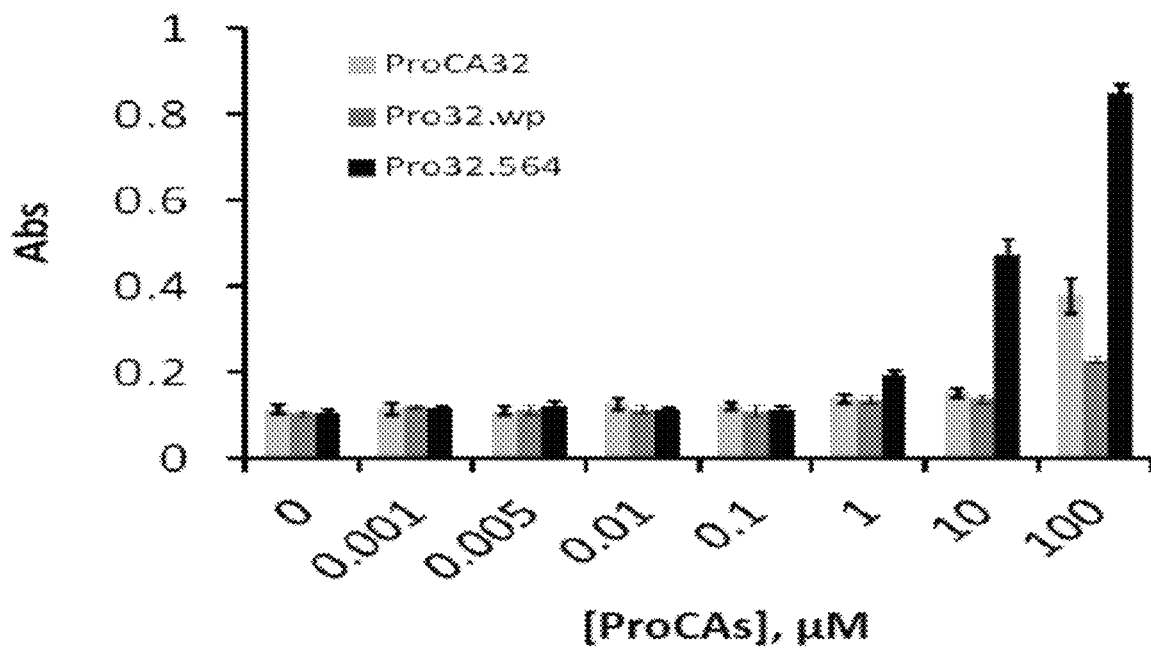
FIG. 9 shows a graph demonstrating a comparison of the binding capability between ProCA32.wp.PSMA and ProCA32.564.PSMA in LNCaP cell lysate by indirect ELISA.

The binding capability of ProCA32.wp.PSMA and ProCA32.564.PSMA and ProCA32 was examined using an enzyme linked immunoabsorbant assay (ELISA). Briefly, LNCaP cell lysates were coated in a 96-well plate and 5% BSA was used as blocking agent. Then, 0-100 μM of ProCA32, ProCA32.564.PSMA and ProCA32wp were added to interact with PSMA in the coated cell lysates. The interaction between ProCA32 variants and PSMA in cell lysates was quantified by ELISA using HRP-conjugated goat-anti-rabbit secondary antibody and one step ELISA kit. FIG. 9 shows a graph demonstrating a comparison of the binding capability between ProCA32.wp.PSMA and ProCA32.564.PSMA in LNCaP cell lysate by indirect ELISA. Without being bound by theory, these results further indicate that PSMA targeted contrast agents bond the PSMA positive cells.

Figure 10:
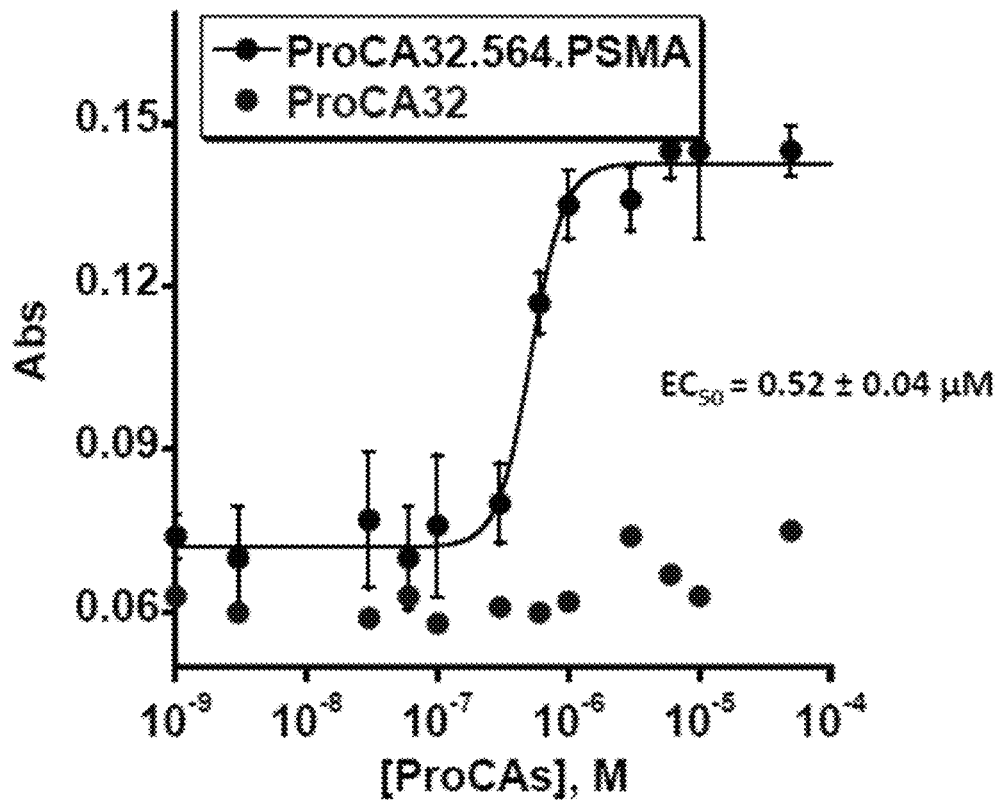
FIG. 10 shows a graph demonstrating targeting affinity of ProCA32.564.PSMA.

The targeting affinity for PSMA was examined. Briefly, LNCaP cell lysate was coated in a 96-well plate and 5% BSA was used as blocking agent. Then, 10-9-10-4 M of ProCA32.564.PSMA (black dots) was added to interact with PSMA in the coated cell lysate. The interaction between ProCA32.564.PSMA and PSMA in cell lysates was quantified by ELISA using HRP-conjugated goat-anti-rabbit secondary antibody and one step ELISA kit. The Kd of ProCA32.564.PSMA to PSMA was determined by Hill equation. ProCA32 (blue dots) was also tested in this experiment using the same experimental conditions. No absorbance enhancement was observed after increasing ProCA32 concentration indicating that ProCA32 itself without targeting moiety cannot bind to PSMA and LNCaP cell lysate. FIG. 10 shows a graph demonstrating targeting affinity of ProCA32.564.PSMA. Without being bound by theory, these results further indicate that PSMA targeted contrast agents bond the PSMA positive cells.

Figures 11, 12A:
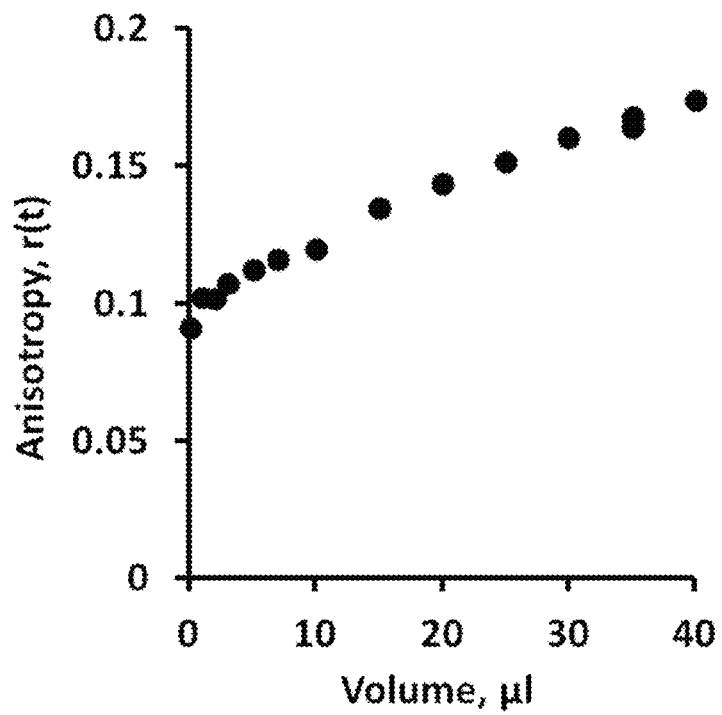
FIG. 11 shows a table demonstrating a summary of relaxivities and metal binding affinities of ProCA32.562.PSMA, ProCA32.564.PSMA, and ProCA32.WP.PSMA.
FIGS. 12A-12B show graphs demonstrating interaction between ProCA32.564.PSMA (FIG. 12A) or ProCA32 (FIG. 12B) and PSMA by anisotropy.

A summary of relaxivities and metal binding affinities of ProCA32.562.PSMA, ProCA32.564.PSMA, and ProCA32.WP.PSMA is shown in FIG. 11.

Figure 12B:
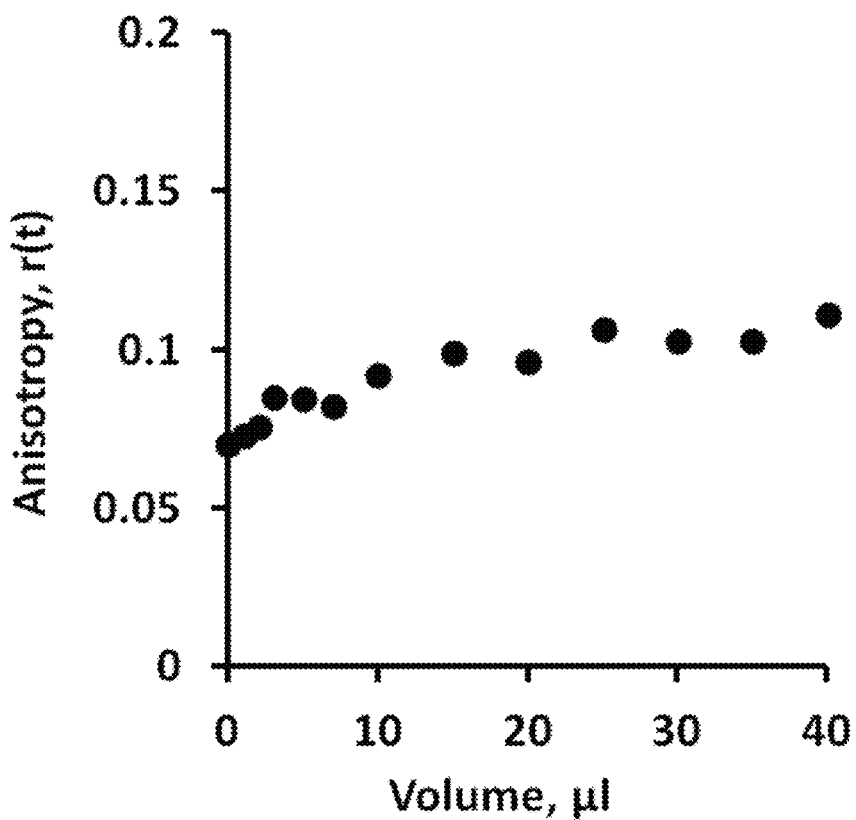

The probe interaction between ProCA32 or ProCA32.564.PSMA and PSMA was examined using anisotropy. The anisotropy 10 nM fluorescein-labeled ProCA32.564.PSMA (left) and ProCA32 (right) were collected using PTI fluorometer using excitation wavelength of 495 nm and emission wavelength of 518 nm in 10 mM HEPES buffer at pH 7.2. Fluorescein labeled ProCA32.564.PSMA has much higher anisotropy change compared with non-targeted ProCA32, indicating the interaction between ProCA32.564.PSMA and PSMA in LNCaP cell lysate. FIGS. 12A-12B show graphs demonstrating interaction between ProCA32.564.PSMA (FIG. 12A) or ProCA32 (FIG. 12B) and PSMA by anisotropy.

The r1 and r2 relaxivities of ProCA32.WP.PSMA was examined. The relaxation rates of protein (r1 and r2) were determined using different concentrations of $Gd^{3+}$ and protein (2:1) using a relaxometer. The relaxation rate for both T1 and T2 were measured using equation 5 (Eq. 5). The slope of the curve is longitudinal ($r_1$) and transverse ($r_2$) relaxivities.

$$r_i = \left(\frac{1}{T_{ia}} - \frac{1}{T_{ib}}\right) / [Gd^{3+}] \; i = 1, 2 \tag{Eq. 5}$$

Figure 13A:
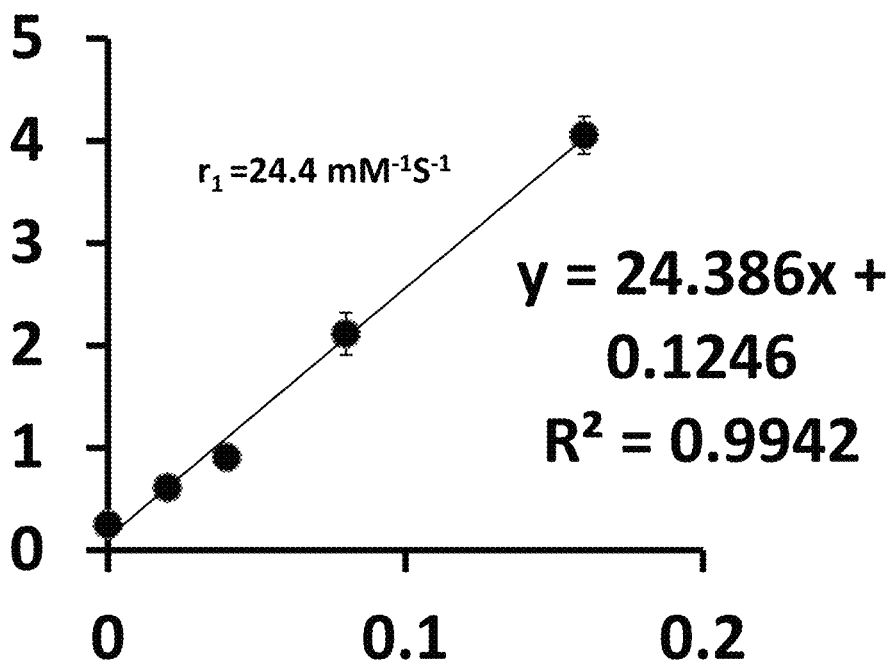
FIGS. 13A-13B show graphs demonstrating the relaxivity (r1, FIG. 13A and r2, FIG. 13B) of ProCA32.WP.PSMA.
Figure 13B:
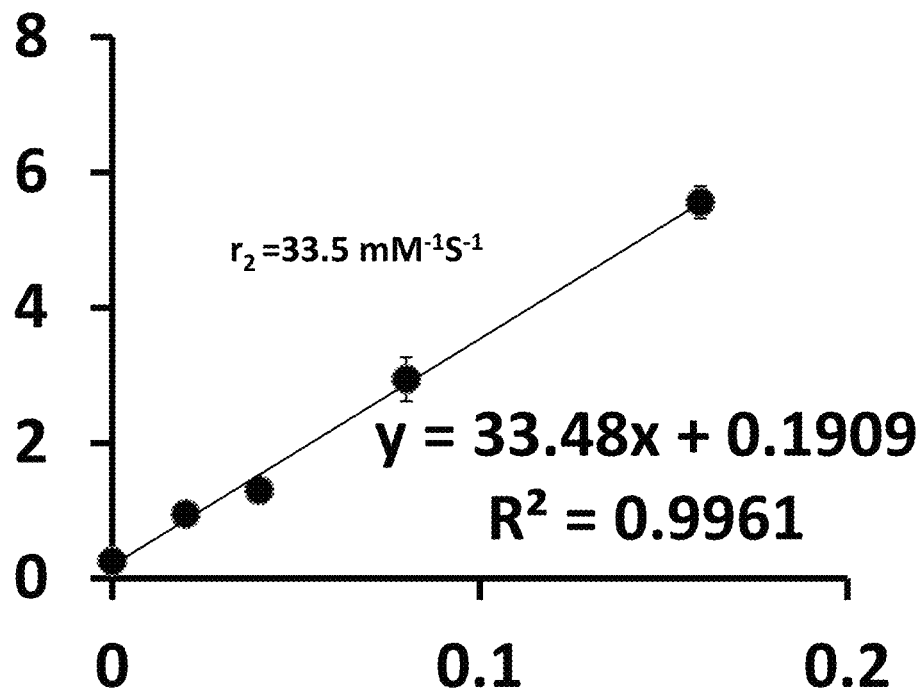

The methods used to examine the relaxivities of ProCA32.WP.PSMA above is described as above]] FIGS. 13A-13B show graphs demonstrating the relaxivity (r1, FIG. 13A and r2, FIG. 13B) of ProCA32.WP.PSMA. Without being bound by theory, these results demonstrate that ProCA32.WP.PSMA has high relaixivity indicating that it is sensitive for in vitro and in vivo MRI applications.

Figure 14A:
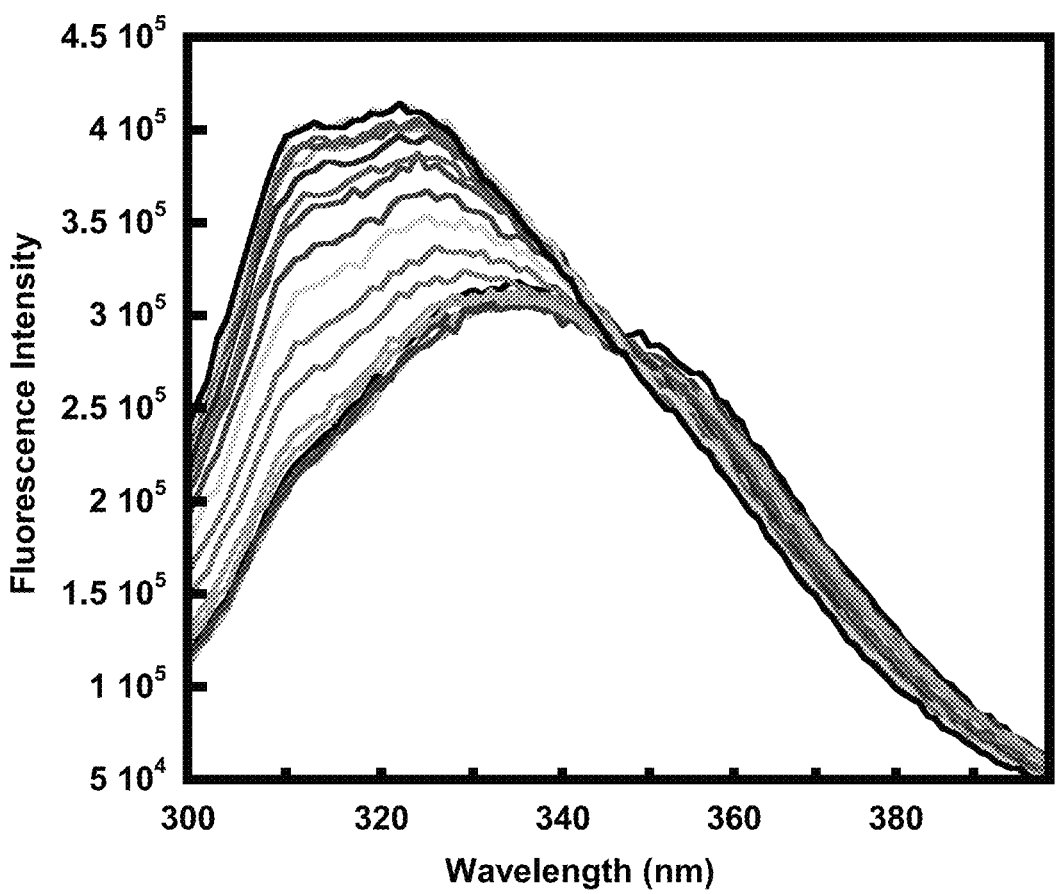
FIGS. 14A-14B show graphs demonstrating $Ca^{2+}$ titration of ProCA32.564 using the Hill Equation.
Figure 14B:
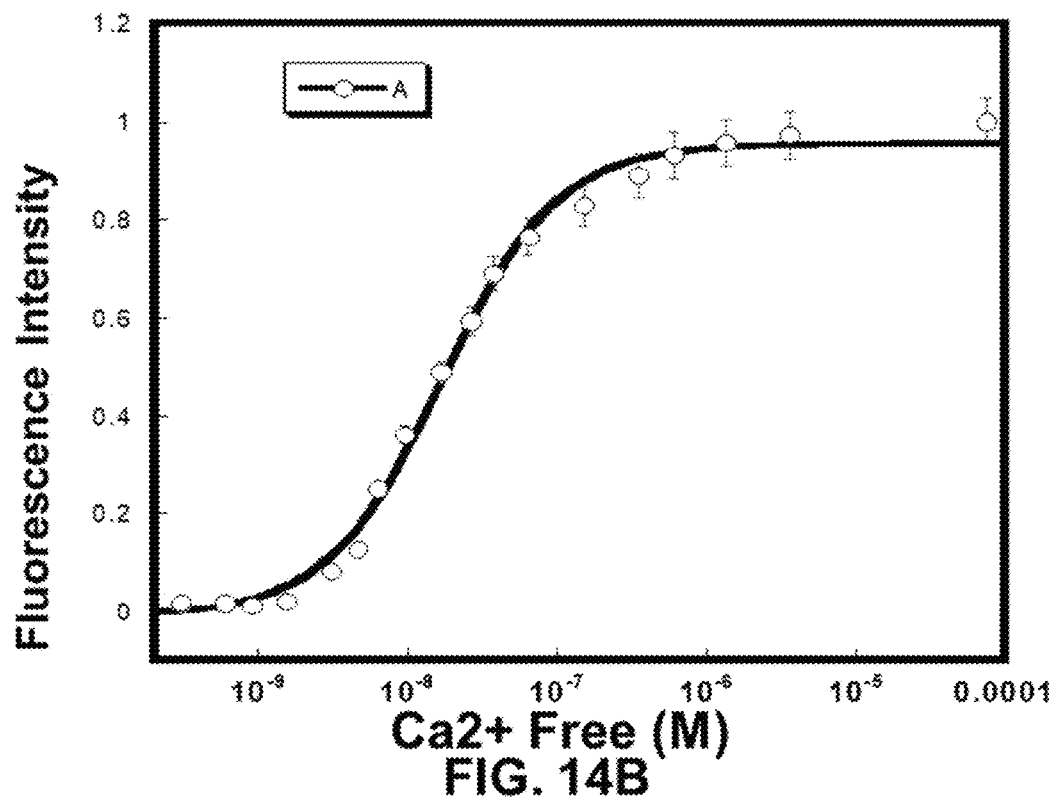

$Ca^{2+}$ titration of ProCA32.564 was performed. 10 μM ProCAs were added into the calcium-buffer system containing 50 mM HEPES, 100 mM NaCl, 5 mM EGTA, at pH 7.2. The system was titrated with different concentrations of $CaCl_2$ to alter the concentration ratio between the Ca-EGTA ([Ca-EGTA]) and free EGTA ($[EGTA]_{free}$). The tryptophan (Trp) fluorescence changes were monitored under the emission spectra between 300 and 390 nm as excited at 280 nm. The free calcium concentration at each titration point was calculated FIGS. 14A-14B show graphs demonstrating $Ca^{2+}$ titration of ProCA32.564 using the Hill Equation (Eq. 2). Without being bound by theory, these results indicate ProCA32.PMSA have lower affinity to Ca2+ compared with Gd3+.

Figure 15A:
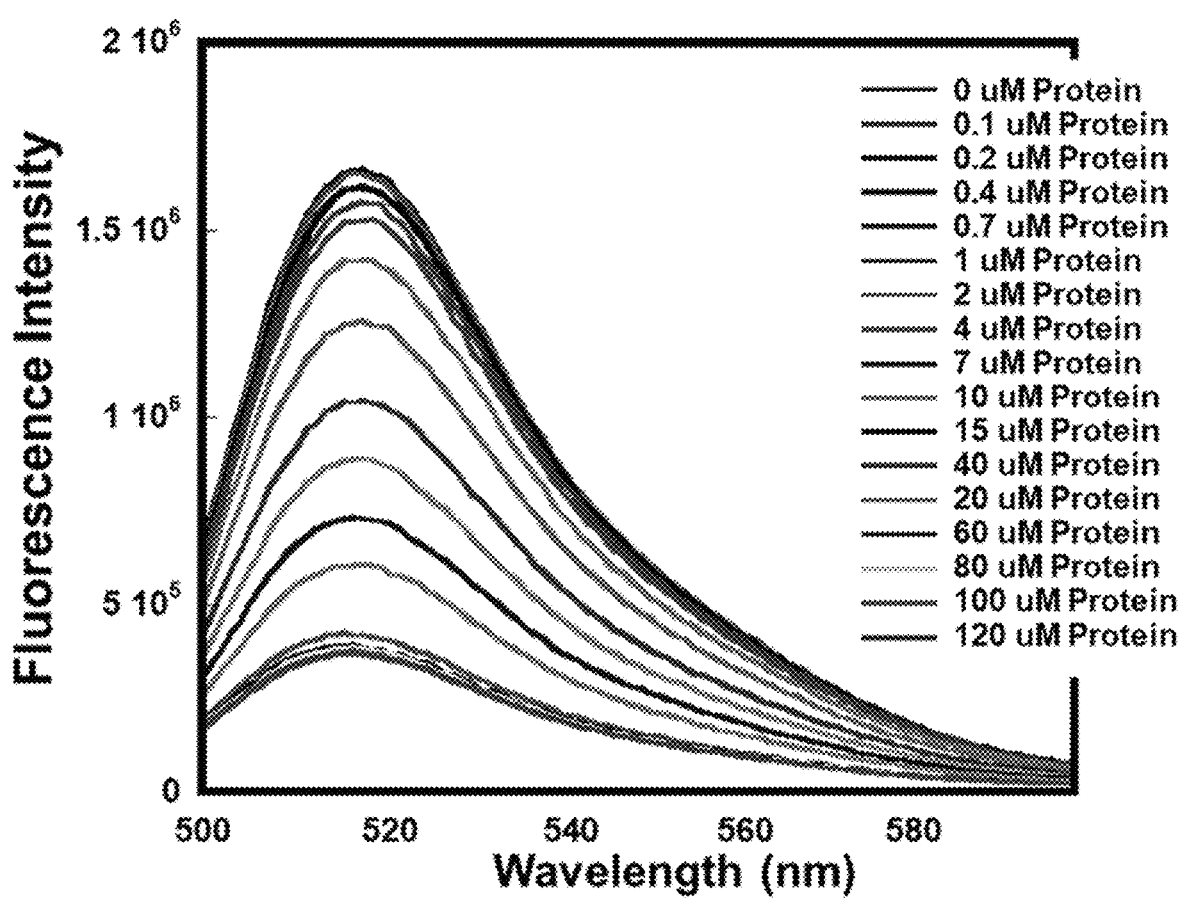
FIGS. 15A-15B show graphs demonstrating Fluozin-1 and ProCA32.564 competition for zinc.
Figure 15B:
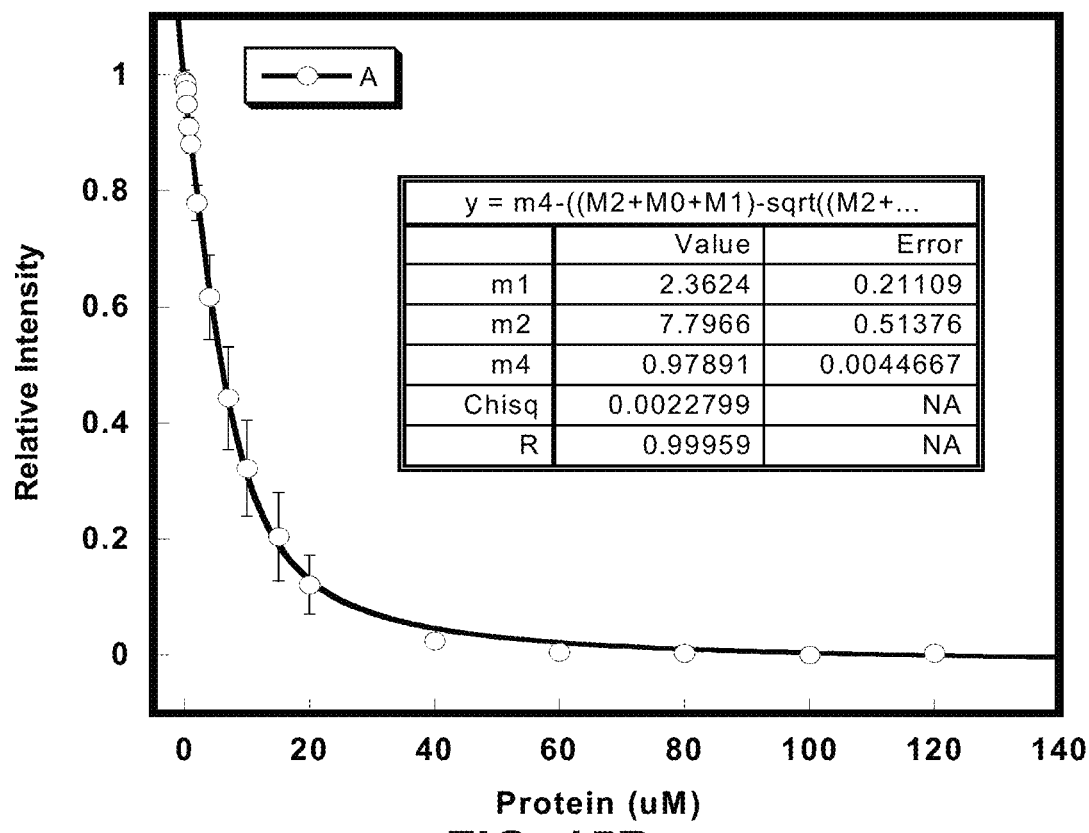

A fluozin-1 zinc competition assay was performed with ProCA32.564. The dissociation constant between $Zn^{2+}$ and PSMA-targeted ProCAs was determined by the fluorescence competition method with some modifications. The fluorescence of 2 μM Fluozin-1 was excited at 495 nm and the emission spectra were collected between 500 and 600 nm in the presence of 2 μM $Zn^{2+}$ and different concentrations of PSMA-targeted ProCAs. The apparent dissociation constant ($K_{dapp}$) was calculated. FIGS. 15A-15B show graphs demonstrating Fluozin-1 and ProCA32.564 competition for zinc.

Without being bound by theory, results indicate ProCA32.PMSA have lower affinity to Zn2+ compared with Gd3+.

Figure 16A:
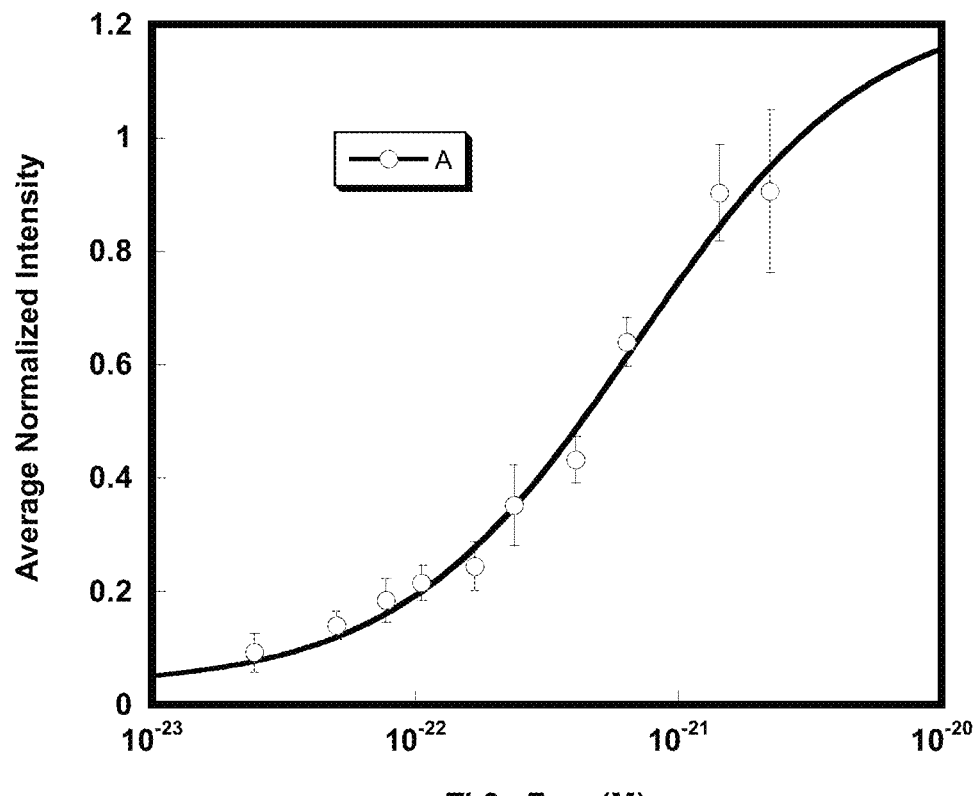
FIGS. 16A-16B demonstrate results of a ProCA32.WP $Tb^{3+}$ titration.
Figures 16B, 17A:
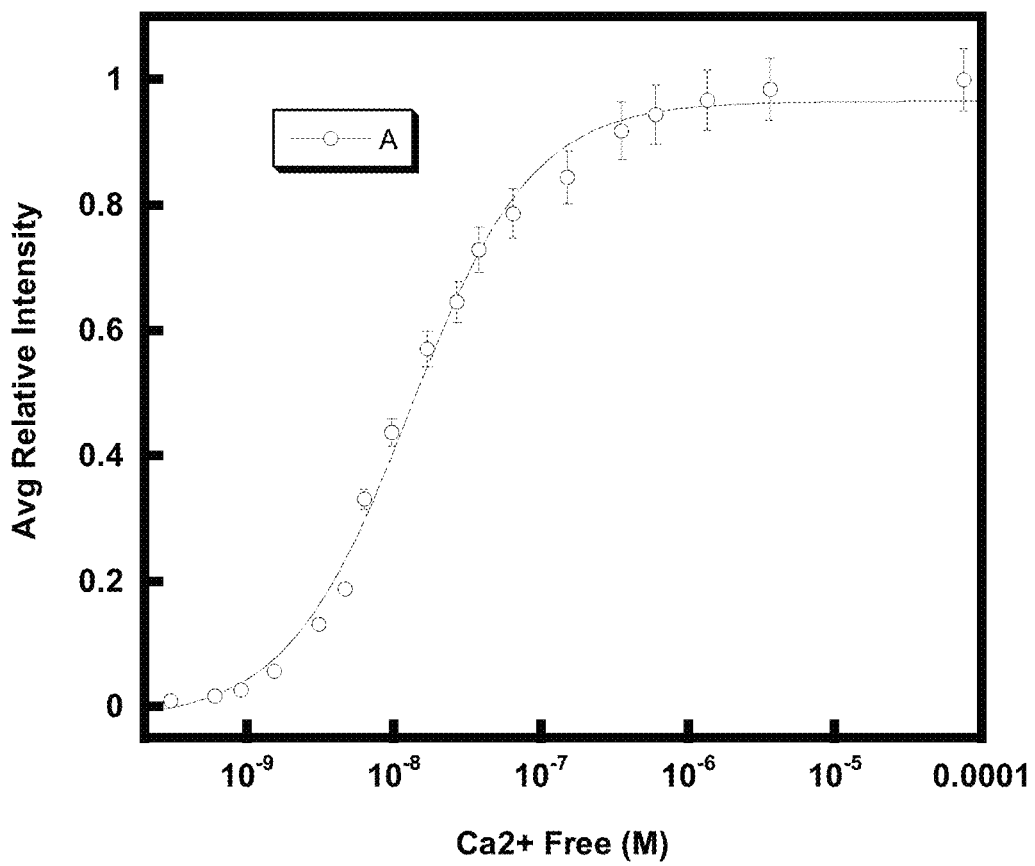
FIGS. 17A-17B show a graph (FIG. 17A) and a table demonstrating results of a $Ca^{2+}$ titration of ProCA32.WP using the Hill Equation.

$Tb^{3+}$ titration assay with ProCA32.WP was performed to examine $Tb^{3+}$ binding as previously described. FIGS. 16A-16B demonstrate results of a ProCA32.WP $Tb^{3+}$ titration. Without being bound by theory, these results demonstrate that ProCA32.WP was observed to have a strong $Tb^{3+}$ affinity.

Figures 17B, 18A:
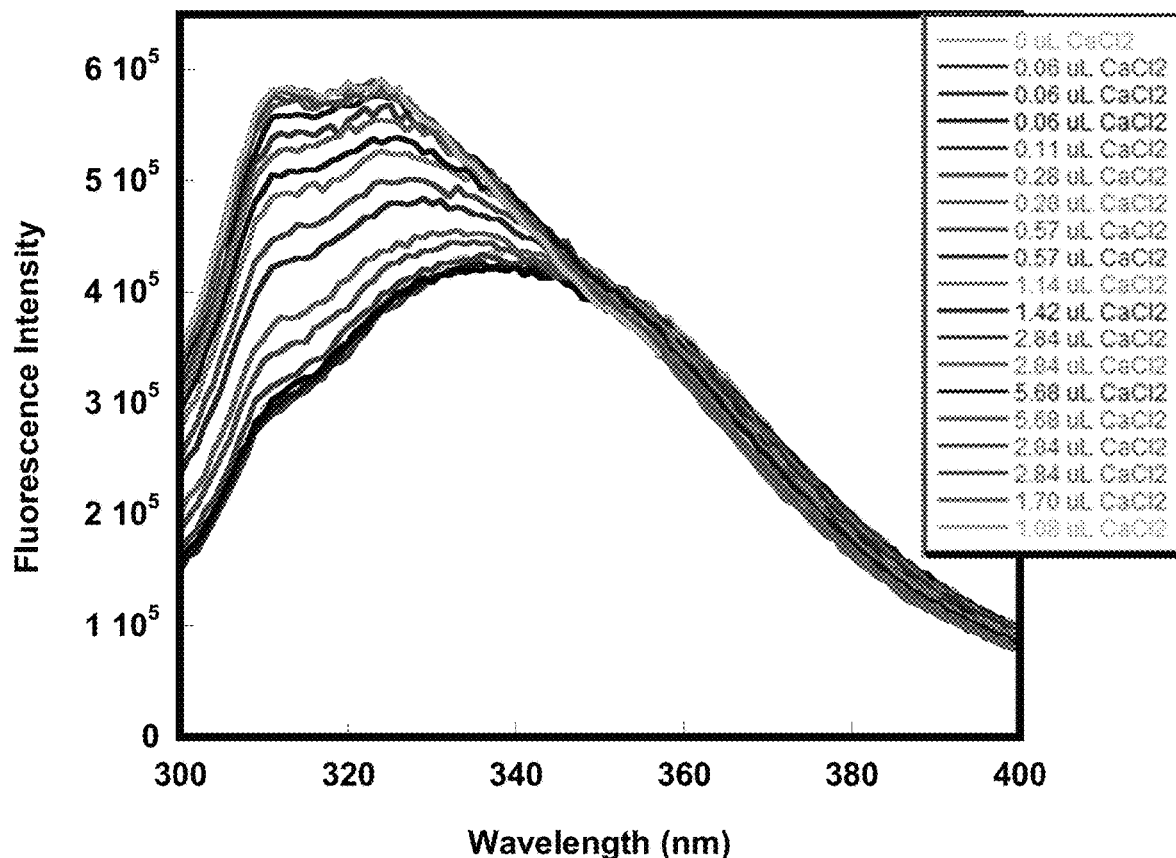
FIGS. 18A-18B show graphs demonstrating $Ca^{2+}$ titration of ProCA32.WP.

$Ca^{2+}$ titration of ProCA32.WP was performed using the Hill Equation (Eq. 2) as previously described. FIGS. 17A-17B show a graph (FIG. 17A) and a table demonstrating results of a $Ca^{2+}$ titration of ProCA32.WP using the Hill Equation. The Average Kd=$1.2 \times 10^{-8}$ M. Without being bound to theory, these results indicate ProCA32.WP.PMSA have lower affinity to Ca2+ compared with Gd3+.

Figure 18B:
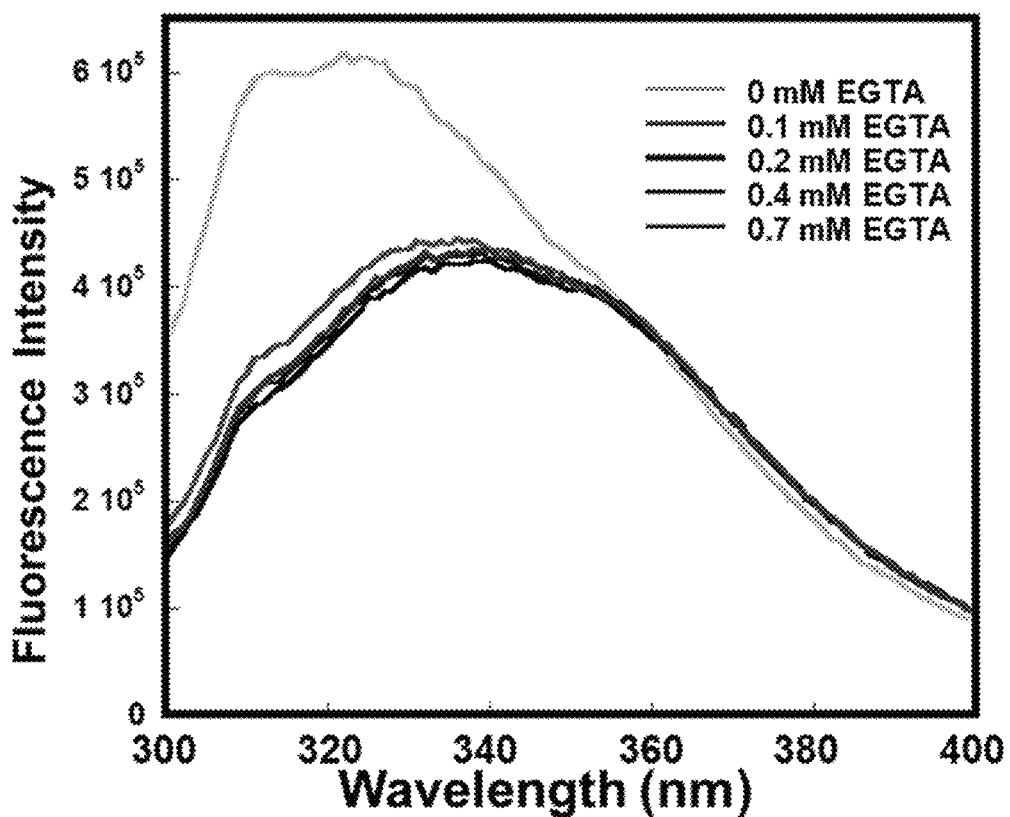
Figure 19:
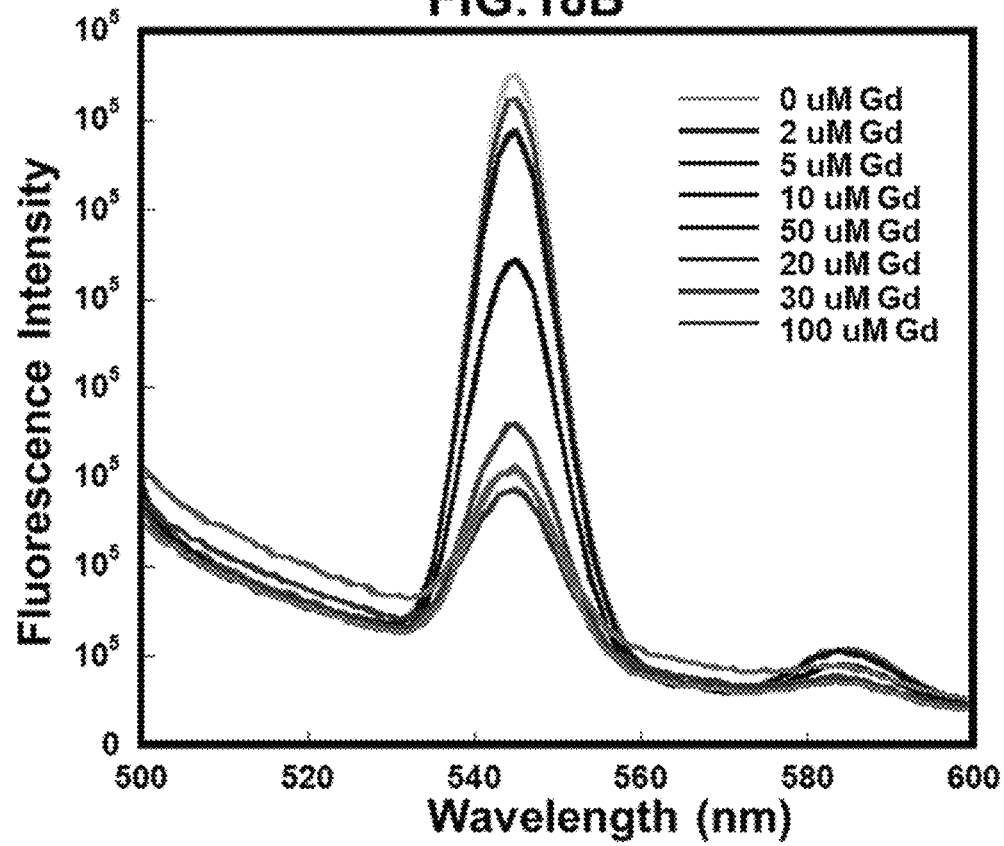
FIG. 19 shows a graph demonstrating $Gd^{3+}$ competition with $Tb^{3+}$ for ProCA32.WP.
Figures 20A, 20B:
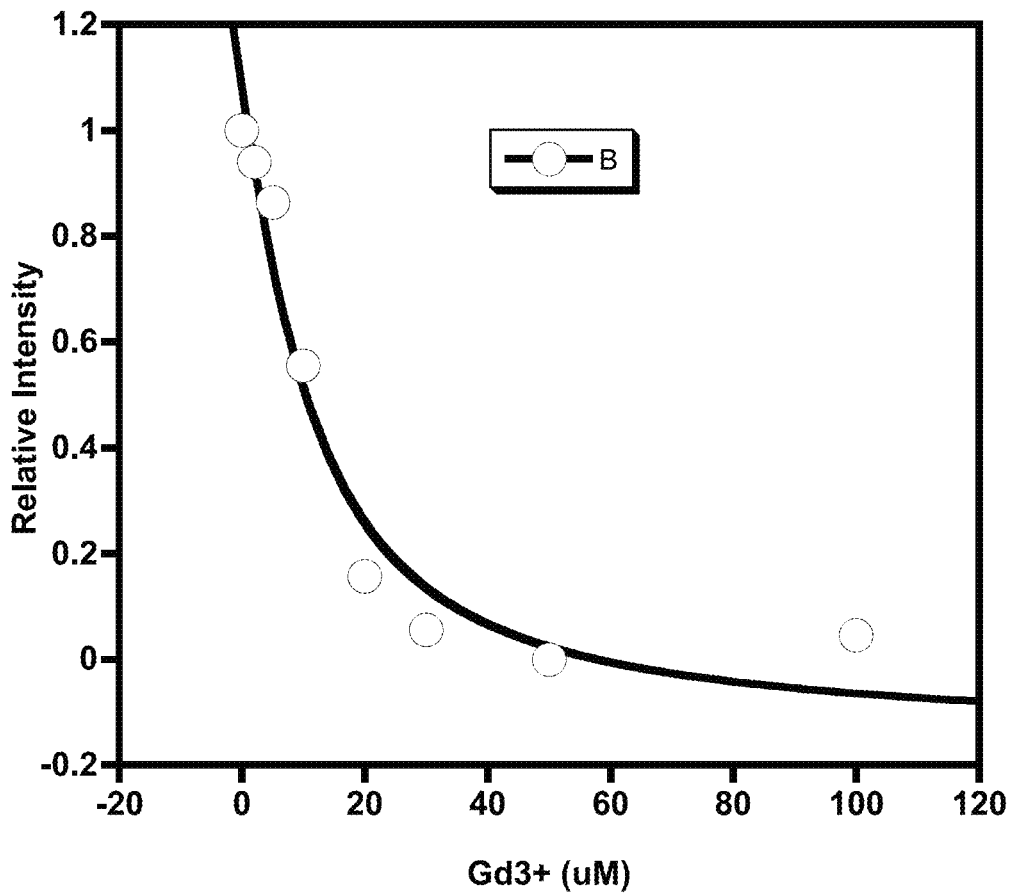
FIGS. 20A-20B demonstrate $Tb^{3+}$ and $Gd^{3+}$ competition for ProCA32.WP.

$Ca^{2+}$ titration of ProCA32.WP was performed as previously described. FIGS. 18A-18B show graphs demonstrating $Ca^{2+}$ titration of ProCA32.WP. Without being bound by theory, these results indicate ProCA32.WP.PMSA have lower affinity to Zn2+ compared with Gd3+. A competition assay for $Gd^{3+}$ and $Tb^{3+}$ for ProCA32.WP was performed. Kd was calculated using Eq. 4. For ProCA32.562, $Kd_{Gd}^3$+ =$2.53 \times 10^{-22}$ M. For ProCA32.WP, $Kd_{app}$=$8.7 \times 0^{-6}$ M, For ProCA32.WP, $Kd_{Gd}^3$+=$2.42 \times 10^{-22}$ M. Without being bound by theory, these results indicate ProCA32.WP and ProCA32.562 have high affinity to Gd3+, allowing it in vitro and in vivo applications with high stability.

Figure 21:
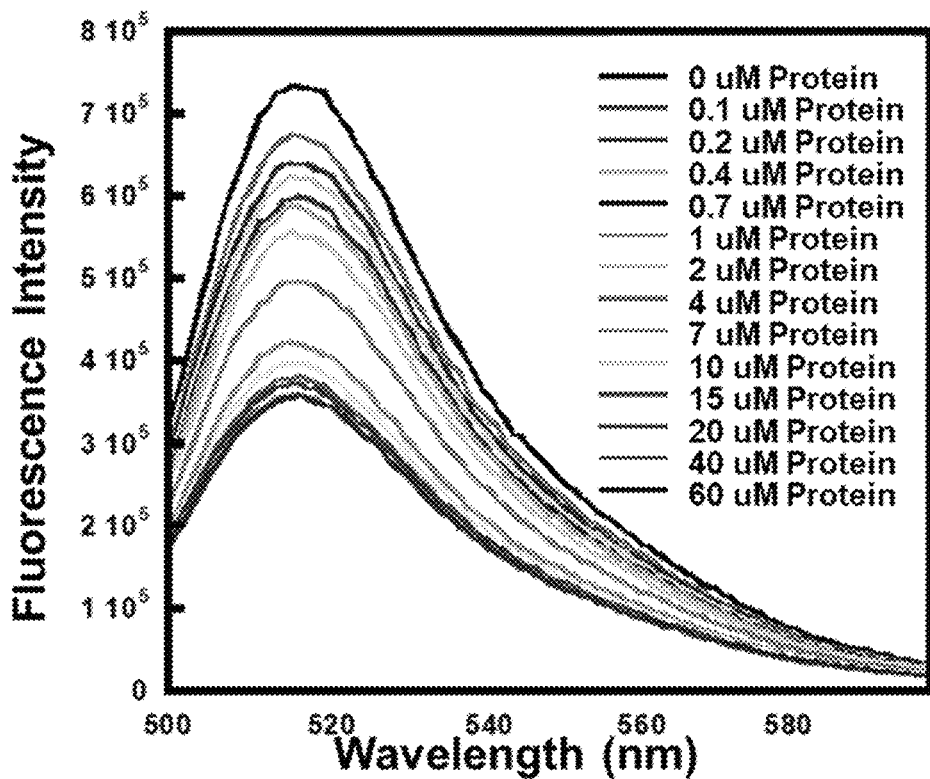
FIG. 21 shows a graph demonstrating Fluozin-1 and ProCA32.WP competition for zinc.
Figure 22A:
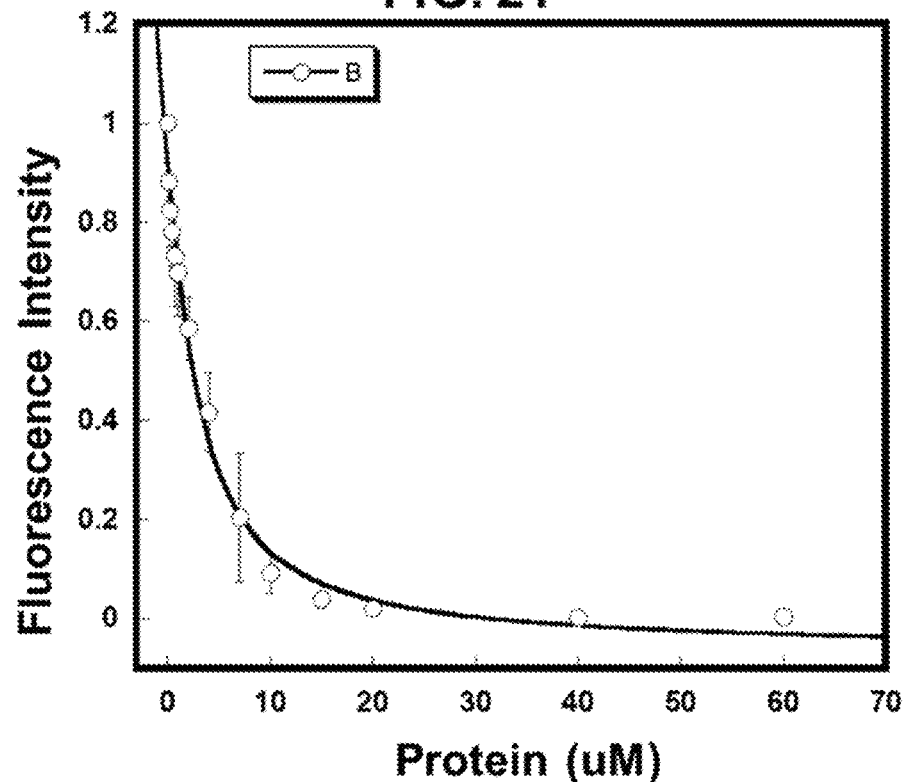
FIGS. 22A-22B demonstrating Fluozin-1 and ProCA32.WP competition for zinc.
Figures 22B, 23:
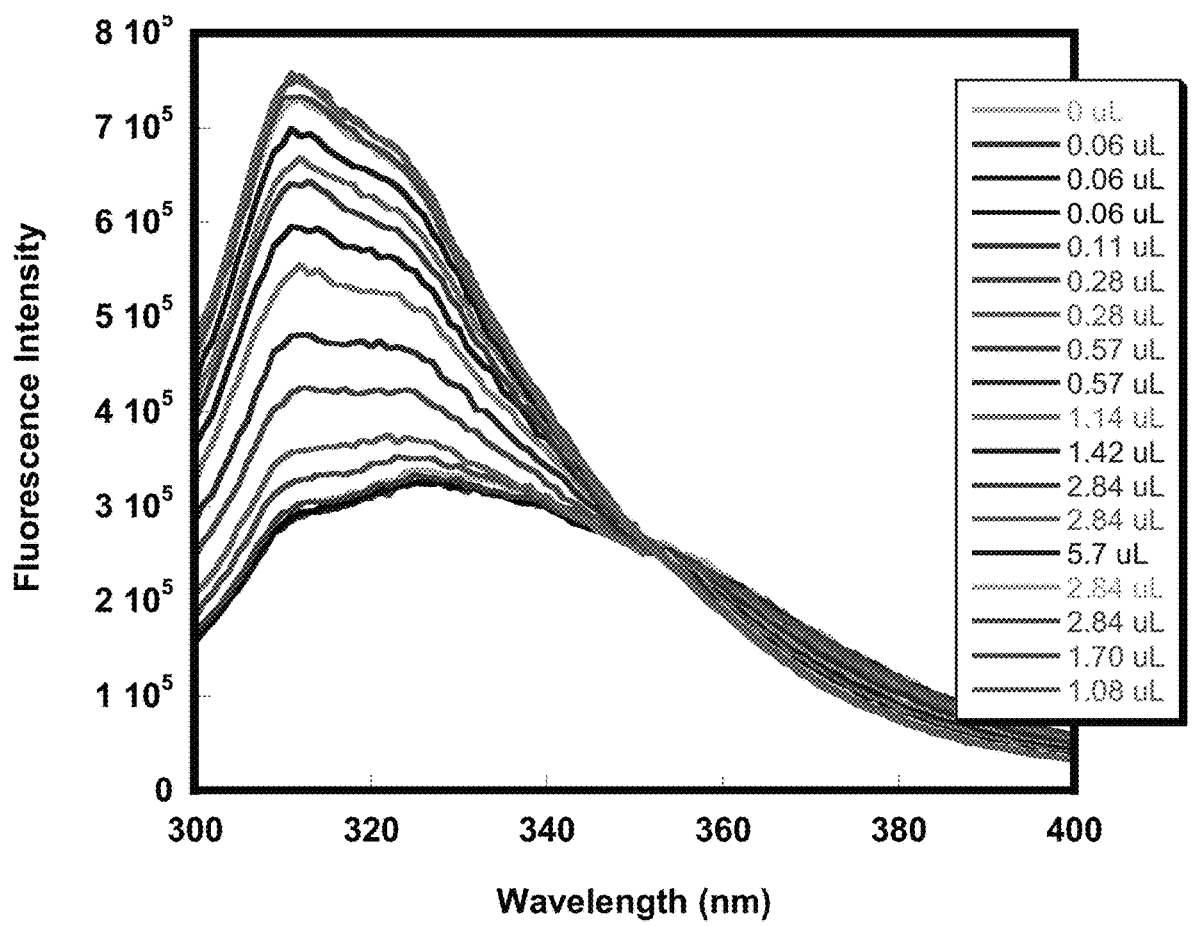
FIG. 23 shows a graph demonstrating $Ca^{2+}$ titration of ProCA32.562.

A fluozin-1 zinc competition assay was performed with ProCA32.WP as previously described. FIGS. 21-22B show graphs demonstrating Fluozin-1 and ProCA32.WP competition for zinc. For ProCA32.WP, $Kd_{Zn}^{2+}$=$1.4 \times 10^{-8}$ M. Without being bound by theory, these results indicate that ProCA32.WP. Have lower affinity to $Zn^{2+}$ compared with $Gd^{3+}$.

Figure 24:
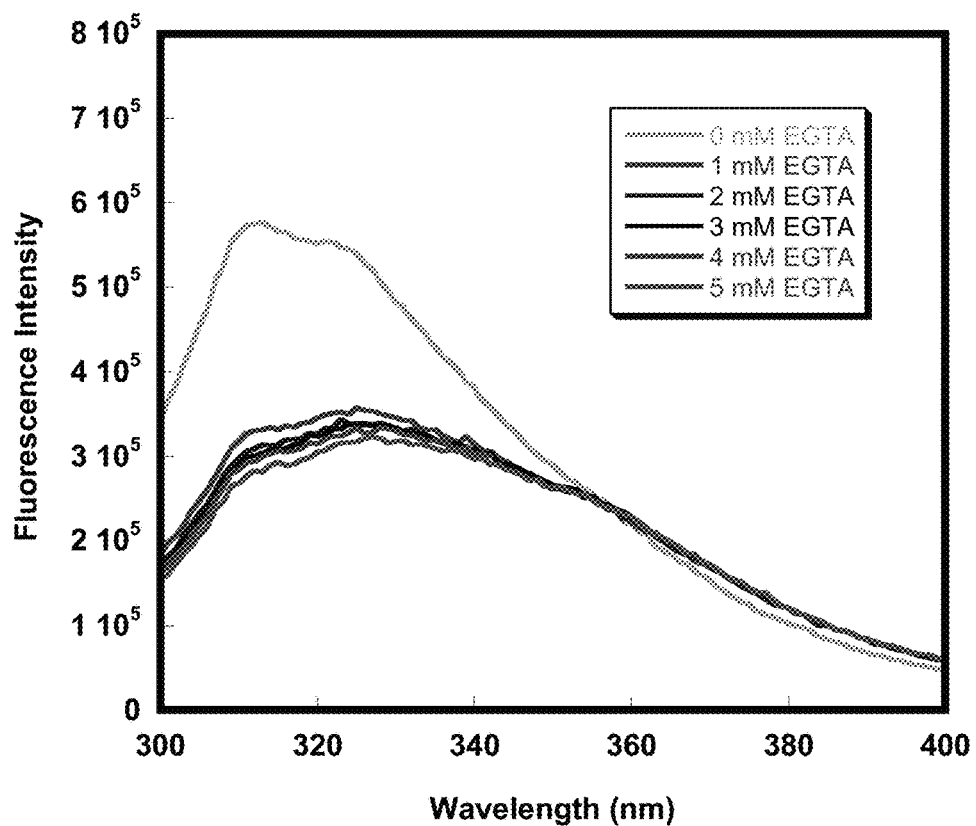
FIG. 24 shows a graph demonstration EGTA titration of ProCA32.562.

$Ca^{2+}$ titration of ProCA32.562. 10 µM ProCAs were added into the calcium-buffer system containing 50 mM HEPES, 100 mM NaCl, 5 mM EGTA, at pH 7.2. The system was titrated with different concentrations of $CaCl_2$ to alter the concentration ratio between the Ca-EGTA ([Ca-EGTA]) and free EGTA ($[EGTA]_{free}$). The tryptophan (Trp) fluorescence changes were monitored under the emission spectra between 300 and 390 nm as excited at 280 nm. The free calcium concentration at each titration point was calculated. FIG. 23 shows a graph demonstrating $Ca^{2+}$ titration of ProCA32.562. FIG. 24 shows a graph demonstration EGTA titration of ProCA32.562. Without being bound by theory, these results indicate ProCA32.562 have lower affinity to $Ca^{2+}$ compared with $Gd^{3+}$.

Figure 25A:
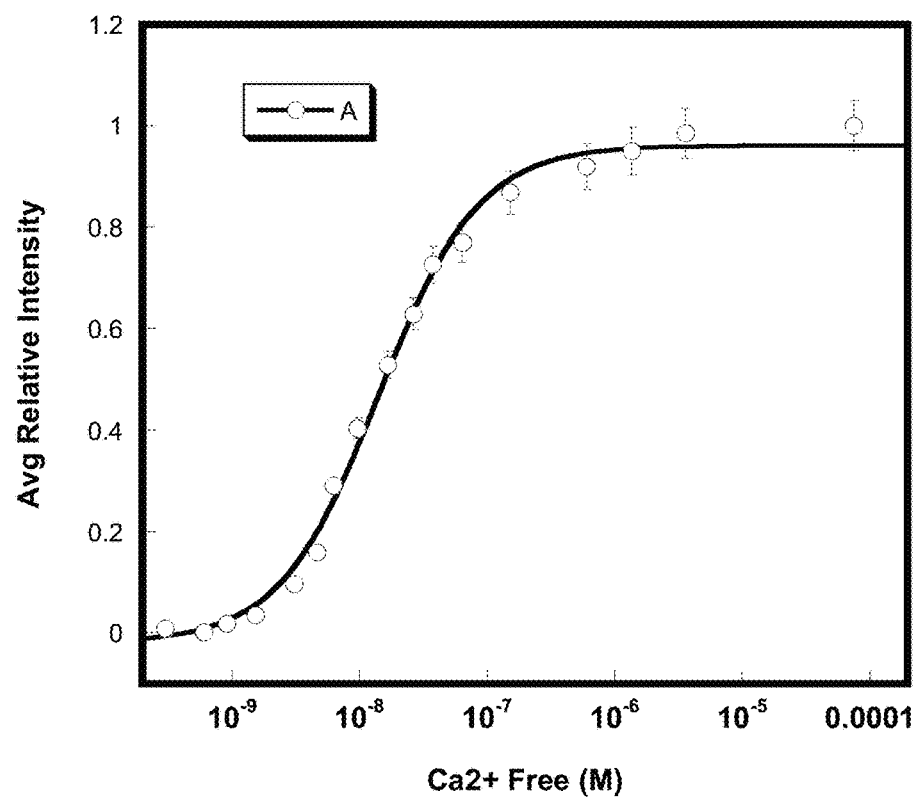
FIGS. 25A-25B demonstrate the results of $Ca^{2+}$ titration of ProCA32.562 using the Hill Equation. The average $Kd=1.4\times10^{-8}M$.
Figures 25B, 26:
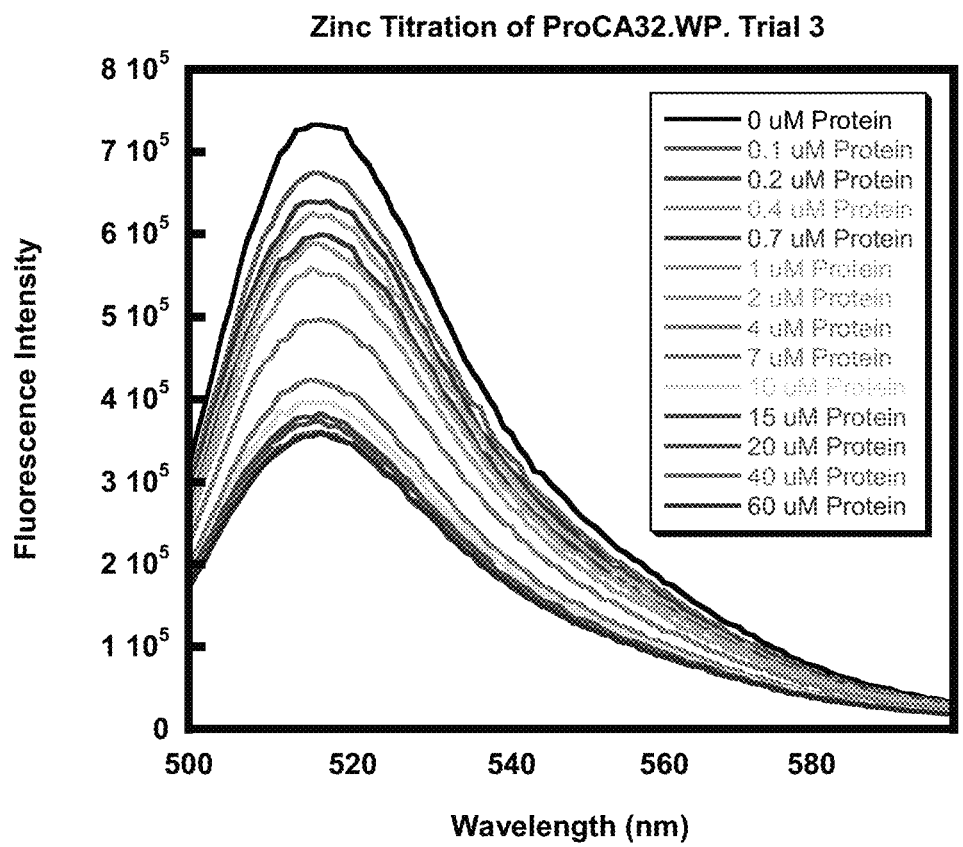
FIG. 26 shows a graph demonstrating Fluozin-1 and ProCA32.562 competition for zinc.

$Ca^{2+}$ titration of ProCA32.562 using the Hill Equation (Eq. 2) as previously described. FIGS. 25A-25B demonstrate the results of $Ca^{2+}$ titration of ProCA32.562 using the Hill Equation. The average Kd=$1.4 \times 10^{-8}$M. Without being bound by theory, these results indicate ProCA32.562 have lower affinity to Ca2+ compared with Gd3+.

Figures 27A, 27B:
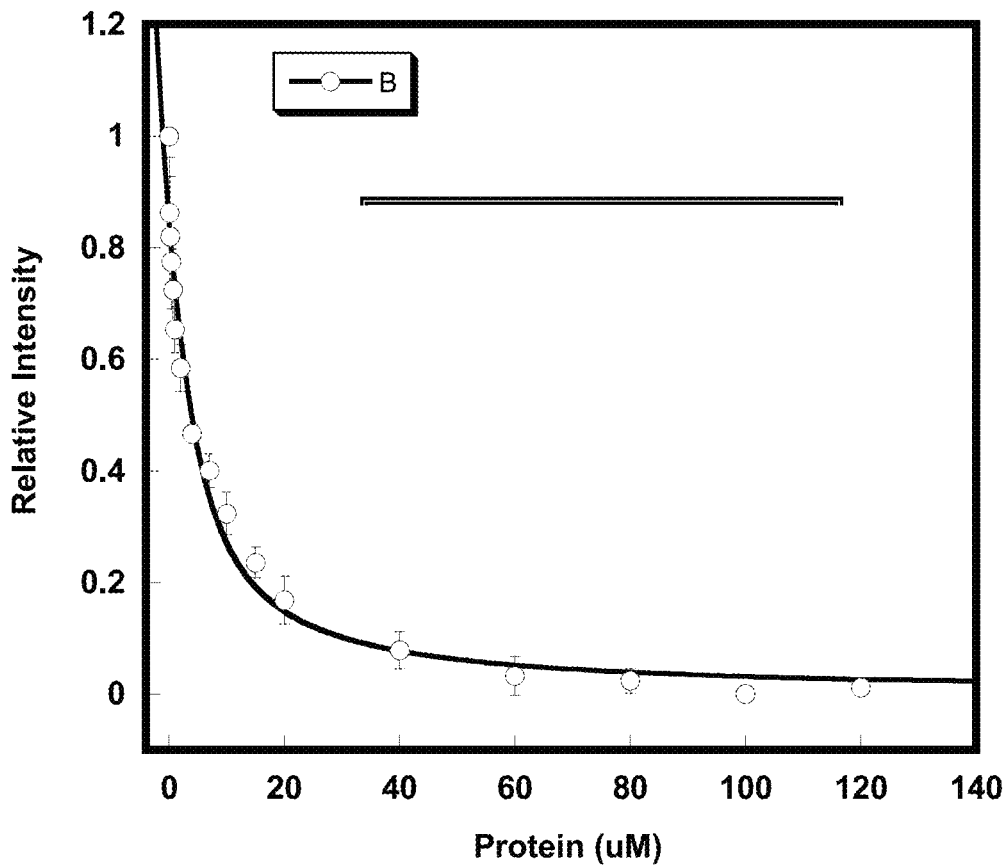
FIGS. 27A-27B demonstrating Fluozin-1 and ProCA32.562 competition for zinc.

A fluozin-1 zinc competition assay was performed with ProCA32.WP as previously described. FIG. 26 shows a graph demonstrating Fluozin-1 and ProCA32.562 competition for zinc. FIGS. 27A-27B demonstrating Fluozin-1 and ProCA32.562 competition for zinc. For ProCA32.WP, $Kd_{Zn}^{2+}$=$2.5 \times 10^{-8}$ M. Without being bound by theory, these results indicate ProCA32.562 have lower affinity to Zn2+ compared with Gd3+.

Figure 28:
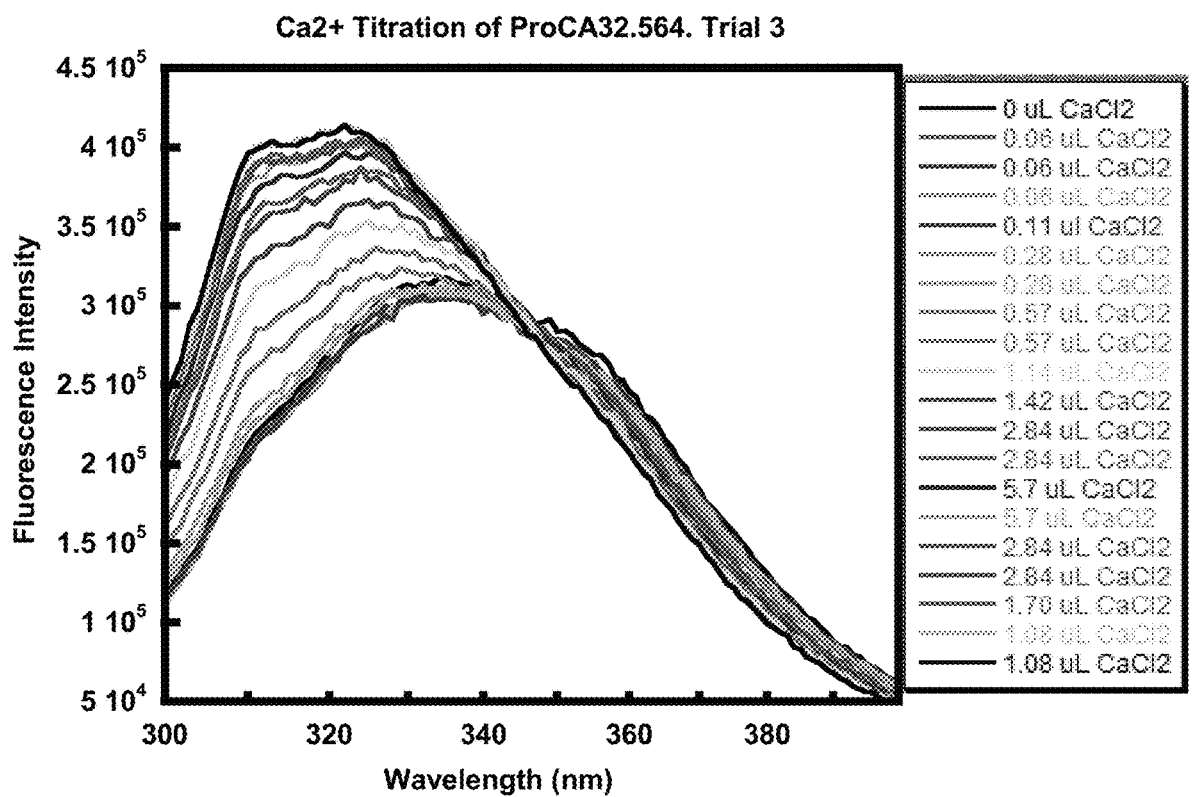
FIG. 28 shows a graph demonstrating $Ca^{2+}$ titration of ProCA32.564.
Figure 29:
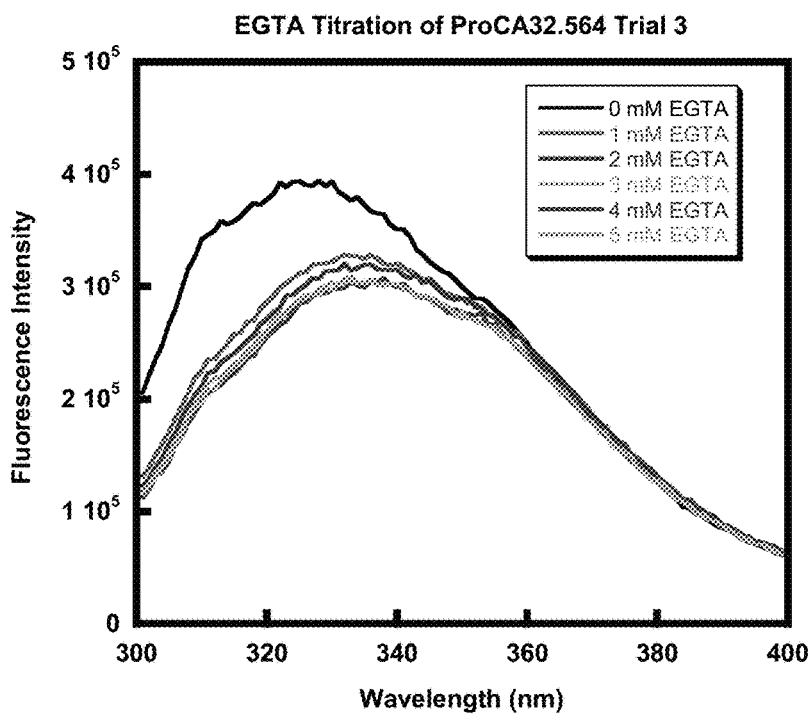
FIG. 29 shows a graph demonstrating EGDTA Titration of ProCA32.564.
Figures 30A, 30B:
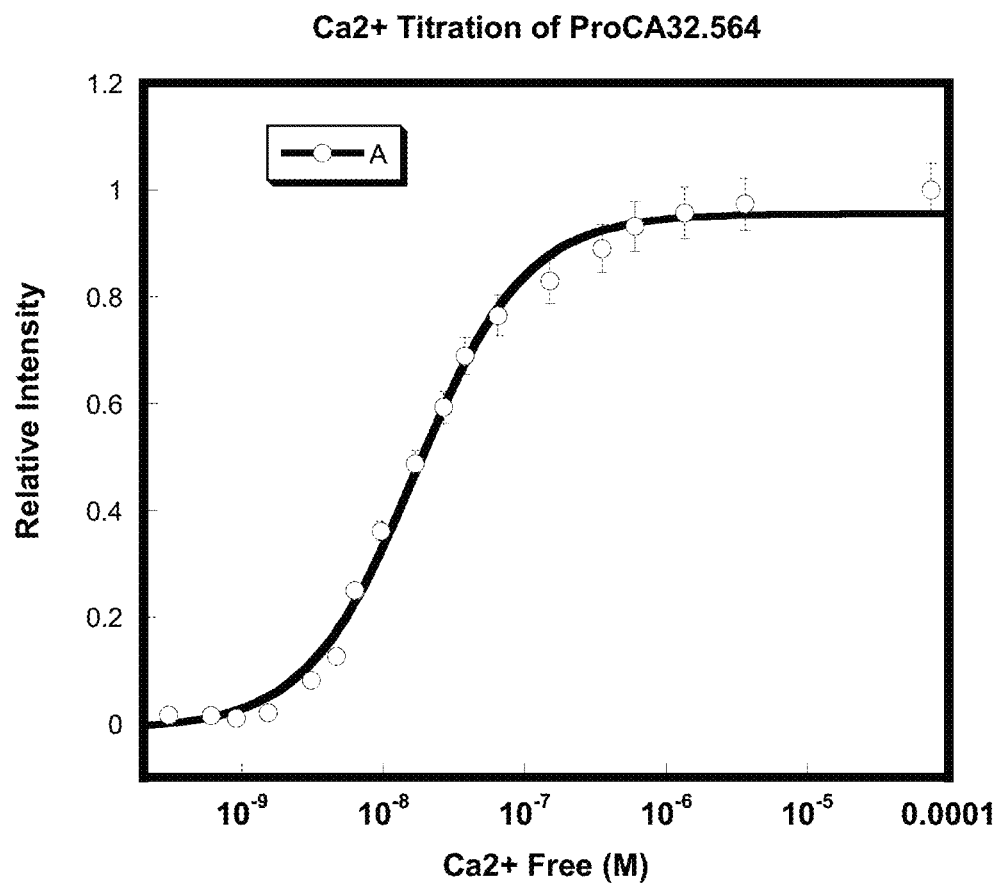
FIGS. 30A-30B demonstrate the results $Ca^{2+}$ titration of ProCA32.564 using the Hill Equation. The average $Kd=1.7\times10^{-8}M$.

A $Ca^{2+}$ titration of ProCA32.564 was performed as previously described. FIG. 28 shows a graph demonstrating $Ca^{2+}$ titration of ProCA32.564. FIG. 29 shows a graph demonstrating EGDTA Titration of ProCA32.564. Without being bound by theory, these results indicate ProCA32.564 have lower affinity to Ca2+ compared with Gd3+. A $Ca^{2+}$ titration of ProCA32.564 using the Hill Equation (Eq 2.) was performed as previously described. FIGS. 30A-30B demonstrate the results $Ca^{2+}$ titration of ProCA32.564 using the Hill Equation. The average Kd=$1.7 \times 10^{-8}$M. Without being bound by theory, these results result indicate ProCA32.564 have lower affinity to $Ca^{2+}$ compared with $Gd^{3+}$.

Figure 31:
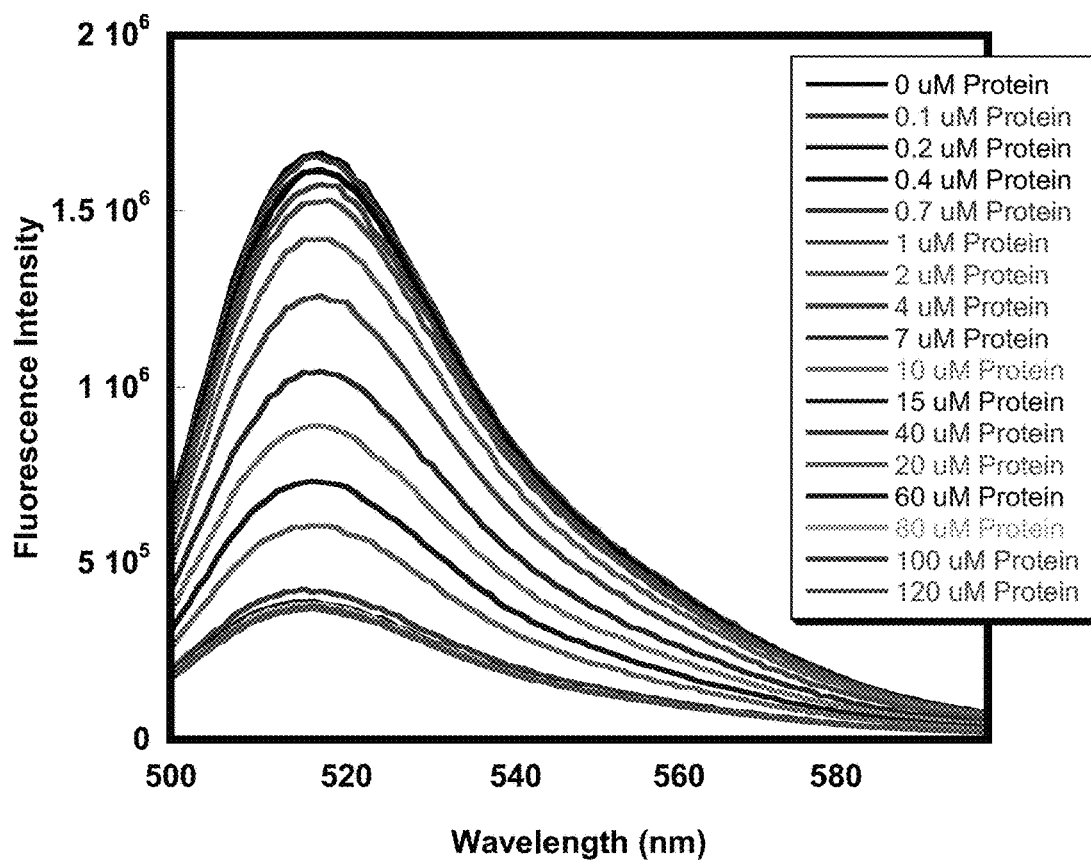
FIG. 31 shows a graph demonstrating Fluozin-1 and ProCA32.564 competition for zinc.

A fluozin-1 zinc competition assay was performed with ProCA32.564 as previously described. FIG. 31 shows a graph demonstrating Fluozin-1 and ProCA32.564 competition for zinc. For ProCA32.WP, $Kd_{Zn}^{2+}$=$1.6 \times 10^{-8}$ M. Without being bound by theory these results indicate ProCA32.562 have lower affinity to $Zn^{2+}$ compared with $Gd^{3+}$.

Figure 32A:
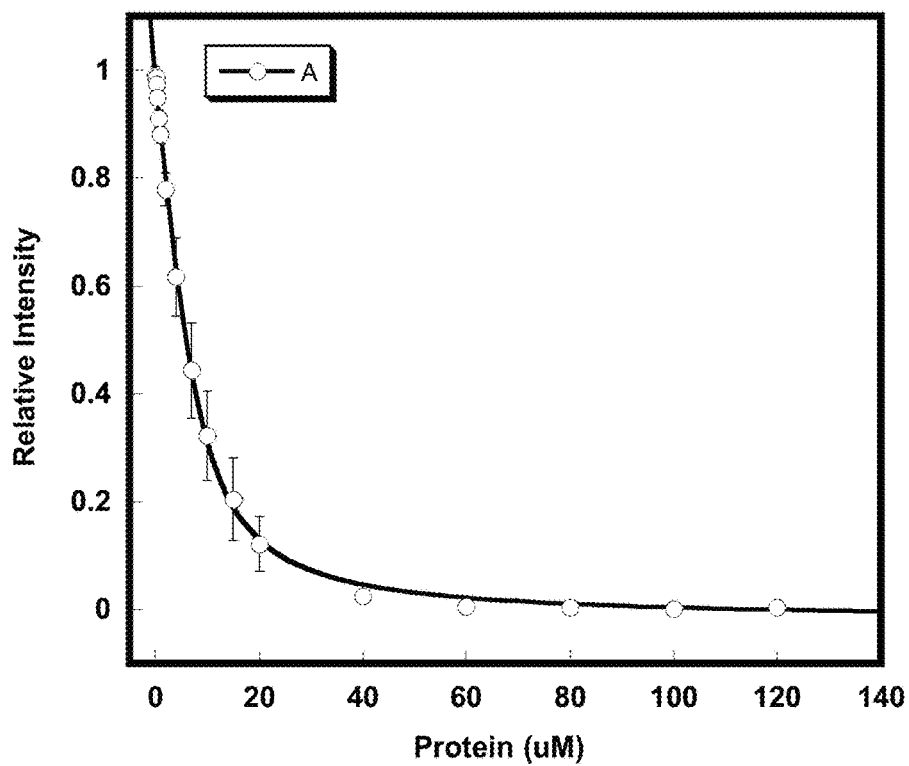

A fluozin-1 zinc competition assay was performed with ProCA32.564 as previously described. FIGS. 32A-32B demonstrating Fluozin-1 and ProCA32.564 competition for zinc. Without being bound by theory, results indicate ProCA32.562 have lower affinity to $Zn^{2+}$ compared with $Gd^{3+}$.

FIG. 33 shows a table demonstrating a summary of relaxivities and metal binding affinities of various targeted protein contrast agents. FIG. 34 shows a table demonstrating association constants for $Ca^{2+}$ for varying PSMA targeted protein contrast agents.

In sum, this Example can demonstrate protein based PSMA-targeted MRI contrast agents having at least one amino acid in the ProCA that can bind directly to a paramagnetic metal ion. The PSMA targeted ProCAs can maintain high relaxivities and metal binding affinity as compared to non-targeted base proteins (e.g. ProCA32 without a targeting moiety). The binding capability of PSMA-targeted MRI contrast agents was demonstrated by cell imaging, fluorescence polarization and ELISA. Among the Protein based contrast agents evaluated, ProCA32.564.PSMA had the best binding affinity (EC50 −0.52±0.04 µM) to PSMA and can provide a molecular based imaging agent for prostate cancer prognosis and diagnosis.

Example 2. VEGFR2 Targeted ProCAs

VEGF and its receptors (VEGFRs) can play a role in angiogenesis, including tumor angiogensis. Signaling though VEGFRs, such as VEGFR2, can influence cell adhesion, sufvival, migration, and vascular permeability. A contrast agent capable of targeting VEGFRs can be useful for evaluating blood vessels, and in particular, the formation and status of tumor blood vessels. This Example can demonstrate a ProCA that can target VEGFR2 and can include a VEGFR2 binding peptide. FIG. 35 shows a table demonstrating Kd values for VEGFR binding peptides.

A ProCA containing ProCA.32 fused directly at its C-terminus to a VEGFR2 binding peptide was generated. The C-terminal ProCA32 was fused with VEGFR2 targeting peptide with GGG flexible peptide linker.

Figure 36A:
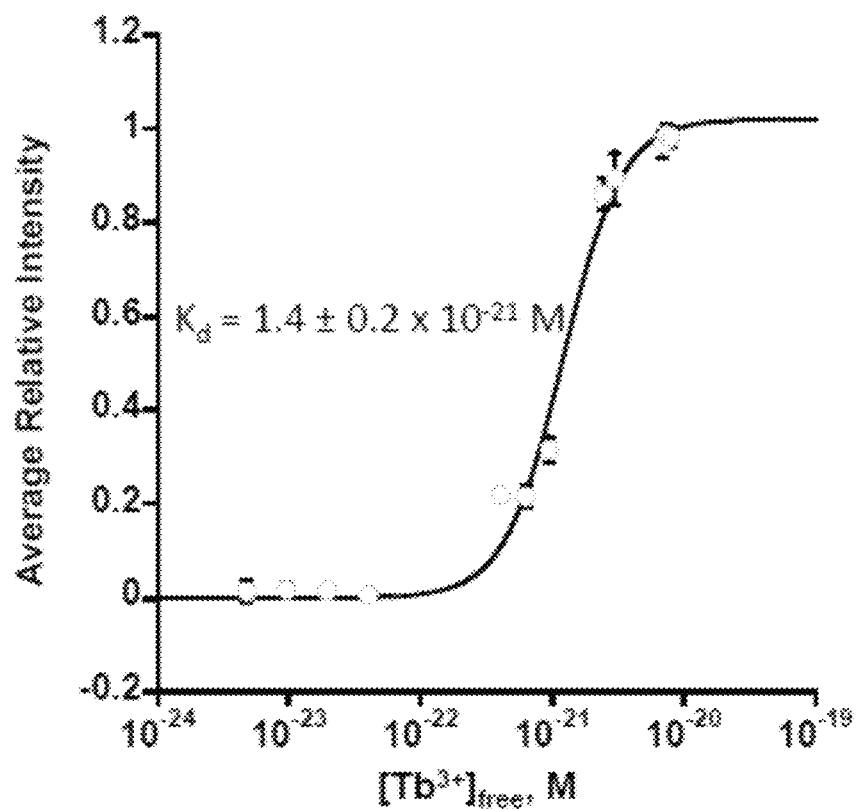
FIGS. 36A-36B show graphs demonstrating the binding affinity of $Ga^{3+}$ (FIG. 36A) and $Tb^{3+}$ (FIG. 36B) for ProCA32.VEGFR.
Figure 36B:
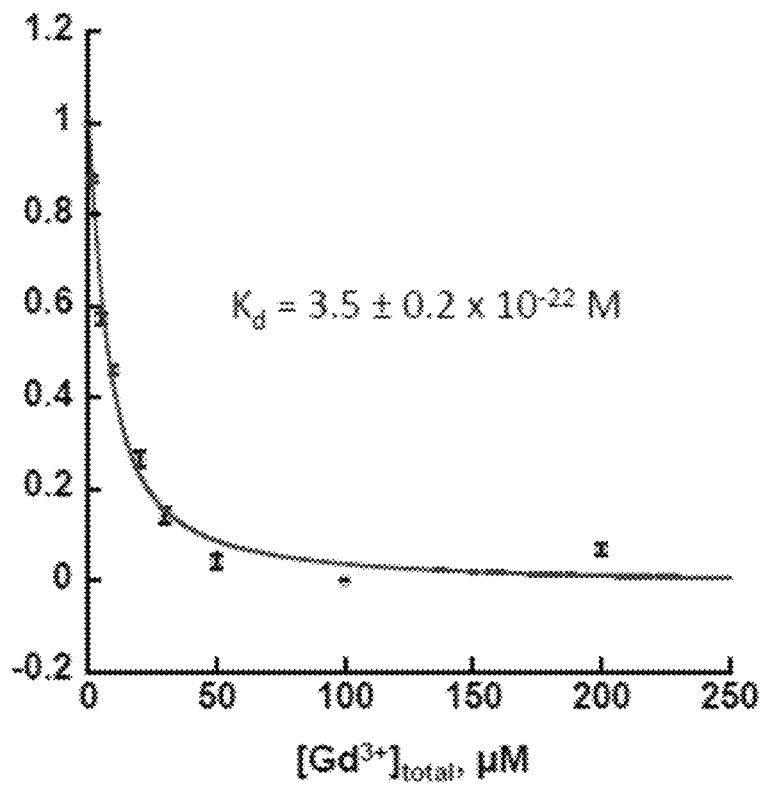
Figure 37:
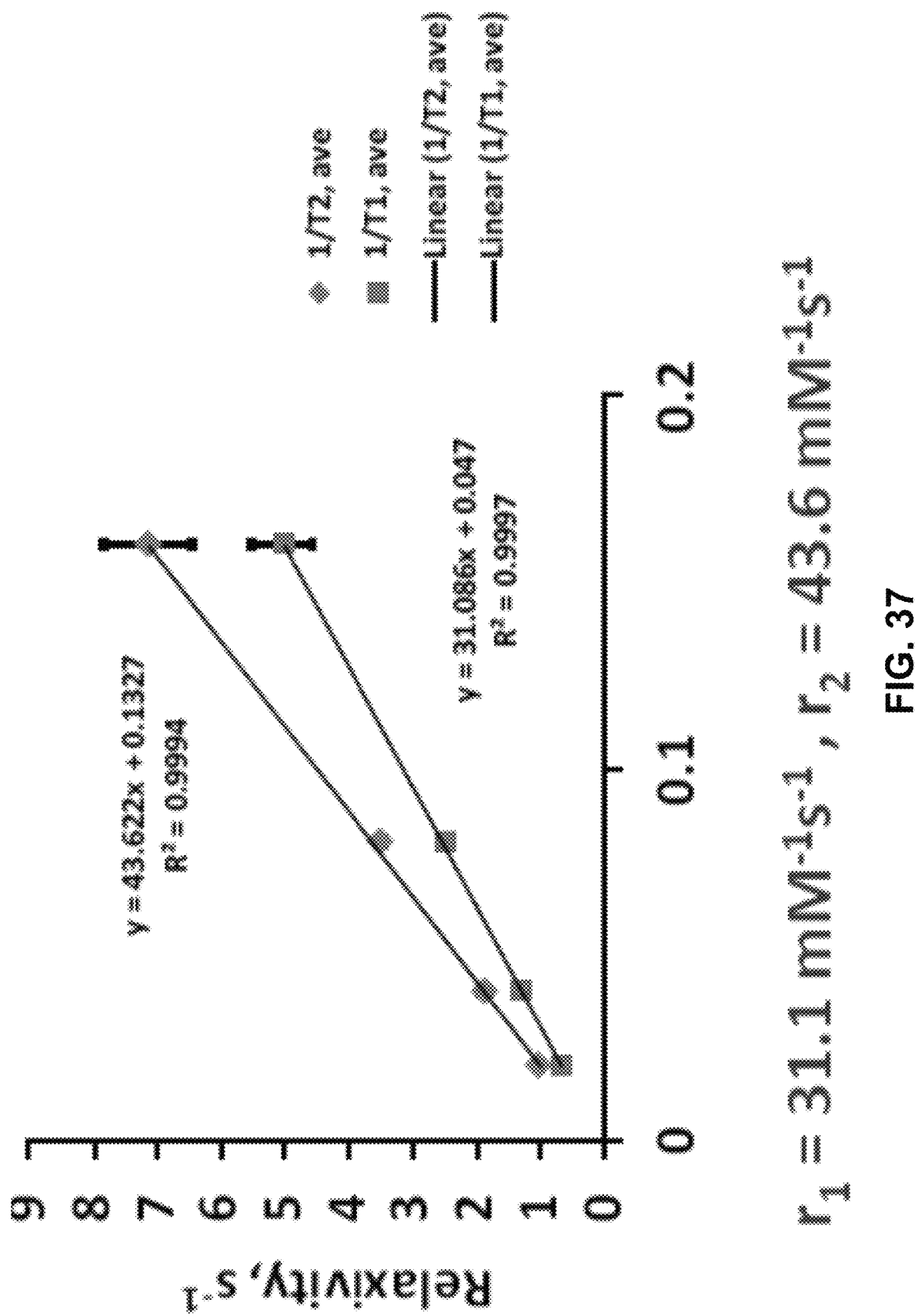
FIG. 37 shows a graph demonstrating the relaxivity of ProCA32.VEGFR at about 37° C.

The binding affinity of $Gd^{3+}$ and $Tb^{3+}$ for ProCA32.VEGFR was evaluated. The methods to determine Gd3+ affinity were similar to that of PSMA targeted ProCAs described above. FIGS. 36A-36B show graphs demonstrating the binding affinity of $Gd^{3+}$ (FIG. 36A) and $Tb^{3+}$ (FIG. 36B) for ProCA32.VEGFR. Without being bound by theory, these results indicate ProCA32.VEGFR have high affinity to Gd3+, allowing it in vitro and in vivo applications with high stability.

The relaxivities of ProCA32.VEGFR was examined using the methods as described for PSMA targeted ProCA32. FIG.

37 shows a graph demonstrating the relxaivity of ProCA32.VEGFR at about 37° C. Without being bound by theory, these results demonstrate that ProCA32.VEGFR have high relaxivity allowing it have sensitive-capacity to visualize subjects under MRI.

Figure 38:
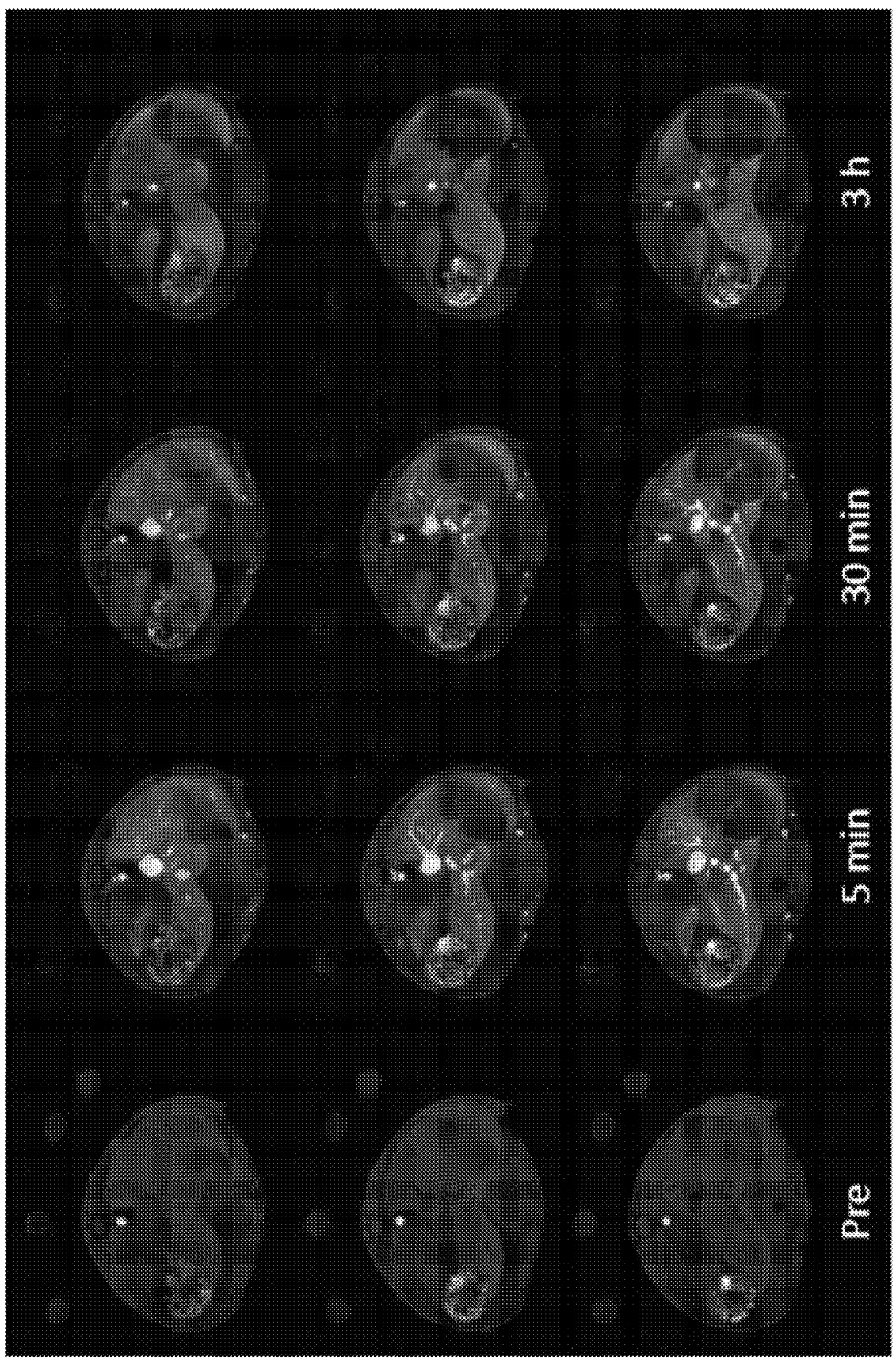
FIG. 38 show MRI contrast imaging of a blood vessel using ProCA32.VEGFR.
Figure 40A:
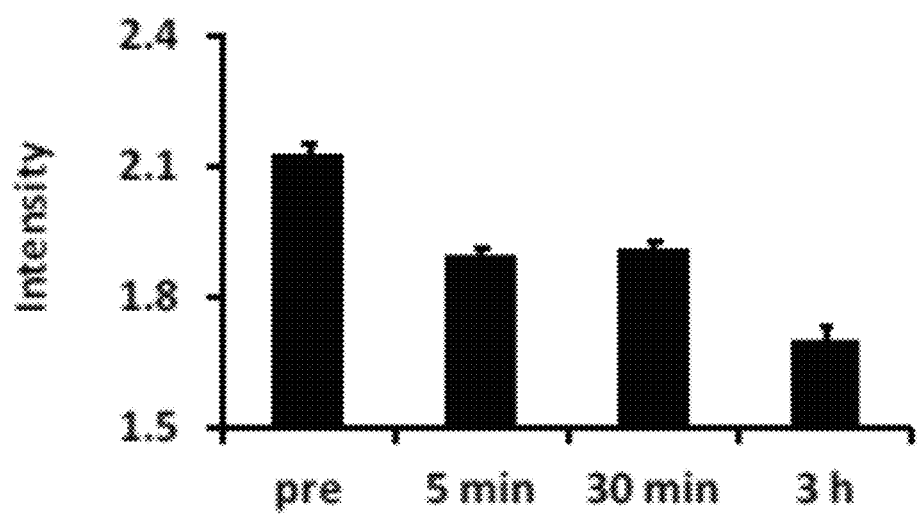
FIGS. 40A-40B show graphs demonstrating VEGFR2 expression in tumors as measured by imaging using ProCA32.VEGFR2.
Figure 40B:
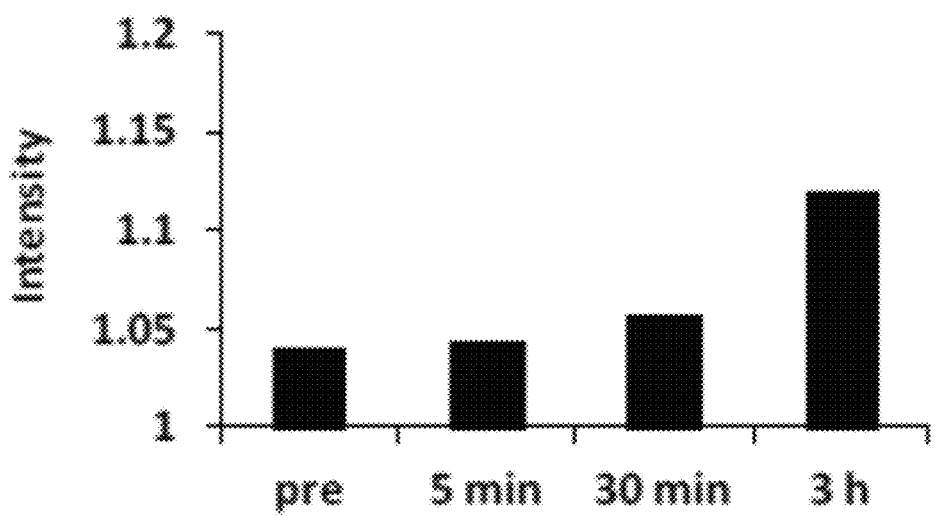

The in vivo imaging capability of ProCA32.VEGFR was examined in a B16LS9 uveal melanoma implantation mouse model. B16LS9 was implanted in the liver of the mice. MRI images were collected before and after injection of ProCA32.VEGFR. FIG. 38 show MRI contrast imaging of a blood vessel using ProCA32.VEGFR. Without being bound by theory, these results demonstrate that ProCA32.VEGFR is able to visualize the blood vessel of the mice by MRI. FIGS. 39A and 39B show imaging VEGFR2 expression in tumors using ProCA32.VEGFR2. FIGS. 40A-40B show graphs demonstrating VEGFR2 expression in tumors as measured by imaging using ProCA32.VEGFR2. Without being bound by theory, the data demonstrated in FIGS. 39-40 indicate ProCA32.VEGFR can image VEGFR2 expression in mice tumors noninvasively using MRI.

In sum, this Example can demonstrate the development of VEGFR targeting ProCAs. The ProCA32.VEGFR was observed to have high r1 and r2 relaxivities. Injection of ProCA32.VEGFR in implanted uveal melanoma model shows enhanced signal in T1-weighted MRI and shows decreased signal in T2-weighed MRI. ProCA32.VEGFR can function as a T1w and T2w dual reagent for the molecular imaging of VEGFR2.

Example 3. CXCR4 Targeted ProCAs

CXCR4 (chemokine receptor type 4) is a chemockine receptor for stromal-derived-factor 1 (SDF-1 or CXCL12). CXCR4 can be aberrantly expressed in cancer cells. CXCR4 has been demonstrated to be expressed in over 23 types of cancer, including but not limited to, breast cancer, ovarian cancer, melanoma, and prostate cancer. Expression of this receptor in cancer cells has been connected to metastasis to tissues containing a high concentration of CXCL12, such as lungs, liver and bone marrow. CXCR4 is present in newly generated neurons during embryogenesis and adult life where it plays a role in neuronal guidance. The levels of the receptor decrease as neurons mature. CXCR4 mutant mice have aberrant neuronal distribution. This has been implicated in disorders such as epilepsy.

V1 peptide is a synthetic peptide derived from the N-terminus of vMIP-II and is a potent antagonist of CXCR4. Zhou et al (2000) Biochem. 39:13545-13550. The N-terminus of the V1 peptide is the major determinant for CXCR4 recognition. Synthetic variants of the V1 peptide have been developed and demonstrate varying affinities for CXCR4. FIG. 41 shows a table demonstrating various V1 and V1 variant peptides.

A CXCR4 targeted ProCA was generated by indirectly linking a V1 peptide or variant thereof via a peptide linker to ProCA32 at its C-terminus. This ProCA is also referred to herein as ProCA32.V1.CXCR4. V1 peptide is a 21 amino acid sequence derived from the N terminal of vMIPII, which has a strong binding affinity to CXCR4. By attaching the V1 peptide to the C terminal of ProCA32, and expressed the ProCA32.V1.CXCR4 using BL21(DE3)pLysS competent cell, the CXCR4 specific targeted protein based contrast agent ProCA32.V1.CXCR4 can be generated.

Figure 42:
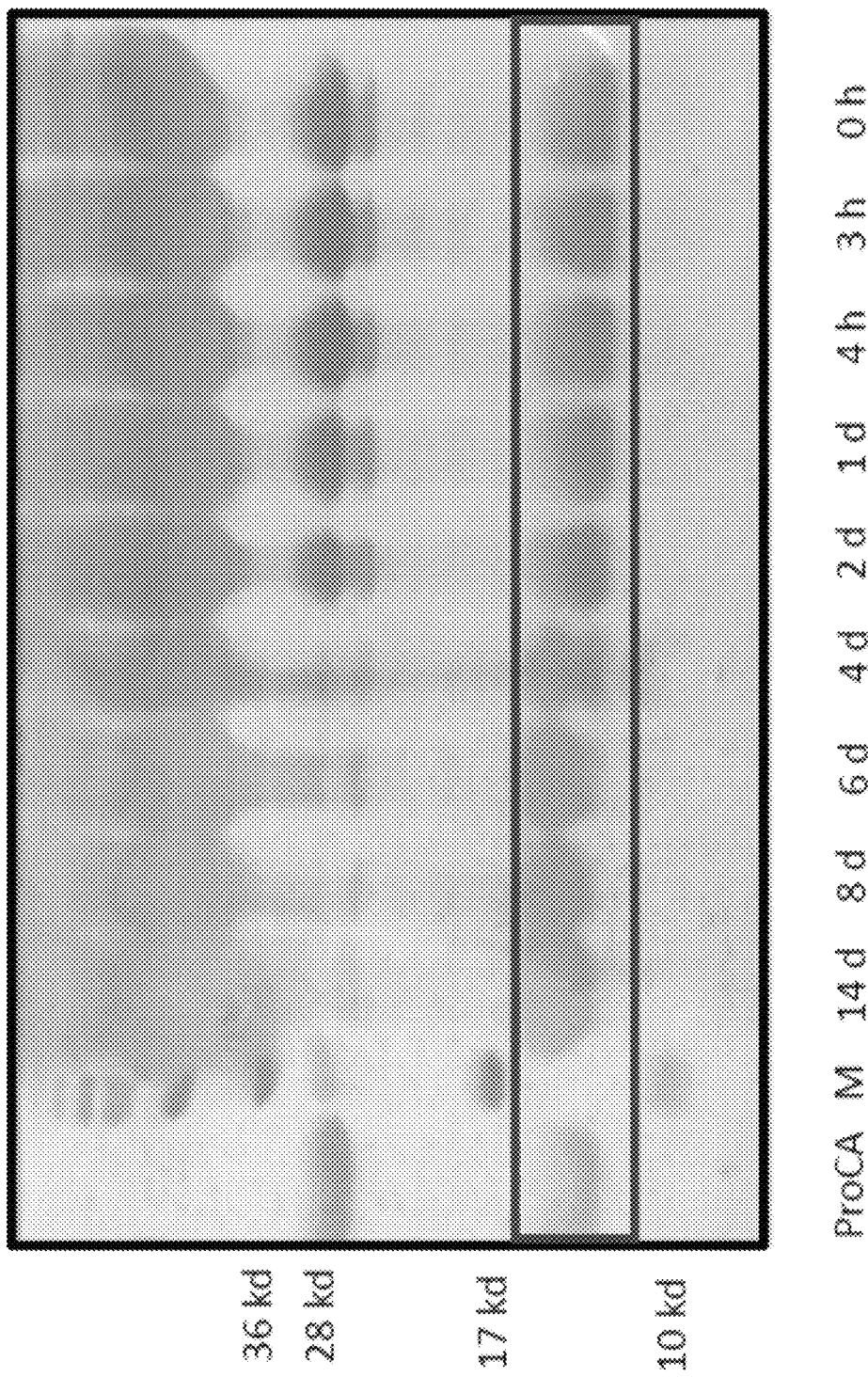
FIG. 42 is an image of a protein gel demonstrating serum stability of a CXCR4 targeted ProCA.

The serum stability of ProCA32.V1.CXCR4 was examined. Briefly, 500 μM of ProCA32.V1.CXCR4 is incubated with mouse serum with equal volume. The mixture solution was incubated at 37° C., and certain volume of the mixture solution incubated for different times were taken out for SDS-PAGE analysis and western-blot analysis as well. FIG. 42 is an image of a protein gel demonstrating serum stability of a CXCR4 targeted ProCA. ProCA32. V1.CXCR4 is stable in 37° C. mouse serum up to 4 days incubation. Without being bound to theory, the in vitro data demonstrates that ProCA32.V1.CXCR4 can be sufficiently stable as a ProCA for in vivo use, such as for use in intravenous administration and applications.

Figure 43A:
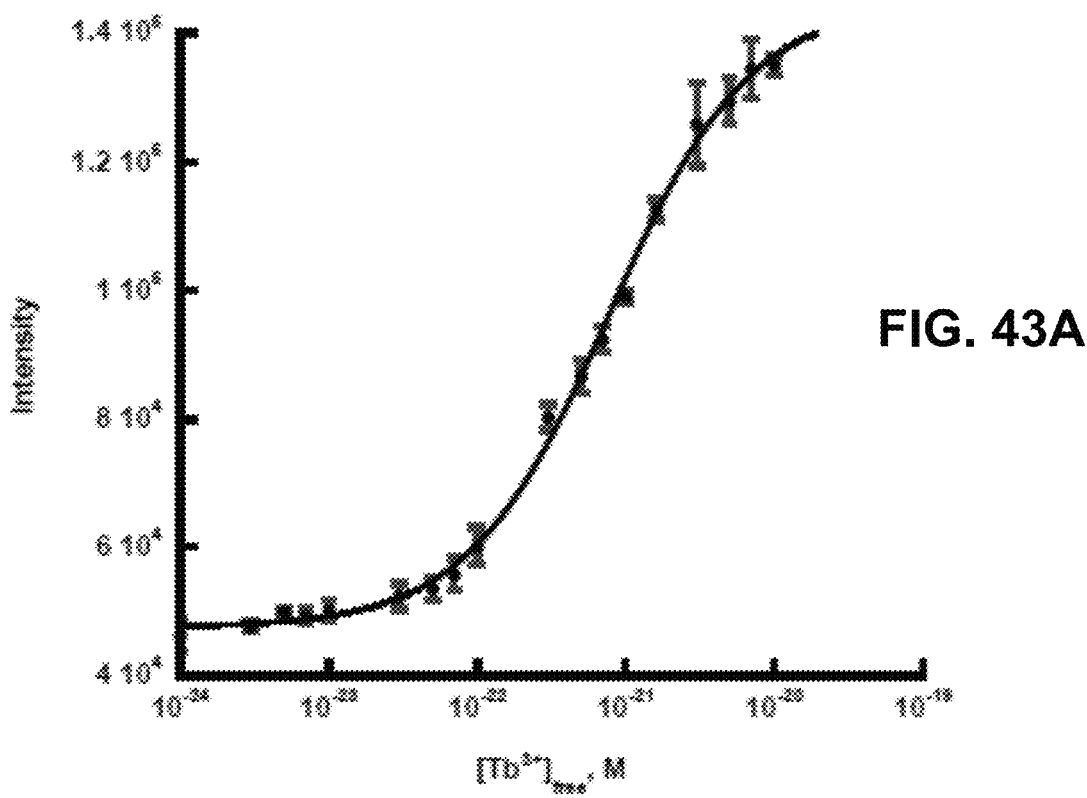
FIGS. 43A-43B show graphs demonstrating Gd3+ affinity.
Figure 43B:
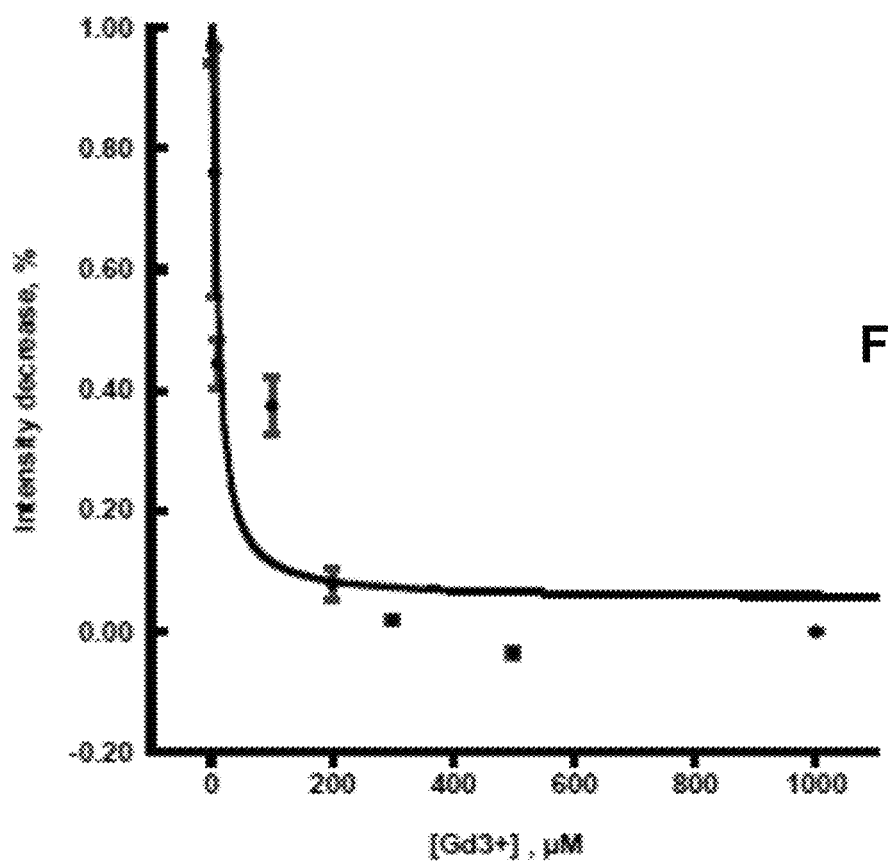

The affinity of ProCA32.V1.CXCR4 for $Gd^{3+}$ was examined. Briefly, A tryptophan residue located close to the ProCA32 binding pocket enable the measurement of Kd value of ProCA32 to terbium using a fluorescence resonance energy transfer (FRET) assay. Following an excitation at 280 nm, the tryptophan will transfer energy to the acceptor terbium if the terbium is in the ProCA32 binding pocket where spatially close enough to the tryptophan residue for the energy transfer. The fluorescence intensity increase at 545 nm reflects the ProCA32 and terbium binding process, by measuring the increase in this wavelength we can calculate the $K_d$ value of ProCA32 binds to terbium. Gadolinium can compete with terbium pre-loaded to ProCA32 binding pocket. Insofar as gadolinium does not have fluorescence property that terbium possesses, By measuring the fluorescence signal decrease as a result gadolinium competition with the pre-loaded terbium present in the binding pocket of ProCA32, the $K_d$ value of gadolinium binding to ProCA32 can be determined. FIGS. 43A-43B show graphs demonstrating $Gd^{3+}$ affinity. The binding affinity of both terbium and gadolinium to ProCA32 was observed to be within a $10^{-22}$ M range that is comparable to the gadolinium binding affinity of small chelators such as DTPA and EGTA.

Figure 44A:
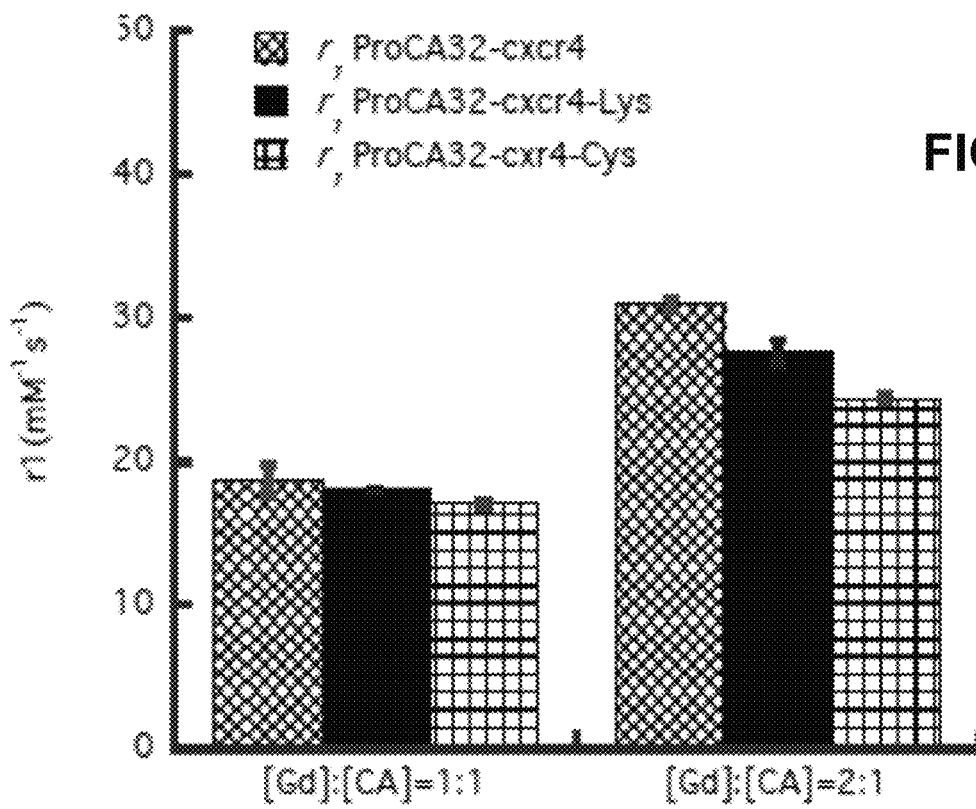
FIGS. 44A-44B show graphs demonstrating r1 (FIG. 44A) and r2 (FIG. 44B) relaxivities of ProCA32.V1.CXCR4.
Figure 44B:
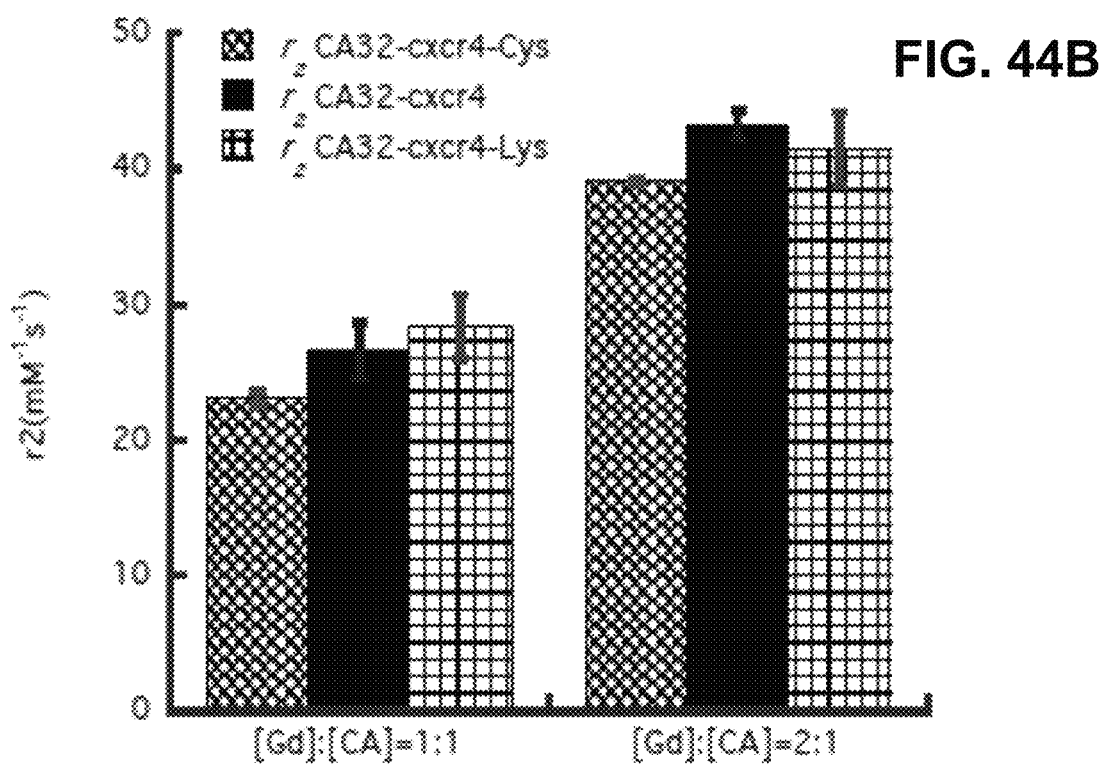

The r1 and r2 relaxivities of ProCA32.V1.CXCR4 were examined. Briefly, both r1 and r2 relaxivities were measured under 1.5 T and 7 T magnetic fields. The 1.5 T relaxometer was used for the ProCA32.V1.CXCR4 relaxivities measurement and a phantom experiment was carried out to measure the protein relaxivities under 7 Tesla magnetic field using a MR scanner. ProCA32.V1.CXCR4 and both the lysine and cysteine PEGylated version of this protein were observed to have similar relaxivities. The T1 relaxivity was observed to be decreased in higher magnetic field and T2 relaxivity was observed to be greater in 7 T than in 1.5 T. FIGS. 44A-44B show graphs demonstrating r1 (FIG. 44A) and r2 (FIG. 44B) relaxivities of ProCA32.V1.CXCR4. The ProCA32.V1.CXCR4 was observed to have a drastic improvement in relaxivity as compared with small chelator based contrast agent and PEGylation of this protein did not affect the relaxivity. Without being bound to theory, it was observed that ProCA32.V1.CXCR4 has superior T1 and T2 relaxivity and is thus suitable for use with new MR pulse sequence techniques that rely on molecules with increased relaxivity. In addition, the improved T2 relaxivity in higher magnetic field can allow ProCA32.V1.CXCR4 to be used as a T2 weighted contrast agent under a higher magnetic field.

Figure 45A:
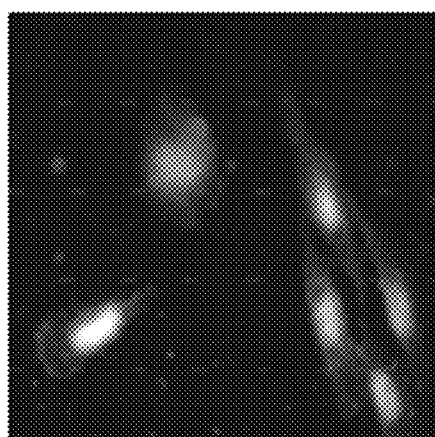
FIGS. 45A-45B show fluorescence micrographic images demonstrating CXCR4 targeting by ProCA32.V1.CXCR4 in vitro.
Figure 45B:
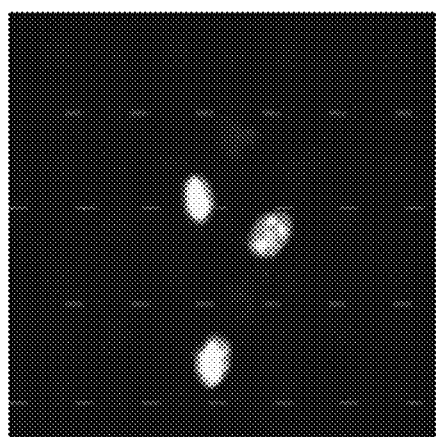
Figure 46A:
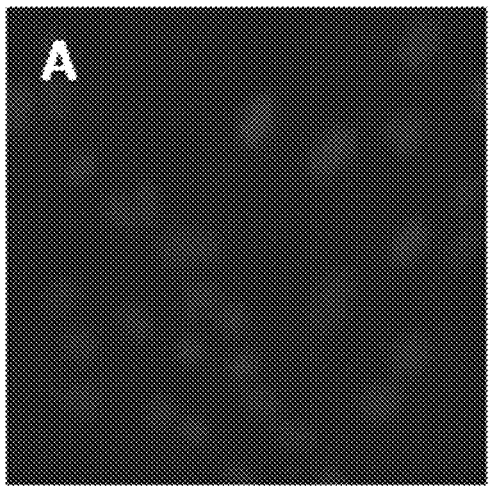
FIGS. 46A-46D show fluorescence micrographic images demonstrating DAPI counter staining (FIG. 46A), fluorescein counter staining for ProCA32.CXCR4 (FIG. 46B), and CXCR4 expression (FIG. 46C). The expression of CXCR4 is represented by red fluorescence generated by a secondary goat-anti-rabbit fluorescent labeled antibody against CXCR4. A composite image of FIGS. 46A-46C is shown in FIG. 46D.
Figure 46B:
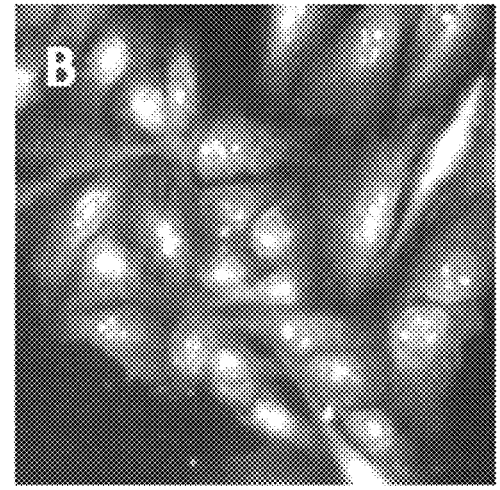
Figure 46C:
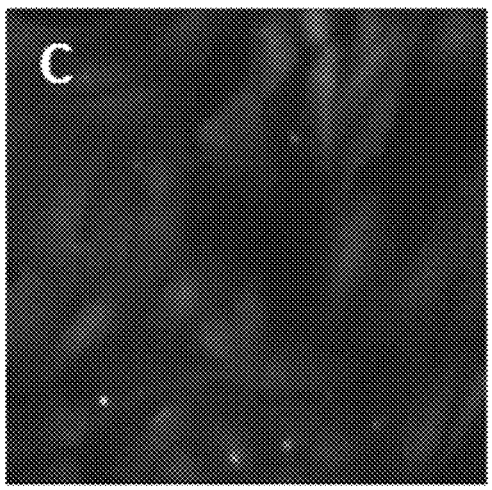
Figure 46D:
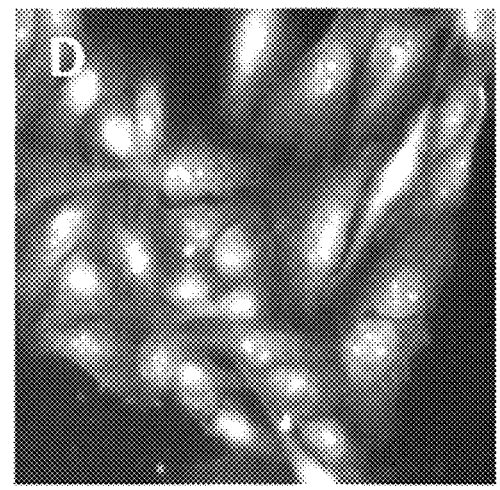
Figure 47A:
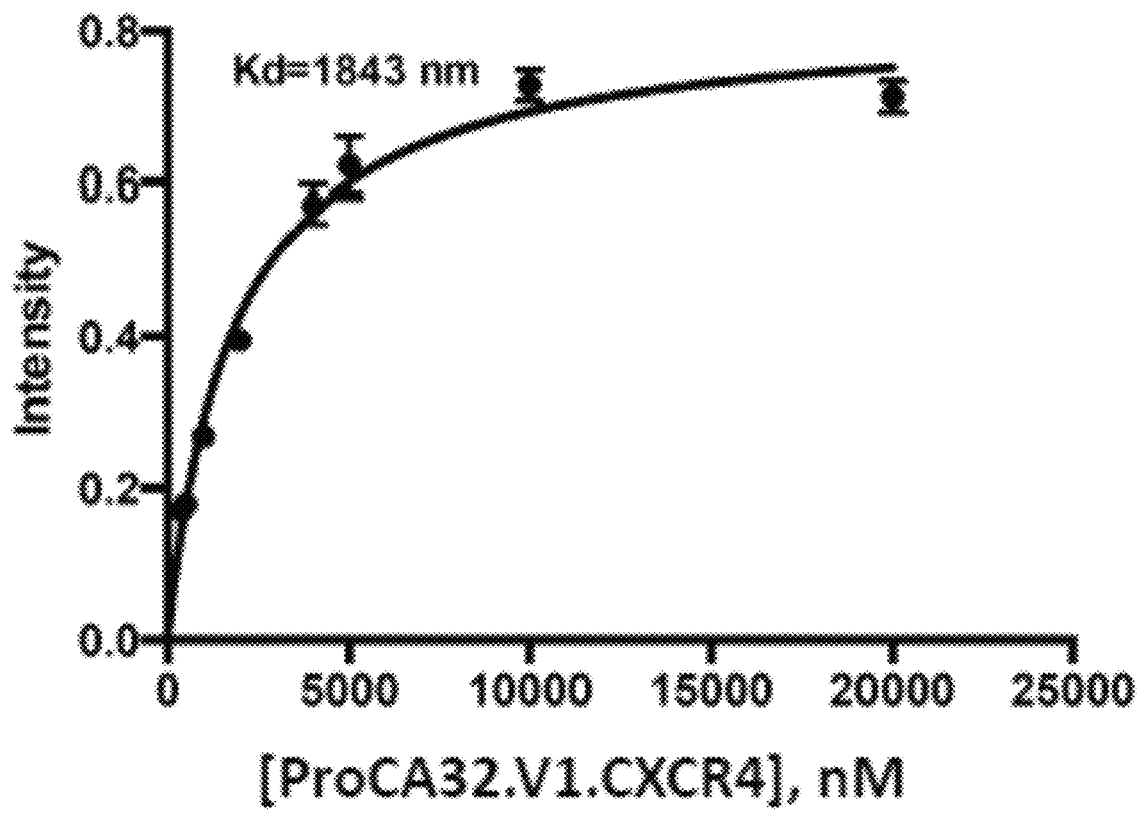
FIGS. 47A-47B demonstrate binding of ProCA32.V1.CXCR4 to CXCR4 positive cells with a dissociation constant of 1843 nM.
Figure 47B:
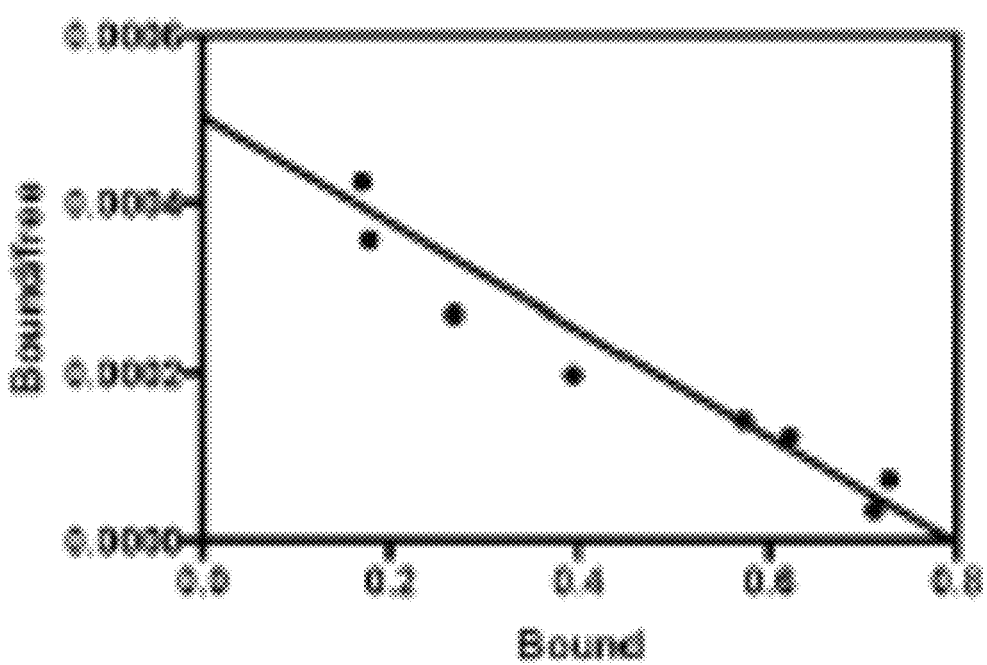

The ability of ProCA32.V1.CXCR4 to target CXCR4 in cells was examined. Briefly, a fluorescence staining of ProCA32.V1.CXCR4 incubated Melanoma 290 cells (CXCR4 high expression cell line) was carried out to examine the CXCR4 targeting capability of ProCA32.V1.CXCR4. ProCA32.V1.CXCR4 was incubated with Me1290 cells and primary antibody that can specifically bind ProCA32.V1.CXCR4 was used to evaluate ProCA32.V1.CXCR4 binding to the Me1290 cells, which express CXCR4. Next the cells were incubated with a fluorecin-labeled secondary antibody that specifically binds the primary antibody. ProCA32.V1.CXCR4 was measured by measuring fluorecin. FIGS. 45A-45B show fluorescence micrographic images demonstrating CXCR4 targeting by ProCA32.V1.CXCR4 in vitro. FIGS. 46A-46D show fluorescence micrographic images demonstrating DAPI counter staining (FIG. 46A), fluorescein counter staining for ProCA32.CXCR4 (FIG. 46B), and CXCR4 expression (FIG. 46C). The expression of CXCR4 is represented by red fluorescence generated by a secondary goat-anti-rabbit fluorescent labeled antibody against CXCR4. A composite image of FIGS. 46A-46C is shown in FIG. 46D. FIGS. 47A-47B demonstrate the in vitro binding affinity of ProCA32.V1.CXCR4.

Figure 48:
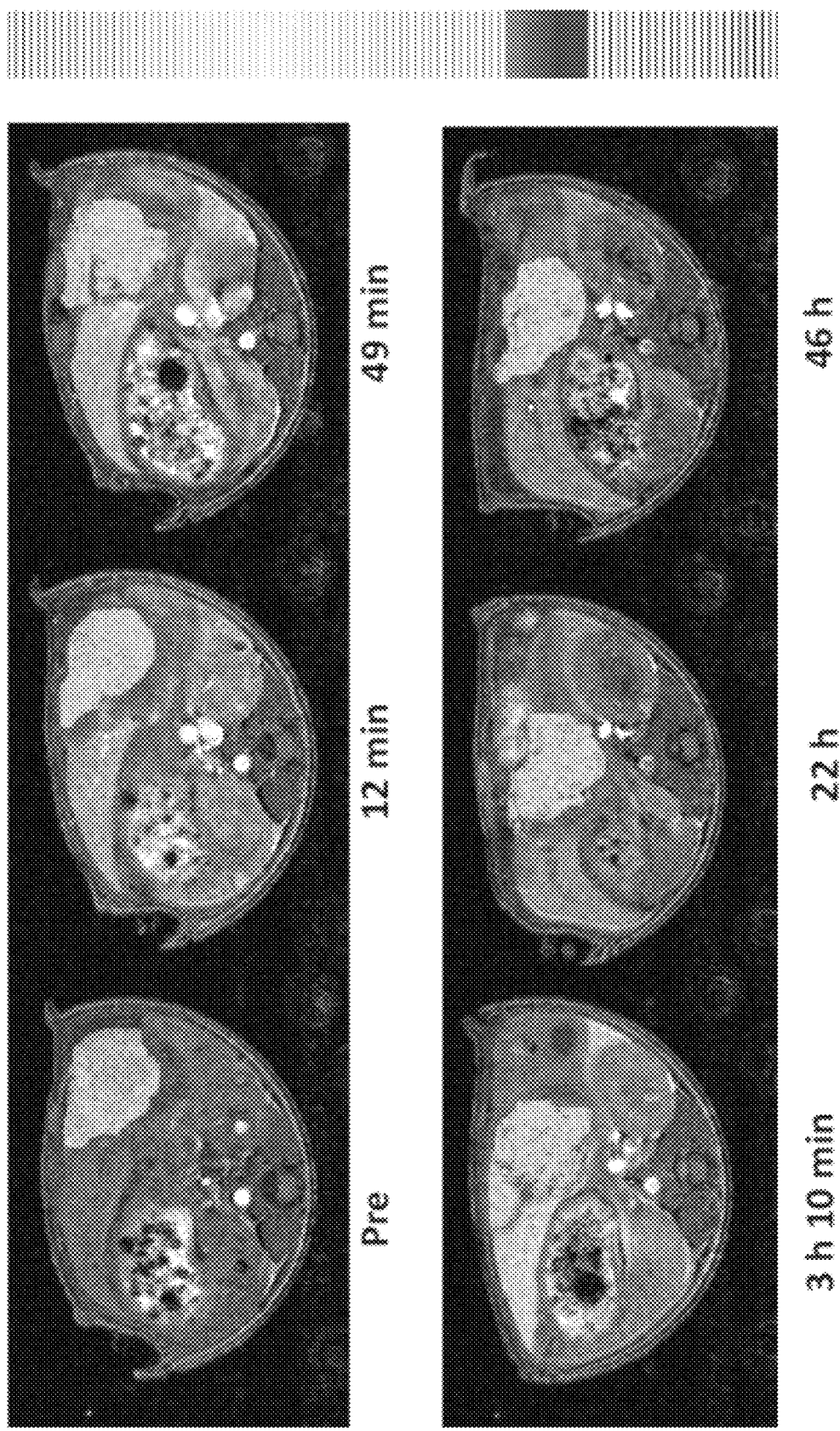
FIG. 48 shows results of gradient echo imaging of Me1290 mice after ProCA32.CXCR4 injection.
Figure 49:
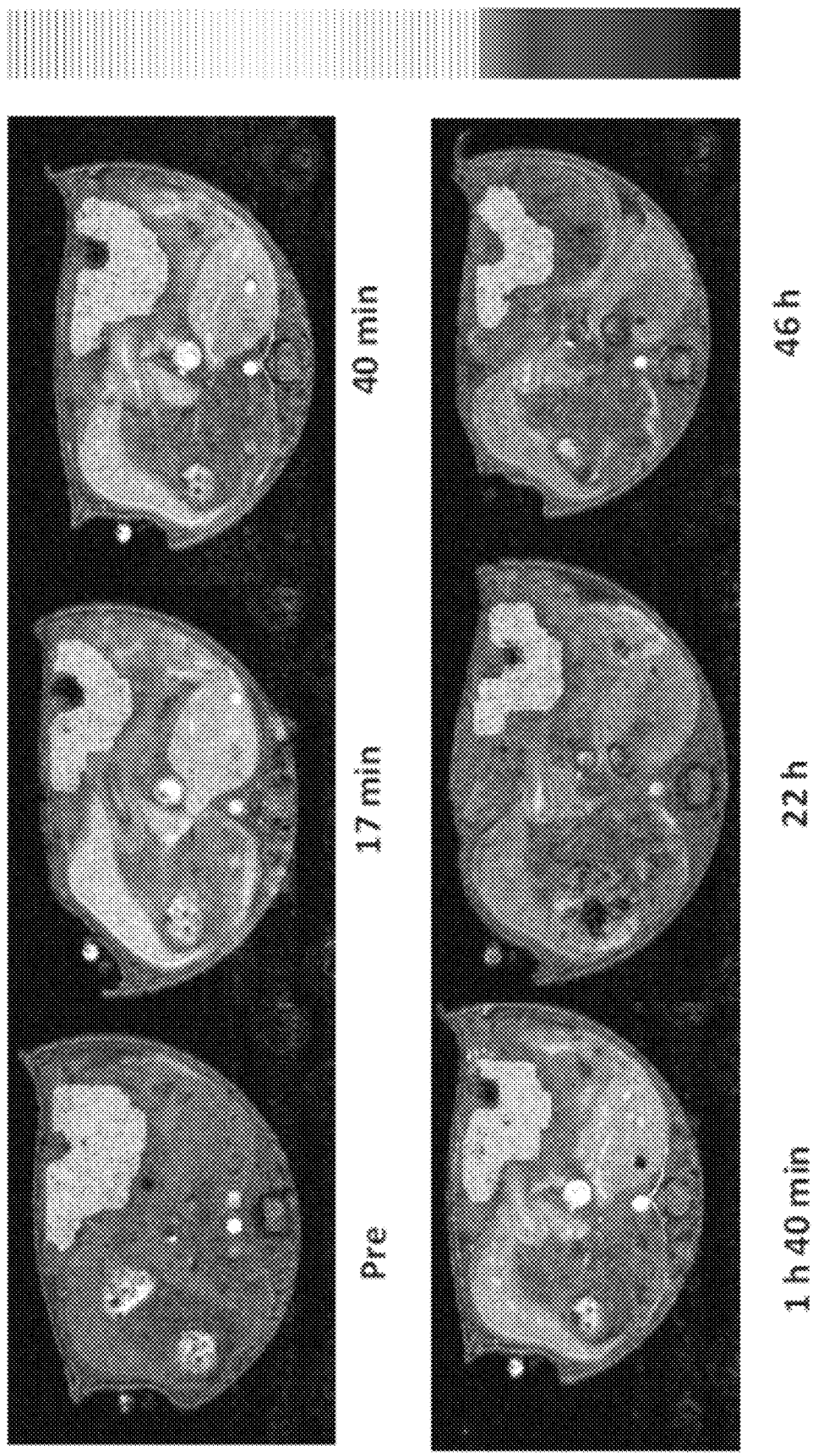
FIG. 49 shows a results of gradient echo imaging of Me1290 after ProCA32 injection.
Figure 50B:
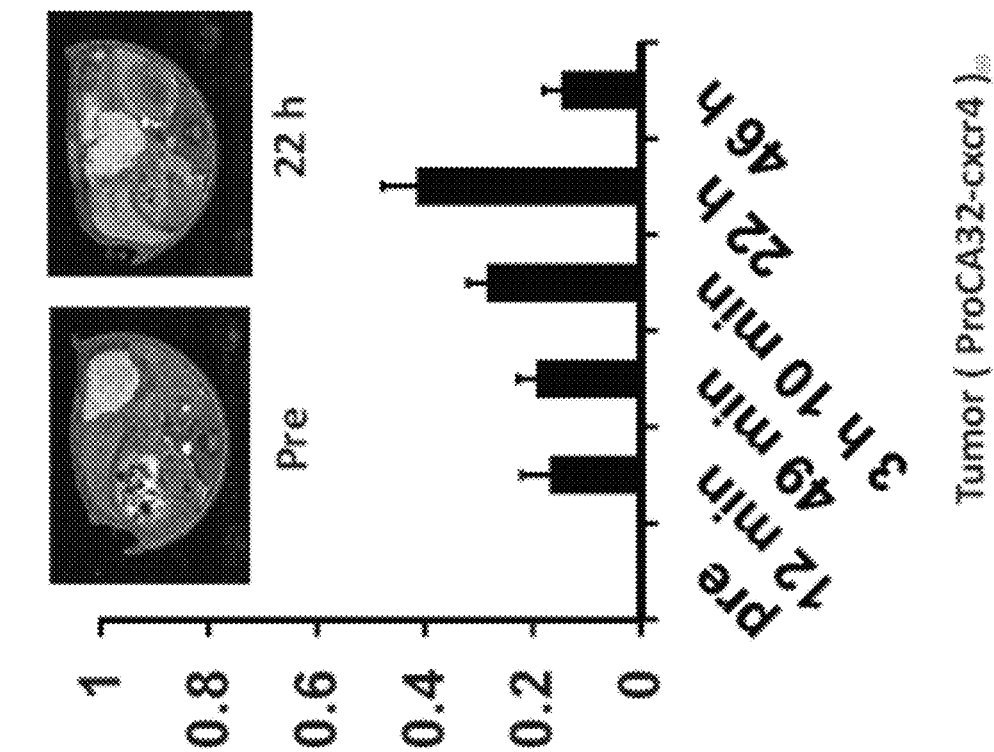
FIGS. 50A-50B show graphs and images demonstrating intensity (SNR) percentage increase of tumor (gradient echo) in mice injected with ProCA32 (FIG. 50A) or ProCA32.CXCR4 (FIG. 50B).
Figure 50A:
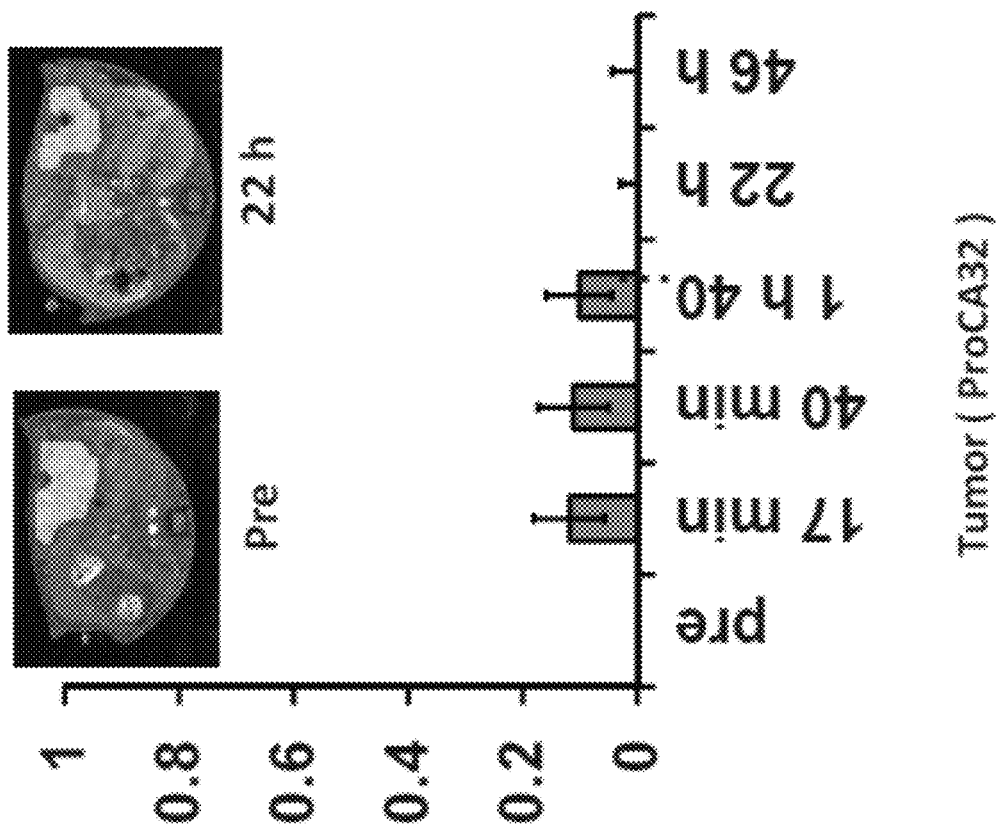

The ProCA32.V1.CXCR4 was examined as contrast agent in Me1290 mice. Briefly, pre-injection scanning and after-injection MR scanning at different time points up to 48 hours after injection was performed and image data was collected for analysis. FIG. 48 shows results of gradient echo imaging of Me1290 mice after ProCA32.CXCR4 injection. FIG. 49 shows a results of gradient echo imaging of Me1290 after ProCA32 injection. FIGS. 50A-50B show graphs and images demonstrating intensity (SNR) percentage increase of tumor (gradient echo) in Me1290 mice injected with ProCA32 (FIG. 50A) or ProCA32.CXCR4 (FIG. 50B).

Figure 51B:
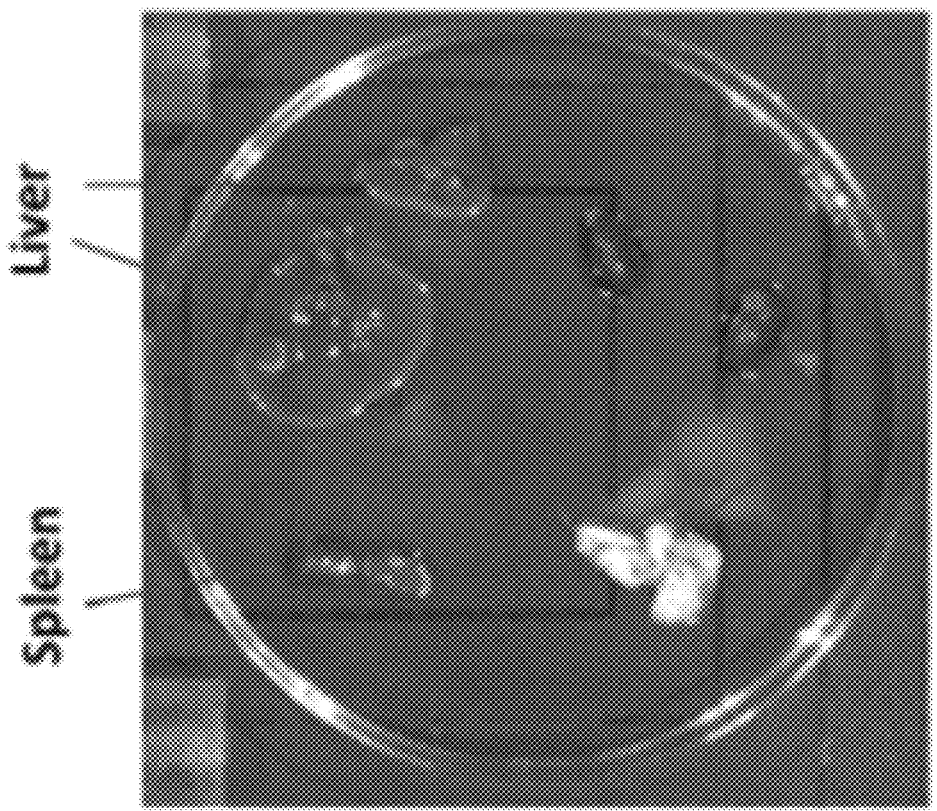
FIGS. 51A-51B show photographs of tumors in mice (FIG. 51A) and organs (FIG. 51B) after being injected subcutaneously and orthotopically to the right ovary with SKOV-3 ovarian cancer cells.
Figure 51A:
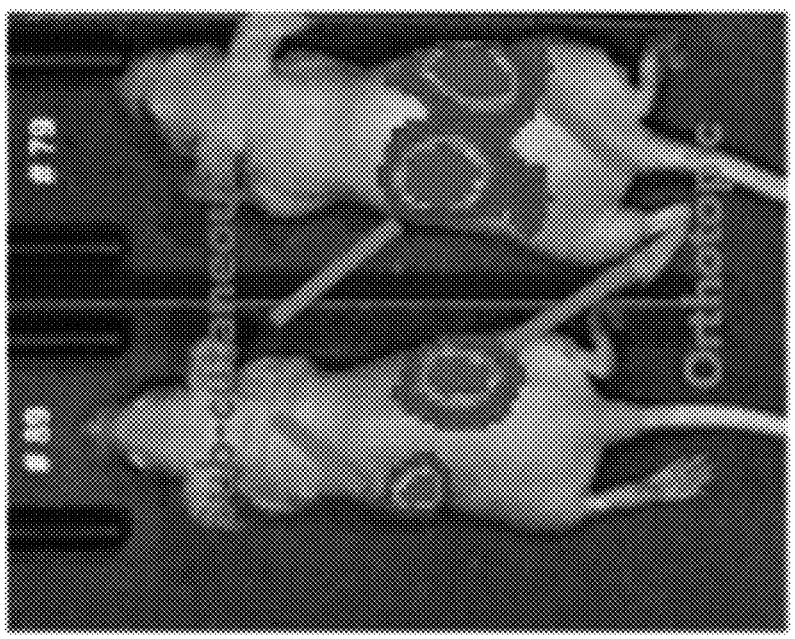
Figure 52:
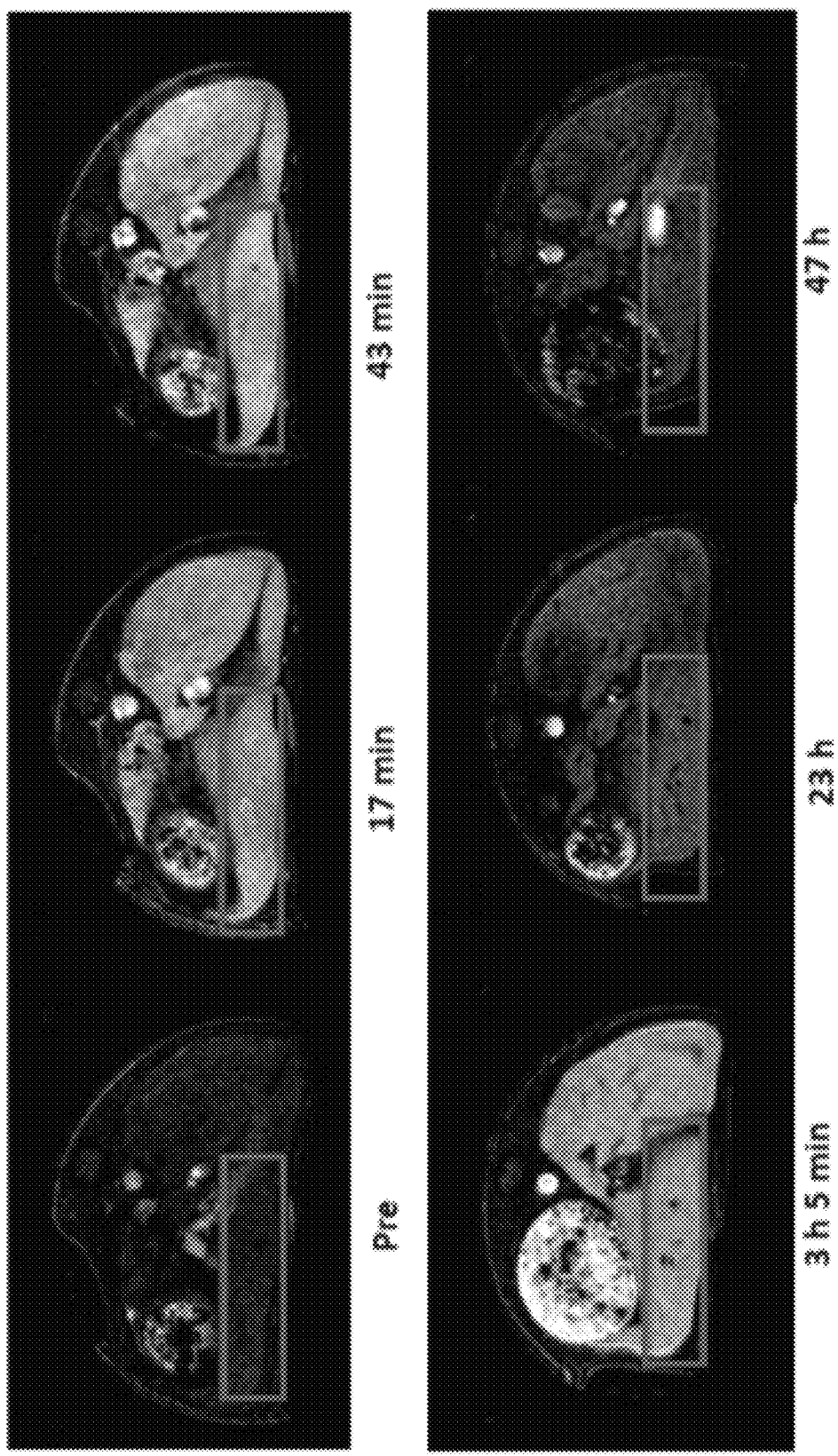
FIG. 52 shows results of T1 weighted imaging (gradient echo) of SKOV3 model mice after ProCA32.V1.CXCR4 injection.
Figure 53:
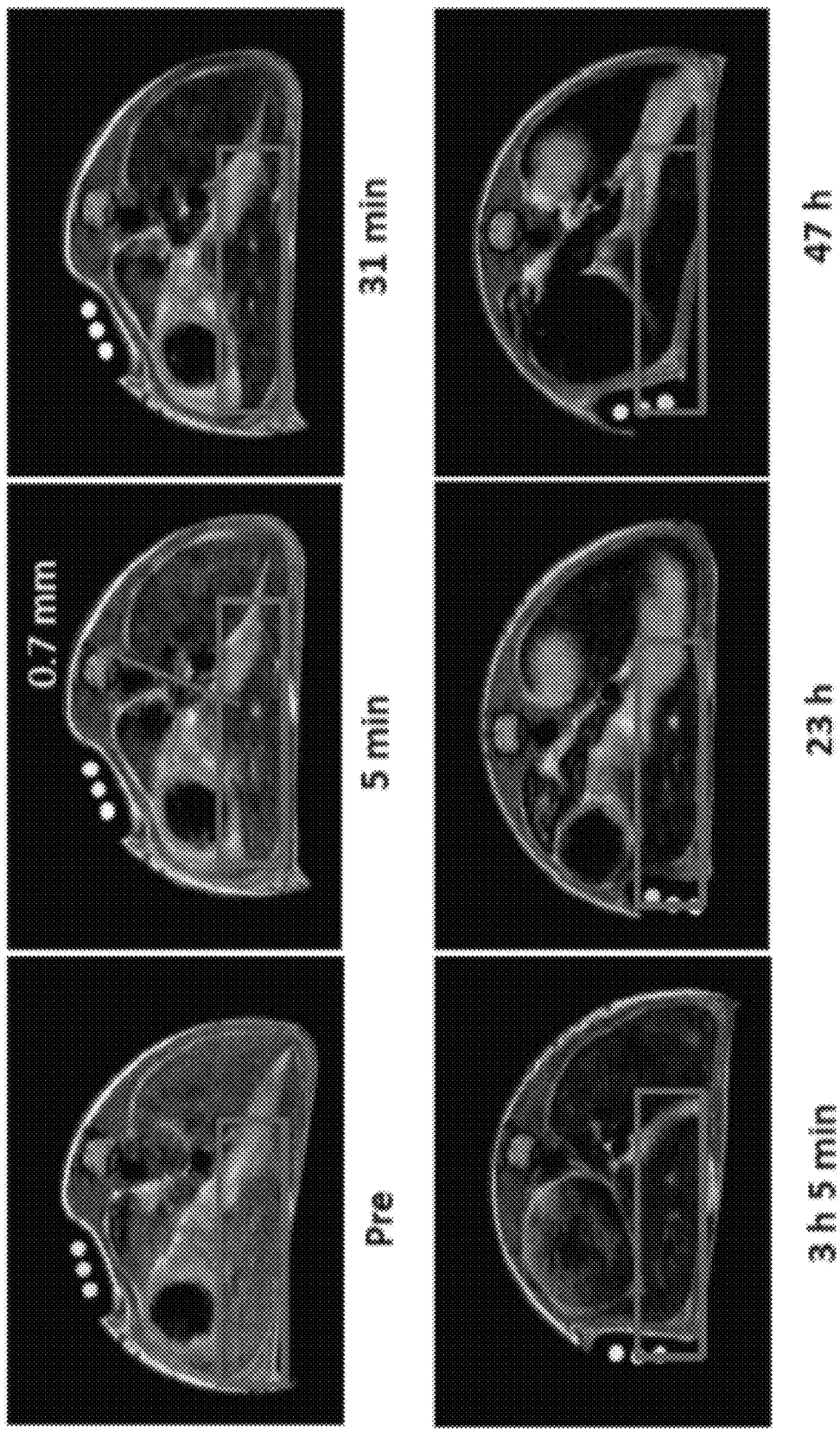
FIG. 53 shows results of T2 weighted imaging (gradient echo) of SKOV3 model mice after ProCA32.V1.CXCR4 injection.
Figure 54:
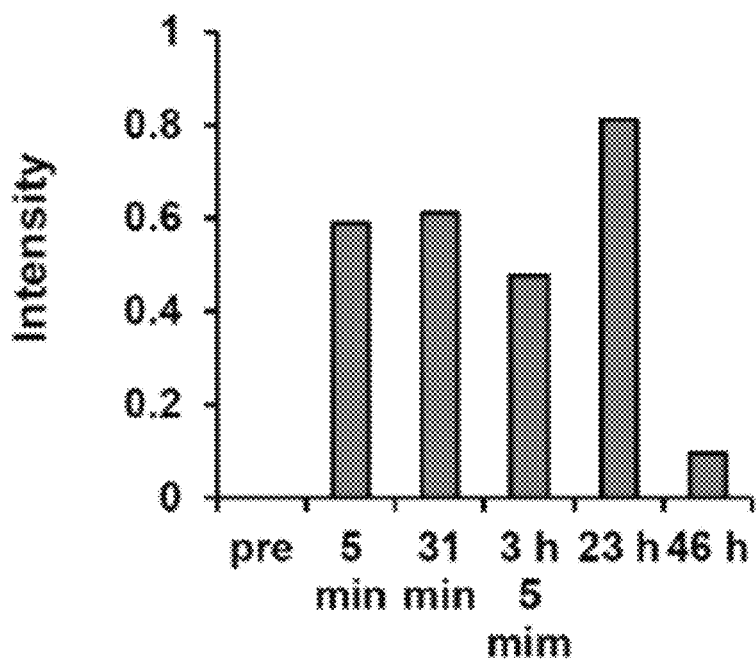
FIG. 54 shows a graph demonstrating the intensity percentage increase of tumors (fast spin echo) metastasis to the liver before (pre) and after injection of ProCA32.CXCR4.

The ProCA32.CXCR4 was also evaluated in a SKOV-3 ovarian cancer metastasis mouse model. The mice were scanned pre-injection and at various time points post-injection in a similar fashion as previously described. FIGS. 51A-51B show photographs of tumors in mice (FIG. 51A) and organs (FIG. 51B) after being injected subcutaneously and orthotopically to the right ovary with SKOV-3 ovarian cancer cells. The ProCA32.CXCR4 was evaluated as a contrast agent in SKOV3 model mice. FIG. 52 shows results of T1 weighted imaging (gradient echo) of SKOV3 model mice after ProCA32.V1.CXCR4 injection. FIG. 53 shows results of T2 weighted imaging (gradient echo) of SKOV3 model mice after ProCA32.V1.CXCR4 injection. FIG. 54 shows a graph demonstrating the intensity percentage increase of tumors (fast spin echo).

FIGS. 90A-F show images demonstrating targeting by ProCA32.CXCR4.

Figure 91:
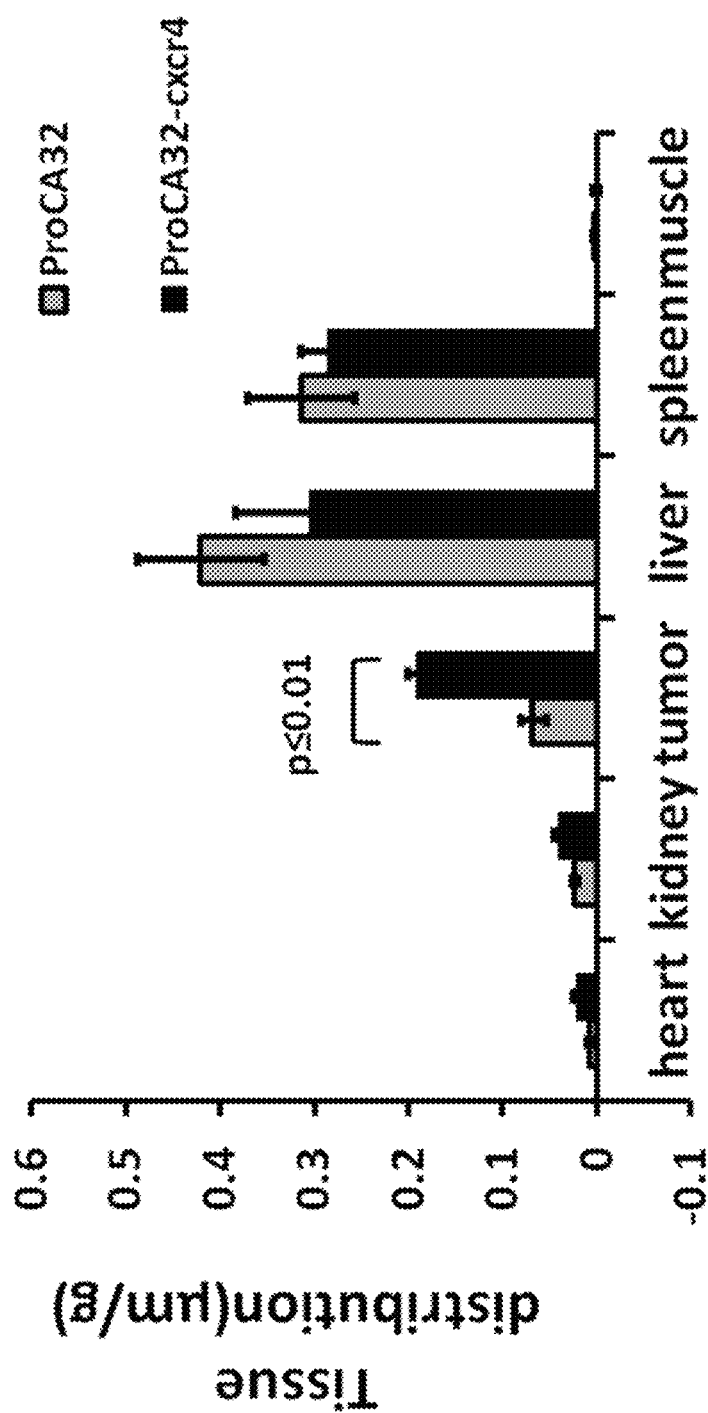
FIG. 91 shows a graph demonstrating tissue distribution of ProCA32.CXCR4.

FIG. 91 shows a graph demonstrating tissue distribution of ProCA32.CXCR4.

Example 4. HER2 and EGFR Targeted ProCAs

Figure 55:
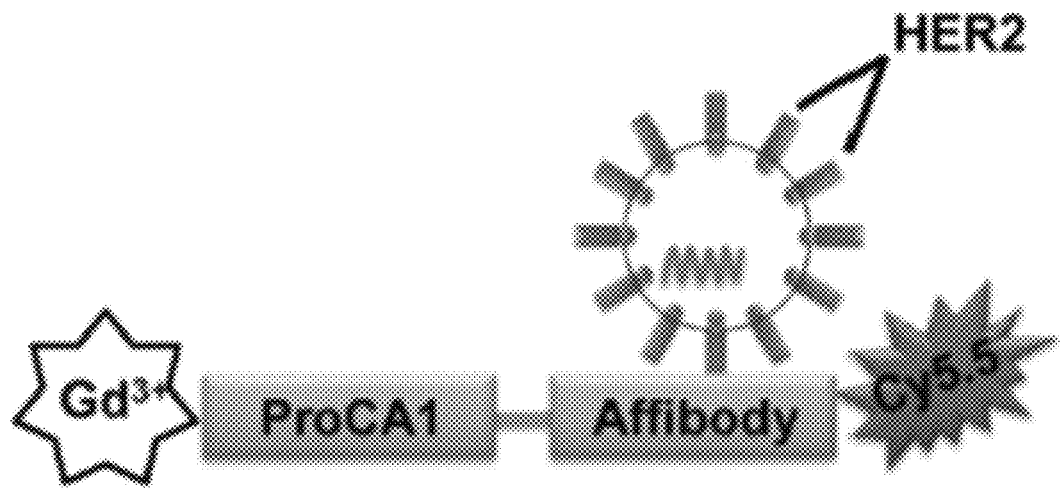
FIG. 55 shows a schematic of one embodiment of a ProCA where the targeting moiety is an affibody, specifically an affibody that can target HER2.
Figure 56A:
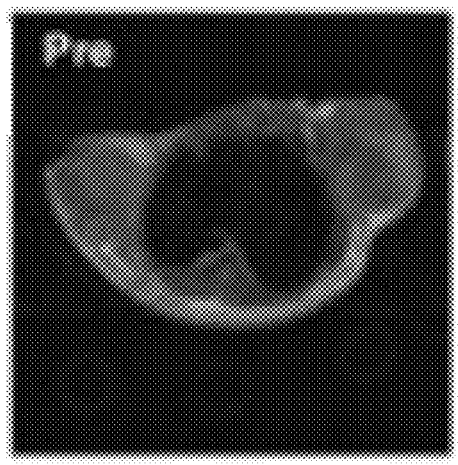
FIGS. 56A-56D show fast spin echo MRI images of mice having HER2 positive and negative tumors after injection with a targeted ProCA that includes an affibody that can bind HER2.
Figure 56B:
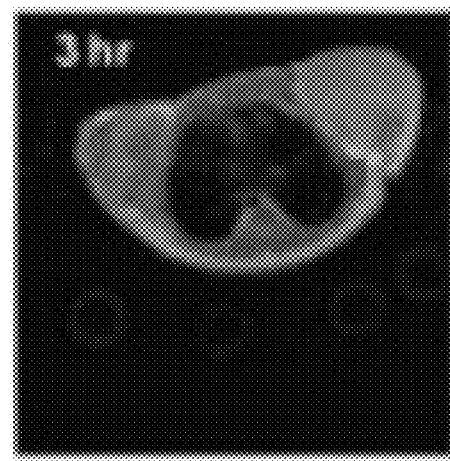
Figure 56C:
Figure 56D:
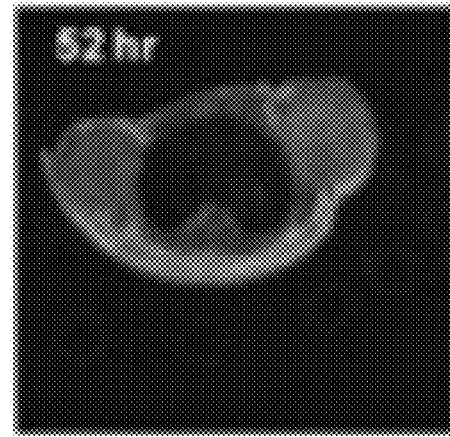
Figure 57A:
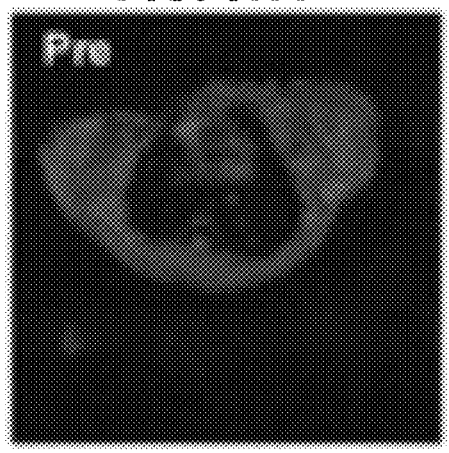
FIGS. 57A-57D show gradient echo MRI images of mice having HER2 positive and negative tumors after injection with a targeted ProCA that includes an affibody that can bind HER2.
Figure 57B:
Figure 57C:
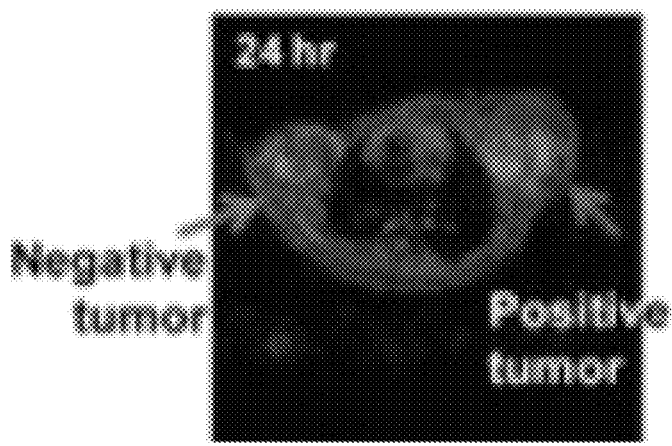
Figure 57D:
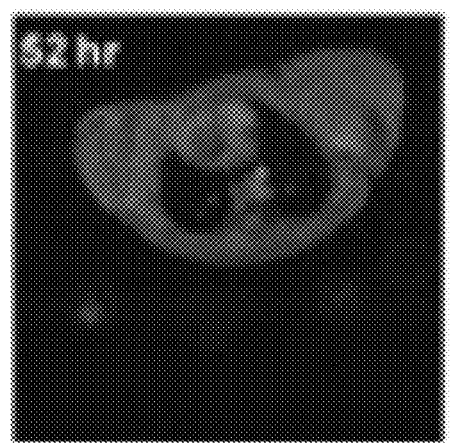

HER2 and EGFR targeting ProCAs were made by indirectly linking a HER2 or EGFR specific affibody to the C-terminus of ProCA1 via a peptide linker as described in Qiao et al, 2014 February; J. Biol. Inorg. Chem. 19(2): 259-270. FIG. 55 shows a schematic of one embodiment of a ProCA where the targeting moiety is an affibody, specifically an affibody that can target HER2.

The HER specific ProCA was evaluated for its ability as a contrast agent. Both HER2 positive and negative tumor cells were inoculated in nude mice as xenografted subcutaneous model. After injection of ProCA1-affi, only HER2 positive tumors shows enhancement under MRI. FIGS. 56A-56D fast spin echo show images of mice having HER2 positive and negative tumors after injection with a targeted ProCA that includes an affibody that can bind HER2. In the experiments demonstrated by FIGS. 56A-56D, images were generated using fast spin echo imaging, in which positive tumor shows highest enhancement at 24 hr. post injection.

Figure 58A:
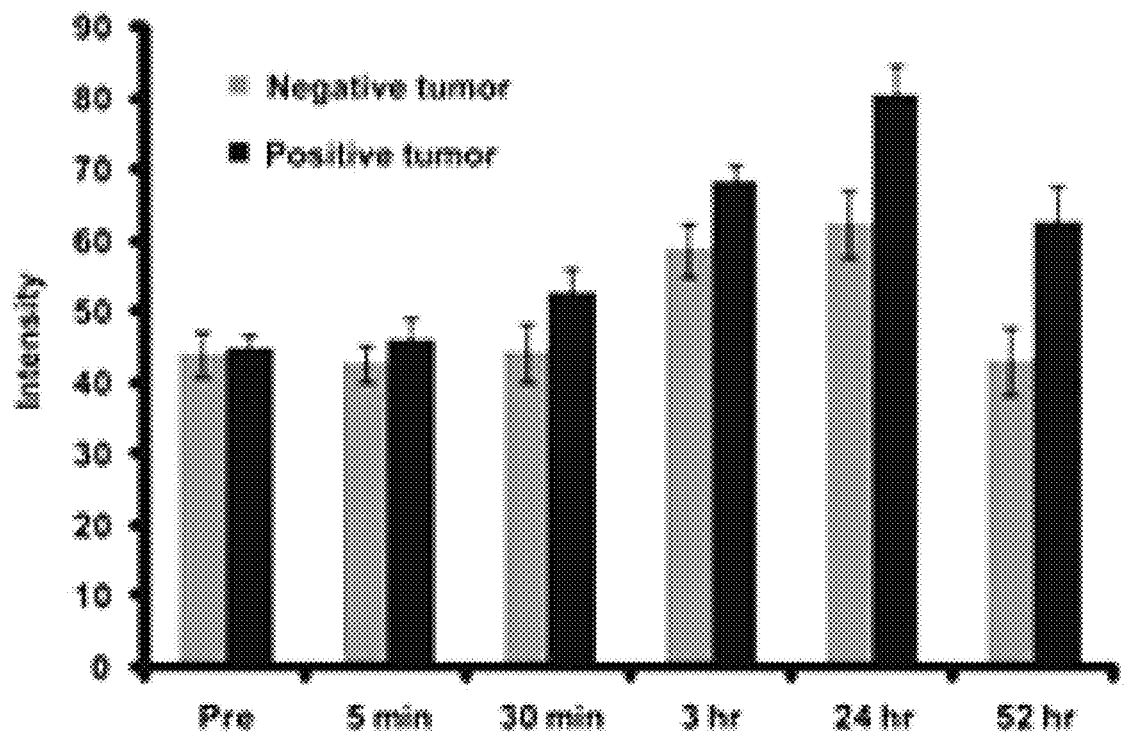
FIGS. 58A-58B show graphs demonstrating signal intensity in HER2 positive and HER2 negative tumors in mouse SKOV-3 metastasis model.
Figure 58B:
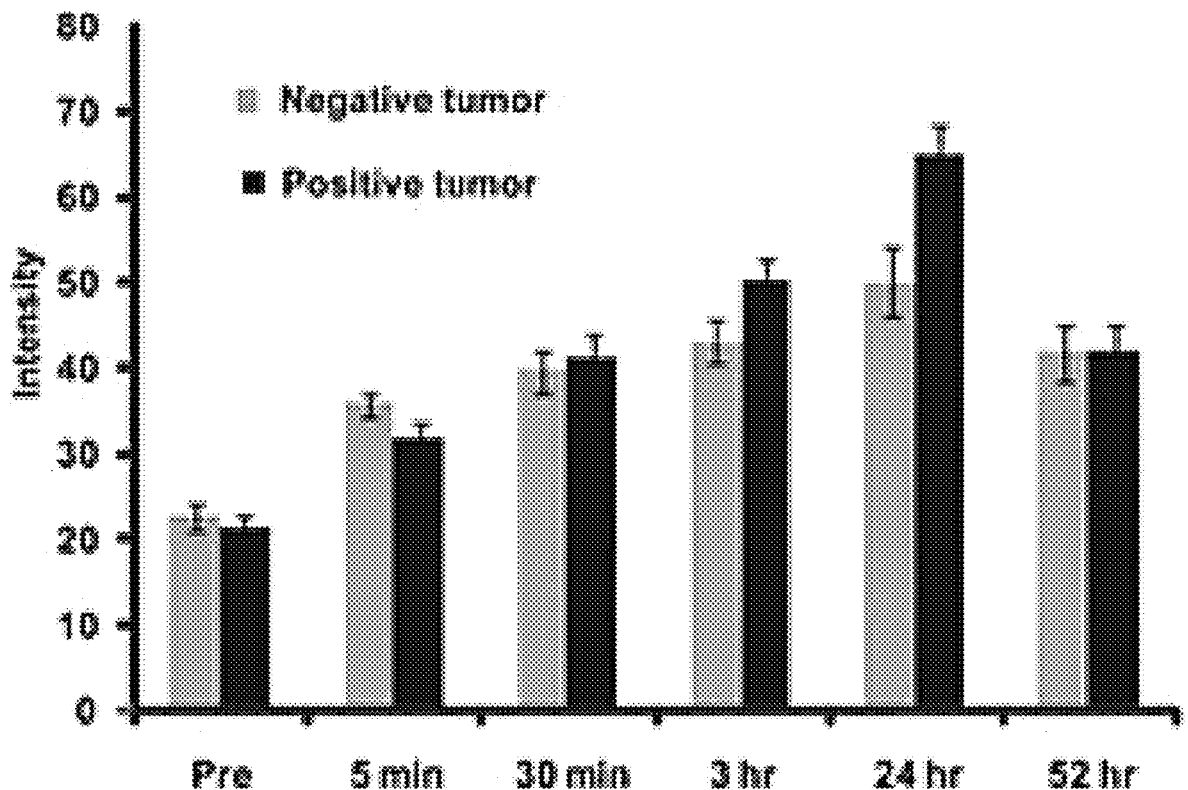

FIGS. 57A-57D show gradient echo images of mice having HER2 positive and negative tumors after injection with a targeted ProCA that includes an affibody that can bind HER2. FIGS. 58A-58B show graphs demonstrating signal intensity in HER2 positive and HER2 negative tumors in mouse SKOV-3 metastasis model. FIGS. 57A-57D shows images in gradient echo, in which a heterogeneous structure of tumors can be visualized. In order to quantitatively analyze the MRI results, we use software Image J to circle the area of interests such as tumors or liver. Then the average intensity of the area will be measured. We selected several adjacent slides with one specific organ or tumor to obtain an average intensity with standard deviation. This statistic analysis makes the results reliable and less false positive.

Example 5. Hydrophilic and Hydrophobic ProCAs

ProCA1 that has no inherent targeting capability can be hydrophilic or hydrophobic modified to add targeting functionality. The ProCA1 was modified with lysine using hydrophilic modification The ProCAs were further modified with PEG.

Figure 59:
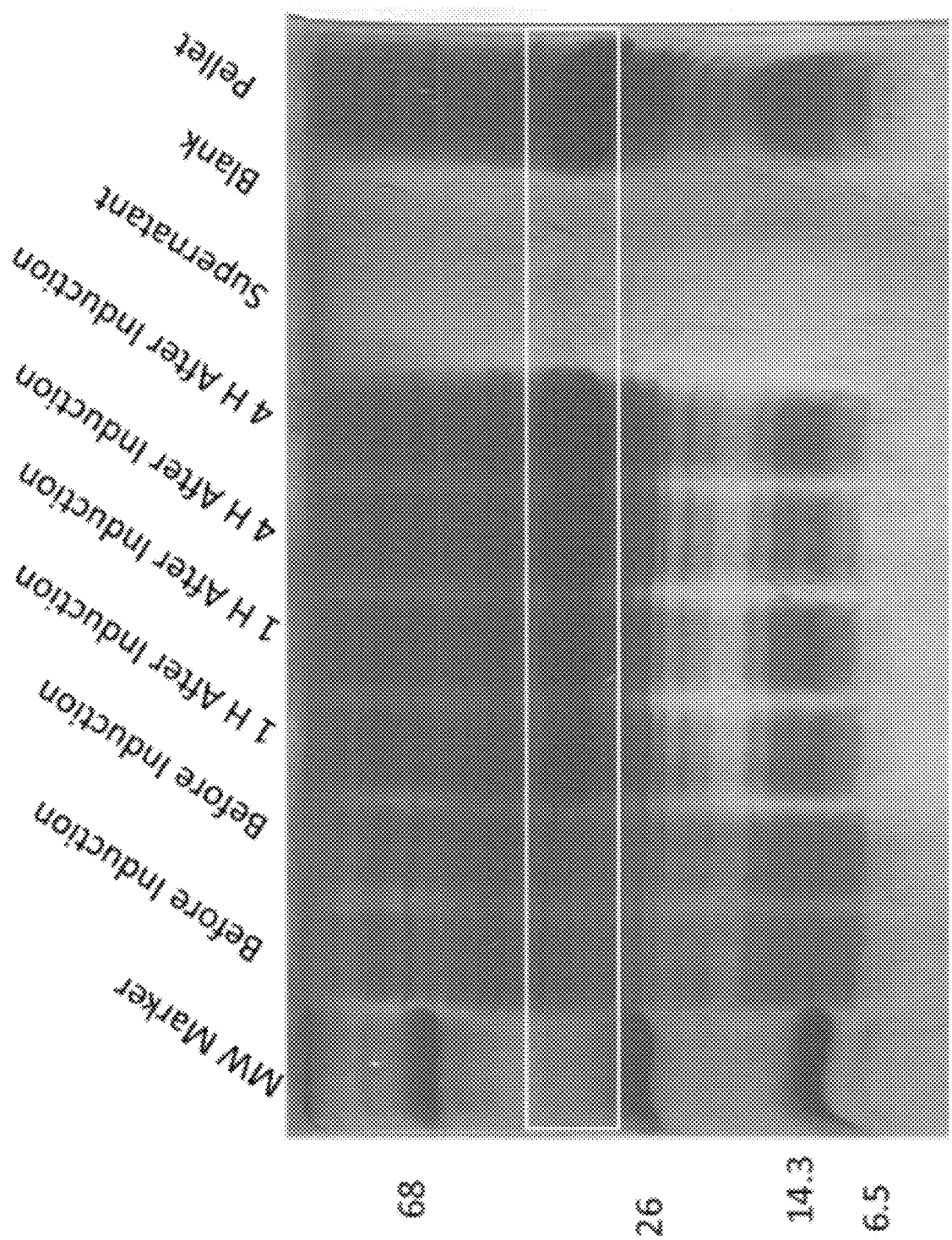
FIG. 59 shows a protein gel demonstrating rat ProCA1 expression. The White box highlights the band of ProCA1 fused with GST. *E. coli* demonstrated no expression before IPTG induction and the protein band of ProCA1 increased after an IPTG induction of 1-4 hours. The ProCA1 band can be detected in the harvested bacteria pellets.
Figure 60:
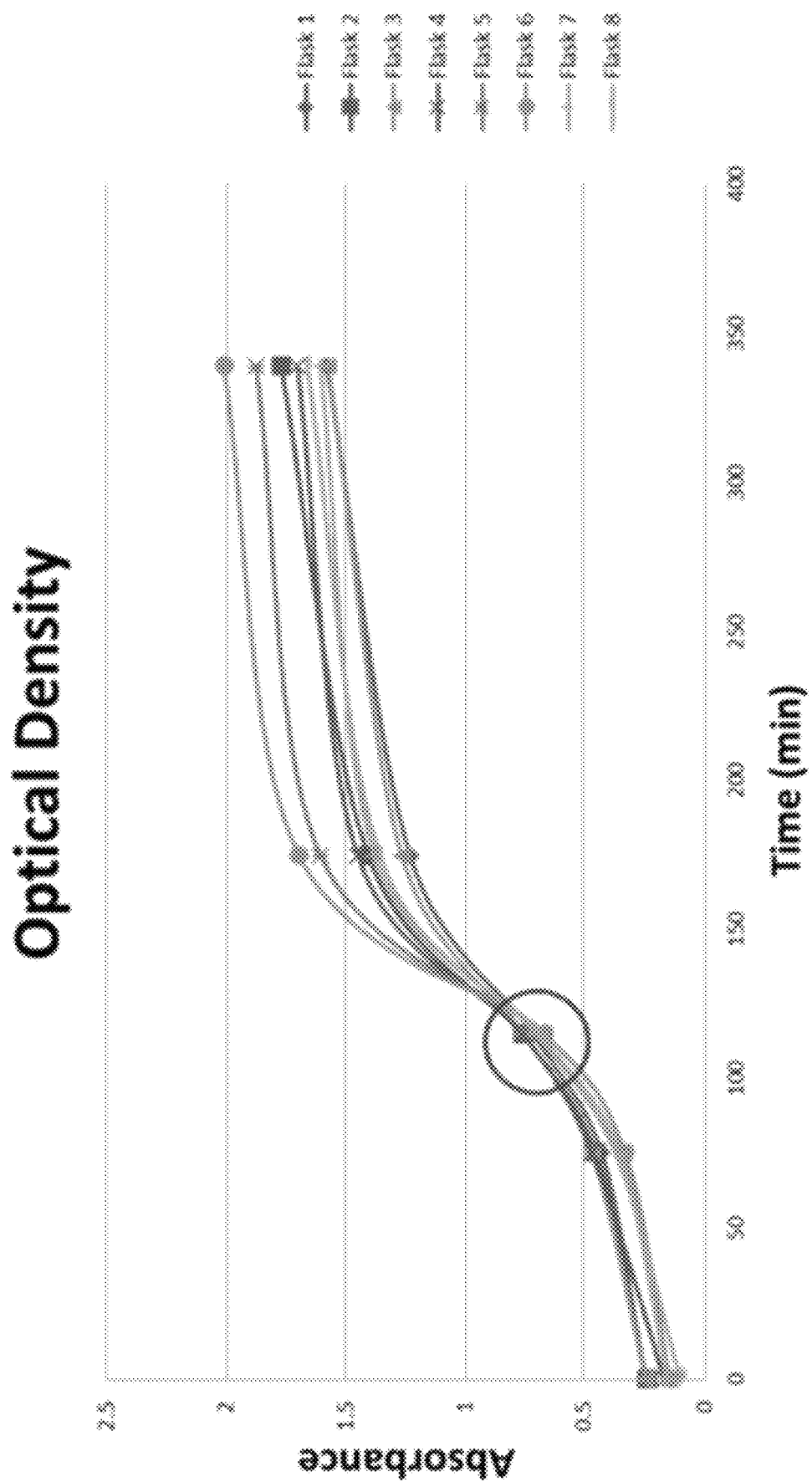
FIG. 60 shows a graph demonstrating an *E. coli* bacteria growth curve over different time points. Red cycle indicate the time points for the induction of ProCA1 expression by IPTG.

Rat ProCA1 was expressed in vitro. FIG. 59 shows a protein gel demonstrating rat ProCA1 expression. The protein is expressed along with the growth of bacterial cells. The optical density increased when the cell numbers increased. When the optical density reaches 0.6-0.8 when cells are active, IPTG was added to induce the protein expression. The optical density will continue increasing after induction. FIG. 60 shows a graph demonstrating rat ProCA1 expression trend.

Figure 61:
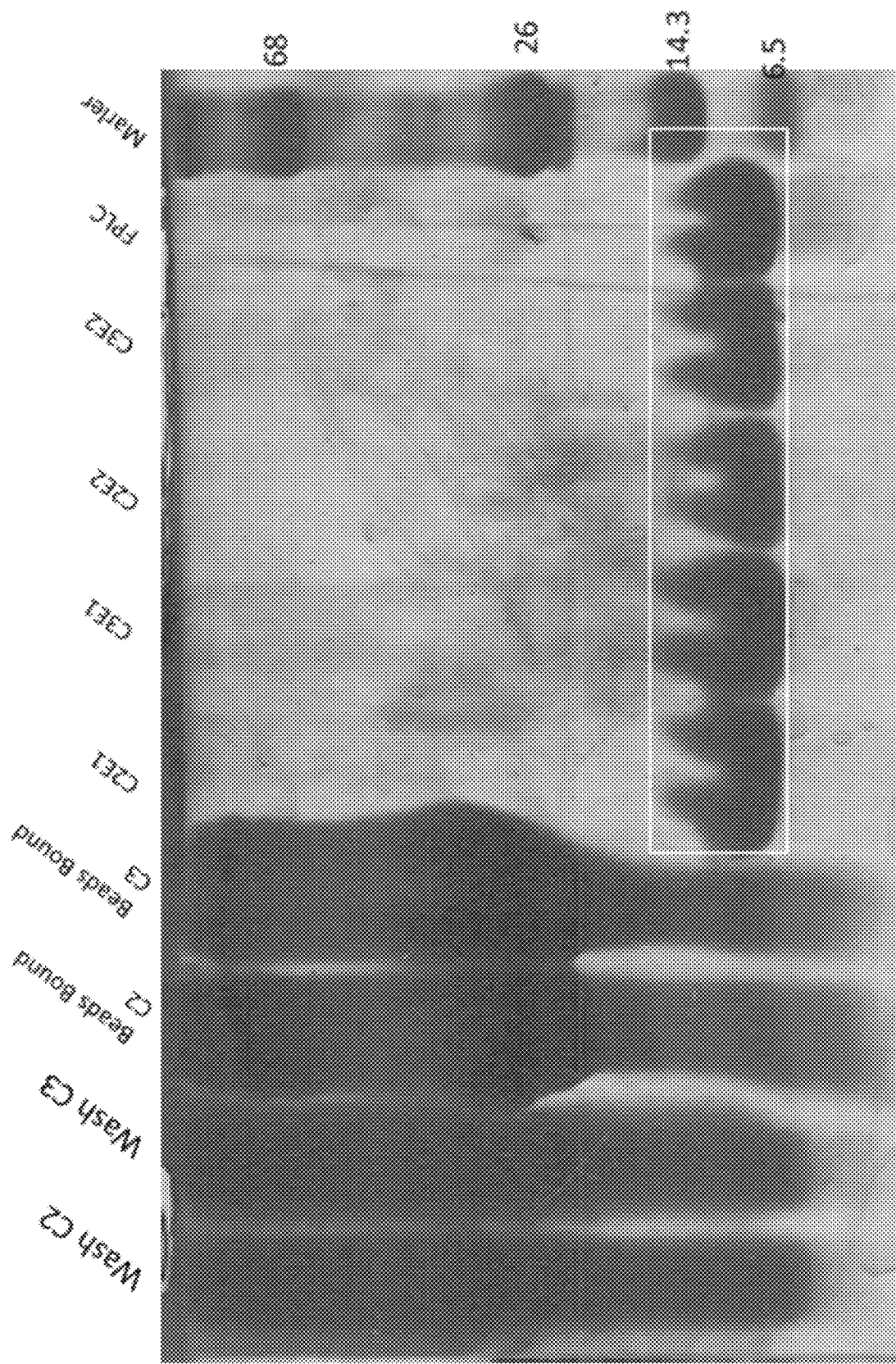
FIG. 61 shows an image of a gel demonstrating purification of Rat ProCA1.
Figure 62:
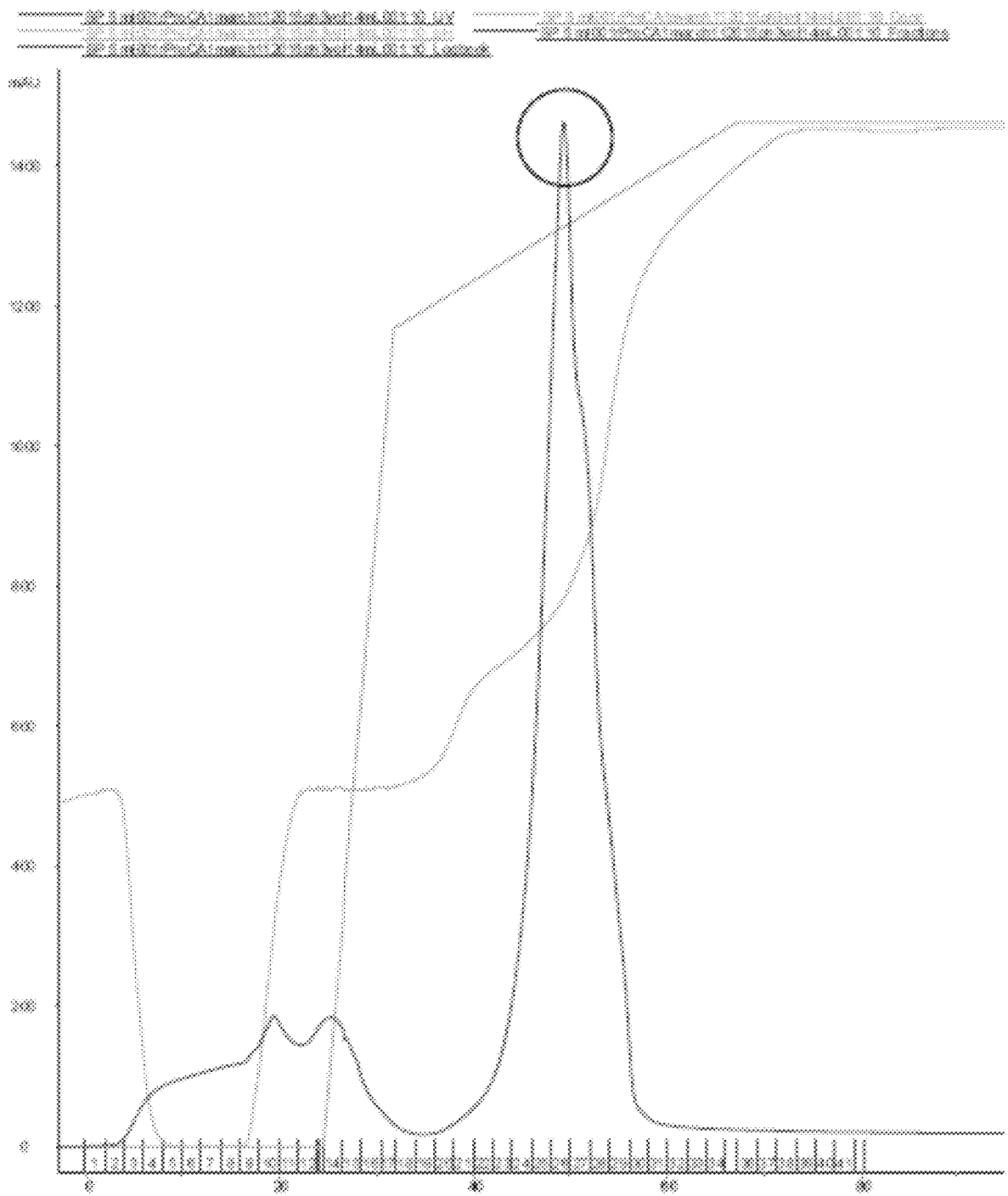
FIG. 62 shows absorbance spectra demonstrating purification of Rat ProCA1 by FPLC.
Figure 63:
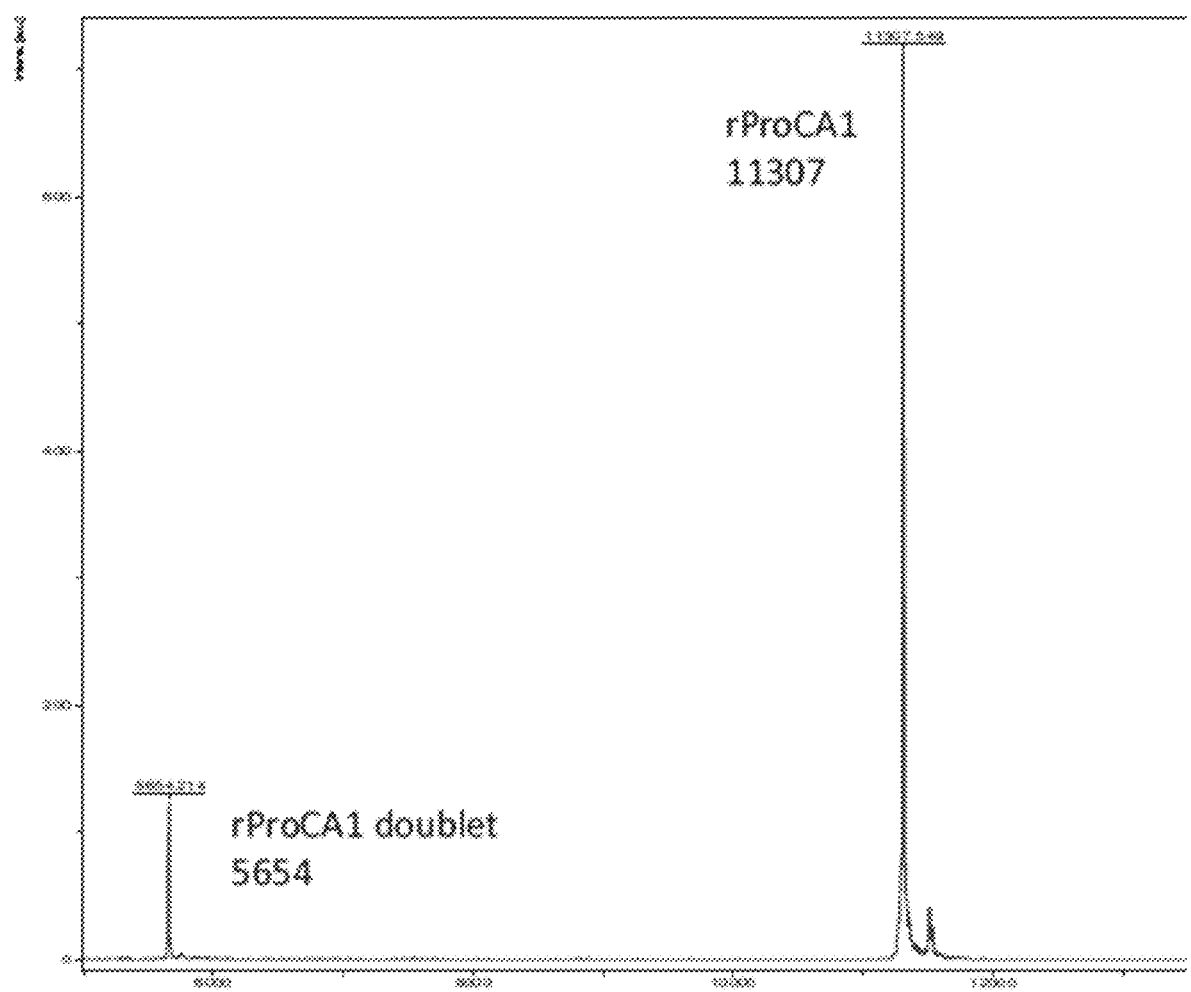
FIG. 63 shows a mass spectra demonstrating that purified rat ProCA1 (rProCA1) have the correct molecular weight of 11 kDa.
Figure 64:
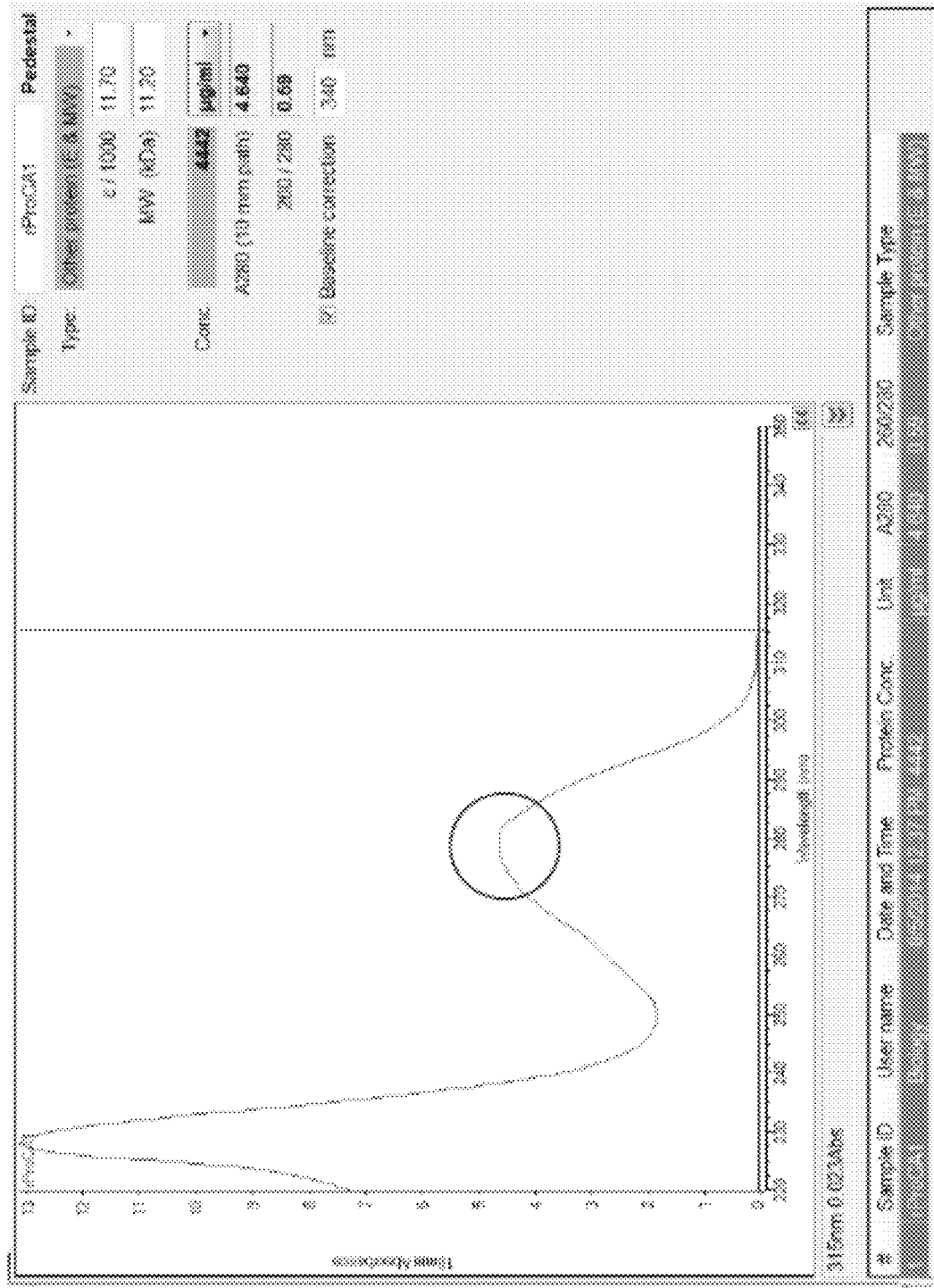
FIG. 64 shows a UV spectra demonstrating purification of rat ProCA1 as demonstrated by absorbance at 280 nm.

Rat ProCA1 was purified from the in vitro culture via bacterial lysis followed by chromatography separation. FIG. 61 shows an image of a gel demonstrating purification of Rat ProCA1. FIG. 62 shows absorbance spectra demonstrating purification of Rat ProCA1. The FPLC instrument is used to monitor protein purification. Protein has absorbance at UV280, so UV detector is used to measure the UV absorbance of flow out from the column. Once the UV increases and form a peak, the protein is eluted out and separated from other impurities. FIG. 63 shows a spectra demonstrating a rat ProCA1 (rProCA1) doublet and rProCA1. FIG. 63 shows a mass spectrum (MS) of ProCA1 to confirm the purity of ProCA1. The mechanism of MS is to trigger one electron of the protein molecule, then the MS machine will detect the molecular weight versus charge. If the molecular is pure, there will be only one peak which equals to the molecular weight of protein. Sometimes, two electrons will be triggered in some molecules, so the reading out will be half of the molecular weight and it is called a doublet. FIG. 64 shows a spectra demonstrating purification of rat ProCA1 as demonstrated by absorbance at 280 nm. Protein will have UV absorbance at UV280. As such a UV scan that includes absorbance at UV280 was conducted of the protein sample and the protein concentration was then calculated.

Example 6. Human Rat ProCA1 and Human ProCA1.Affibody

ProCA1 was originally based on CD2 domain 1. To apply the protein to humans the CD2 sequence was used to generate a human ProCA1 (hProCA1). Human ProCA1 was produced by modifying human CD2 to include a paramagnetic metal (e.g., $Gd^{3+}$) binding site. This binding site was generated by mutating the human CD2 sequence to include the N15E, D17N, L60D, T64D and K66D mutations.

The human ProCA1-Affi contrast agent was further examined in SKOV-3 model mice. Briefly, the human ProCA1-affi was injected into mouse with SKOV-3 tumor. MRI was used to scan to image any enhancement in tumor region. FIGS. 65A-65D show MRI scans demonstrating imaging of HER2 positive and negative tumors in SKOV-3 tumors on mice pre and at various time points post administration of a human ProCA1-Affi. FIG. 66 shows a graph demonstrating signal intensity of HER2 positive and negative SKOV-3 tumors on mice pre and at various time points post administration of a humanized ProCA1-Affi.

The humanized ProCA1-Affi contrast agent was further examined in MDA-MB-231 tumors on mice. Briefly, the modified ProCA1-affi was injected into mouse with MDA-MB-231 tumor. MRI was scanned to see less enhancement in tumor with less HER2 expression FIGS. 67A-67D show MRI scans demonstrating imaging of HER2 positive and negative MFS-MB-231 tumors on mice pre and at various time points post administration of a humanized ProCA1-Affi. FIG. 68 shows a graph demonstrating signal intensity of HER2 positive and negative MFS-MB-231 tumors on mice pre and at various time points post administration of a humanized ProCA1-Affi.

Example 7. Variants of ProCA1

Figure 69:
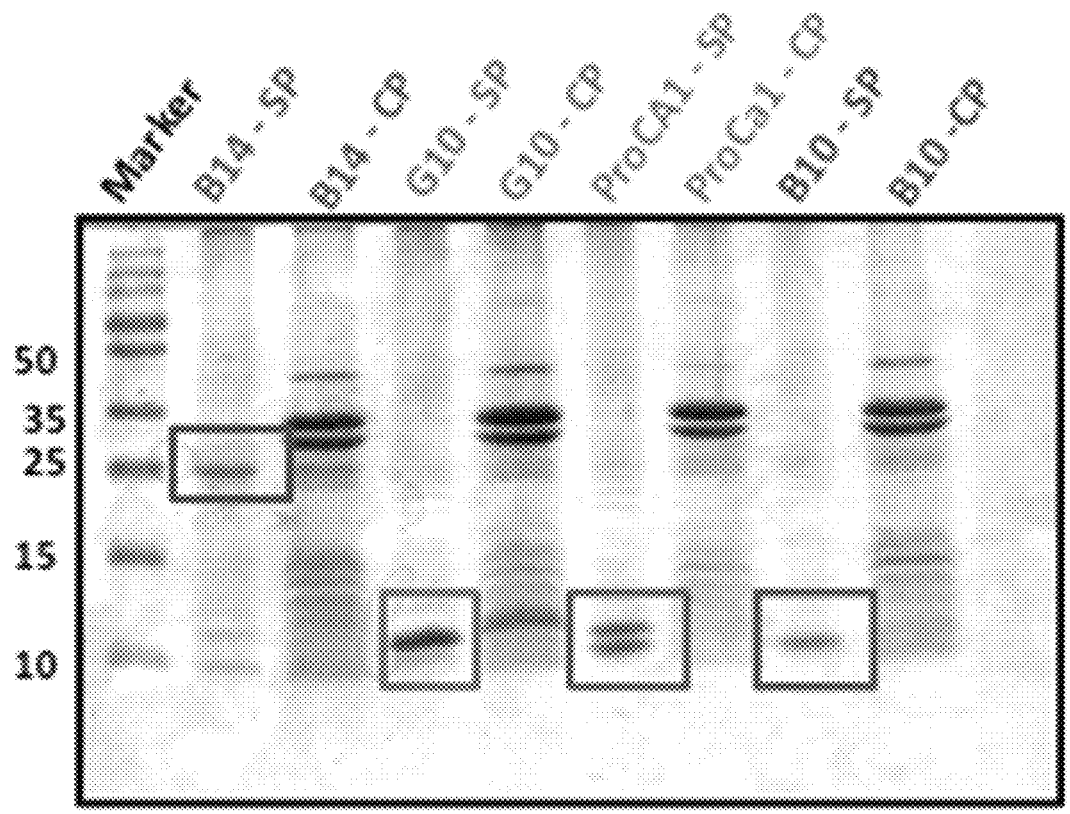
FIG. 69 shows an image of a protein gel demonstrating purification of various variants of ProCA1 by unfolding using 8M urea. After washed by detergent, bacteria pellet was dissolved in 8 M Urea. The supernatants (SP) and pellets (CP) in this solution were separated by centrifuge. The distribution of ProCA1.B14 (B14), ProCA1.B10 (B10) and ProCA1.G10 (G10) were visualized by SDS PAGE. The boxes indicate the band of these proteins.
Figure 70:
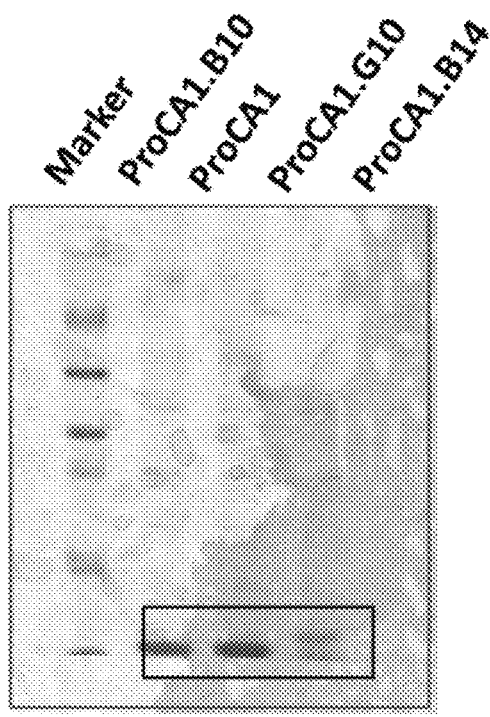
FIG. 70 shows an image of a protein gel demonstrating the purified of various variants of ProCA1 by unfolding methods.

ProCA1 was modified to generate ProCA1 variants. ProCA1.B10, ProCA1.G10, and ProCA1.B14 were generated by inserting 14 amino acid bombesin (B14), 10 amino acid bombesin (B10) and Gastrin releasing peptide (GRP) peptide (G10) in the middle of ProCA1 through flexible peptide linkers. FIG. 69 shows an image of a protein blot demonstrating purification of various variants of ProCA1 by unfolding using 8M urea. FIG. 70 shows an image of a protein gel demonstrating purification of various variants of ProCA1 by unfolding using 8M urea. FIG. 71 shows a table demonstrating the concentration of the purified ProCA (7E15) and the ProCA1.G10 and ProCA1.B10 variants.

Figure 72:
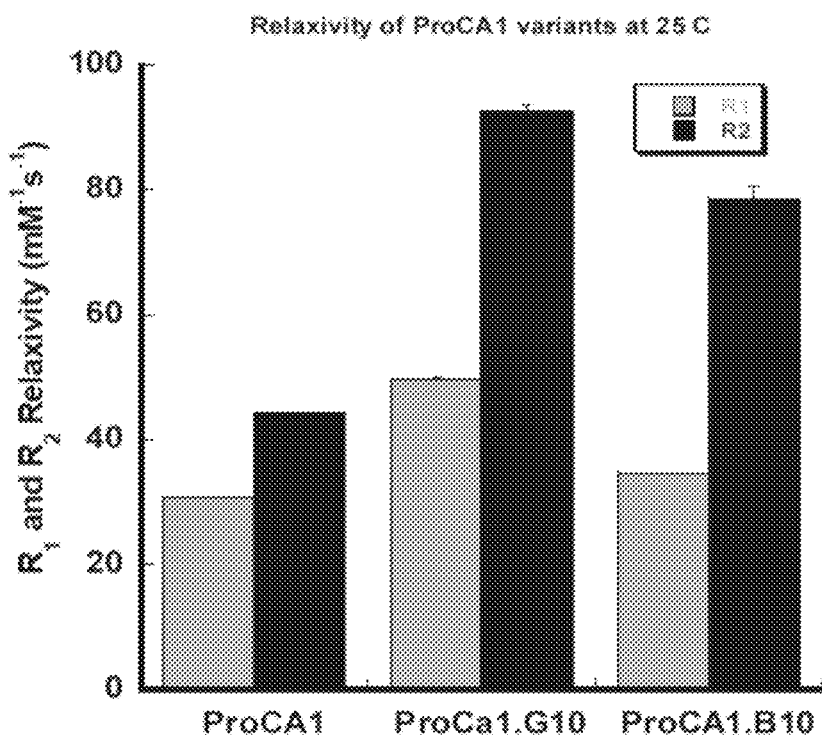
FIG. 72 shows a graph demonstrating relaxivity of ProCA1 variants at about 25° C.
Figure 73:
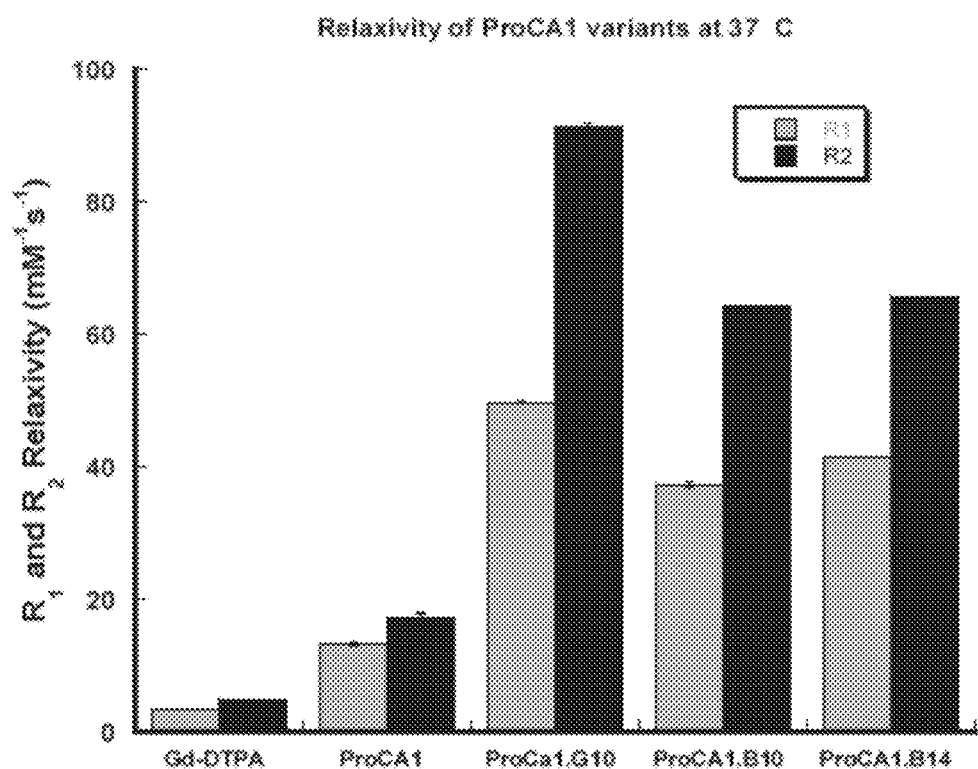
FIG. 73 shows a graph demonstrating relaxivity of ProCA1 variants at about 37° C.

The relaxivity of ProCA1 variants were analyzed as previously described for PSMA targeted ProCAs. FIG. 72 shows a graph demonstrating relaxivity of ProCA1 variants at about 25° C. FIG. 73 shows a graph demonstrating relaxivity of ProCA1 variants at about 37° C. Without being bound by theory, ProCAs have high relaixivity allow them to visualize subjects in vitro and in vivo by MRI.

Figures 74, 75:
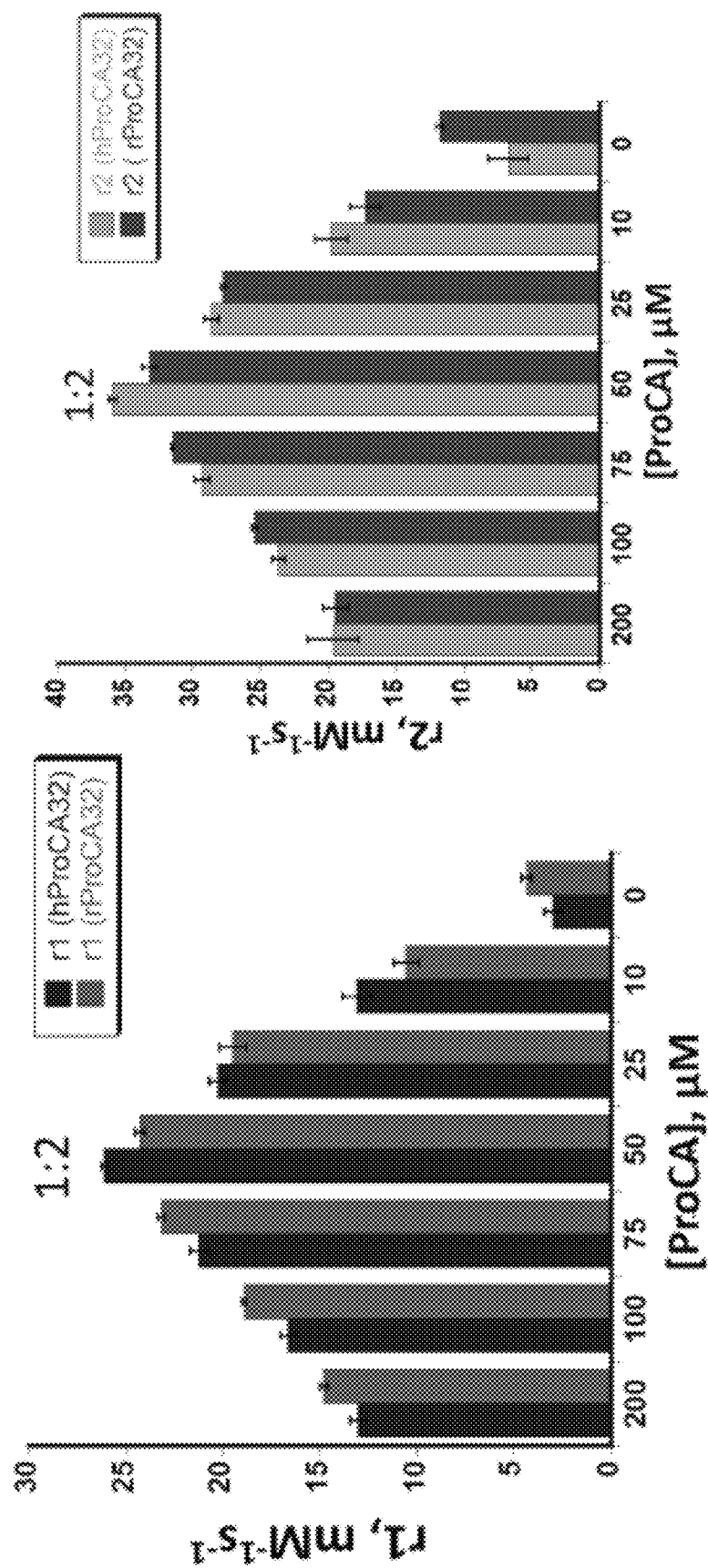
FIG. 74 shows a graph demonstrating r1 relaxivity of rat and human ProCA32.
FIG. 75 shows a graph demonstrating r2 relaxivity of rat and human ProCA32.

Example 8. ProCA32

α-Parvalbumin was modified with a S56D and F103W mutation to make a ProCA, which is referred to herein as ProCA32. ProCA32 was purified as previously described for PSMA targeted ProCAs. The relaxtivities of ProCA32 were examined as previously described for PSMA targeted ProCAs. FIG. 74 shows a graph demonstrating r1 relaxivity of rat and human ProCA32. FIG. 75 shows a graph demonstrating r2 relaxivity of rat and human ProCA32. the relaxivity of rat of human ProCA32 are similar.

Figure 77:
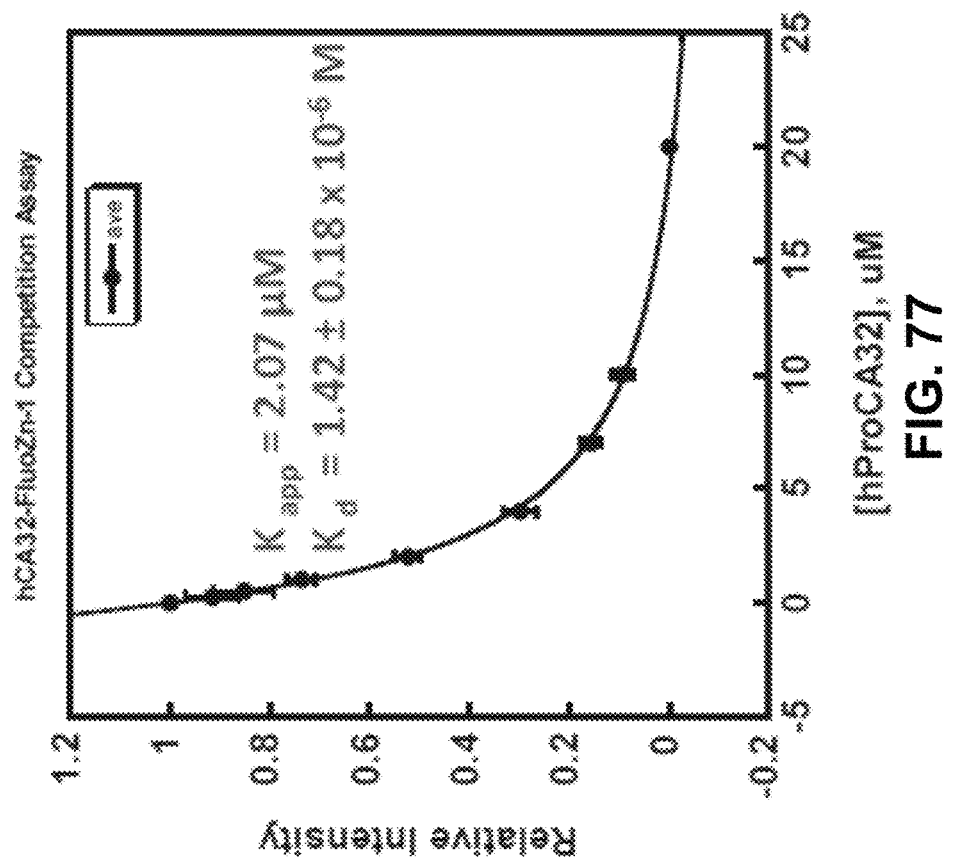
FIG. 77 shows a graph demonstrating results of an hCA32-FluoZn-1 competition assay.
Figure 76:
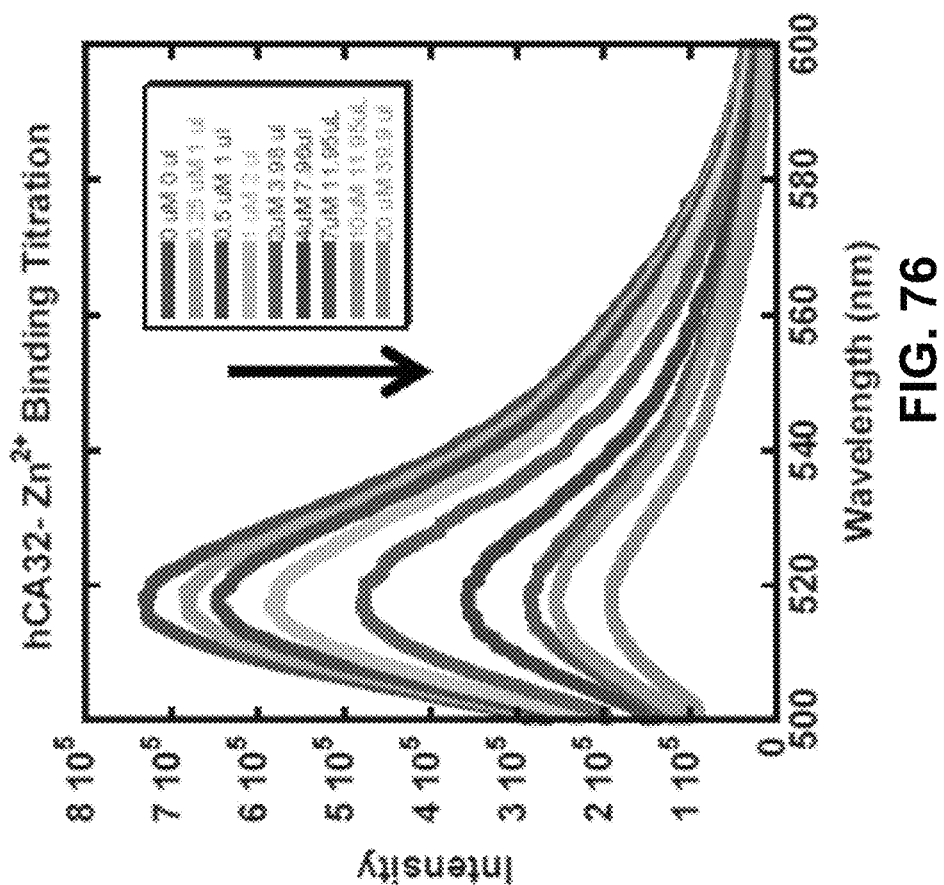
FIG. 76 shows a graph demonstrating hCA32 $Zn^{2+}$ binding titration.
Figure 79:
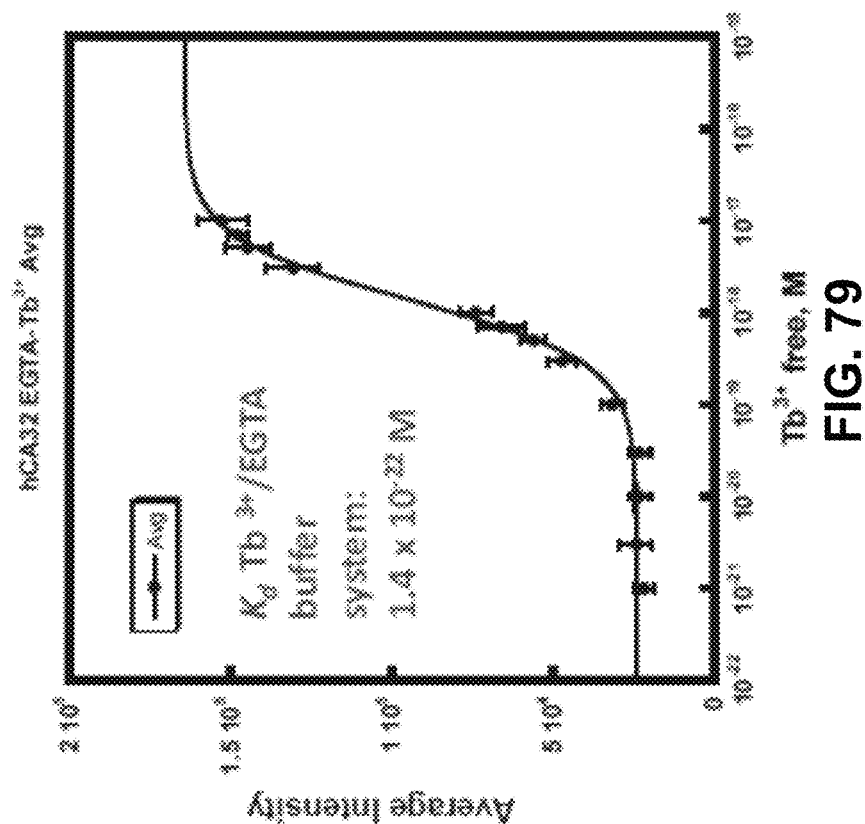
FIG. 79 shows a graph demonstrating hCA32 EGTA-$Tb^{3+}$ Avg.
Figure 78:
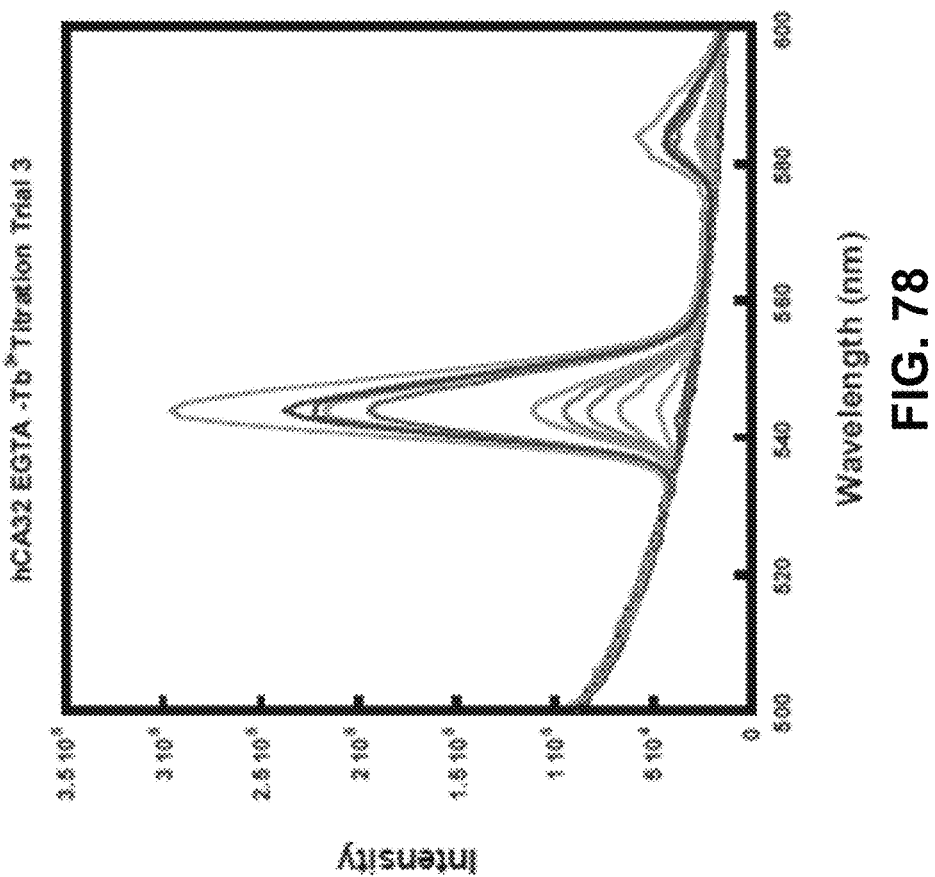
FIG. 78 shows a graph demonstrating results of an hCA32 EGTA $Tb^{3+}$ titration assay.
Figure 81:
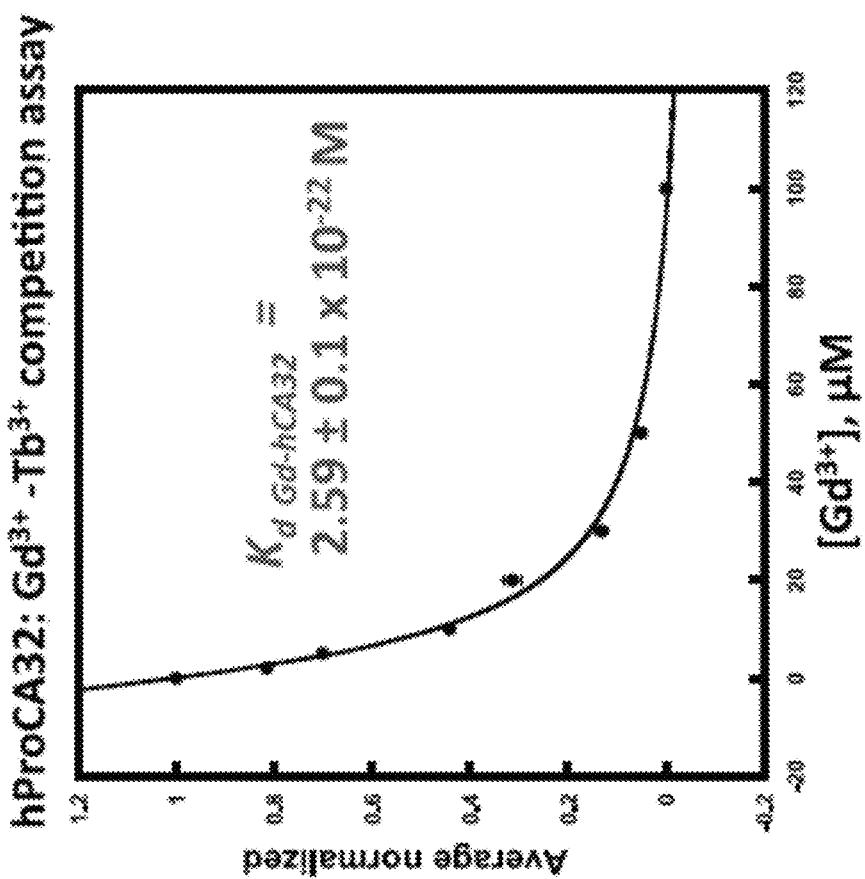
FIG. 81 shows a graph demonstrating results from a hProCA32: Gd3+-Tb3+ competition assay.
Figure 80:
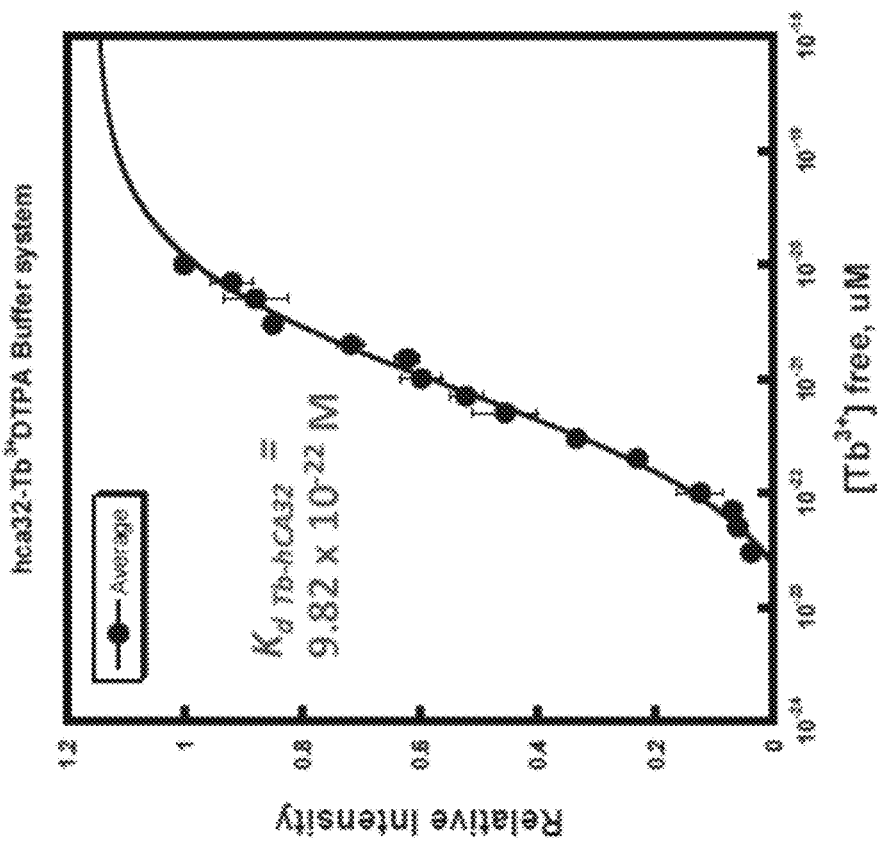
FIG. 80 shows a graph demonstrating hCA32-$Tb^{3+}$ DTPA buffer system.

The metal binding capabilities of ProCA32 were examined using the methods as previously described for PSMA targeted ProCAs. FIG. 76 shows a graph demonstrating hCA32 $Zn^{2+}$ binding titration. FIG. 77 shows a graph demonstrating results of an hCA32-FluoZn-1 competition assay. FIG. 78 shows a graph demonstrating results of an hCA32 EGTA $Tb^{3+}$ titration assay. FIG. 79 shows a graph demonstrating hCA32 EGTA-$Tb^{3+}$ Avg. FIG. 80 shows a graph demonstrating hCA32-$Tb^{3+}$ DTPA buffer system. FIG. 81 shows a graph demonstrating results from a hProCA32: Gd3+-Tb3+ competition assay. FIG. 82 shows a table demonstration various metal binding affinities for ProCA32 and hCA32. Without being bound by theory, these results indicate ProCA32 is stable for in vitro and in vivo applications.

Figure 83:
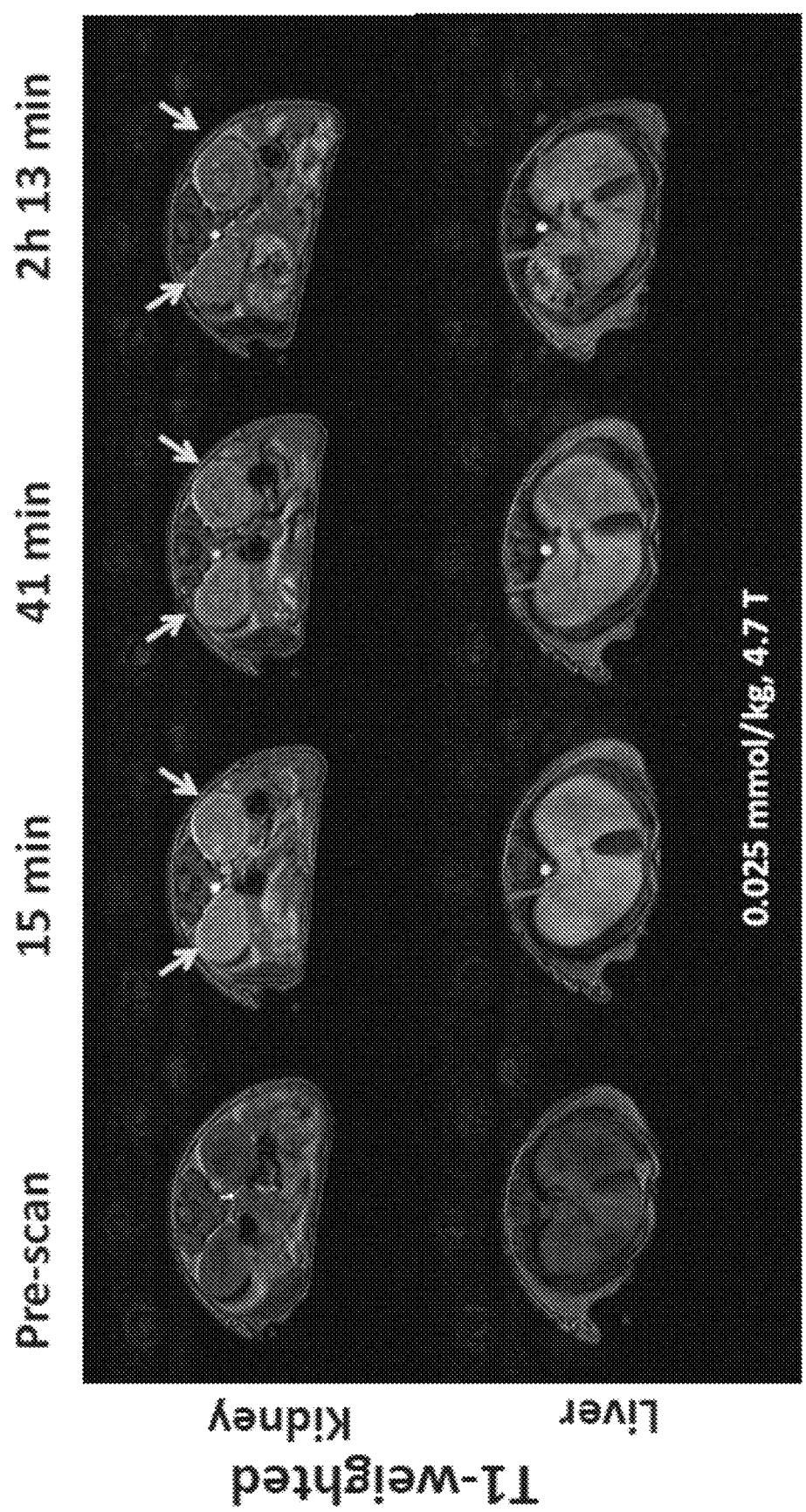
FIG. 83 shows T1 weighted images in liver and kidney of mice before and after administration of hProCA32.
Figure 84:
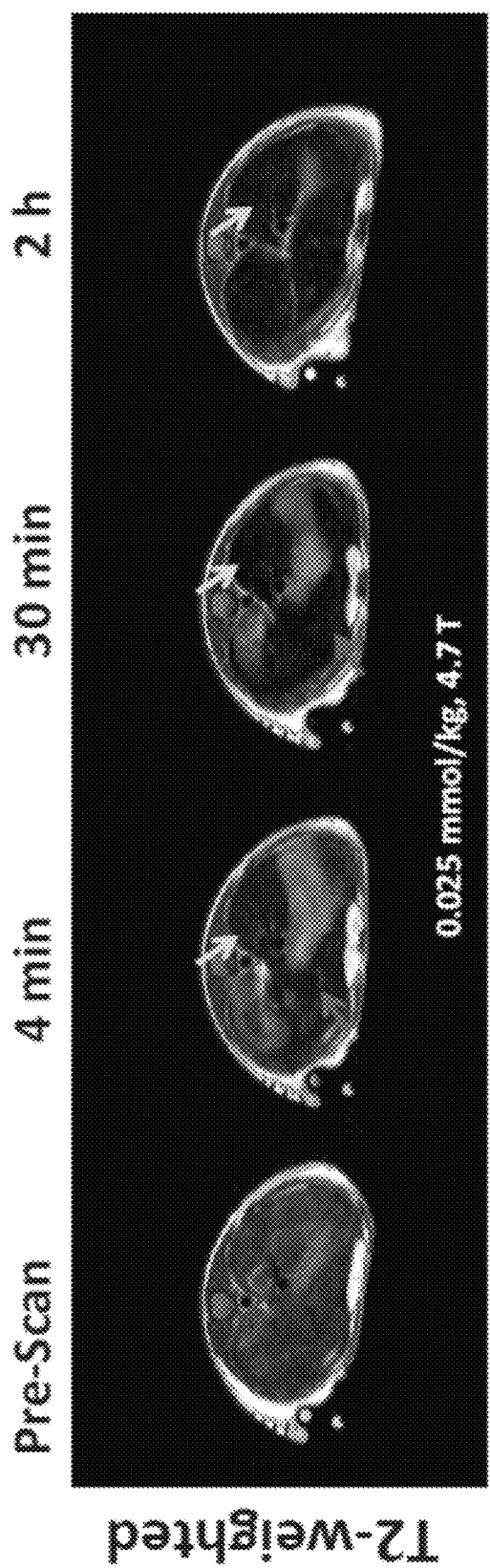
FIG. 84 shows T2 weighted images in liver and kidney of mice before and after administration of hProCA32.
Figure 85A:
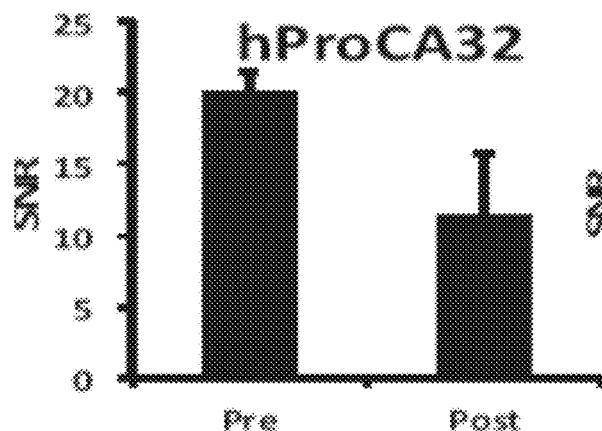
FIGS. 85A-85D show SNR of T1 (FIGS. 85C and 85D) and T2 (FIGS. 85A and 85B) weighted liver pre and post injection of hProCA32 or rat ProCA32.
Figure 85B:
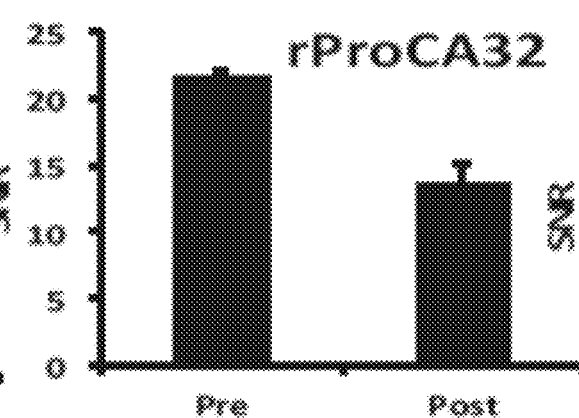
Figure 85C:
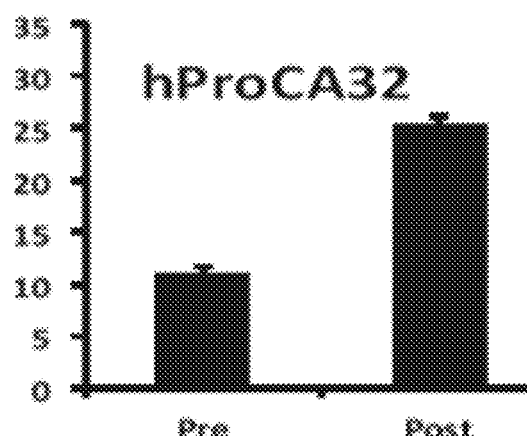
Figure 85D:
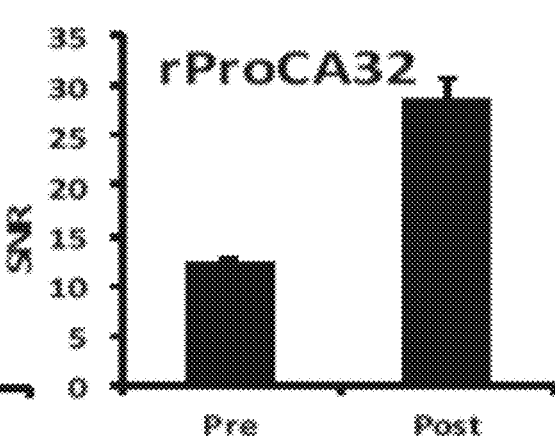

The ability of ProCA32 to function as a contrast agent was examined in vivo. Human ProCA32 were IV injected in mice to evaluate its in vivo capacity. MRI were collected before injection and different time points after injection. FIG. 83 shows T1 weighted images in liver and kidney of mice before and after administration of hProCA32. FIG. 84 shows T2 weighted images in liver and kidney of mice before and after administration of hProCA32. FIGS. 85A-85D show SNR of T1 (FIGS. 85C and 85D) and T2 (FIGS. 85A and 85B) weighted liver pre and post injection of hProCA32. Without being bound by theory, these results suggest human ProCA32 have the capacity to alter the MRI signal in both T1 weighted and T2 weighted MRI. It is also able to visualize the metastatic live tumor with a size less than 1 mm mice liver. hProCA32 can also be used to identify and evaluate other diseases in the liver.

Example 9

The targeted ProCAs can have a sequence that is 50-100% (or any range within) identical to any one of SEQ ID NOS:

CaMBom:
```
                                            SEQ ID NO: 70
ADQLTEEQIAEFKEAFSLFDKDGDGTITTKELGTVMRSLGQNPTEAELQD

MINEVDADGDGTIDFPEFLTMMARKMKDTGGNQWAVGHLMGGDSEEEIRE

AFRVFDKDGDGYISAAELRHVMTNLGEKLTDEEVDEMIREADIDGDGQVN

YEEFVQMMTAK
```

Example 10. Collagen, Liver Fibrosis, and Liver Cancer Targeted ProCAs

Collagen is the major fibrous protein in the extracellular matrix (ECM) and in connective tissue and it is the single most abundant protein in the body. There are at least 16 types of collagen, but 80-90 percent of the collagen in the body consists of types I, II, and III.

Collagen type I is one of the major diagnostic biomarker and therapeutic target for many chronic diseases including chronic liver diseases (e.g. liver fibrosis), different types of cancers and metastasis, heart failure, and pulmonary fibrosis. Early diagnosis of liver fibrosis will lead to effective treatment and can stop its further progression to major clinical consequences including cirrhosis and hepatocellular carcinoma (HCC) which affect large populations worldwide. Uveal melanoma, the most common primary intraocular tumor, has a 40% risk of metastasizing to the liver. Hepatic metastases, which occur in 95% of patients with uveal melanoma metastasis, result in death in almost all cases. To date, there is no reliable noninvasive imaging method for early detection and staging of fibrosis as well as primary liver cancer and hepatic metastases with high sensitivity and specificity. MRI has several unique advantages for monitoring slow progression and detection of fibrosis and metastasis with high resolution without using radiation, however, there is a pressing unmet medical need to develop MRI contrast agents with desired sensitivity and collagen specificity to overcome high heterogeneous liver background as well as proper in vivo properties and reduced toxicity.

Figure 87A:
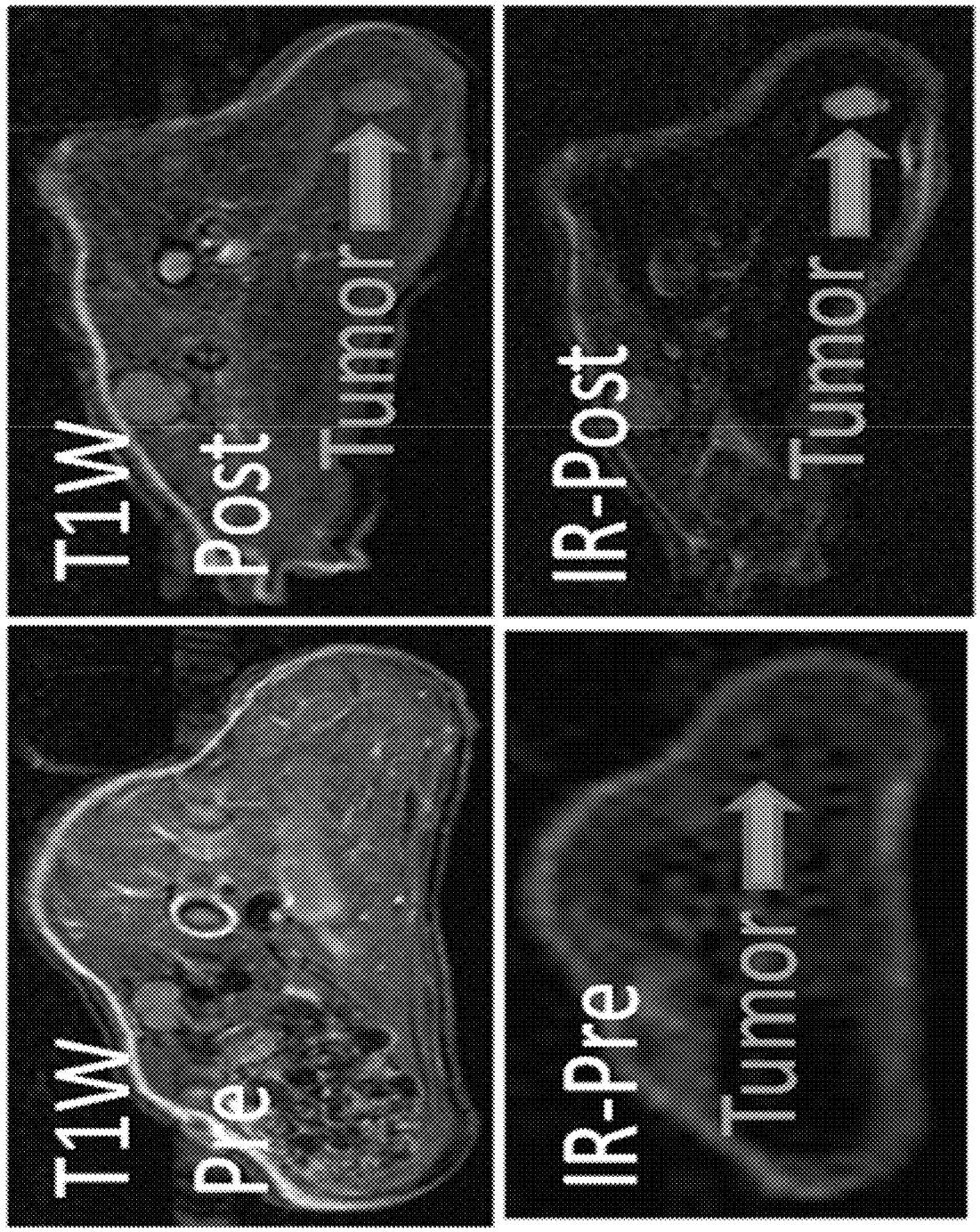
FIGS. 87A-B show images (FIGS. 87A and C-H) and a graph (FIG. 87B) demonstrating the tumor enhancement after injection of rProCA32.collagen with 6-fold enhancement in the relative contrast after injection using inversion recovery, $T_1$ and $T_2$-weighted sequence (FIGS. 87A-87B), stage II nodular metastatic melanoma to liver trichrome with associated blue patches of collagen (FIG. 87C), Stage II infiltrative pattern of melanoma metastasis to liver (FIG. 87D), (Collagen is highlighted in blue surrounding islands of melanoma), Collagen stained with picrosirius red in liver tissues shows different growth patterns with different collagen levels demonstrated by collagen proportionate area (CPA) (FIGS. 87E and 87F), Uveal melanoma tumor implanted into the liver (FIG. 87F), and IHC staining of liver tissue with tumor with rProCA32.collagen (red) shows heterogeneous distribution of the contrast agent in the liver with tumor (FIG. 87F).
Figure 87B:
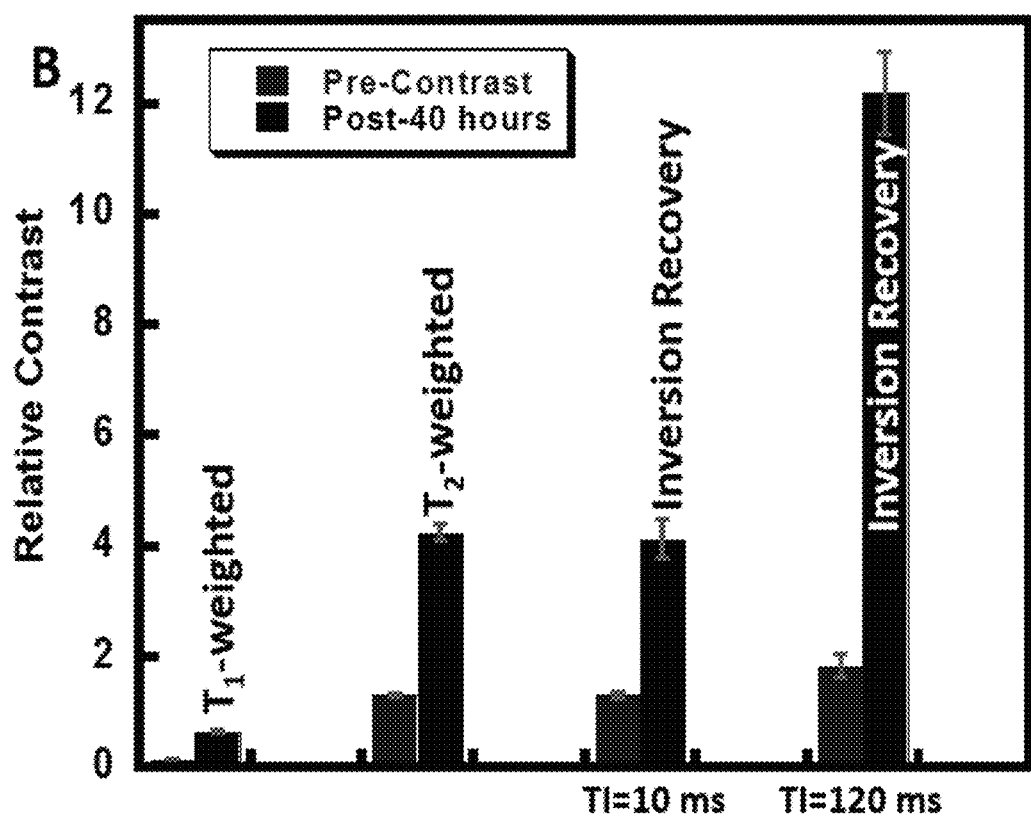

A protein-based MRI contrast agent, rat ProCA32.collagen (rProCA32.collagen) was designed that can have collagen type I targeting capability (parent targeting peptide in Table 2) at the C-terminal of rat ProCA32 with three Glycines as a flexible linker to diagnose and stage liver fibrosis and metastasis of uveal melanoma tumors in the liver. rProCA32.collagen exhibits the highest relaxivity values for $r_1$ and $r_2$ per $Gd^{3+}$ at both 1.5 and 7.0 T magnetic field strengths and are 14-20-fold higher than clinically used contrast agents. The uniqueness of both high $r_1$ and $r_2$ relaxivity values enables us to achieve both $T_1$ and T2 imaging after a single injection of rProCA32.collagen. More important, we can greatly improve dynamic range in detection with a 6-fold enhancement in the relative contrast for the implanted liver uveal melanoma tumor in mouse taken advantage of both relaxation property and imaging methodology. FIGS. 87A-87H summarizes the results. FIGS. 87A-87H. FIGS. 87A and 87B. Shows the tumor enhancement after injection of rProCA32.collagen with 6-fold enhancement in the relative contrast after injection using inversion recovery, $T_1$ and $T_2$-weighted sequence. FIG. 87C. Stage II nodular metastatic melanoma to liver trichrome with associated blue patches of collagen. FIG. 87D. Stage II infiltrative pattern of melanoma metastasis to liver. Collagen is highlighted in blue surrounding islands of melanoma. FIGS. 87E and 87F. Collagen stained with picrosirius red in liver tissues shows different growth patterns with different collagen levels demonstrated by collagen proportionate area (CPA). G. Uveal melanoma tumor implanted into the liver. FIG. 87H. IHC staining of liver tissue with tumor with rProCA32.collagen (red) shows heterogeneous distribution of the contrast agent in the liver with tumor.

Figure 88A:
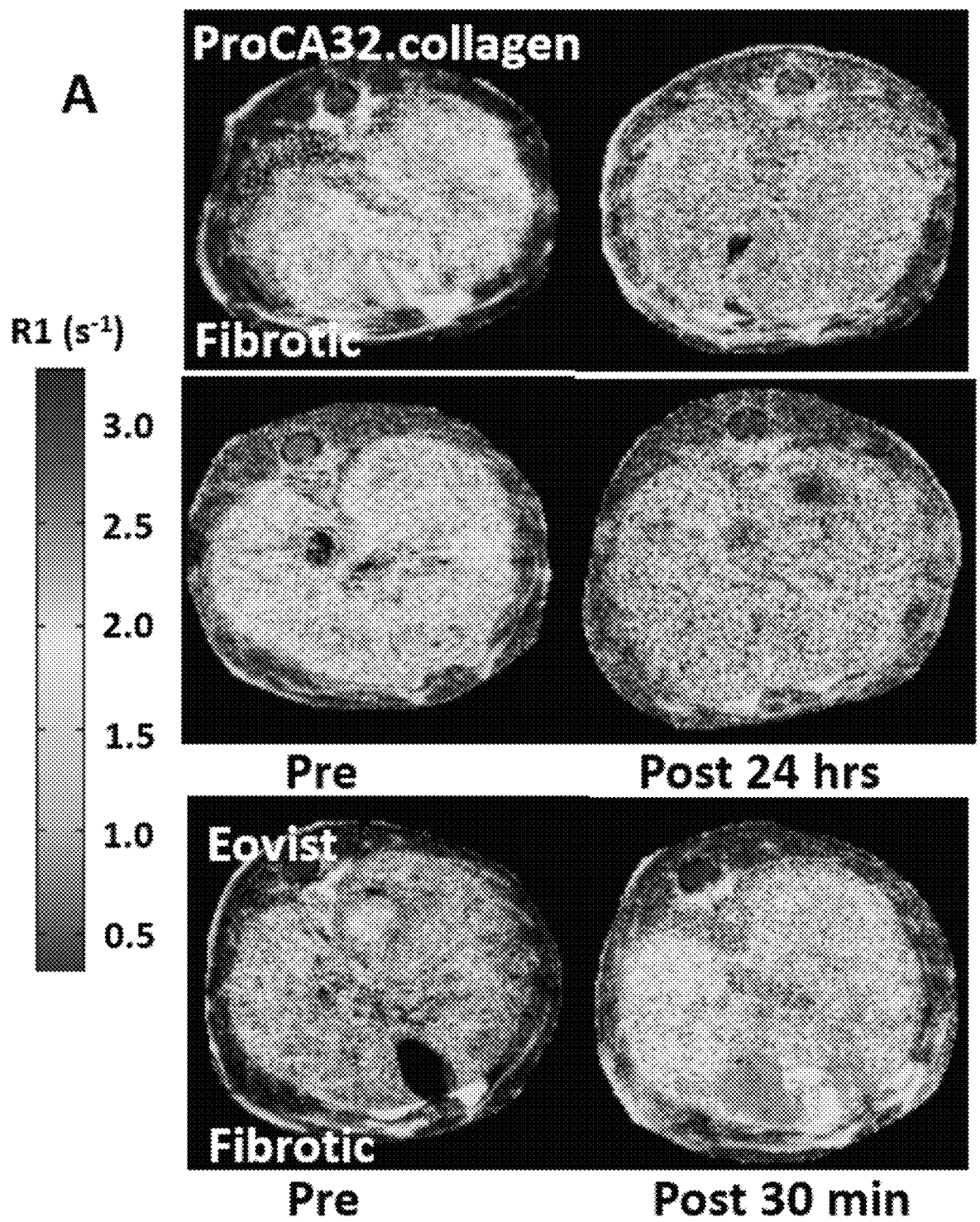

In addition, rProCA32.collagen can to detect early stage of mouse liver fibrosis with 6-fold increase in change in relaxation rate ($\Delta R1$) at 7.0 T compared to Eovist which has not been achieved using clinical contrast agents. Both liver metastasis and early stage liver fibrosis have been verified by histological analysis. It is further demonstrated that the addition of collagen type I targeting moiety does not reduce its strong metal binding affinity to $Gd^{3+}$ and $10^{11}$-fold higher selectivity towards $Gd^{3+}$ over $Zn^{2+}$ compared to Eovist which is very important for reducing metal toxicity. The development of collagen targeting contrast agent is expected to have broad applications in detection and staging of fibrosis in chronic diseases and liver metastasis from various types of cancer and probing heterogeneous microenvironment changes upon disease progression and treatment. FIGS. 88A-88H demonstrates a summary of the results collected for rProCA32.collagen. FIG. 88A. Demonstrates the R1 map of fibrotic and normal liver before and after injection of rProCA32.collagen (24 hours) and Eovist (30 min). FIG. 88B. R1 values of fibrotic and normal liver before and 24 hours after injection of rProCA32.collagen. FIG. 88C. Demonstrates the percent increase rate in R1 of normal and fibrotic liver before and after injection of rProCA32.collagen (24 hours) and Eovist (30 min and 24 hours). FIG. 88D. $\Delta R1$ of Eovist (30 min and 24 h post injection) and rProCA32.collagen (24 hours post injection) of fibrotic and normal liver. FIG. 88E. Representative Sirius Red histology of normal and FIG. 88F. fibrotic liver tissues. Based on NASH/CRN staging system: FIG. 88E is 0-Normal and FIG. 88F is 1A-Mild, zone 3, perisinusoidal. Both shown in FIGS. 88E and 88F were injected with rProCA32.collagen. The fibrotic liver which was injected with Eovist showed the same stage (1A-Mild or 3 based on Ishak). Based on collagen proportional area (CPA) analysis, the stage is 3 in Ishak system. FIGS. 88G and 88H. Immunofluorescence staining of fibrotic liver tissue with rProCA32.collagen and rProCA32 (red) and collagen type I (green) along with nucleus (blue). rProCA32.collagen interaction with collagen type I can only be seen in FIG. 88G in yellow.

In order to test the capability of rProCA32.collagen in detection of early liver fibrosis, BALB/c mice were injected with thioacetamide (TAA) twice a week to induce liver fibrosis for 12 weeks (i.p. injection), then TAA concentration increased gradually from 100 mg/kg to 200 mg/kg. Balb/c mice were fed with 10% alcohol in drinking water for 12 weeks. After 12 weeks of TAA treatment, mice were euthanized and livers were dissected for analysis.

For detailed MRI scans, four different time points were chosen to scan the entire fibrotic and normal liver after injection of rProCA32.collagen (100 µL, 5 mM) into tail vein of each mouse. T1 mapping MRI was used to image the fibrotic and normal liver in order to quantify T1 relaxation time and R1 relaxation rate for liver fibrosis detection. Three hours after injection of rProCA32.collagen, a significance enhancement was observed in R1 (decrease in T1) of normal liver compared to fibrotic liver. When the MRI scan was continued for 24 hours, R1 increased further for fibrotic liver however, it significantly decreased in normal liver which suggests that the targeted contrast agent is being washed away from normal liver, however it stays in fibrotic liver, therefore, 24 hours can be selected as the optimum time point in order to detect fibrotic liver from normal liver. As the scan continued the contrast agent was washed away further which resulted in decrease of R1 at 72 hours.

At the 24 hour time point, rProCA32.collagen was observed to exhibit the greatest targeting capability for detection of fibrotic liver. FIG. 88B shows the effect of contrast agent in T1 reduction and subsequent increase in R1. Non-targeted rat ProCA32 (rProCA32) and Eovist, a widely used clinical contrast agent were also tested for detection of liver fibrosis. After 3 hours post injection of rProCA32, fibrotic liver showed a considerable enhancement in R1 which was different from rProCA32.collagen. Since rProCA32 is a non-targeted agent, it functions differently from rProCA32.collagen which has the collagen type I targeting capability. rProCA32.collagen needs longer times (24 hours) to show its effect on fibrotic liver, and rProCA32 has shorter effect (3 hours). In addition, targeted contrast agent has more sensitivity than the non-targeted agent based on the R1 increase at 3 hour and 24 hour time points. Eovist with the same volume and concentration was used to image liver fibrosis, however, it failed to show the same liver enhancement, therefore it can be concluded that Eovist is not sensitive enough to detect early stage fibrosis.

Among the reported agents, rProCA32.collagen was observed to have the highest $r_1$ (21 mM-1s-1) and $r_2$ (108 $mM^{-1}\ s^{-1}$) at the high magnetic field 7.0 T. Thus, the developed contrast agent can be applied to both medical related low and high magnetic field strengths. First, rProCA32.collagen at lower dosage results in significant increase in R1 map at 7.0 T MRI while Eovist did not result in any significant R1 increase for stage 3 fibrotic mouse liver. Rat rProCA32.collagen exhibits approximately 3-10 fold higher $\Delta R1$ (3-24 hours after injection) than that of clinical contrast agent, Eovist. More importantly, rProCA32.collagen does not result in any significant increase in R1 and $\Delta R1$ for normal mouse suggesting that our contrast agent has strong targeting capability for collagen type I. Detailed histological analysis using Sirius Red staining and quantitative analysis of collagen proportional area (CPA) by Pathologist Dr. Brad Farris at Emory University confirmed the early stage of liver fibrosis (Mild-1A) based on the NASH/CRN scoring system, and stage 3 (Ishak scoring system).

In order to further confirm the targeting capability of rProCA32.collagen, each mouse was dissected and each organ was separated and dissolved in high concentration of nitric acid. Then ICP-OES was used to measure the $Gd^{3+}$ concentration with the help of $Gd^{3+}$ standards. The $Gd^{3+}$ concentration in spleen, heart, kidney and liver was measured with the instrument. Based on the measurements, fibrotic liver 72 hours after injection of rProCA32.collagen showed the highest $Gd^{3+}$ concentration among other organs which demonstrates the targeting capability of rProCA32.collagen towards collagen type I in fibrotic liver. Furthermore, fibrotic liver after injection of rProCA32 (non-targeted) also showed high amounts of $Gd^{3+}$ compared to other organs, however, it was much lower than the rProCA32.collagen. Overall, the $Gd^{3+}$ injection dosage per gram of tissue in fibrotic liver with ProCA32.collagen was approximately 2-fold higher than rProCA32 which shows the targeting capability of rProCA32.collagen (FIGS. 89A-89B).

We claim:

1. A protein contrast agent comprising:
   a parvalbumin polypeptide, wherein the parvalbumin polypeptide has the amino acid sequence comprising SEQ ID NO: 10, wherein the parvalbumin polypeptide contains a paramagnetic metal binding site consisting of one or more amino acid residues of SEQ ID NO: 10, and wherein the protein contrast agent further comprises a Prostate-Specific Membrane Antigen (PSMA)-targeting moiety directly fused or indirectly linked via a peptide linker to a terminus of the parvalbumin polypeptide.

2. The protein contrast agent of claim 1, further comprising a paramagnetic ion, wherein the paramagnetic ion is directly bound to at least one amino acid of the parvalbumin polypeptide.

3. The protein contrast agent of claim 2, wherein the paramagnetic ion is Gd3+.

4. The protein contrast agent of claim 1, wherein the protein contrast agent is PEGylated.

5. The protein contrast agent of claim 1, wherein the PSMA-targeting moiety has an amino acid sequence selected from SEQ ID Nos: 14-28.

6. A pharmaceutical composition comprising:
   the protein contrast agent according to claim 1; and
   a pharmaceutically acceptable carrier.

7. A method of generating a magnetic resonance image in a subject, the method comprising:
   administering an amount of the protein contrast agent according to claim 1 or a pharmaceutical formulation thereof to a subject; and
   imaging at least a portion of the subject using magnetic resonance imaging.

8. The protein contrast agent of claim 1, wherein the PSMA-targeting moiety is directly fused or indirectly linked via a peptide linker to the C terminus of the parvalbumin polypeptide.

* * * * *

SEQUENCE LISTING

```
<160> NUMBER OF SEQ ID NOS: 70

<210> SEQ ID NO 1
<211> LENGTH: 101
<212> TYPE: PRT
<213> ORGANISM: Artificial Sequence
<220> FEATURE:
<223> OTHER INFORMATION: a CD2 protein

<400> SEQUENCE: 1

Thr Asn Ala Leu Glu Thr Trp Gly Ala Leu Gly Gln Asp Ile Asn Leu
1               5                   10                  15

Asp Ile Pro Ser Phe Gln Met Ser Asp Ile Asp Asp Ile Lys Trp
            20                  25                  30

Glu Lys Thr Ser Asp Lys Lys Ile Ala Gln Phe Arg Lys Glu Lys
        35                  40                  45

Glu Thr Phe Lys Glu Lys Asp Thr Tyr Glu Leu Leu Lys Asn Gly Thr
    50                  55                  60

Leu Lys Ile Lys His Leu Lys Thr Asp Asp Gln Asp Ile Tyr Lys Val
65                  70                  75                  80

Ser Ile Tyr Asp Thr Lys Gly Lys Asn Val Leu Glu Lys Ile Phe Asp
                85                  90                  95

Leu Lys Ile Gln Glu
            100

<210> SEQ ID NO 2
<211> LENGTH: 101
<212> TYPE: PRT
<213> ORGANISM: Artificial Sequence
<220> FEATURE:
<223> OTHER INFORMATION: a CD2 protein

<400> SEQUENCE: 2

Thr Asn Ala Leu Glu Thr Trp Gly Ala Leu Gly Gln Asp Ile Glu Leu
1               5                   10                  15

Asn Ile Pro Ser Phe Gln Met Ser Asp Asp Ile Asp Asp Ile Lys Trp
            20                  25                  30

Glu Lys Thr Ser Asp Lys Lys Ile Ala Gln Phe Arg Lys Glu Lys
        35                  40                  45

Glu Thr Phe Lys Glu Lys Asp Thr Tyr Glu Leu Asp Lys Asn Gly Asp
    50                  55                  60

Leu Asp Ile Lys His Leu Lys Thr Asp Asp Gln Asp Ile Tyr Lys Val
65                  70                  75                  80

Ser Ile Tyr Asp Thr Lys Gly Lys Asn Val Leu Glu Lys Ile Phe Asp
                85                  90                  95

Leu Lys Ile Gln Glu
            100
```

```
<210> SEQ ID NO 3
<211> LENGTH: 101
<212> TYPE: PRT
<213> ORGANISM: Artificial Sequence
<220> FEATURE:
<223> OTHER INFORMATION: a  CD2 potein

<400> SEQUENCE: 3

Gly Ser Arg Asp Ser Gly Thr Val Trp Gly Ala Leu Gly His Gly Ile
1               5                   10                  15

Glu Leu Asn Ile Pro Asn Phe Gln Met Thr Asp Asp Ile Asp Glu Val
                20                  25                  30

Arg Trp Glu Arg Gly Ser Thr Leu Val Ala Glu Phe Lys Arg Lys Met
            35                  40                  45

Lys Pro Phe Leu Lys Ser Gly Ala Phe Glu Ile Asp Ala Asn Gly Asp
        50                  55                  60

Leu Asp Ile Lys Asn Leu Thr Arg Asp Asp Ser Gly Thr Tyr Asn Val
65                  70                  75                  80

Thr Val Tyr Ser Thr Asn Gly Thr Arg Ile Leu Asn Lys Ala Leu Asp
                85                  90                  95

Leu Arg Ile Leu Glu
            100

<210> SEQ ID NO 4
<211> LENGTH: 123
<212> TYPE: PRT
<213> ORGANISM: Artificial Sequence
<220> FEATURE:
<223> OTHER INFORMATION: ProCA1.B14

<400> SEQUENCE: 4

Met Arg Asp Ser Gly Thr Val Trp Gly Ala Leu Gly His Gly Ile Glu
1               5                   10                  15

Leu Asn Ile Pro Asn Phe Gln Met Thr Asp Asp Ile Asp Glu Val Arg
                20                  25                  30

Trp Glu Arg Gly Ser Thr Leu Val Ala Glu Phe Lys Arg Lys Met Lys
            35                  40                  45

Pro Phe Leu Lys Ser Gly Gly Ser Gly Gly Glu Gln Arg Leu Gly Asn
        50                  55                  60

Gln Trp Ala Val Gly His Leu Met Gly Gly Ser Gly Gly Ala Phe Glu
65                  70                  75                  80

Ile Asp Ala Asn Gly Asp Leu Asp Ile Lys Asn Leu Thr Arg Asp Asp
                85                  90                  95

Ser Gly Thr Tyr Asn Val Thr Val Tyr Ser Thr Asn Gly Thr Arg Ile
                100                 105                 110

Leu Asn Lys Ala Leu Asp Leu Arg Ile Leu Glu
            115                 120

<210> SEQ ID NO 5
<211> LENGTH: 119
<212> TYPE: PRT
<213> ORGANISM: Artificial Sequence
<220> FEATURE:
<223> OTHER INFORMATION: ProCA1.B10

<400> SEQUENCE: 5

Met Arg Asp Ser Gly Thr Val Trp Gly Ala Leu Gly His Gly Ile Glu
1               5                   10                  15

Leu Asn Ile Pro Asn Phe Gln Met Thr Asp Asp Ile Asp Glu Val Arg
```

```
                    20                  25                  30

Trp Glu Arg Gly Ser Thr Leu Val Ala Glu Phe Lys Arg Lys Met Lys
            35                  40                  45

Pro Phe Leu Lys Ser Gly Gly Ser Gly Gly Gly Asn Gln Trp Ala Val
        50                  55                  60

Gly His Leu Met Gly Gly Ser Gly Gly Ala Phe Glu Ile Asp Ala Asn
 65                  70                  75                  80

Gly Asp Leu Asp Ile Lys Asn Leu Thr Arg Asp Asp Ser Gly Thr Tyr
                    85                  90                  95

Asn Val Thr Val Tyr Ser Thr Asn Gly Thr Arg Ile Leu Asn Lys Ala
                100                 105                 110

Leu Asp Leu Arg Ile Leu Glu
            115

<210> SEQ ID NO 6
<211> LENGTH: 119
<212> TYPE: PRT
<213> ORGANISM: Artificial Sequence
<220> FEATURE:
<223> OTHER INFORMATION: ProCA1.G10

<400> SEQUENCE: 6

Met Arg Asp Ser Gly Thr Val Trp Gly Ala Leu Gly His Gly Ile Glu
 1               5                  10                  15

Leu Asn Ile Pro Asn Phe Gln Met Thr Asp Asp Ile Asp Glu Val Arg
                    20                  25                  30

Trp Glu Arg Gly Ser Thr Leu Val Ala Glu Phe Lys Arg Lys Met Lys
            35                  40                  45

Pro Phe Leu Lys Ser Gly Gly Ser Gly Gly Gly Asn His Trp Ala Val
        50                  55                  60

Gly His Leu Met Gly Gly Ser Gly Gly Ala Phe Glu Ile Asp Ala Asn
 65                  70                  75                  80

Gly Asp Leu Asp Ile Lys Asn Leu Thr Arg Asp Asp Ser Gly Thr Tyr
                    85                  90                  95

Asn Val Thr Val Tyr Ser Thr Asn Gly Thr Arg Ile Leu Asn Lys Ala
                100                 105                 110

Leu Asp Leu Arg Ile Leu Glu
            115

<210> SEQ ID NO 7
<211> LENGTH: 100
<212> TYPE: PRT
<213> ORGANISM: Artificial Sequence
<220> FEATURE:
<223> OTHER INFORMATION: rProCA1(rat ProCA1)

<400> SEQUENCE: 7

Met Arg Asp Ser Gly Thr Val Trp Gly Ala Leu Gly His Gly Ile Glu
 1               5                  10                  15

Leu Asn Ile Pro Asn Phe Gln Met Thr Asp Asp Ile Asp Glu Val Arg
                    20                  25                  30

Trp Glu Arg Gly Ser Thr Leu Val Ala Glu Phe Lys Arg Lys Met Lys
            35                  40                  45

Pro Phe Leu Lys Ser Gly Ala Phe Glu Ile Asp Ala Asn Gly Asp Leu
        50                  55                  60

Asp Ile Lys Asn Leu Thr Arg Asp Asp Ser Gly Thr Tyr Asn Val Thr
 65                  70                  75                  80
```

```
Val Tyr Ser Thr Asn Gly Thr Arg Ile Leu Asn Lys Ala Leu Asp Leu
                85                  90                  95

Arg Ile Leu Glu
            100

<210> SEQ ID NO 8
<211> LENGTH: 98
<212> TYPE: PRT
<213> ORGANISM: Artificial Sequence
<220> FEATURE:
<223> OTHER INFORMATION: ProCA1 human ProCA1; hProCA1

<400> SEQUENCE: 8

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Ala Phe Glu Ile Asp Ala Asn Gly Asp Leu Asp Ile
    50                  55                  60

Lys Asn Leu Thr Arg Asp Asp Ser Gly Thr Tyr Asn Val Thr Val Tyr
65                  70                  75                  80

Ser Thr Asn Gly Thr Arg Ile Leu Asn Lys Ala Leu Asp Leu Arg Ile
                85                  90                  95

Leu Glu

<210> SEQ ID NO 9
<211> LENGTH: 110
<212> TYPE: PRT
<213> ORGANISM: Artificial Sequence
<220> FEATURE:
<223> OTHER INFORMATION: rProCA32 (rat ProCA32)

<400> SEQUENCE: 9

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser
            100                 105                 110

<210> SEQ ID NO 10
<211> LENGTH: 110
<212> TYPE: PRT
<213> ORGANISM: Artificial Sequence
<220> FEATURE:
<223> OTHER INFORMATION: ProCA32 (human ProCA32)

<400> SEQUENCE: 10

Met Ser Met Thr Asp Leu Leu Asn Ala Glu Asp Ile Lys Lys Ala Val
1               5                   10                  15
```

Gly Ala Phe Ala Thr Asp Ser Phe Asp His Lys Lys Phe Phe Gln
            20                  25                  30

Met Val Gly Leu Lys Lys Ser Ala Asp Val Lys Val Phe
            35                  40                  45

His Met Leu Asp Lys Asp Lys Asp Gly Phe Ile Glu Glu Asp Glu Leu
 50                  55                  60

Gly Phe Ile Leu Lys Gly Phe Ser Pro Asp Ala Arg Asp Leu Ser Ala
 65                  70                  75                  80

Lys Glu Thr Lys Met Leu Met Ala Ala Gly Asp Lys Asp Gly Asp Gly
                 85                  90                  95

Lys Ile Gly Val Glu Glu Trp Ser Thr Leu Val Ala Glu Ser
                100                 105                 110

<210> SEQ ID NO 11
<211> LENGTH: 101
<212> TYPE: PRT
<213> ORGANISM: Artificial Sequence
<220> FEATURE:
<223> OTHER INFORMATION: Rat CD2 domain 1

<400> SEQUENCE: 11

Thr Asn Ala Leu Glu Thr Trp Gly Ala Leu Gly Gln Asp Ile Asn Leu
 1               5                  10                  15

Asp Ile Pro Ser Phe Gln Met Ser Asp Asp Ile Asp Asp Ile Lys Trp
            20                  25                  30

Glu Lys Thr Ser Asp Lys Lys Lys Ile Ala Gln Phe Arg Lys Glu Lys
            35                  40                  45

Glu Thr Phe Lys Glu Lys Asp Thr Tyr Glu Leu Leu Lys Asn Gly Thr
 50                  55                  60

Leu Lys Ile Lys His Leu Lys Thr Asp Asp Gln Asp Ile Tyr Lys Val
 65                  70                  75                  80

Ser Ile Tyr Asp Thr Lys Gly Lys Asn Val Leu Glu Lys Ile Phe Asp
                 85                  90                  95

Leu Lys Ile Gln Glu
            100

<210> SEQ ID NO 12
<211> LENGTH: 101
<212> TYPE: PRT
<213> ORGANISM: Artificial Sequence
<220> FEATURE:
<223> OTHER INFORMATION: Rat CD2 domain

<400> SEQUENCE: 12

Thr Asn Ala Leu Glu Thr Trp Gly Ala Leu Gly Gln Asp Ile Glu Leu
 1               5                  10                  15

Asp Asn Pro Ser Phe Gln Met Ser Asp Asp Ile Asp Asp Ile Lys Trp
            20                  25                  30

Glu Lys Thr Ser Asp Lys Lys Lys Ile Ala Gln Phe Arg Lys Glu Lys
            35                  40                  45

Glu Thr Phe Lys Glu Lys Asp Thr Tyr Glu Leu Asp Lys Asn Gly Asp
 50                  55                  60

Leu Asp Ile Lys His Leu Lys Thr Asp Asp Gln Asp Ile Tyr Lys Val
 65                  70                  75                  80

Ser Ile Tyr Asp Thr Lys Gly Lys Asn Val Leu Glu Lys Ile Phe Asp
                 85                  90                  95

Leu Lys Ile Gln Glu

```
<210> SEQ ID NO 13
<211> LENGTH: 75
<212> TYPE: PRT
<213> ORGANISM: Artificial Sequence
<220> FEATURE:
<223> OTHER INFORMATION: ProCA2

<400> SEQUENCE: 13

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asp Gly Thr Ile Asp
    50                  55                  60

Phe Pro Glu Phe Leu Thr Met Met Ala Arg Lys
65                  70                  75

<210> SEQ ID NO 14
<211> LENGTH: 12
<212> TYPE: PRT
<213> ORGANISM: Artificial Sequence
<220> FEATURE:
<223> OTHER INFORMATION: a PSMA targeting moiety

<400> SEQUENCE: 14

Trp Gln Pro Asp Thr Ala His His Trp Ala Thr Leu
1               5                   10

<210> SEQ ID NO 15
<211> LENGTH: 18
<212> TYPE: PRT
<213> ORGANISM: Artificial Sequence
<220> FEATURE:
<223> OTHER INFORMATION: a PSMA targeting moiety

<400> SEQUENCE: 15

Ala Glu Trp Trp Gln Pro Asp Thr Ala His His Trp Ala Thr Leu Pro
1               5                   10                  15

Asp Pro

<210> SEQ ID NO 16
<211> LENGTH: 15
<212> TYPE: PRT
<213> ORGANISM: Artificial Sequence
<220> FEATURE:
<223> OTHER INFORMATION: a PSMA targeting moiety

<400> SEQUENCE: 16

Ser His Ser Phe Ser Val Gly Ser Gly Asp His Ser Pro Phe Thr
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: a PSMA targeting moiety

<400> SEQUENCE: 17

Gly Arg Phe Thr Gly Gly Thr Gly Arg Leu Leu Arg Ile Ser
```

```
<210> SEQ ID NO 18
<211> LENGTH: 15
<212> TYPE: PRT
<213> ORGANISM: Artificial Sequence
<220> FEATURE:
<223> OTHER INFORMATION: a PSMA targeting moiety

<400> SEQUENCE: 18

Leu Ser Phe Phe Ser Cys Trp Leu Arg Arg Ser Phe Ser Leu Thr
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: a PSMA targeting moeity

<400> SEQUENCE: 19

Leu Pro Ile Phe Lys Val Asp Phe Gly Asp His Ser Pro Phe Thr
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: a PSMA targeting moiety

<400> SEQUENCE: 20

Ala Arg Met Phe Leu Leu Phe Leu Met Ala Cys Ile Gly Cys Tyr
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: a PSMA targeting moiety

<400> SEQUENCE: 21

Ser His Ser Phe Ser Val Gly Ser Gly Asp Ser Pro Phe Thr
1               5                   10

<210> SEQ ID NO 22
<211> LENGTH: 15
<212> TYPE: PRT
<213> ORGANISM: Artificial Sequence
<220> FEATURE:
<223> OTHER INFORMATION: a PSMA targeting moiety

<400> SEQUENCE: 22

Ser His Ser Phe Ser Val Gly Ser Gly Ser Gly Asp His Ser Pro
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: a PSMA targeting moiety

<400> SEQUENCE: 23

Glu Val Pro Arg Leu Ser Leu Leu Ala Val Phe Leu Val Val Met
1               5                   10                  15
```

<210> SEQ ID NO 24
<211> LENGTH: 15
<212> TYPE: PRT
<213> ORGANISM: Artificial Sequence
<220> FEATURE:
<223> OTHER INFORMATION: a PSMA targeting moiety

<400> SEQUENCE: 24

Glu Val Pro Arg Leu Ser Leu Leu Ala Val Phe Leu Cys Asn Gly
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: a PSMA targeting moiety

<400> SEQUENCE: 25

Glu Val Pro Arg Leu Ser Leu Leu Ala Val Phe Leu Val Ala Asn
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: a PSMA targeting moiety

<400> SEQUENCE: 26

Gly Arg Phe Leu Thr Gly Gly Thr Gly Arg Leu Leu Arg Ile Ser
1               5                   10                  15

<210> SEQ ID NO 27
<211> LENGTH: 18
<212> TYPE: PRT
<213> ORGANISM: Artificial Sequence
<220> FEATURE:
<223> OTHER INFORMATION: a PSMA targeting moiety

<400> SEQUENCE: 27

Met Ala Glu Trp Gln Pro Asp Thr Ala His His Trp Ala Thr Leu Pro
1               5                   10                  15

Asp Pro

<210> SEQ ID NO 28
<211> LENGTH: 14
<212> TYPE: PRT
<213> ORGANISM: Artificial Sequence
<220> FEATURE:
<223> OTHER INFORMATION: a PSMA targeting moiety

<400> SEQUENCE: 28

Ser His Ser Phe Ser Val Gly Ser Gly Asp Gly Ser Pro Phe
1               5                   10

<210> SEQ ID NO 29
<211> LENGTH: 25
<212> TYPE: PRT
<213> ORGANISM: Artificial Sequence
<220> FEATURE:
<223> OTHER INFORMATION: a VEGFR2 targeting moiety 1

<400> SEQUENCE: 29

Gly Asp Ser Arg Val Cys Trp Glu Asp Ser Trp Gly Gly Glu Val Cys

```
1               5                   10                  15
Phe Arg Tyr Asp Pro Gly Gly Gly Lys
            20                  25

<210> SEQ ID NO 30
<211> LENGTH: 22
<212> TYPE: PRT
<213> ORGANISM: Artificial Sequence
<220> FEATURE:
<223> OTHER INFORMATION: a VEGFR2 targeting moiety

<400> SEQUENCE: 30

Ala Gly Pro Lys Trp Cys Glu Glu Asp Trp Tyr Tyr Cys Met Ile Thr
1               5                   10                  15
Gly Thr Gly Gly Gly Lys
            20

<210> SEQ ID NO 31
<211> LENGTH: 22
<212> TYPE: PRT
<213> ORGANISM: Artificial Sequence
<220> FEATURE:
<223> OTHER INFORMATION: a VEGFR2 targeting moiety

<400> SEQUENCE: 31

Ala Gly Pro Thr Trp Cys Glu Asp Asp Trp Tyr Tyr Cys Trp Leu Pro
1               5                   10                  15
Gly Thr Gly Gly Gly Lys
            20

<210> SEQ ID NO 32
<211> LENGTH: 50
<212> TYPE: PRT
<213> ORGANISM: Artificial Sequence
<220> FEATURE:
<223> OTHER INFORMATION: Homo-bivalent VEGFR2 (targeting moiety 1) +
      VEGFR2 (targeting moiety 1)

<400> SEQUENCE: 32

Gly Asp Ser Arg Val Cys Trp Glu Asp Ser Trp Gly Gly Glu Val Cys
1               5                   10                  15
Phe Arg Tyr Asp Pro Gly Gly Gly Lys Gly Asp Ser Arg Val Cys Trp
            20                  25                  30
Glu Asp Ser Trp Gly Gly Glu Val Cys Phe Arg Tyr Asp Pro Gly Gly
        35                  40                  45
Gly Lys
    50

<210> SEQ ID NO 33
<211> LENGTH: 44
<212> TYPE: PRT
<213> ORGANISM: Artificial Sequence
<220> FEATURE:
<223> OTHER INFORMATION: Homo-bivalent VEGFR2 (targeting moiety 3) +
      VEGFR2 (targeting moiety 3)

<400> SEQUENCE: 33

Ala Gly Pro Thr Trp Cys Glu Asp Asp Trp Tyr Tyr Cys Trp Leu Pro
1               5                   10                  15
Gly Thr Gly Gly Gly Lys Ala Gly Pro Thr Trp Cys Glu Asp Asp Trp
            20                  25                  30
Tyr Tyr Cys Trp Leu Pro Gly Thr Gly Gly Gly Lys
        35                  40
```

<210> SEQ ID NO 34
<211> LENGTH: 47
<212> TYPE: PRT
<213> ORGANISM: Artificial Sequence
<220> FEATURE:
<223> OTHER INFORMATION: Hetero-bivalent VEGFR2 (targeting moiety 1) +
      VEGFR2 (targeting moiety 2)

<400> SEQUENCE: 34

Gly Asp Ser Arg Val Cys Trp Glu Asp Ser Trp Gly Gly Glu Val Cys
1               5                   10                  15

Phe Arg Tyr Asp Pro Gly Gly Gly Lys Ala Gly Pro Lys Trp Cys Glu
            20                  25                  30

Glu Asp Trp Tyr Tyr Cys Met Ile Thr Gly Thr Gly Gly Lys
        35                  40                  45

<210> SEQ ID NO 35
<211> LENGTH: 47
<212> TYPE: PRT
<213> ORGANISM: Artificial Sequence
<220> FEATURE:
<223> OTHER INFORMATION: Hetero-bivalent VEGFR2 (targeting moiety 1) +
      VEGFR2 (targeting moiety 3)

<400> SEQUENCE: 35

Gly Asp Ser Arg Val Cys Trp Glu Asp Ser Trp Gly Gly Glu Val Cys
1               5                   10                  15

Phe Arg Tyr Asp Pro Gly Gly Gly Lys Ala Gly Pro Thr Trp Cys Glu
            20                  25                  30

Asp Asp Trp Tyr Tyr Cys Trp Leu Pro Gly Thr Gly Gly Lys
        35                  40                  45

<210> SEQ ID NO 36
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 36

Leu Gly Ala Ser Trp His Arg Pro Asp Lys Cys Cys Leu Gly Tyr Gln
1               5                   10                  15

Lys Arg Pro Leu Pro
            20

<210> SEQ ID NO 37
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 37

Ala Gly Ala Ser Trp His Arg Pro Asp Lys Cys Cys Leu Gly Tyr Gln
1               5                   10                  15

Lys Arg Pro Leu Pro
            20

<210> SEQ ID NO 38
<211> LENGTH: 21
<212> TYPE: PRT
<213> ORGANISM: Artificial Sequence
<220> FEATURE:

<223> OTHER INFORMATION: a CXCR4 targeting moiety

<400> SEQUENCE: 38

Leu Gly Ala Ser Ala His Arg Pro Asp Lys Cys Cys Leu Gly Tyr Gln
1               5                   10                  15

Lys Arg Pro Leu Pro
            20

<210> SEQ ID NO 39
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 39

Leu Gly Ala Ser Trp His Ala Pro Asp Lys Cys Cys Leu Gly Tyr Gln
1               5                   10                  15

Lys Arg Pro Leu Pro
            20

<210> SEQ ID NO 40
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 40

Leu Gly Ala Ser Trp His Arg Pro Asp Ala Cys Cys Leu Gly Tyr Gln
1               5                   10                  15

Lys Arg Pro Leu Pro
            20

<210> SEQ ID NO 41
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 41

Leu Gly Ala Ser Trp His Arg Pro Asp Lys Ala Cys Leu Gly Tyr Gln
1               5                   10                  15

Lys Arg Pro Leu Pro
            20

<210> SEQ ID NO 42
<211> LENGTH: 21
<212> TYPE: PRT
<213> ORGANISM: Artificial Sequence
<220> FEATURE:
<223> OTHER INFORMATION: aCXCR4 targeting moiety

<400> SEQUENCE: 42

Leu Gly Ala Ser Trp His Arg Pro Asp Lys Cys Cys Leu Gly Tyr Ala
1               5                   10                  15

Lys Arg Pro Leu Pro
            20

<210> SEQ ID NO 43
<211> LENGTH: 21
<212> TYPE: PRT
<213> ORGANISM: Artificial Sequence

```
<220> FEATURE:
<223> OTHER INFORMATION: a CXCR4 targeting moiety

<400> SEQUENCE: 43

Leu Gly Ala Ser Trp His Arg Pro Asp Lys Cys Cys Leu Gly Tyr Gln
1               5                   10                  15

Lys Ala Pro Leu Pro
            20

<210> SEQ ID NO 44
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 44

Leu Gly Ala Ser Trp His Arg Pro Asp Lys Ala Ala Leu Gly Tyr Gln
1               5                   10                  15

Lys Arg Pro Leu Pro
            20

<210> SEQ ID NO 45
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 45

Leu Gly Ala Ser Trp His Arg Pro Asp Lys Gly Cys Leu Gly Tyr Gln
1               5                   10                  15

Lys Arg Pro Leu Pro
            20

<210> SEQ ID NO 46
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 46

Leu Gly Ala Ser Trp His Arg Pro Asp Lys Phe Cys Leu Gly Tyr Gln
1               5                   10                  15

Lys Arg Pro Leu Pro
            20

<210> SEQ ID NO 47
<211> LENGTH: 21
<212> TYPE: PRT
<213> ORGANISM: Artificial Sequence
<220> FEATURE:
<223> OTHER INFORMATION: a CXCR4 targeting moiety

<400> SEQUENCE: 47

Leu Gly Ala Ser Trp His Arg Pro Asp Lys Ala Gly Leu Gly Tyr Gln
1               5                   10                  15

Lys Arg Pro Leu Pro
            20

<210> SEQ ID NO 48
<211> LENGTH: 21
<212> TYPE: PRT
```

<213> ORGANISM: Artificial Sequence
<220> FEATURE:
<223> OTHER INFORMATION: a CXCR4 targeting moiety

<400> SEQUENCE: 48

Leu Gly Ala Ser Trp His Arg Pro Asp Lys Ala Phe Leu Gly Tyr Gln
1               5                   10                  15

Lys Arg Pro Leu Pro
            20

<210> SEQ ID NO 49
<211> LENGTH: 17
<212> TYPE: PRT
<213> ORGANISM: Artificial Sequence
<220> FEATURE:
<223> OTHER INFORMATION: a CXCR4 targeting moiety

<400> SEQUENCE: 49

Met Leu Gly Ala Ser Trp His Arg Pro Asp Lys Cys Cys Leu Gly Tyr
1               5                   10                  15

Gln

<210> SEQ ID NO 50
<211> LENGTH: 17
<212> TYPE: PRT
<213> ORGANISM: Artificial Sequence
<220> FEATURE:
<223> OTHER INFORMATION: a CXCR4 targeting moiety

<400> SEQUENCE: 50

Met Leu Gly Ala Ser Trp His Arg Pro Asp Lys Phe Cys Leu Gly Tyr
1               5                   10                  15

Gln

<210> SEQ ID NO 51
<211> LENGTH: 17
<212> TYPE: PRT
<213> ORGANISM: Artificial Sequence
<220> FEATURE:
<223> OTHER INFORMATION: a CXCR4 targeting moiety

<400> SEQUENCE: 51

Met Leu Gly Ala Ser Trp His Arg Pro Asp Lys Cys Phe Leu Gly Tyr
1               5                   10                  15

Gln

<210> SEQ ID NO 52
<211> LENGTH: 17
<212> TYPE: PRT
<213> ORGANISM: Artificial Sequence
<220> FEATURE:
<223> OTHER INFORMATION: a CXCR4 targeting moiety

<400> SEQUENCE: 52

Met Leu Gly Ala Ser Trp His Arg Pro Asp Lys Ala Cys Leu Gly Tyr
1               5                   10                  15

Gln

<210> SEQ ID NO 53
<211> LENGTH: 17
<212> TYPE: PRT
<213> ORGANISM: Artificial Sequence
<220> FEATURE:
<223> OTHER INFORMATION: a CXCR4 targeting moiety

<400> SEQUENCE: 53

Met Leu Gly Ala Ser Trp His Arg Pro Asp Lys Cys Ala Leu Gly Tyr
1               5                   10                  15

Gln

<210> SEQ ID NO 54
<211> LENGTH: 58
<212> TYPE: PRT
<213> ORGANISM: Artificial Sequence
<220> FEATURE:
<223> OTHER INFORMATION: a HER2 targeting moiety

<400> SEQUENCE: 54

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 55
<211> LENGTH: 58
<212> TYPE: PRT
<213> ORGANISM: Artificial Sequence
<220> FEATURE:
<223> OTHER INFORMATION: a EGFR targeting moiety

<400> SEQUENCE: 55

Val Asp Asn Lys Phe Asn Lys Glu Met Trp Ala Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 56
<211> LENGTH: 14
<212> TYPE: PRT
<213> ORGANISM: Artificial Sequence
<220> FEATURE:
<223> OTHER INFORMATION: Bombesin, B14

<400> SEQUENCE: 56

Glu Gln Arg Leu Gly Asn Gln Trp Ala Val Gly His Leu Met
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Bombesin, B10

<400> SEQUENCE: 57

Gly Asn Gln Trp Ala Val Gly His Leu Met
1               5                   10

```
<210> SEQ ID NO 58
<211> LENGTH: 10
<212> TYPE: PRT
<213> ORGANISM: Artificial Sequence
<220> FEATURE:
<223> OTHER INFORMATION: Gastrin-releasing peptide

<400> SEQUENCE: 58

Gly Asn His Trp Ala Val Gly His Leu Met
1               5                   10

<210> SEQ ID NO 59
<211> LENGTH: 17
<212> TYPE: PRT
<213> ORGANISM: Artificial Sequence
<220> FEATURE:
<223> OTHER INFORMATION: a Collagen Type I targeting moiety

<400> SEQUENCE: 59

Lys Lys Trp His Cys Tyr Thr Tyr Phe Pro His His Tyr Cys Val Tyr
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: a collagen type I targeting moiety

<400> SEQUENCE: 60

Lys Lys Trp His Cys Tyr Thr Tyr Phe Pro His His Tyr Cys Val Tyr
1               5                   10                  15

Tyr

<210> SEQ ID NO 61
<211> LENGTH: 17
<212> TYPE: PRT
<213> ORGANISM: Artificial Sequence
<220> FEATURE:
<223> OTHER INFORMATION: a collagen type I targeting moiety

<400> SEQUENCE: 61

Lys Lys Trp His Cys Tyr Thr Tyr Phe Pro His His Tyr Cys Val Tyr
1               5                   10                  15

Trp

<210> SEQ ID NO 62
<211> LENGTH: 17
<212> TYPE: PRT
<213> ORGANISM: Artificial Sequence
<220> FEATURE:
<223> OTHER INFORMATION: a collagen type I targeting moiety

<400> SEQUENCE: 62

Lys Lys Trp His Cys Tyr Thr Tyr Phe Pro His His Tyr Cys Val Tyr
1               5                   10                  15

Phe

<210> SEQ ID NO 63
<211> LENGTH: 17
<212> TYPE: PRT
<213> ORGANISM: Artificial Sequence
<220> FEATURE:
<223> OTHER INFORMATION: a collagen type I targeting moiety
```

```
<400> SEQUENCE: 63

Gly Lys Trp His Cys Tyr Thr Tyr Phe Pro His His Tyr Cys Val Tyr
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: a collagen type I targeting moiety

<400> SEQUENCE: 64

Gly Lys Trp His Cys Tyr Thr Lys Phe Pro His His Tyr Cys Leu Tyr
1               5                   10                  15

Gly

<210> SEQ ID NO 65
<211> LENGTH: 17
<212> TYPE: PRT
<213> ORGANISM: Artificial Sequence
<220> FEATURE:
<223> OTHER INFORMATION: a collagen type I targeting moiety

<400> SEQUENCE: 65

Gly Lys Trp His Cys Tyr Thr Tyr Phe Pro His His Tyr Cys Leu Tyr
1               5                   10                  15

Gly

<210> SEQ ID NO 66
<211> LENGTH: 12
<212> TYPE: PRT
<213> ORGANISM: Artificial Sequence
<220> FEATURE:
<223> OTHER INFORMATION: an integrin alphaVbeta3 targeting moiety

<400> SEQUENCE: 66

Arg Gly Asp Arg Gly Asp Arg Gly Asp Arg Gly Asp
1               5                   10

<210> SEQ ID NO 67
<211> LENGTH: 4
<212> TYPE: PRT
<213> ORGANISM: Artificial Sequence
<220> FEATURE:
<223> OTHER INFORMATION: a linker where X is no amino acid or first
      amino acid of attached sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 67

Gly Gly Gly Xaa
1

<210> SEQ ID NO 68
<211> LENGTH: 5
<212> TYPE: PRT
<213> ORGANISM: Artificial Sequence
<220> FEATURE:
<223> OTHER INFORMATION: a linker

<400> SEQUENCE: 68
```

```
Gly Gly Ser Gly Gly
1               5

<210> SEQ ID NO 69
<211> LENGTH: 4
<212> TYPE: PRT
<213> ORGANISM: Artificial Sequence
<220> FEATURE:
<223> OTHER INFORMATION: a linker

<400> SEQUENCE: 69

Gly Ser Gly Ser
1

<210> SEQ ID NO 70
<211> LENGTH: 161
<212> TYPE: PRT
<213> ORGANISM: Artificial Sequence
<220> FEATURE:
<223> OTHER INFORMATION: CaMBom ProCA

<400> SEQUENCE: 70

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asp Gly Thr Ile Asp
    50                  55                  60

Phe Pro Glu Phe Leu Thr Met Met Ala Arg Lys Met Lys Asp Thr Gly
65                  70                  75                  80

Gly Asn Gln Trp Ala Val Gly His Leu Met Gly Gly Asp Ser Glu Glu
                85                  90                  95

Glu Ile Arg Glu Ala Phe Arg Val Phe Asp Lys Asp Gly Asp Gly Tyr
            100                 105                 110

Ile Ser Ala Ala Glu Leu Arg His Val Met Thr Asn Leu Gly Glu Lys
        115                 120                 125

Leu Thr Asp Glu Glu Val Asp Glu Met Ile Arg Glu Ala Asp Ile Asp
    130                 135                 140

Gly Asp Gly Gln Val Asn Tyr Glu Glu Phe Val Gln Met Met Thr Ala
145                 150                 155                 160

Lys
```

UNITED STATES PATENT AND TRADEMARK OFFICE
CERTIFICATE OF CORRECTION

PATENT NO. : 11,426,471 B2
APPLICATION NO. : 17/015633
DATED : August 30, 2022
INVENTOR(S) : Jenny Jie Yang et al.

Page 1 of 1

It is certified that error appears in the above-identified patent and that said Letters Patent is hereby corrected as shown below:

In the Specification

Column 19, Table 1:
Please delete:
"MSMTDLLSAEDIKKAIGAFTAADSFDHKKFFQMVGLKKKSADDVKKVFHILDKD
KD55GFIEEDELGSILKGFSSDARDLSAKETKTLMAAGDKDGDGKIGVEEWSTLVAES"

And insert:
-- MSMTDLLNAEDIKKAVGAFSATDSFDHKKFFQMVGLKKKSADDVKKVFHMLDKDKDG
FIEEDELGFILKGFSPDARDLSAKETKMLMAAGDKDGDGKIGVEEWSTLVAES --

Signed and Sealed this
First Day of July, 2025

Coke Morgan Stewart
*Acting Director of the United States Patent and Trademark Office*